(12) United States Patent
Iguchi

(10) Patent No.: US 9,169,518 B2
(45) Date of Patent: Oct. 27, 2015

(54) PRIMER SET FOR DETECTING EGFR EXON 21 POLYMORPHISM AND APPLICATION THEREOF

(75) Inventor: Aki Iguchi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 300 days.

(21) Appl. No.: 13/284,322

(22) Filed: Oct. 28, 2011

(65) Prior Publication Data

US 2012/0107816 A1    May 3, 2012

(30) Foreign Application Priority Data

Oct. 29, 2010  (JP) ................................. 2010-243876
Oct. 27, 2011  (JP) ................................. 2011-235784

(51) Int. Cl.
  *C12Q 1/68*  (2006.01)

(52) U.S. Cl.
  CPC ........ *C12Q 1/6886* (2013.01); *C12Q 2525/161* (2013.01); *C12Q 2535/125* (2013.01); *C12Q 2600/156* (2013.01)

(58) Field of Classification Search
  None
  See application file for complete search history.

(56) References Cited

FOREIGN PATENT DOCUMENTS

| EP | 1881079 A1 | 1/2008 | |
|---|---|---|---|
| JP | 2008-529532 | 8/2008 | ............. C12N 15/09 |
| JP | 2008-534025 A | 8/2008 | |
| JP | 2009-544283 A | 12/2009 | |
| WO | WO 0047766 A1 * | 8/2000 | |
| WO | 2006/106316 A2 | 10/2006 | |
| WO | 2008/009740 A1 | 1/2008 | |
| WO | WO 2010/001969 | 1/2010 | ............. C12N 15/09 |

OTHER PUBLICATIONS

Uhara et al. Clinica Chimica Acta (2009) 401: 68-72.*
Moiseyenko et al. Onkologie (Apr. 9, 2010) 33: 231-238.*
Sarkar et al. Analytical Biochemistry (1990) 186(1): 64-68.*
GenBank Accession No. NM_005228.2 (2003).*
Endo et al., "Epidermal growth factor receptor gene mutation in non-small cell lung cancer using highly sensitive and fast TaqMan PCR assay," Lung Cancer, 50: 375-384 (2005).
Paez et al., "EGFR Mutations in Lung Cancer: Correlation with Clinical Response to Gefitinib Therapy," Science, 304: 1497-1500 (2004).
Sasaki et al., "EGFR Mutation Status in Japanese Lung Cancer Patients: Genotyping Analysis Using LightCycler," Clinical Cancer Research, 11: 2924-2929 (2005).
Willmore-Payne et al., "Detection of epidermal growth factor receptor and human epidermal growth factor receptor 2 activating mutations in lung adenocarcinoma by high-resolution melting amplicon analysis: correlation with gene copy number, protein expression, and hormone receptor expression," Human Pathology, 37: 755-763 (2006).
Extended European Search Report issued in corresponding European Patent Application No. 11187129.9 dated Jan. 13, 2012.
Hoshi et al., "Rapid Detection of Epidermal Growth Factor Receptor Mutations in Lung Cancer by the Smart-Amplification Process", Clin. Cancer Res., 13:4974-4983 (2007).
Inukai et al., "Presence of Epidermal Growth Factor Receptor Gene T790M Mutation as a Minor Clone in Non-Small Cell Lung Cancer", Can. Res., 66:7854-7858 (2006).
Mitsudomi et al., "Mutations of the Epidermal Growth Factor Receptor Gene Predict Prolonged Survival After Gefitinib Treatment in Patients With Non-Small-Cell Lung Cancer With Postoperative Recurrence", Journal of Clinical Oncology, 23(11):2513-2520 (Apr. 10, 2005).
Office Action issued in corresponding Japanese Patent Application No. 2011-235784 dated Dec. 2, 2014.

* cited by examiner

*Primary Examiner* — Angela M Bertagna
(74) *Attorney, Agent, or Firm* — Morgan, Lewis & Bockius LLP

(57) ABSTRACT

The invention provides a primer set for detecting a polymorphism in EGFR exon 21 L858R. The primer set has a P1 oligonucleotide and a P2 oligonucleotide and can performing amplification by using a region including the 172792nd base of SEQ ID NO: 1 as a template. As a base that is complementary to the 172792nd base of SEQ ID NO: 1, the P1 oligonucleotide has cytosine and the P2 oligonucleotide has adenine. The melting temperature of the P1 oligonucleotide is higher than the melting temperature of the P2 oligonucleotide, and/or the P1 oligonucleotide is one or more bases longer than the P2 oligonucleotide. The invention further provides a polymorphism detection primer, a polymorphism detection method using the primer set, a method of evaluating a EGFR tyrosine kinase inhibitor using the primer set, a primer used in the polymorphism detection method, and a kit including the primer set.

24 Claims, 4 Drawing Sheets

PRIMER SET FOR DETECTING EGFR EXON 21 POLYMORPHISM AND APPLICATION THEREOF

CROSS-REFERENCE TO RELATED APPLICATION

This application claims priority under 35 USC 119 from Japanese Patent Application No. 2010-243876 filed on Oct. 29, 2010 and Japanese Patent Application No. 2011-235784 filed on Oct. 27, 2011, the disclosures of which are incorporated by reference herein.

SEQUENCE LISTING SUBMISSION VIA EFS-WEB

A computer readable text file, entitled "068022-5138-SequenceListing.txt," created on or about Oct. 27, 2011 with a file size of about 238 kb contains the sequence listing for this application and is hereby incorporated by reference in its entirety.

BACKGROUND

Field of the Invention

The present invention relates to a primer set for detecting EGFR exon 21 polymorphism and an application of the primer set.

It has been thought that epidermal growth factor receptor (EGFR) plays an important role in lung cancer. Medicaments which can suppress functions of EGFR have been utilized in the field of lung cancer therapy. EGFR tyrosine kinase inhibitors, such as gefitinib, erlotinib, or the like, which are used to treat non-small cell lung cancer patient, have been known as such medicaments. These medicaments are not only used for lung cancer, but also tried to apply for adenocarcinoma. However, in some group of patients, effects of EGFR tyrosine kinase inhibitors seem sometime not enough. Also, in another group of patients, although EGFR tyrosine kinase inhibitors induce reactions at the beginning, there are cases in which their effects gradually decrease against expectations.

For these reasons, factors for predicting effects of EGFR tyrosine kinase inhibitors have explored for use of the inhibitors, and EGFR gene mutation has been found as such an important factor. Examples of a known predictive factor include a mutation of EGFR exon 20, at codon 790 (T790M) (JP 2008-529532, Cancer Research, Vol. 66, No. 16, 2006, pp. 7854-7858), a mutation of exon 18, at codon 719 (G719X) (Cancer Research, Vol. 66, No. 16, 2006, pp. 7854-7858).

A mutation from leucine to arginine of EGFR exon 21, at codon 858 (EGFR exon 21 L858R) has been specifically thought to enhance a tumor reduction effect of gefitinib. Because the EGFR mutation is found in a high percentage (approximately 45%) of lung cancers, it is important as a predictive factor to be referred before dosing.

A direct sequencing method (J. Clin. Oncology, Vol 23, No 11 (April 10), 2005: pp. 2513-2520), or SMAP (SMart-Ablification Process) method (Clin Cancer Res 2007; Vol. 13 (17) Sep. 1, 2007: pp. 4974-4983) has been known as a technique for detecting EGFR exon 21 L858R.

Meanwhile, a mutation detection method, which includes preferentially amplifying nucleic acid sequences having mutated bases, by using both mutant type and wild type (normal type) primers in one reaction, has been known as an easy, sensitive, and reliable method of detecting mutations (WO 2010/001969).

SUMMARY

Samples used in actual tests are soluble DNA which is derived from plasma or serum. High specificity is required to detect mutations in such DNA. In the case of the direct sequencing method, however, the specificity is usually thought as about 10%, which may not be likely enough to detect mutations in soluble DNA. Meanwhile, although the SMAP method may be sufficient in view of sensitivity, designing of materials such as primers may not be easy, and actual manipulation may be complicated.

The present invention was made in consideration of these circumstances. The present invention relates to providing a probe which may enable to easily detect a polymorphism of EGFR exon 21 with high sensitivity as well as application of the probe.

One exemplary embodiment of a first aspect of the present invention is [1] a primer set for detecting a polymorphism in EGFR exon 21, the primer set comprising a P1 oligonucleotide and a P2 oligonucleotide and being capable of performing amplification by using a region in SEQ ID NO: 1 as a template, the region comprising the 172792nd base of SEQ ID NO: 1, the P1 oligonucleotide having a length of from 10 bases to 50 bases and having cytosine as a base that is complementary to the 172792nd base of SEQ ID NO: 1, the P2 oligonucleotide having a length of from 10 bases to 50 bases and having adenine as a base that is complementary to the 172792nd base of SEQ ID NO: 1, and the P1 oligonucleotide and the P2 oligonucleotide satisfying at least one of the following relationships: the melting temperature of the P1 oligonucleotide is higher than the melting temperature of the P2 oligonucleotide, or the P1 oligonucleotide is one or more bases longer than the P2 oligonucleotide.

Another exemplary embodiment of the first aspect of the present invention is [2] the primer set of [1], wherein at least one of the P1 oligonucleotide or the P2 oligonucleotide comprises, at a position that is different from the position of the base that is complementary to the 172792nd base of SEQ ID NO: 1, at least one base that is non-complementary to the base sequence of SEQ ID NO: 1.

Another exemplary embodiment of the first aspect of the present invention is [3] the primer set of [1] or [2], wherein at least one of the P1 oligonucleotide or the P2 oligonucleotide comprises, at a position that is different from the position of a base that is complementary to the 172792nd base of SEQ ID NO: 1, an additional sequence that is formed of two to ten sequential bases that are non-complementary to the base sequence of SEQ ID NO: 1 and is located at the 5' terminus of the oligonucleotide strand.

Another exemplary embodiment of the first aspect of the present invention is [4] the primer set of any one of [1] to [3], wherein at least one of the P1 oligonucleotide or the P2 oligonucleotide comprises, at a position that is different from the position of the base that is complementary to the 172792nd base of SEQ ID NO: 1, either a mismatch base or a sequence of two to twenty mismatch bases that are non-complementary to the base sequence of SEQ ID NO: 1.

Another exemplary embodiment of the first aspect of the present invention is [5] the primer set of any one of [1] to [4], wherein at least one of the P1 oligonucleotide or the P2 oligonucleotide comprises the base that is complementary to the 172792nd base of SEQ ID NO: 1 at one of the first to third positions from its 3' terminus.

Another exemplary embodiment of the first aspect of the present invention is [6] the primer set of any one of [1] to [5], wherein the melting temperature of the P1 oligonucleotide is 0.1° C. to 20° C. higher than the melting temperature of the P2 oligonucleotide.

Another exemplary embodiment of the first aspect of the present invention is [7] the primer set of any one of [1] to [6], further comprising a primer that is homologous to a sequence that is in a region located further toward the 5' terminus side than a template nucleic acid sequence in the base sequence of SEQ ID NO: 1, wherein the template nucleic acid sequence is complementary to the P1 oligonucleotide or the P2 oligonucleotide.

Another exemplary embodiment of the first aspect of the present invention is [8] the primer set of any one of [1] to [7], comprising at least one of oligonucleotides of SEQ ID NO: 2 to SEQ ID NO: 11 as the P1 oligonucleotide and at least one of oligonucleotides of SEQ ID NO: 12 to SEQ ID NO: 21 as the P2 oligonucleotide.

One exemplary embodiment of a second aspect of the present invention is [9] a primer for detecting a polymorphism in EGFR exon 21, the primer being capable of performing amplification by using a region in SEQ ID NO: 1 as a template, the region comprising the 172792nd base of SEQ ID NO: 1, and the primer being an oligonucleotide having a length of from 10 bases to 50 bases and having cytosine as a base that is complementary to the 172792nd base of SEQ ID NO: 1.

Another exemplary embodiment of the second aspect of the present invention is [10] the primer of [9], comprising, at a position that is different from the position of the base that is complementary to the 172792nd base of SEQ ID NO: 1, at least one base that is non-complementary to the base sequence of SEQ ID NO: 1.

Another exemplary embodiment of the second aspect of the present invention is [11] the primer of [9] or [10], comprising, at a position that is different from the position of the base that is complementary to the 172792nd base of SEQ ID NO: 1, one or more bases that are non-complementary to the base sequence of SEQ ID NO: 1, wherein the one or more non-complementary bases are selected from the group consisting of:
  an additional sequence that is formed of two to ten sequential bases and is located at the 5' terminus of the primer;
  a mismatch base; and
  a sequence of two to twenty mismatch bases.

Another exemplary embodiment of the second aspect of the present invention is [12] the primer of any one of [9] to [11], comprising the base that is complementary to the 172792nd base of SEQ ID NO: 1 at one of the first to third positions from its 3' terminus.

One exemplary embodiment of a third aspect of the present invention is [13] method of detecting a polymorphism in EGFR gene comprising:
  (I) performing amplification by contacting the primer set of any one of [1] to [8] with a nucleic acid sample comprising a nucleic acid and using the nucleic acid as a template;
  (II) obtaining a hybrid formed of a single-stranded nucleic acid and a probe by contacting the single-stranded nucleic acid with the probe, the single-stranded nucleic acid being obtained by the amplification and the probe being capable of detecting a polymorphism in EGFR exon 21;
  (III) measuring a change of a signal based on dissociation of the hybrid by changing the temperature of a sample comprising the hybrid in order to dissociate the hybrid;
  (IV) determining, as a melting temperature, a temperature at which the hybrid dissociates based on the signal variation; and
  (V) checking for presence of the EGFR exon 21 L858R or assessing an abundance ratio of a nucleic acid having the EGFR exon 21 L858R based on the melting temperature.

Another exemplary embodiment of the third aspect of the present invention is [14] the method of [13], wherein the amplification and the obtaining of the hybrid are performed concurrently.

One exemplary embodiment of a fourth aspect of the present invention is [15] a method of evaluating an EGFR tyrosine kinase inhibitor comprising:
  detecting a polymorphism in the EGFR gene by the method of [13] or [14]; and
  evaluating a resistance of a source of the nucleic acid sample to the EGFR tyrosine kinase inhibitor or an effect of the EGFR tyrosine kinase inhibitor based on a result of the detection.

One exemplary embodiment of a fifth aspect of the present invention is [16] a primer adapted for use in the method of [13] or [14], the primer being the P1 oligonucleotide of any one of SEQ ID NO: 2 to SEQ ID NO: 11 or the P2 oligonucleotide of any one of SEQ ID NO: 12 to SEQ ID NO: 21.

One exemplary embodiment of a sixth aspect of the present invention is [17] a kit comprising the primer set of any one of [1] to [8].

Another exemplary embodiment of the sixth aspect of the present invention is [18] the kit of [17], further comprising a probe which can detect EGFR exon 21 L858R.

DETAILED DESCRIPTION

Primer Set

Figure 1A:
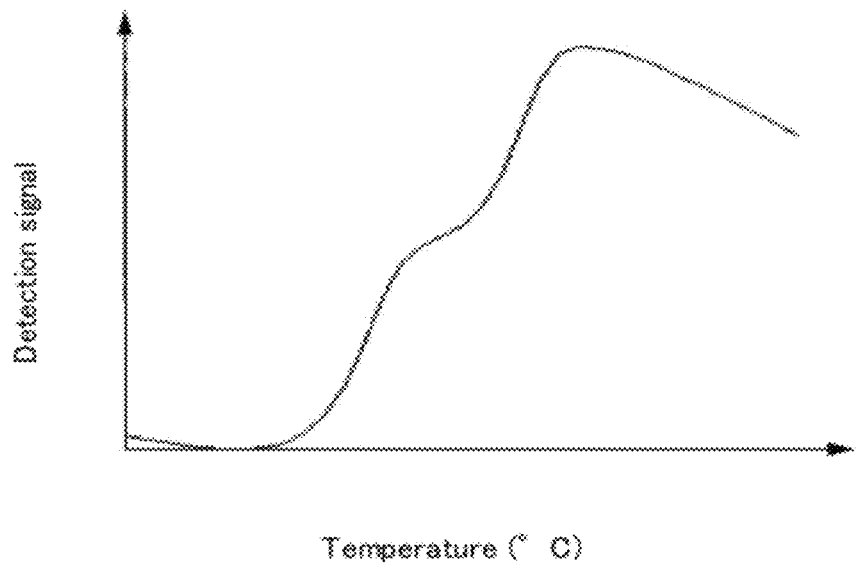
FIG. 1A is an example of a melting curve of a nucleic acid mixture.

The primer set of one exemplary embodiment of one aspect of the invention detects a polymorphism in EGFR exon 21. The primer set has at least a P1 oligonucleotide and a P2 oligonucleotide and is capable of performing amplification by using a region in SEQ ID NO: 1 as a template, in which the region has at least the 172792nd base of SEQ ID NO: 1.

The P1 oligonucleotide has a length of from 10 bases to 50 bases and has cytosine (C) as a base that is complementary to the 172792nd base of SEQ ID NO: 1.

The P2 oligonucleotide has a length of from 10 bases to 50 bases and has adenine (A) as a base that is complementary to the 172792nd base of SEQ ID NO: 1.

The melting temperature (Tm) of the P1 oligonucleotide is higher than the melting temperature of the P2 oligonucleotide, and/or the P1 oligonucleotide is one or more bases longer than the P2 oligonucleotide.

The primer set has the P1 oligonucleotide, that is the mutant type primer having C as a base that is complementary to the 172792nd base of SEQ ID NO: 1 and can be used to detect a polymorphism of EGFR exon 21, and the P2 oligonucleotide, that is the wild type primer having A as a base that is complementary to the 172792nd base of SEQ ID NO: 1, in which the melting temperature of the P1 oligonucleotide is higher than the melting temperature of the P2 oligonucleotide, and/or the P1 oligonucleotide is one or more bases longer than the P2 oligonucleotide. By using these two oligonucleotides as primers in one reaction system, a polymorphism of EGFR exon 21 may be detected easily and with high sensitivity.

The "EGFR exon 21 L858R" herein means a mutation in exon 21 of EGFR gene, in which leucine in the codon 858 is mutated to arginine.

The "polymorphism of EGFR exon 21" herein means the "EGFR exon 21 L858R".

The "base sequence of the EGFR exon 21" herein means the sequence of SEQ ID NO: 1, that is Gene ID: 1956 of GenBank accession No. NC000007 (version: NC000007.13), 55086724-55275030.

The "mutation of EGFR exon 21 L858R" herein means the mutation in which the 172792nd base of SEQ ID NO: 1 is mutated from thymine (T) to guanine (G).

The position at 172792nd of the base sequence shown in SEQ ID NO: 1 is specifically referred to as a "mutated site."

A "template nucleic acid sequence" herein means a part of base sequence shown in SEQ ID NO: 1 as a template, to which a primer anneals to perform amplification of a nucleic acid.

The "melting temperature (Tm)" means a temperature at which double strand nucleic acid is dissociated. This temperature is usually defined as the temperature at which an increase of an absorbance of a sample at a wavelength of 260 nm reaches 50% relative to total increase of the absorbance achievable by increasing temperature of the sample. That is, when double strand nucleic acid, such as a DNA solution, is heated, the absorbance at 260 nm increases. This occurs because of a melting of DNA, which is a phenomenon that a hydrogen bond between both strands of a double strand DNA is loosed by heating, and then the double strand DNA is dissociated to single strand DNA. When all double strand DNA is dissociated and becomes single strand DNA, its absorbance may be about 1.5 times higher than the absorbance at the beginning of heating (absorbance of double strand DNA only), and thereby completion of melting can be determined Tm is defined based on this phenomenon.

The term "step" includes not only an independent step but also a step which cannot be clearly distinguished from another step, provided that an expected effect of the step is achieved thereby.

Indications of a numerical range using "from m to n" herein indicate a numerical value range including a numerical value indicated as a lower limit of the range ("m") as a minimum value, and a numerical value indicated as an upper limit of the range ("n") as a maximum value.

When referring to an amount of component in a composition, if the composition includes plural substances which are within the scope of the component, the amount means sum of the amounts of the plural substances in the composition, unless otherwise noted.

Primer Set

The primer set has at least the P1 oligonucleotide, that is a mutant type primer, and the P2 oligonucleotide, that is the wild type primer.

The P1 oligonucleotide can perform amplification by using a region in SEQ ID NO: 1 as a template, in which the region includes the base located at the mutated site of the 172792nd position in SEQ ID NO: 1. The P1 oligonucleotide has a length of from 10 bases to 50 bases and has cytosine as a base that is complementary to the 172792nd base of SEQ ID NO: 1.

The P2 can perform amplification by using a region in SEQ ID NO: 1 as a template, in which the region includes the base located at the mutated site of the 172792nd position in SEQ ID NO: 1. The P2 oligonucleotide has a length of from 10 bases to 50 bases and has adenine as a base that is complementary to the 172792nd base of SEQ ID NO: 1.

The P1 oligonucleotide and the P2 oligonucleotide are required to be under at least one of the relationships that the P1 oligonucleotide has higher Tm than the P2 oligonucleotide, or that the P1 oligonucleotide is longer than the P2 oligonucleotide. The P1 oligonucleotide may have higher affinity to a template nucleic acid sequence than the P2 oligonucleotide and may have stronger binding property to a template nucleic acid sequence when at least one of the relationships is satisfied. As a result of that, when nucleic acid is amplified in one reaction by using both the P1 oligonucleotide and the P2 oligonucleotide as primers, amplification with the P1 oligonucleotide may be preferential, and thereby the polymorphism of the mutant type EGFR exon 21 can be detected easily and with high sensitivity.

Either one or both of the relationship with respect to Tms and the relationship with respect to base lengths may be satisfied.

When the P1 oligonucleotide has higher Tm than the P2 oligonucleotide, difference of Tms between the P1 oligonucleotide and the P2 oligonucleotide is not particularly limited. For example, it may be preferably from 0.1° C. to 20° C., more preferably from 0.1° C. to 10° C., and still more preferably from 0.1° C. to 5° C. In this range, false positive may be suppressed. The Tm herein means a Tm of a hybrid, which hybrid is composed of base sequences having a substantially complete complementarity.

When Tm is adjusted by GC content, relatively high Tm can be established by, for example, relatively increasing GC content. In embodiments, it may be preferable to set the GC content of the P1 oligonucleotide to be higher than that of the P2 oligonucleotide. Alternatively, Tm may be set by adjusting both primer length and GC content. Alternatively, by incorporating, for example, modification to use LNA as RNA analog, PNA as peptide nucleic acid, BNA as crosslinked nucleic acid or the like, into a sequence of an oligonucleotide, Tm of the oligonucleotide may be set to be relatively higher than another oligonucleotide which does not include such modifications.

When the P1 oligonucleotide is one or more base longer than the P2 oligonucleotide, the P1 oligonucleotide has higher affinity to a template sequence. Accordingly, amplification with the P1 oligonucleotide may be preferentially performed comparing to amplification with the P2 oligonucleotide.

The relationship with respect to Tms or the relationship with respect to base lengths may be preferably achieved by that at least one of the P1 oligonucleotide or the P2 oligonucleotide has, at a position that is different from the position of the base that is complementary to the 172792nd base of SEQ ID NO: 1, at least one base that is non-complementary to the base sequence of SEQ ID NO: 1. This may enable to make these relationships be adjustable through construction of sequences.

Tm or base length of the oligonucleotides may be adjusted by selecting positions of insertion or addition in the oligonucleotide, number of base, type of base and the like for the non-complementary base at a position that is different from the mutated site. In view of this, the base may be put either in the P1 oligonucleotide or the P2 oligonucleotide, or may be put in both.

When one or more bases are added to extend the length of the P1 oligonucleotide, it may be preferable that the base(s) is added to the site of 5' terminus side from the mutated site, and may be more preferably added to the site of 5' terminus side from the region complementary to the template nucleic acid sequence of the P1 oligonucleotide, and thereby, for example, false positive may be suppressed.

When the P1 oligonucleotide is made longer than the P2 oligonucleotide, the difference between the oligonucleotides is not particularly limited. In embodiments, the difference may be from one base to 20 bases, preferably from one base to 10 bases, and more preferably from one base to 5 bases.

Bases added to extend the length of the P1 oligonucleotide may be or may not be complementary to the base sequence shown in SEQ ID NO: 1. When the base is not complementary to the base sequence shown in SEQ ID NO: 1, the base may be or may not be continued to an additional sequence explained below.

When each of the oligonucleotides is "capable of performing amplification by using a region in SEQ ID NO: 1 as a template, in which the region includes the 172792nd base of SEQ ID NO: 1", it means that when the oligonucleotide is used as a primer for the amplification reaction such as PCR (polymerase chain reaction), the oligonucleotide anneals to a predefined region including the mutated site, and can amplify a sequence which is complementary to the sequence having the mutated site. Accordingly, each of the oligonucleotides may be a sequence fully complementary to the base sequence shown in SEQ ID NO: 1, a partially complementary sequence to the base sequence shown in SEQ ID NO: 1, or a sequence having a partially non-complementary base (mismatch base), as long as it can anneal to the predefined region including the mutated site in the base sequence shown in SEQ ID NO: 1. The mismatch base means a nucleic acid base which does not form a proper pair of G-C or A-T, and specifically means a nucleic acid base which result in a mismatch base pair of G-G, G-A, G-T, A-A, A-C, C-T, C-C, or T-T.

For example, as described in below, it may be preferable that each of the oligonucleotides is a partially complementary sequence, or a sequence having a partially mismatched base, as long as the relationship with respect to Tms or the relationship with respect to base lengths are not disturbed. When such sequence is used, for example, sensitivity to detect mutation may be increased and false positive may be decreased.

Length of each of the oligonucleotides may be in the range of from 10 bases to 50 bases, and may be preferably in the range of from 15 bases to 40 bases, and may be more preferably in the range of from 18 bases to 25 bases, as long as relationships with respect to Tms or with respect to base lengths described above are not impaired. The length in this range, for example, may increase detection sensitivity, and may suppress false positive efficiently. The base length is adjustable along with other structural characteristics of the P1 oligonucleotide.

The non-complementary bases other than the base that is complementary to the mutated site may be an additional sequence that is formed of two to ten sequential bases and is located at the 5' terminus of the oligonucleotide strand. Such additional sequence, for example, may increase detection sensitivity or may suppress false positive.

An additional sequence which may be added to the P1 oligonucleotide and the P2 oligonucleotide respectively may be from 3 bases to 10 bases, preferably from 4 bases to 9 bases, and more preferably from 5 bases to 7 bases, which are non-complementary to the base sequence shown in SEQ ID NO: 1. When the additional sequence is added to 5' terminus, for example, sensitivity may be increased, and annealing of each primer to each other template nucleic acid sequence may be efficiently suppressed, or amplification efficiency may be increased. Also, when the length of the additional sequence is in this range, for example, false positive may be suppressed, or amplification efficiency may be increased.

In the P1 oligonucleotide and the P2 oligonucleotide, the additional sequence may be same or different length, and may have same or different base sequence. In embodiments, it may be preferable that the additional sequences have different base sequence. The GC content of base sequence of the additional sequence may be preferably about from 40% to 60%, but not particularly limited thereto. When the GC content is in this range, for example, amplification efficiency of the mutant type sequence or the wild type sequence may be maintained. Also, when the additional sequence is added to both the P1 oligonucleotide and the P2 oligonucleotide, the GC content of the additional sequence of the P1 oligonucleotide may be preferably made higher. In this case, sensitivity for the mutant type sequence detection may be increased.

The P1 oligonucleotide may have, as a base complementary to the mutated site of EGFR exon 21 L858R, a base (cytosine) in its 3' region. In the P1 oligonucleotide, it may be preferable that either first to third base in the 3' terminus is a base that is complementary to a base at the mutated site. When the base complementary to a base at the mutated site is placed in such position, for example, detection sensitivity may be increased, or false positive may be suppressed.

Note that the "first base in the 3' terminus" herein means the base at the 3' terminus, and the "third base in the 3' terminus" means the third base counted in the direction of 3' to 5', when the base at 3' terminus is defined as the first base.

On the other hand, the P2 oligonucleotide may have, as a base complementary to the mutated site of EGFR exon 21 L858R, a base (adenine) in its 3' region. In the P1 oligonucleotide, it may be preferable that either first to third base in the 3' terminus is a base that is complementary to a base at the mutated site. When the base complementary to a base at the mutated site is placed in such position, for example, detection sensitivity may be increased, or false positive may be suppressed.

The distance (base position) of the base complementary to the mutated site from the 3' terminus in the P1 oligonucleotide may be the same or different from that in the P2 oligonucleotide. In embodiments, the distance of the base complementary to the mutated site from the 3' terminus may be preferably same in the P1 oligonucleotide and the P2 oligonucleotide. When the distance is same in the P1 oligonucleotide and the P2 oligonucleotide, for example, detection sensitivity may be increased or false positive may be suppressed.

In embodiments, one base or 2-20 sequential bases may be a mismatch base(s) which is(/are) a non-complementary base(s) which reside(s) at other than the mutated site in the oligonucleotide strand. When such a mismatch base(s) is(/are) introduced, for example, detection sensitivity may be increased or false positive may be suppressed.

Although the total number of such mismatch bases may be varied depending on a base sequence constituting each of the oligonucleotides, the total number may be preferably 10 or less, more preferably 5 or less, and still more preferably 3 or less. When the number of the mismatch base is in such range, it may be advantageous, for example, detection sensitivity may be increased or false positive may be suppressed.

Such mismatch base may be preferably placed in a position of 5' terminus side from the mutated site. Especially, at least one base from third to seventh base located in 5' terminus side from the mutated site may be preferably made as the mismatch base, and at least one base from third to fifth base located in 5' terminus side from the mutated site may be more preferably made as the mismatch base. When such position is employed, for example, detection sensitivity may be increased or false positive may be suppressed.

When both the P1 oligonucleotide and the P2 oligonucleotide have mismatch bases, it may be preferable that a position of a mismatch base in the P1 oligonucleotide and a position of a mismatch base in the P2 oligonucleotide are not corresponding to each other. Positions of the mismatch bases may be different. It may be preferably 1-6 bases apart, and more preferably 2-3 bases apart. Also, for example, when both the P1 oligonucleotide and the P2 oligonucleotide have mismatch bases, it may be preferable that a position of the mismatch base in the P1 oligonucleotide is at a farther 3' terminus side, compared to a position of the mismatch base in the P2 oligonucleotide. When positions of mismatch bases in the P1 oligonucleotide and the P2 oligonucleotide are correlated as such, for example, false positive may be suppressed.

Any base that is non-complimentary to the base sequence shown in SEQ ID NO: 1 can be employed as a mismatch base. In embodiments, adenine (A) or thymine (T) may preferable because of their relatively weak binding activities. When "A" or "T" is employed, for example, false positive may be suppressed.

Note that there are polymorphisms around the mutated site of the EGFR exon 21, which are not related to the polymorphisms to be detected herein. If necessary, mutations may be added to bases, which are not a target of detection, in both the P1 oligonucleotide and the P2 oligonucleotide to invalidate effects resulting from such unrelated polymorphisms. Such bases are referred to as "invalidation mutation" herein.

The additional sequence may be added in both or one of the P1 oligonucleotide and the P2 oligonucleotide. Also, the mismatch base may be added in both or one of the P1 oligonucleotide and the P2 oligonucleotide.

The primer set for polymorphism detection includes at least one P1 oligonucleotide and at least one P2 oligonucleotide. In embodiments, two or more of both or one of the P1 oligonucleotide and the P2 oligonucleotide may be included in the primer set as long as relationship with respective to Tms or the relationship with respective to base lengths described above are not generally disturbed.

Examples of P1 oligonucleotide are shown in Table 1, and examples of the P2 oligonucleotide are shown in Table 2. Note that the underlined "A" or "T" in Tables 1 and 2 means mismatch bases, and capital alphabets in the 5' terminus side means additional sequences. A base at the 3' terminus side in the respective oligonucleotide in Tables 1 and 2 is a base that is complimentary to the base at the mutated site. Also, "(a)" in Tables 1 and 2 means the invalidation mutation. Note that the Tms are calculated with MELTCALC®.

TABLE 1

|  | (5'→3') | mer | Tm (° C.) | SEQ ID No. |
|---|---|---|---|---|
| Mt-R2 | cacccagcagtttggccc | 18 | 57.7 | 2 |
| Mt-R3 | ACACTacccagc(a)gtttggcAc | 22 | 59.1 | 3 |

TABLE 1-continued

|  | (5'→3') | mer | Tm (° C.) | SEQ ID No. |
|---|---|---|---|---|
| Mt-R4 | ACACTacccagc(a)gtttggAcc | 22 | 54.2 | 4 |
| Mt-R5 | TTAGTAGacccagc(a)gtttggccc | 24 | 54.2 | 5 |
| Mt-R6 | CTATTccagc(a)gtttggccc | 20 | 55.0 | 6 |
| Mt-R7 | ACACTacccagc(a)gtttAgccc | 22 | 54.5 | 7 |
| Mt-R8 | TTAGTAGTTCcagc(a)gtttggccc | 24 | 58.5 | 8 |
| Mt-A | CTGTGacccagc(a)gtttgAccc | 22 | 59.4 | 9 |
| Mt-B | ATGTGacccagc(a)gtttgTcccg | 23 | 61.1 | 10 |
| Mt-C | CTAccgcacccagc(a)gtttgTccc | 24 | 63.4 | 11 |

TABLE 2

|  | (5'→3') | mer | Tm (° C.) | SEQ ID No. |
|---|---|---|---|---|
| Wt-R1 | acccagcagtttggccag | 18 | 56.5 | 12 |
| Wt-R5 | ATTCACTccagc(a)gtttggcca | 22 | 58.5 | 13 |
| Wt-R6 | ATACAcagc(a)gtttggcca | 19 | 53.4 | 14 |
| Wt-R7 | GACTAcccagc(a)gtttAgcca | 21 | 55.7 | 15 |
| Wt-R7-2 | GACTAcccagc(a)gttAggcca | 21 | 57.4 | 16 |
| Wt-R7-3 | GACTAcccagc(a)gtAtggcca | 21 | 57.4 | 17 |
| Wt-R8 | ATTCACTGTAgc(a)gtttggcca | 22 | 56.3 | 18 |
| Wt-A | GACTAcccagc(a)gtttgcTa | 20 | 53.3 | 19 |
| Wt-B | ACTAcccagc(a)gAttggccag | 21 | 58.8 | 20 |
| Wt-C | GACTAgcacccagc(a)gtAtggcca | 24 | 61.9 | 21 |

The P1 oligonucleotide and the P2 oligonucleotide may be respectively selected based on Tm and the like. Both Mt-R2 and Wt-R1 shown above are oligonucleotides having predetermined base lengths and are identical to the base sequence shown in SEQ ID NO: 1 except to the mutated site. Any oligonucleotides other than Mt-R2 and Wt-R1 have at least one mismatch base (namely, at least one base that is non-complementary to the base sequence shown in SEQ ID NO: 1).

Specific examples of combinations of the P1 oligonucleotide and the P2 oligonucleotide include those shown in the following Table 3. Among these, combinations of Nos. 5-7, in which each combination includes primers which have additional sequences with identical lengths together with mismatch bases in different positions, may be preferable in view of increasing detection sensitivity, suppressing false positive and the like.

TABLE 3

| No. | Mutant type(Mt) | Wild type(Wt) |
|---|---|---|
| 1 | Mt-R2 | Wt-R1 |
| 2 | Mt-R5 | Wt-R5 |
| 3 | Mt-R6 | Wt-R6 |
| 4 | Mt-R8 | Wt-R8 |
| 5 | Mt-R7 | Wt-R7-3 |

TABLE 3-continued

| No. | Mutant type(Mt) | Wild type(Wt) |
|---|---|---|
| 6 | Mt-R4 | Wt-R7 |
| 7 | Mt-R7 | Wt-R5 |
| 8 | Mt-R5 | Wt-R7 |
| 9 | Mt-R3 | Wt-A |
| 10 | Mt-A | Wt-R7-2 |
| 11 | Mt-B | Wt-B |
| 12 | Mt-C | Wt-C |

In embodiments, the primer set may further include a forward primer (F primer) in addition to the P1 oligonucleotide, which is a mutant primer, and the P2 oligonucleotide, which is a wild type primer. The F primer is homologous to a region located further toward the 5' terminus side than a template nucleic acid sequence in the base sequence of SEQ ID NO: 1.

The P1 oligonucleotide and the P2 oligonucleotide are both reverse primers with respect to the base sequence shown in SEQ ID NO: 1. The F primer is a forward primer which acts as a pairing primer to the P1 oligonucleotide and the P2 oligonucleotide.

Because the F primer anneals to a region different from the base site to be detected, it can amplify a template nucleic acid regardless of whether the base site is the mutant type or the normal type. Therefore, when F primer is co-existed, amplicons having original template nucleic acid sequences will also be obtained, thereby reliability to detect mutations may be further increased.

The length of the F primer is preferably in a range of from 10 bases to 50 bases, more preferably in a range of from 15 bases to 40 bases, and still more preferably in a range of from 16 bases to 35 bases, but not specifically limited thereto. The F primer may anneal to a sequence complementary to a region which is 5' side from the template nucleic acid sequence to which the P1 oligonucleotide and the P2 oligonucleotide anneal. Sequence of the F primer is not specifically limited, and can be designed according to general means for designing primers well-known in the art.

Primer for Polymorphism Detection

The primer for detecting polymorphism in EGFR exon 21 of one exemplary embodiment of one aspect of the invention includes either the P1 oligonucleotide or the P2 oligonucleotide among the primer set. One individual type of oligonucleotide, or alternatively, two or more types of oligonucleotides which are different in terms of base length, position of mismatch base, GC content and/or the like, may be included in the primer.

Details of the P1 oligonucleotide and the P2 oligonucleotide as the primer for detecting polymorphism are respectively the same as those in the primer set.

Method of Detecting a Polymorphism

The method of detecting a polymorphism in the EGFR gene of one exemplary embodiment of one aspect of the invention includes at least:

(I) performing amplification by contacting the primer set with a nucleic acid sample containing at least a nucleic acid and using the nucleic acid as a template (amplification);

(II) obtaining a hybrid formed of a single-stranded nucleic acid and a probe by contacting the single-stranded nucleic acid with the probe, the single-stranded nucleic acid being obtained by the amplification and the probe being capable of detecting a polymorphism in EGFR exon 21 (hybridization);

(III) measuring a change of a signal based on dissociation of the hybrid by changing the temperature of a sample contacting the hybrid in order to dissociate the hybrid (measurement);

(IV) determining, as a melting temperature, a temperature at which the hybrid dissociates based on the signal variation (Tm determination); and (V) checking for presence of the EGFR exon 21 L858R or assessing an abundance ratio of a nucleic acid having the EGFR exon 21 L858R based on the melting temperature. (polymorphism check/assessment).

In the method of detecting a polymorphism, preferential amplification of a nucleic acid having the mutant type sequence may be achieved by the use of the primer set, which includes the P1 oligonucleotide and the P2 oligonucleotide, to one sample. Nucleic acids which are obtained by the amplification may be further subjected to a hybridization process using detecting probes, a Tm determination, and a polymorphism check/assessment. Accordingly, even if a content of the nucleic acid having the mutant type sequence in a sample is small, the nucleic acid having the mutant type sequence may be preferentially amplified so that the nucleic acid having the mutant type sequence may be detected with high sensitivity and polymorphism may be checked and/or assessed.

A nucleic acid sample used in the method of detecting a polymorphism is not particularly limited, as long as it contains a nucleic acid which can be a template. One example thereof is a sample which contains a nucleic acid derived from a biological sample. Examples of the biological sample include whole blood, oral cells such as those from oral mucosa, somatic cells such as those from such as nail, hair or the like, germ cells, sputum, amniotic fluid, paraffin embedded tissues, urine, gastric juice, gastric lavage fluid and the like, and suspensions of any of these. In embodiments, a reaction solution resulted from a nucleic acid amplification performed as described above, which utilizes nucleic acid from a biological sample as a template, may be used as the nucleic acid sample, and an amplicon contained in the reaction solution may also be used as the template nucleic acid.

The sample may be any of, for example, a sample which is unclear contains a nucleic acid having a target base site which is not known for whether the mutant type or the normal type, a sample which is readily known as containing both a nucleic acid having the mutant type sequence and a nucleic acid having the normal type sequence, and a sample which possibly contains a nucleic acid having the mutant type sequence or a nucleic acid having the normal type sequence. Origin of nucleic acid in a sample, for example, origin of DNA, RNA, and the like is not limited. Examples thereof include a cell such as various cancer cells, a virus, mitochondria, and the like. In embodiments, the method may be specifically preferably applied to a sample having a nucleic acid of the mutant type and nucleic acid of the normal type. Examples of such sample include a biological sample such as various cancer cells, and specific examples thereof include a leukemia cell and the like. Since cancer cells in blood include both cells having the mutant type nucleic acid and cells having normal type nucleic acid, the method of detecting a polymorphism of this exemplary embodiment may be preferably applied to nucleic acid samples derived from such cells, because the method may achieve required sensitivity. Method to collect the samples, method to prepare the nucleic acids, and the like is not limited, and conventional methods well-known in the art may be employed.

Nucleic acids derived from biological samples described above may be isolated, for example, by conventional methods well-known in the art. For example, a commercially available genomic DNA isolation kit (trade name: GFX GENOMIC BLOOD DNA PURIFICATION KIT, available from GE healthcare bioscience) and the like may be utilized to isolate genomic DNA from whole blood.

The nucleic acid in the sample may be single-stranded or double-stranded. Examples of the template nucleic acid include DNA, and RNA, such as total RNA or mRNA. Examples of template nucleic acid include a nucleic acid contained in a sample such as a biological sample. A nucleic acid which is contained in the sample may be a nucleic acid originally contained in the biological samples, or alternatively, in view of increasing detectability, it may be an amplicon which is a product made by a nucleic acid amplification method using a nucleic acid in a biological sample as a template. Specific examples include an amplicon made by a nucleic acid amplification method with use of a nucleic acid originally contained in a biological sample as a template, and an amplicon made by a nucleic acid amplification method with use of a cDNA as a template, in which the cDNA is generated from RNA originally contained in the biological sample by reverse transcription-PCR (RT-PCR:Reverse Transcription PCR). These amplicons may be used as template nucleic acids. The length of such amplicon may be, for example, in a range of from 50 bases to 1000 bases, and preferably in a range of from 80 bases to 200 bases, but not limited thereto.

In the amplification, the nucleic acid sample and the primer set are made to contact, and amplification is performed with use of a nucleic acid contained in a sample as a template. In this step, the P1 oligonucleotide and the P2 oligonucleotide in the primer set each anneal to a template nucleic acid sequence in one sample (one reaction solution), and then amplification of the nucleic acid is started.

A nucleic acid amplification method employed in the amplification is not specifically limited. Examples thereof include PCR (Polymerase Chain Reaction), NASBA (Nucleic acid sequence based amplification), TMA (Transcription-mediated amplification), and SDA (Strand Displacement Amplification). Among these, PCR may be preferable. Conditions for the nucleic acid amplification method is not particularly limited, and conventional methods well-known in the art can be employed.

In the amplification, a ratio of an addition amount of the nucleic acid sample to an amount of the amplification reaction system (for example, a reaction solution) is not particularly limited. In embodiments, when the nucleic acid sample is a biological sample (for example, whole blood sample), a lower limit of the addition ratio may be preferably 0.01 v/v % or more, more preferably 0.05 v/v % or more, and still more preferably 0.1 v/v % or more. Also, an upper limit of the ratio is not particularly limited. In embodiments, it may be preferably 2 v/v % or less, more preferably 1 v/v % or less, and still more preferably 0.5 v/v % or less.

In embodiments, when an optical detection which uses a labeled probe is employed in the detection of mutation which is explained below, a ratio of an addition amount of a biological sample, such as whole blood sample in the reaction, to an amount of the amplification reaction system may be preferably, for example, in a range of from 0.1 w/w % to 0.5 w/w %. In this range, generation of sediment caused by denaturation may be sufficiently suppressed, and sensitivity in an optical method may be increased. Also, inhibition of PCR caused by contaminant in whole blood may also be suppressed, and further increase of amplification efficiency may be expected.

Prior to beginning of the amplification reaction, albumin may be preferably added to the reaction system. By such addition of albumin, for example, influences caused by sediment or turbidity may be further decreased and amplification efficiency may be further increased.

In the reaction system, a ratio of an addition amount of albumin to an amount of the reaction system may be, for example, from 0.01 w/w % to 2 w/w %, preferably from 0.1 w/w % to 1 w/w %, and more preferably from 0.2 w/w % to 0.8 w/w %. Examples of the albumin include, but not particularly limited to, bovine serum albumin (BSA), human serum albumin, rat serum albumin, and horse serum albumin. These albumins may be respectively used individually or in a combination of two or more of these.

Amplification in the amplification step is herein explained with PCR as an example, but the invention is not limited thereto. Conditions of the PCR are not particularly limited, and PCR can be performed by conventional well-known method in the art. For example, conditions and methods disclosed in WO 2010/001969 may be preferably employed.

Firstly, a PCR reaction solution containing a template nucleic acid and the primers is prepared. In the PCR reaction solution of above, a ratio of an addition amount of each primer to an amount of the PCR reaction solution is not particularly limited. In embodiments, the mutant type primer (P1 oligonucleotide) may be preferably added so that the ratio becomes in a range of from 0.01 µmol/L to 10 µmol/L, more preferably from 0.05 µmol/L to 5 µmol/L, and still more preferably from 0.1 µmol/L to 1 µmol/L. In embodiments, the normal type primer (P2 oligonucleotide) may be preferably added so that the ratio becomes in a range of from 0.01 µmol/L to 10 µmol/L, more preferably 0.05 µmol/L to 5 µmol/L, and still more preferably 0.1 µmol/L to 0.5 µmol/L. A ratio between the addition amount of the mutant type primer (P1) and that of the wild type primer (P2) in terms of mole (P1:P2) may be, for example, in a range of from 1:0.001 to 1:10, more preferably from 1:0.01 to 1:2, and still more preferably from 1:0.1 to 1:1. When such addition amount ratio and molar ratio are applied to each primer, sensitivity may be increased and false positive may be suppressed.

When the F primer is used in addition to the mutant type P1 oligonucleotide and the wild type P2 oligonucleotide, for example, a ratio of an addition amount of the F primer to an amount of the PCR reaction solution may be preferably in a range of from 0.01 µmol/L to 10 µmol/L, more preferably from 0.05 µmol/L to 5 µmol/L, and still more preferably from 0.1 µmol/L to 1 µmol/L. A ratio between the addition amount of the mutant type primer (P1) and the addition amount of the F primer (F) in terms of mole (P1:F) may be, for example, preferably in a range of from 1:0.001 to 1:10, more preferably from 1:0.01 to 1:2, and still more preferably from 1:0.1 to 1:1. When such addition amount ratio and molar ratio are applied, sensitivity may be increased.

Other components in the reaction solution is not particularly limited. Examples of the component are well-known in the art, and content ratio therebetween is also not particularly limited. Examples of the component include a DNA polymerase, nucleotides such as nucleoside triphosphate (dNTP), and a solvent. Order of addition for each component to the reaction solution is not limited.

The DNA polymerase is not particularly limited. For example, conventional well-known polymerase derived from heat-resistant bacteria can be used. Specific examples of commercially available DNA polymerase include DNA polymerase derived from Thermus aquaticus (U.S. Pat. No. 4,889,818 and U.S. Pat. No. 5,079,352) (trade name: Taq polymerase), DNA polymerase derived from Thermus thermophilus) (WO 91/09950) (rTth DNA polymerase), DNA polymerase derived from Pyrococcus furiosus (WO 92/9689) (Pfu DNA polymerase: available from Stratagene), and DNA polymerase derived from Thermococcus litoralis) (EP 0455430) (Trademark: Vent; available from New England Biolabs), and the heat-resistant DNA polymerase derived from Thermus aquaticus may be preferable among these.

A ratio of an addition amount of the DNA polymerase to an amount of the PCR reaction solution is not particularly limited as long as it is a ratio usually used in the art for amplifying a target nucleic acid.

Examples of the nucleoside triphosphate usually used include dNTP (For example, dATP, dGTP, dCTP, dTTP, dUTP and the like). A ratio of an addition amount of the dNTP to an amount of the PCR reaction solution is not particularly limited as long as it is a ratio usually used in the art for amplifying a target nucleic acid.

Examples of the solvent include a buffer such as Tris-HCl, Tricine, MES, MOPS, HEPES, and CAPS, and commercially available PCR buffers or buffers included in PCR kits can be directly used. The PCR reaction solution may further contain glycerol, heparin, betaine, KCl, $MgCl_2$, $MgSO_4$, and/or the like.

The PCR includes: (1) dissociating double nucleic acid into single-stranded nucleic acid; (2) annealing primers to a template nucleic acid sequence; and (3) elongating nucleic acid sequences from primers by a polymerase. Conditions for each step are not particularly limited. For example, in the dissociation step, a condition of 90-99° C. for 1-120 sec. may be preferable, and a condition of 92-95° C. for 1-60 sec. may be more preferable. In the annealing step, for example, a condition of 40-70° C. for 1-300 sec. may be preferable, and a condition of 50-70° C. for 5-60 sec. may be more preferable. In the elongation step, for example, a condition of 50-80° C. for 1-300 sec. may be preferable, and a condition of 50-80° C. for 5-60 sec. may be more preferable. The number of cycles is not particularly limited. When the three steps are defined as one cycle, for example, 30 cycles or more may be preferable. There is no particular upper limit to the number of cycles. For example, total number of cycles may be 100 cycles or less, preferably 70 cycles or less, and more preferably 50 cycles or less. Change of a temperature in each step may be, for example, automatically regulated by using thermal cycler or the like.

In the hybridization step, a probe which can detect a polymorphism of EGFR exon 21 and a single-stranded nucleic acid obtained in the amplification step are contacted to obtain a hybrid.

The probe which can detect a polymorphism of EGFR exon 21 is not particularly limited as long as it has (i) a nucleic acid sequence of a region which includes the 172792nd base of SEQ ID NO: 1 or (ii) a nucleic acid sequence which can hybridize to a sequence which is complementary to the nucleic acid sequence (i).

The length of probe is not particularly limited. In embodiments, it may be preferably from 5 mer to 50 mer, more preferably from 10 mer to 30 mer. When the length of probe is in such range, for example, detection sensitivity may be increased.

The probe is not particularly limited as long as it includes a base that is complementary to the mutated site. The base complementary to the mutated site may be preferably located at the fourth to the fifteenth position from the 5' terminus of the probe. When the base complementary to the mutated site is located at such positions in the probe, for example, detection sensitivity may be increased.

Sequence of the probe is not limited. The mutated site in the sequence of the probe may be a base corresponding to the mutant type, or may be a base corresponding to the wild type. In embodiments, the sequence of the polymorphism detection probe may be preferably one that has the base corresponding to the mutant type, more preferably one that is 90-100% identical to the sequence which is complementary to the base sequence shown in SEQ ID NO: 1 except for the base located at the mutated site, and particularly preferably 100% identical to the sequence which is complementary to the base sequence shown in SEQ ID NO: 1 except for the base located at the mutated site. When the sequence of the polymorphism detection probe corresponds to the mutant type, detection sensitivity may be increased.

When the polymorphism detection probe is used to be present together with primers in the amplification step, the 3' terminus side of the probe may be preferably fluorescent labeled as described below, or a phosphate group is added to the 3' terminus of the probe, in view of preventing that the primer is being a target of DNA polymerase, which will cause elongation of probe itself.

In view of the detection efficiency, the polymorphism detection probe may be preferably a labeled probe.

Specific examples of a labeling substance for labeling the probe include a fluorescent dye and a fluorophore. Specific example of the labeled probe is a probe labeled with a fluorescent dye, which emits fluorescence by itself (that is, when it is not hybridized with a complementary sequence,) and the decreases fluorescence (for example quenches) by hybridization (that is, when it is hybridized with a complementary sequence).

A probe which utilizes such quenching phenomenon is usually referred to as a fluorescence quenching probe. The probe is preferably labeled with a fluorescent dye on its base located in 3' region (for example 3' terminus) or 5' region (for example 5' terminus) of the oligonucleotide, and the base to be labeled is preferably cytosine (C). In this case, it may be preferable that a base sequence of the labeled probe is designed so that a base in a target sequence, which is a base pairing with the terminal base C of the labeled probe or a base which is 1-3 bases far from the base pairing with the terminal base C of the labeled probe, becomes guanine (G). Such probe is usually referred to as guanine quenching probe, and is known as Q PROBE®.

When the guanine quenching probe is hybridized with a target sequence, the fluorescent dye-labeled terminal C comes close to the G in the target sequence, and thereby luminescence of the fluorescent dye is weakened (luminescent intensity is decreased). When utilizing such probe, hybridization and dissociation may be easily checked according to changes of the signal. Also, the labeling substance of above can usually bind to phosphate groups of nucleotides.

Other than the detection method using Q PROBE®, means for detection well-known in the art may be applied. Examples of such means for detection include Taq-man Probe method and RFLP method.

The fluorescent dye is not particularly limited. Examples of the fluorescent dye include fluorescein, phosphor, rhodamine and polymethine dye derivatives. Examples of commercially available products of such fluorescent dyes include, BODIPY FL (trademarks, manufactured by Molecular Probes Inc.), FLUOREPRIME (trade name, manufactured by Amersham Pharmacia), FLUOREDITE (trade name, manufactured by Millipore Corporation), FAM (manufactured by ABI), Cy3 and Cy5 (manufactured by Amersham Pharmacia) and TAMRA (manufactured by Molecular Probes Inc.). The combination of fluorescent dyes used for plural fluorescent dyes is not particularly limited as long as, for example, the fluorescent dyes are detectable under different detection conditions, and examples thereof include a combination of any of PACIFIC BLUE (described above), that can be detected at a detection wavelength of from 450 nm to 480 nm, TAMRA (described above), that can be detected at a detection wavelength of from 585 nm to 700 nm, and BODIPY FL (described above), that can be detected at a detection wavelength of from 515 nm to 555 nm.

When the probe is a probe labeled with a labeling substance such as the fluorescent dye, an unlabeled probe having an identical sequence to the labeled probe may be used. This may enable to regulate a signal strength (such as a fluorescent intensity) to be detected. In embodiments, a phosphate may be added onto a 3' terminus of the unlabeled probe.

Timing for adding the probe to the reaction system is not particularly limited. For example, it can be before amplification, at the beginning of the amplification, in the middle of amplification reaction, or after amplification. In embodiments, it may be preferable to perform the addition before the amplification or at the beginning of the amplification in view of sequentially perform the amplification and hybridization. Namely, the amplification and the obtaining of the hybrid may be preferably performed concomitantly for processing efficiency.

The amount of the probe to be added to the reaction system is not particularly limited. For example, the amount of the probe added may be preferably in the range of from 10 to 400 nmol per liter of the reaction system, and more preferably in the range of from 20 to 200 nmol per liter of the reaction system.

Means and conditions of hybridization applied for obtaining the hybrid formed of the polymorphism detection probe and the single-stranded nucleic acid obtained by the amplification are not particularly limited. Conditions for obtaining single-stranded nucleic acids by denaturing double strand nucleic acids and conditions for hybridizing the single-stranded nucleic acid sequences with each other, which are well-known in the art, can be applied as they are.

In embodiments, heating temperature for dissociation may be preferably, for example, in a range of from 85° C. to 95° C., but not limited thereto as long as the amplified product of above can be dissociated at the temperature. Usually, duration of heating may be preferably in a range of from 1 sec. to 10 min., and more preferably from 1 sec. to 5 min, but not particularly limited thereto. Dissociated single-stranded nucleic acid sequence and a polymorphism detection probe can be hybridized, for example, by lowering the heating temperature after dissociation. Condition for temperature may be, for example, in a range of from 40° C. to 50° C.

Note that the term "single-stranded nucleic acid obtained by the amplification" herein includes single-stranded nucleic acids originally contained in a nucleic acid sample to be examined.

In the measuring step, a signal change is measured based on dissociation of the hybrid, by changing temperature of the sample containing the hybrid in order to dissociate the hybrid.

Signal value which indicates dissociation of the hybrid of a single-stranded nucleic acid obtained by the amplification and the polymorphism detection probe, can be measured with absorbance at a wavelength of 260 nm. In embodiments, it may be preferably measured by measuring the signal of a labeling substance. When measuring of the signal of a labeling substance is employed, for example, detection sensitivity may be increased.

Examples of the labeled probe include a labeled probe showing a signal by itself, but not showing a signal when hybridized, and a labeled probe not showing a signal by itself, but showing a signal when hybridized. The former probe does not show a signal when hybridized with a target sequence (for example, when double strand DNA is formed), but shows a signal when the probe is dissociated by heating. The latter probe shows a signal when hybridized with a target sequence (for example, when double strand DNA is formed), but the signal may be decreased (quenched) when the probe is dissociated by heating. Accordingly, by detecting the signal of the label with a specific condition for the signal (absorption wavelength and the like), progress of dissociation of the hybrid may be monitored, and Tm can be determined, in a similar manner to measurement of absorbance at 260 nm.

Signal changes based on dissociation of the hybrid may be made by changing a temperature of a reaction solution. For example, heating the reaction solution, i.e. a hybrid between the single strand DNA and the labeled probe, and a change of signal value associated with increase of the temperature is measured. As described in above, for example, if a probe having C as a terminal base which is labeled (guanine quenching probe) is used, when the probe is hybridized with a single strand DNA, fluorescence is decreased (or quenched), and when the probe is dissociated, fluorescence is emitted. Thus, for example, by gradually heating a hybrid having decreased fluorescence (or quenched), increase of fluorescent intensity associated with increase of the temperature can be measured. Note that when the labeled probe is used, the signal value can be measured by, for example, conditions according to the labeling substance of the labeled probe.

The temperature range to measure a change of fluorescent intensity is, for example, room temperature to 85° C., preferably in a range of from 25° C. to 70° C. for starting temperature, and for example, from 40° C. to 105° C. for terminating temperature, but not specifically limited thereto. Also, increasing rate of temperature is, for example, in a range of from 0.1° C./sec. to 20° C./sec., and preferably from 0.3° C./sec. to 5° C./sec., but not specifically limited thereto.

In the Tm determination, Tm is determined by analyzing a signal change obtained in the measuring step, and then assessed. Specifically, for example, an amount of change for fluorescent intensity per unit time is calculated from the obtained fluorescence for each temperature. When an amount of change is defined as [−d(increased amount of fluorescent intensity)/dt], for example, the temperature showing the lowest value can be determined as a Tm. Also, an amount of change is defined as [d(increased amount of fluorescent intensity)/t], for example, the temperature showing the highest value can be determined as a Tm. On the other hand, when a labeled probe used is not a quenching probe, but is a probe which does not show a signal by itself and shows a signal when hybridized, a decrease of fluorescent intensity can be measured.

Tm can be calculated, for example, by MELTCALC software (meltcalc.com/) and the like which are well-known in the art, and also Nearest Neighbor Method can be used for determination.

In the polymorphism check/assessment, based on the determined Tm, presence of the EGFR exon 21 L858R is checked or abundance ratio of a nucleic acid having the EGFR exon 21 L858R is assessed.

The kind of the 172792nd base of SEQ ID NO: 1 which corresponds to EGFR exon 21 L858R, i.e. whether the genotype is the mutant type or the wild type, is identified by the Tm obtained in the Tm determining step. It is understood from results of analysis of Tm that a Tm which indicates dissociation a hybrid of full complementary strands (match) may be higher than that of a hybrid of one base-different strands (mismatch). Therefore, by determining Tms of both a hybrid of full complementary strands and a hybrid of one base-different strands in advance, genotype of the target base site may be determined.

For example, when a base of the target base site is presumed to be the mutant type, and a probe complementary to the target sequence containing the mutant type is used, the target base may be identified as the mutant type if Tm of a formed hybrid is identical to the Tm of the hybrid of full complementary strands. Also, if Tm of a formed hybrid is identical to the Tm of the hybrid of one base-different strands (lower than the Tm of the hybrid of full complementary strands), the target base can be identified as normal type. If both Tms are detected, for example, it can be determined that a nucleic acid of mutation type and a nucleic acid of normal type co-exist.

As described in above, signal change caused by increase of the temperature can be measured by increasing a temperature of a reaction solution which contains the probe, i.e. by heating a hybrid. Alternatively, for example, signal change caused by hybridization can be measured. That is, when decreasing a temperature of a reaction solution which contains the probe to form a hybrid, signal change caused by decrease of the temperature can be measured.

In a specific example, when a labeled probe which shows a signal by itself but not shows a signal when hybridized (for example guanine quenching probe) is used, the probe emits fluorescence when a single-stranded nucleic acid and a labeled probe are dissociated, but when the probe is hybridized by lowering the temperature, the fluorescence is decreased (or quenched). Thus, for example, by gradually lowering the temperature of the reaction solution, decrease of fluorescent intensity can be measured. On the other hand, when a labeled probe which does not show a signal by itself but shows a signal when hybridized is used, the probe does not emit fluorescence when a single strand DNA and a probe are dissociated, but when the probe is hybridized by lowering the temperature, the probe emits fluorescence. Thus, for example, by gradually lowering the temperature of the reaction solution, increase of fluorescent intensity can be measured.

To quantitatively measure the abundance ratio between the mutant type and the wild type nucleic acid sequences in EGFR exon 21, it may be preferable to make a standard curves for the mutant type and the wild type nucleic acids respectively in advance, and assess each abundance ratio based on the standard curves.

Explanation follows regarding a detection amount curve generation method.

First, for example, plural nucleic acid mixtures are prepared that each have different abundance ratios of two types of nucleic acid, a wild-type nucleic acid Wt and a mutant nucleic acid Mt. Melting curves are obtained with a melting curve analysis instrument for each of the plural nucleic acid mixtures.

Figure 1B:
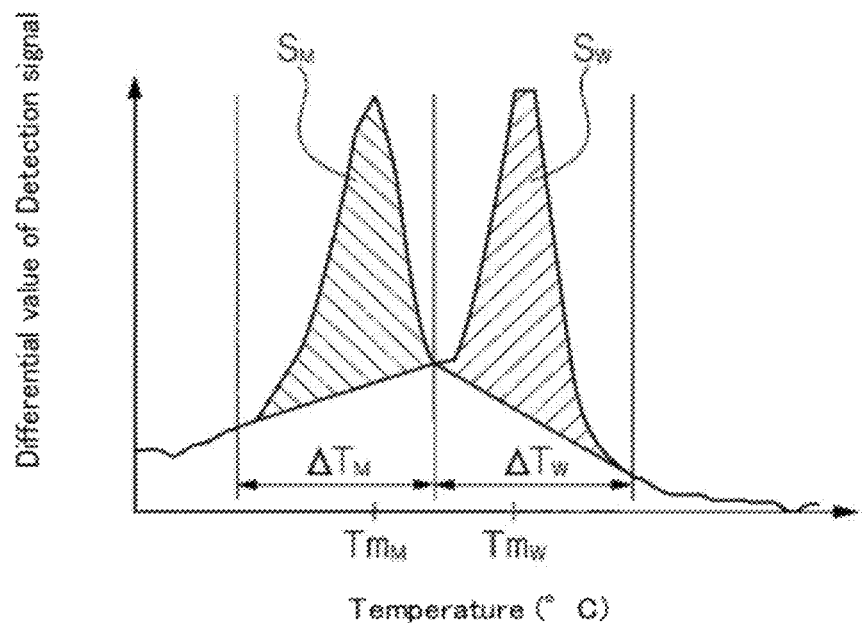
FIG. 1B is an example of a differential melting curve of a nucleic acid mixture.

FIG. 1A illustrates a melting curve expressing the relationship for a single nucleic acid mixture of a detection signal, such as a degree of light absorption or fluorescence intensity, to temperature. FIG. 1B illustrates a melting curve (also called a differential melting curve) expressing the relationship of the differential values of the detection signal to temperature. The melting temperature $Tm_W$ of the nucleic acid Wt and the melting temperature $Tm_M$ of the mutant nucleic acid Mt are detected from the peaks of the differential melting curve. Temperature ranges are then set to contain $Tm_W$ and $Tm_M$, respectively.

As a temperature range $\Delta T_W$ containing $Tm_M$ a temperature range can be set, for example, with a lower limit at the temperature at which the differential value of the detection signal reaches a minimum between $Tm_W$ and $Tm_M$, and an upper limit at the temperature corresponding to the tail of the detection signal peak. As the temperature range $\Delta T_M$ containing $Tm_M$, a temperature range can be set, for example, with an upper limit at the temperature at which the differential value of the detection signal reaches a minimum between $Tm_W$ and $Tm_M$, and with a lower limit at a temperature corresponding to the tail of the detection signal peak.

The temperature range $\Delta T_W$ and the temperature range $\Delta T_M$ can be set so as to have the same width as each other (for example 10° C.) or set to have different widths from each other (for example a temperature range $Tm_W$ of 10° C., and a temperature range $Tm_M$ of 7° C.). The temperature range $\Delta T_W$ and the temperature range $\Delta T_M$ can be set with widths from minus X° C. to plus X° C. from the temperature range Tm or the temperature range Tw, respectively, (for example, 15° C. or less, or preferably 10° C. or less).

Then, for each of the temperature range $\Delta T_W$ and the temperature range $\Delta T_M$, respectively, a surface area is derived of an area bounded by a straight line passing through a point corresponding to the lower limit and a point corresponding to the upper limit of the respective temperature range of the differential melting curve and bounded by the differential melting curve itself (the shaded regions in FIG. 1B). A specific example of a method that can be employed for deriving the surface area is set out below. Derivation can be made according to the following Equality (1), in which f (T) is a differential value of the detection signal at temperature T, and B (T) is a base value at temperature T.

Surface Area $S=\{f(T_{s+1})-B(T_{s+1})\}+\{f(T_{s+2})-B(T_{s+2})\}$
and so on up to $\{f(T_{e-1})-B(T_{e-1})\}$    Equality (1)

In Equality (1), $T_s$ is the lower limit value of each of the temperature ranges, and $T_e$ is the upper limit value thereof. The base value B (T) at each temperature T is a value derived according to the following Equality (2), and represents the background level included in the detection signal. Influence from background included in the detection signal is removed by subtracting this base value from the differential value of the detection signal.

$B(T)=a \times (T-T_s)+f(T_s)$    Equality (2)

In Equality (2), $a=\{f(T_e)-f(T_s)\}/(T_e-T_s)$.

Figure 2:
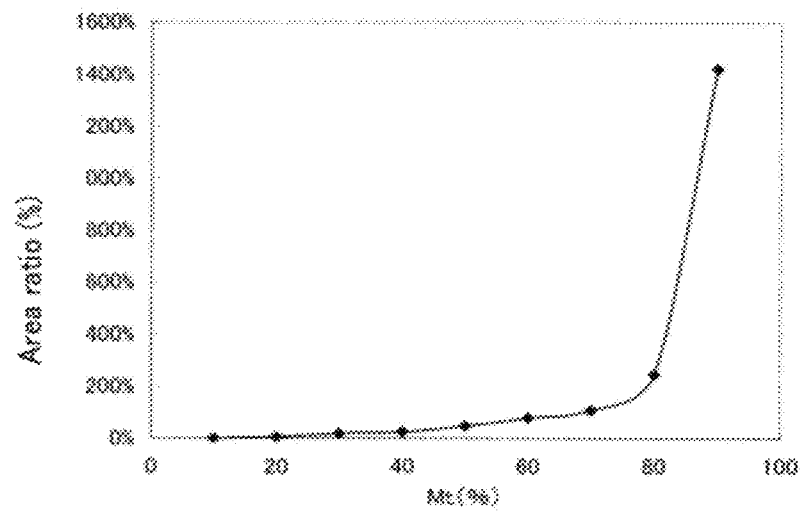
FIG. 2 is an example of a standard curve.
Figure 3:
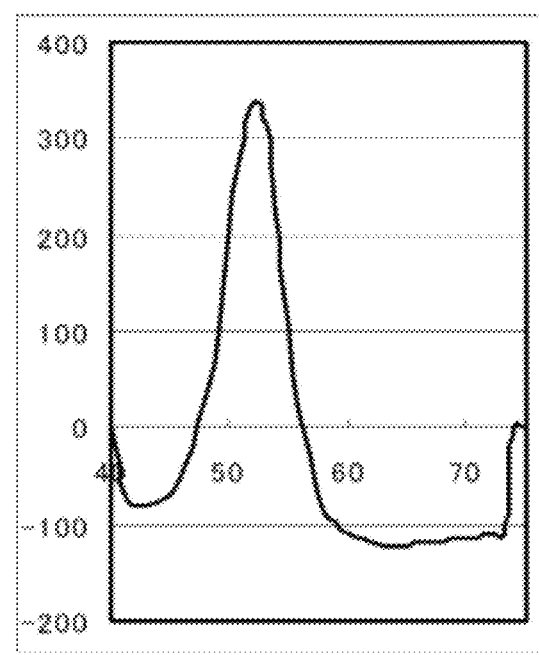
FIG. 3 is a melting curve of a nucleic acid mixture having no mutation, obtained by a primer set related to examples of the present invention.
Figure 4:
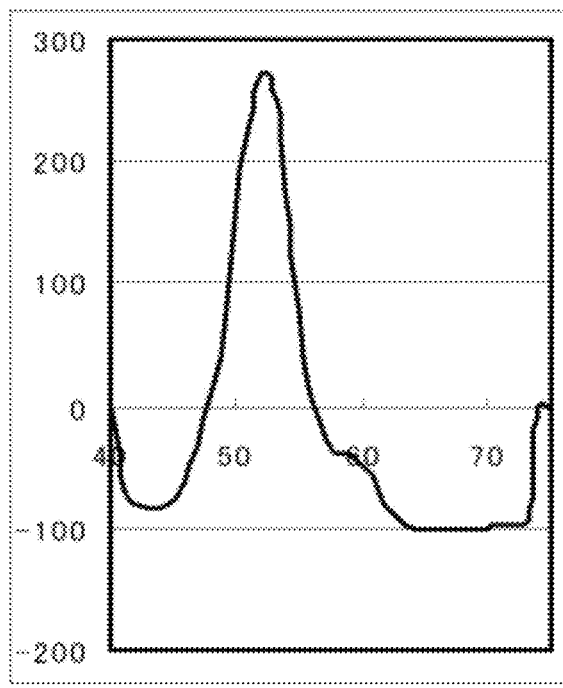
FIG. 4 is a melting curve of a nucleic acid mixture having a mutation content of 0.1%, obtained by a primer set related to an exemplary embodiment of the present invention.
Figure 5:
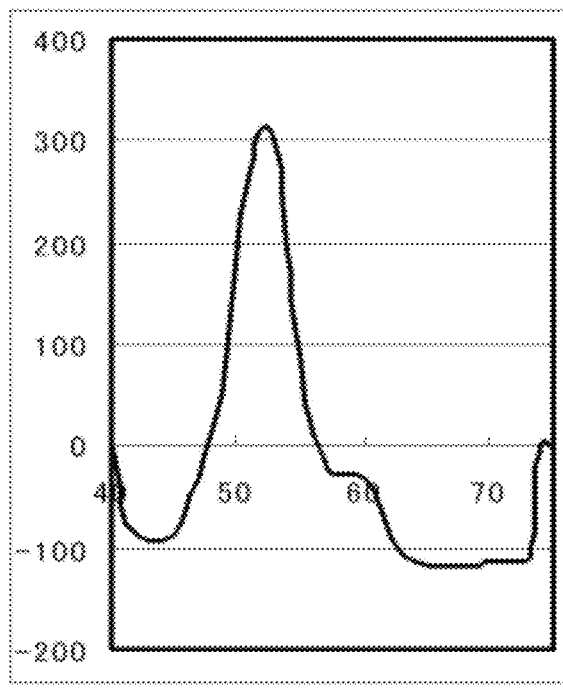
FIG. 5 is a melting curve of a nucleic acid mixture having a mutation content of 0.3%, obtained by a primer set related to an exemplary embodiment of the present invention.
Figure 6:
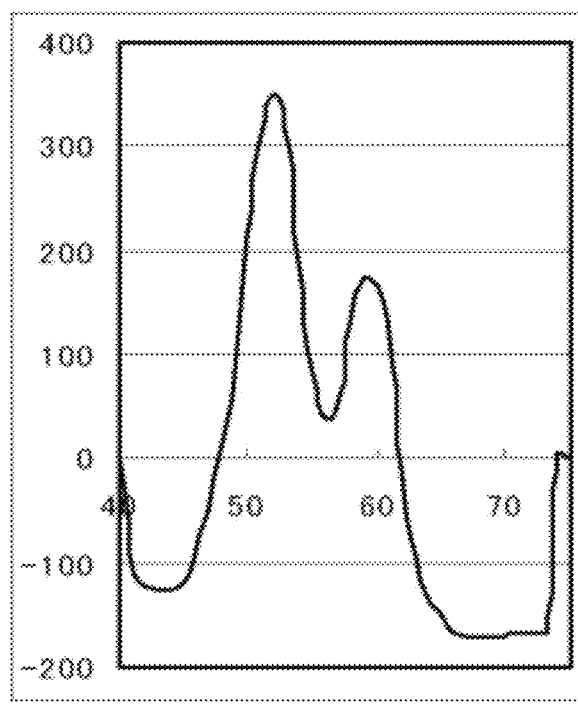
FIG. 6 is a melting curve of a nucleic acid mixture having a mutation content of 1%, obtained by a primer set related to an exemplary embodiment of the present invention.

For each nucleic acid mixture the surface area $S_W$ over the temperature range $\Delta T_W$ and the surface area $S_M$ over the temperature range $\Delta T_M$ are derived according to Equality (1) and Equality (2). A detection amount curve is then generated expressing the relationship between the area ratios and the abundance ratios for each of the nucleic acid mixtures. FIG. 2 illustrates an example of a detection amount curve, with the abundance ratio (the proportion of nucleic acid Mt to the total nucleic acid mixture) on the horizontal axis and the area ratio ($S_M/S_W$) on the vertical axis. A detection amount curve such as this is stored in the memory 26. The area ratio may also be defined as ($S_W/S_M$).

The area ratio is calculated from a melting curve and a differential melting curve obtained from actual samples, and abundance ratio of a base sequence having a polymorphism in actual samples can be determined based on the standard curves prepared as above.

The abundance ratio may be calculated according to each peak of the wild type and the mutant type. In embodiments, presence of polymorphism (whether existed or not) in EGFR gene may be simply checked by checking for presence of any of the peaks.

Method of Evaluating EGFR Tyrosine Kinase Inhibitor

The method for evaluating EGFR tyrosine kinase inhibitor of one exemplary embodiment of one aspect of the invention includes at least:

detecting a polymorphism in the EGFR gene by the method of detecting a polymorphism in an EGFR gene (gene polymorphism detecting step); and evaluating a resistance of a source of the nucleic acid sample to the EGFR tyrosine kinase inhibitor or an effect of the EGFR tyrosine kinase inhibitor based on a result of the detection (effect evaluating step).

In the method of detecting a polymorphism, because EGFR exon 21 L85R is detected easily and with high sensitivity by using the primer set to detect a polymorphism of EGFR exon 21, EGFR tyrosine kinase inhibitor can be evaluated easily and with high sensitivity based on the polymorphism in the EGFR exon 21.

Details of the gene polymorphism detection in the method for evaluating EGFR tyrosine kinase inhibitor are the same as those of the method of detecting polymorphism in EGFR gene explained above.

It has been known that the reactivity of EGFR tyrosine kinase may be varied depending on polymorphisms in EGFR exon 21. Specifically, when EGFR gene is wild type, it may be assessed that tumor regression effect by EGFR tyrosine kinase inhibitor can be expected.

As such, by applying the method of evaluating the EGFR tyrosine kinase inhibitor, effects of EGFR tyrosine kinase inhibitor may be predicted easily with high sensitivity.

Kit

The kit for detecting a polymorphism in EGFR gene of one exemplary embodiment of one aspect of the invention includes at least the primer set including the P1 oligonucleotide and the P2 oligonucleotide.

The primer set included in the reagent kit can be used to detect a polymorphism in EGFR gene easily with high sensitivity, thereby a polymorphism in EGFR gene may be detected more easily.

The P1 oligonucleotide and the P2 oligonucleotide which form the primer set may be individually contained in different vials, or contained in one vial together. The term "different vial" herein means a vial which enables to keep the P1 oligonucleotide and the P2 oligonucleotide to be separated, and does not necessarily mean individual vials which can be handled independently.

The kit may further include F primer, which is a primer complementary to a complementary sequence of the 5' terminus side from the template nucleic acid sequence for the P1 oligonucleotide and the P2 oligonucleotide. Descriptions about F primer can be applied to F primer, without any modifications. The kit includes such primer set which can detect a polymorphism in EGFR gene with high sensitivity, thereby a polymorphism in EGFR gene may be detected more easily with high sensitivity.

The F primer may be contained in a vial different from a vial for a primer set, or contained in one vial together with the primer set.

The kit may further include a polymorphism detection probe which can detect a polymorphism of EGFR exon 21. Details of the polymorphism detection probe in the kit are the same as described above. By using the probe, nucleic acid amplification with a primer set and detection with a probe may be easily performed concurrently or sequentially to detect polymorphisms in samples from subjects.

The polymorphism detection probe may be contained in a vial different from a vial for a primer set, or contained in one vial together with the primer set.

In addition to the above, the kit may include reagents or buffers required for amplification, such as a polymerase, reagents or buffers required for hybridization, diluents for diluting samples, and/or the like. Further, the kit may preferably include instructions for various reagents, and/or the instructions can be supplementary included in the kit.

EXAMPLES

In the following, the invention is described in further detail with reference to examples. However, the examples are not be construed as limiting the invention. The terms "part" and "%" are based on mass, unless indicated otherwise.

Evaluation Example 1

Example 1

To detect a polymorphism of EGFR exon 21, nucleic acid samples which are respectively a mixture of a mutant type plasmid and a wild type plasmid were prepared. The mutant type plasmid (hereinafter, referred to as "mt") was prepared by cutting a plasmid having a sequence of 172643rd to 172941st bases of SEQ ID NO: 1 in which the 172792nd base of SEQ ID NO: 1 is "G" using a restriction enzyme which cuts the plasmid at a position other than the 172792nd base and linearizing the cut plasmid. The wild type plasmid (hereinafter, referred to as "wt") was prepared by cutting a plasmid having a sequence of 172643rd to 172941st bases of SEQ ID NO: 1 in which the 172792nd base of SEQ ID NO: 1 is "T" using a restriction enzime which cuts the plasmid at a position other than the 172792nd base and linearizing the cut plasmid. The mutant type plasmid and the wild type plasmid were mixed in predetermined ratios, so that plural nucleic acid samples were prepared. The content of mt in the nucleic acid samples were 3%, 1%, and 0% respectively.

To detect a polymorphism of EGFR exon 21, a mutant type primer (hereinafter, referred to as "Mt primer") mt-R2, which includes a sequence complementary to 172792nd-172807th of the sequence shown in SEQ ID NO: 1 and has "C" as a base that is complementary to the 172792nd base (see Table 1 or 5), and a wild type primer (hereinafter, referred to as "Wt primer") wt-R1, which includes a sequence complementary to 172792nd-172807th of the sequence shown in SEQ ID NO: 1 and has "A" as a base that is complementary to the 172792nd base (see Table 2 or 5) were prepared.

As shown in Table 4, 1 μL, of nucleic acid sample ($2\times10^4$ copies/test) and 244, of PCR reaction solution containing Mt primer and Wt primer were added in a tube, and subjected to PCR using a thermal cycler (trade name: MASTERCYCLER EP GRADIENT S, available from Eppendorf). The PCR condition was one process of 95° C. for 60 sec., followed by 50 cycles of 95° C. for 1 sec and 60° C. for 15 sec.

Then, the tube containing the PCR reaction solution was transferred to i-densy (trade name, available from Arkray), and subjected to a treatment at 95° C. for 1 sec., and a treatment at 40° C. for 60 sec., and then the change of the fluorescence intensity over time was measured while increasing the temperature from 40° C. to 75° C. at a temperature increasing rate of 1° C. per 3 seconds. Since TAMRA (manufactured by Molecular Probes Inc.) was herein used as a fluorescent dye, excitation wavelengths in a range from 520 nm to 555 nm and detection wavelengths in a range from 585 nm to 700 nm were employed.

TABLE 4

| Formulation (μl) | 1 test |
|---|---|
| dH$_2$O | 33.84 |
| 0.94 U/μl Taq Pol | 2 |

TABLE 4-continued

| Formulation (μl) | 1 test |
|---|---|
| 100 mM MgCl$_2$ | 0.75 |
| 1M KCl | 1.25 |
| 1M Tris-HCl (pH 8.6) | 1.25 |
| 2.5 mM dNTP | 4 |
| 20% BSA | 0.5 |
| 80% Glycerol | 1.56 |
| 100 μM probe | 0.1 |
| 100 μM Foward primer | 0.5 |
| 100 μM Mt primer | 0.125 |
| 100 μM Wt Primer | 0.125 |
| Template Nucleic acid (5000 copy/μl) | 4 |
| | 50 |

For the probe, the 3T-EGFR-858-R2 (ttggccCgcccaaaatc-(TAMRA): SEQ ID NO: 22, the "C" is a base corresponding to the mutated site) which recognizes 172782th-172798th of the sequence shown in SEQ ID NO: 1, was used. For the F primer (forward primer), the EGFR-L858R-F2 (aggaacg-tactggtgaaaacaccgc: SEQ ID NO: 23), corresponding to 172739th-172764th of the sequence shown in SEQ ID NO: 1, was used. As the template nucleic acid sequence, wild type DNA of EGFR exon 21 (available from Roche, human genome) and the mixture plasmid (mixed with 1% or 3% of mt) were used.

The graph showing an amount of change for fluorescent value of the probe was obtained by Tm analysis. The Tm was determined from actual value, the starting temperature and the terminating temperature of analysis were respectively set to Tm±5° C., the area analysis method was used for the analysis, and abundance ratio of the mutant amplicon to the wild type amplicon was calculated as the area ratio with the following formula. The result is shown in Table 5.

Area ratio=(area of a peak obtained by association and dissociation of mt template and probe)/(area of a peak obtained by association and dissociation of wt template and probe).

Examples 2 to 8

Polymorphism detections using the primer sets of Examples 2 to 8 were respectively performed in the similar manner as Example 1 except that the combination of the mutant type primer the wild type primer was changed as shown in the following Table 5. Results thereof are shown in Table 5.

Comparative Example 1

A polymorphism detection was performed for Comparative example 1 in the similar manner as Example 1 except that the wild type primer was not used and the formulation of the reaction system was adjusted with an equivalent amount of water. Results thereof are shown in Table 5.

TABLE 5

| | Primer set (Mt/Wt) | mt (%) | Region 1 (WT) | Region 1 (mt) | Area ratio |
|---|---|---|---|---|---|
| Comparative example 1 | Mt-R2/none | 0 | 0.0 | 1013.0 | |
| | | 1 | 0.0 | 943.0 | |
| | | 3 | 0.0 | 1090.5 | |
| Example 1 | MT-R2/Wt-R1 | 0 | 493.0 | 189.0 | 38.3 |
| | | 1 | 370.0 | 290.5 | 78.5 |
| | | 3 | 386.0 | 387.5 | 100.4 |

TABLE 5-continued

| | Primer set (Mt/Wt) | mt (%) | Region 1 (WT) | Region 1 (mt) | Area ratio |
|---|---|---|---|---|---|
| Example 2 | Mt-R5/Wt-R5 | 0 | 942.5 | 429.5 | 45.6 |
| | | 1 | 596.5 | 794.0 | 133.1 |
| | | 3 | 479.5 | 877.0 | 182.9 |
| Example 3 | Mt-R6/Wt-R6 | 0 | 807.5 | 67.4 | 8.3 |
| | | 1 | 433.5 | 1077.5 | 248.6 |
| | | 3 | 330.5 | 1093.5 | 330.9 |
| Example 4 | Mt-R8/Wt-R8 | 0 | 856.0 | 312.2 | 36.5 |
| | | 1 | 537.5 | 929.0 | 172.8 |
| | | 3 | 452.0 | 1228.5 | 271.8 |
| Example 5 | Mt-R7/Wt-R7-3 | 0 | 753.5 | 0.0 | 0.0 |
| | | 1 | 307.0 | 97.0 | 31.6 |
| | | 3 | 125.8 | 206.5 | 164.1 |
| Example 6 | Mt-R4/Wt-R7 | 0 | 162.0 | 0.0 | 0.0 |
| | | 1 | 51.1 | 205.5 | 402.2 |
| | | 3 | 0.5 | 173.0 | 34600.0 |
| Example 7 | Mt-R7/Wt-R5 | 0 | 1123.0 | 0.0 | 0.0 |
| | | 1 | 526.5 | 5.4 | 1.0 |
| | | 3 | 283.6 | 56.2 | 19.8 |
| Example 8 | Mt-R5/Wt-R7 | 0 | 33.5 | 470.0 | 1403.0 |
| | | 1 | 12.5 | 590.5 | 4724.0 |
| | | 3 | 2.8 | 379.5 | 13553.6 |

As shown in Table 5, when both the mutant type primer and the wild type primer, the base lengths or Tms of which being different, were used in one reaction for detecting a polymorphism, the mt content of 0%, 1%, and 3% each can be detected dose dependently, compared to single use of the mutant type primer. It shows that, by using the primer set of the examples, a polymorphism in nucleic acid samples, i.e. EGFR exon 21 L858R, can be detected with high sensitivity.

Especially, when a mutant type primer, which has a mismatch mutation in addition to an additional sequence, is used together with a wild type primer, (Examples 5-7), false positive for the sample having the mt content of 0% can be suppressed. It shows that false positive can also be suppressed well on detection of EGFR exon 21 L858R in addition that high sensitivity is achieved.

Evaluation Example 2

Detection of polymorphism was performed to samples having the mt content of 0%, 0.1%, 0.3%, or 1%, with a primer set of the Example 5.

The template nucleic acid having 5,000 copies/μL (20,000 copies/test) and the primer set of Example 5 were used. Full automatic SNPs test machine (trade name: i-densy, available from Arkray) and i-densy Pack UNIVERSAL (trade name, available from Arkray) which includes DNA polymerase were used for PCR and Tm analysis. Conditions for PCR and Tm analysis employed herein were same as those in Evaluation example 1 to perform the Tm analysis. Graphs obtained by Tm analyses are shown in FIGS. 3-6. Note that, in FIGS. 3-6, the vertical axis indicates temperature derivative value of fluorescent intensity, and the horizontal axis indicates temperature, respectively.

As shown in FIGS. 3-6, when the primer set of Example 5 is used for detecting a polymorphism, a peak of the mutant type, which is located around 60° C., is observed as the size depending on the mt content. Thus, by using the primer set of Example 5, polymorphism can be detected with sensitivity depending on the abundance ratio of the mutant type, even if the mt content is 1% or less.

As is understood from the above, polymorphism in EGFR exon 21 can be detected easily with high sensitivity by utilizing the present invention.

All publications, patent applications, and technical standards mentioned in this specification are herein incorporated by reference to the same extent as if such individual publication, patent application, or technical standard was specifically and individually indicated to be incorporated by reference. It may be obvious to those having skill in the art that many changes may be made in the above-described details of the preferable embodiments of the present invention. It is intended that the scope of the invention be defined by the following claims and their equivalents.

What is claimed is:

1. A kit comprising:
 (i) a primer set comprising a P1 oligonucleotide and a P2 oligonucleotide,
  the P1 oligonucleotide having a length of from 22 bases to 50 bases and comprising a sequence selected from the group consisting of SEQ ID NO: 4, 5, 6, 7 and 8,
  the P2 oligonucleotide having a length of from 19 bases to 50 bases and comprising a sequence selected from the group consisting of SEQ ID NO: 13, 14, 15, 17 and 18, and
  the P1 oligonucleotide and the P2 oligonucleotide satisfying at least one of the following relationships: the melting temperature of the P1 oligonucleotide is higher than the melting temperature of the P2 oligonucleotide, or the P1 oligonucleotide is one or more bases longer than the P2 oligonucleotide, and
 (ii) a labeled probe configured to detect epidermal growth factor receptor (EGFR) exon 21 L858R.

2. The kit of claim 1, wherein at least one of the P1 oligonucleotide or the P2 oligonucleotide comprises the base that is complementary to the 172792nd base of SEQ ID NO: 1 at one of the first to third positions from its 3' terminus.

3. The kit of claim 1, wherein the melting temperature of the P1 oligonucleotide is 0.1° C. to 20° C. higher than the melting temperature of the P2 oligonucleotide.

4. The kit of claim 1, further comprising a primer that is homologous to a sequence that is in a region located further toward the 5' terminus side than a template nucleic acid sequence in the base sequence of SEQ ID NO: 1, wherein the template nucleic acid sequence is complementary to the P1 oligonucleotide or the P2 oligonucleotide.

5. The kit of claim 1, wherein the P1 oligonucleotide consists of a sequence selected from the group consisting of SEQ ID NO: 4, 5, 6, 7 and 8, and the P2 oligonucleotide consists of a sequence selected from the group consisting of SEQ ID NO: 13, 14, 15, 17 and 18.

6. The kit of claim 1, wherein the P1 oligonucleotide consists of a sequence selected from the group consisting of SEQ ID NO: 4, 5, 6, 7 and 8.

7. The kit of claim 1, wherein the P2 oligonucleotide consists of a sequence selected from the group consisting of SEQ ID NO: 13, 14, 15, 17 and 18.

8. The kit of claim 1, wherein the labeled probe has a length of from 5 bases to 50 bases and comprises a region of SEQ ID NO: 1, including the 172792nd base of SEQ ID NO: 1.

9. The kit of claim 1, wherein the labeled probe has a length of from 5 bases to 50 bases and hybridizes to a sequence that is complementary to a region of SEQ ID NO: 1, including the 172792nd base of SEQ ID NO: 1.

10. The kit of claim 1, wherein the labeled probe is labeled with a fluorescent dye or a fluorophore.

11. A kit comprising:
 (i) a primer having a length of from 19 bases to 50 bases and comprising a sequence selected from the group consisting of SEQ ID NO: 4, 5, 6, 7, 8, 13, 14, 15, 17 and 18, and
 (ii) a labeled probe configured to detect epidermal growth factor receptor (EGFR) exon 21 L858R.

12. The kit of claim 11, wherein the primer comprises the base that is complementary to the 172792nd base of SEQ ID NO: 1 at one of the first to third positions from its 3' terminus.

13. The kit of claim 11, wherein the primer consists of a sequence selected from the group consisting of SEQ ID NO: 4, 5, 6, 7, 8, 13, 14, 15, 17 and 18.

14. The kit of claim 11, wherein the primer consists of SEQ ID NO: 4.

15. The kit of claim 11, wherein the primer consists of SEQ ID NO: 5.

16. The kit of claim 11, wherein the primer consists of SEQ ID NO: 6.

17. The kit of claim 11, wherein the primer consists of SEQ ID NO: 7.

18. The kit of claim 11, wherein the primer consists of SEQ ID NO: 8.

19. The kit of claim 11, wherein the labeled probe has a length of from 5 bases to 50 bases and comprises a region of SEQ ID NO: 1, including the 172792nd base of SEQ ID NO: 1.

20. The kit of claim 11, wherein the labeled probe has a length of from 5 bases to 50 bases and hybridizes to a sequence that is complementary to a region of SEQ ID NO: 1, including the 172792nd base of SEQ ID NO: 1.

21. The kit of claim 11, wherein the labeled probe is labeled with a fluorescent dye or a fluorophore.

22. A method of detecting a polymorphism in the EGFR gene comprising:
 (I) performing amplification by contacting the primer set of the kit of claim 1 with a nucleic acid sample comprising a nucleic acid and using the nucleic acid as a template;
 (II) obtaining a hybrid formed of a single-stranded nucleic acid and the labeled probe of the kit of claim 1 by contacting the single-stranded nucleic acid with the probe, the single-stranded nucleic acid being obtained by the amplification;
 (III) measuring a change of a signal based on dissociation of the hybrid by changing the temperature of a sample comprising the hybrid in order to dissociate the hybrid;
 (IV) determining, as a melting temperature, the temperature at which the hybrid dissociates based on the change of the signal; and
 (V) checking for presence of the EGFR exon 21 L858R mutation or assessing an abundance ratio of a nucleic acid having the EGFR exon 21 L858R mutation based on the melting temperature.

23. The method of claim 22, wherein the amplification and the obtaining of the hybrid are performed concurrently.

24. A method of evaluating an EGFR tyrosine kinase inhibitor comprising:
 detecting a polymorphism in the EGFR gene by the method of claim 22; and
 evaluating resistance of a source of the nucleic acid sample to the EGFR tyrosine kinase inhibitor or efficacy of the EGFR tyrosine kinase inhibitor based on the result of the detection.

\* \* \* \* \*

SEQUENCE LISTING

```
<160> NUMBER OF SEQ ID NOS: 23

<210> SEQ ID NO 1
<211> LENGTH: 188307
<212> TYPE: DNA
<213> ORGANISM: Homo sapiens

<400> SEQUENCE: 1
cccccggcgc agcgcggccg cagcagcctc cgcccccgc acggtgtgag cgcccgacgc       60
ggccgaggcg gccggagtcc cgagctagcc ccggcggccg ccgccgccca gaccggacga      120
caggccacct cgtcggcgtc cgcccgagtc cccgcctcgc cgccaacgcc acaaccaccg      180
cgcacggccc cctgactccg tccagtattg atcgggagag ccggagcgag ctcttcgggg      240
agcagcgatg cgaccctccg ggacggccgg ggcagcgctc ctggcgctgc tggctgcgct      300
ctgcccggcg agtcgggctc tggaggaaaa gaaaggtaag ggcgtgtctc gccggctccc      360
gcgccgcccc cggatcgcgc cccggacccc gcagcccgcc caaccgcgca ccggcgcacc      420
ggctcggcgc ccgcgccccc gcccgtcctt tcctgtttcc ttgagatcag ctgcgccgcc      480
gaccgggacc gcgggaggaa cgggacgttt cgttcttcgg ccgggagagt ctggggcggg      540
cggaggagga gacgcgtggg acaccgggct gcaggccagg cggggaacgg ccgccgggac      600
ctccggcgcc ccgaaccgct cccaactttc ttccctcact ttccccgccc agctgcgcag      660
gatcggcgtc agtgggcgaa agccgggtgc tggtgggcgc ctggggccgg ggtcccgcac      720
gtgcgccccg cgctgtcttc ccaggcgcg acggggtcct ggcgcgcacc cgaggggcgg      780
gcgctgccca cccgccgaga ctgcactgtt tagggaagct gaggaaggaa cccaaaaata      840
cagcctcccc tcggaccccg cgggacaggc ggctttctga gaggacctcc ccgcctccgc      900
cctccgcgca ggtctcaaac tgaagccggc gcccgccagc ctggccccgg cccctctcca      960
ggtccccgcg atcctcgttc cccagtgtgg agtcgcagcc tcgacctggg agctgggaga     1020
actcgtctac caccacctgc ggctcccggg gaggggtggt gctggcggcg gttagtttcc     1080
tcgttggcaa aaggcaggtg gggtccgacc cgcccccttgg gcgcagaccc cggccgctcg     1140
cctcgcccgg tgcgccctcg tcttgcctat ccaagagtgc cccccacctc ccggggaccc     1200
cagctccctc ctgggcgccc gcgccgaaag cccccaggctc tccttcgatg gccgcctcgc     1260
ggagacgtcc gggtctgctc cacctgcagc ccttcggtcg cgcctgggct tcgcggtgga     1320
gcgggacgcg gctgtccggc cactgcaggg ggggatcgcg ggactcttga gcggaagccc     1380
cggaagcaga gctcatcctg gccaacacca tggtgtttca aaatgggggct cacagcaaac     1440 ttctcctcaa aacccggaga ctttctttct tggatgtctc ttttttgctgt ttgaagaatt     1500 tgagccaacc aaaatattaa acctgtctta cacacacaca cacacacaca cacacacaca     1560
caccggattg ctgtccctgg ttcaagtgtg ccaagtgtgc agacagaaca tgagcgagtc     1620
tggcttcgtg actaccgacc ataaacccac ttgacagggg aaacatgcct tggaaggttt     1680
aattgcacaa ttccaacctt gagctgcgcg ggttccaaga gccaggcccg tacttgctgt     1740
tgatgtcatt ggcttgggga gttggggttt ggtgcccagc gcggtcgttg ggggaggggc     1800
aaggcataga acagtggttc ccagaccttg ctgcacattg gaattacctg ggattaaaaa     1860
```

```
aaaaaaaatc aaaacaaaaa ccagtgtctg gctcccgccc ccagacattc tgatttaatt   1920 ggcatgggc  aagacctgga cttgggattt tttttaatgc tcttcatgtg atctgttggg   1980
cagccagatt tggggatcac tagacggaag aaggattgtt aaagtctccg agatgttac    2040 ttgccaatgc taagagctct ttgaggacat ctggaattgt tacaatattg ccaaatatag   2100
gaaagaggga aaaggtagag tgtgattcca ataataaagg attccgcttt tcattgaagg   2160
aactggtgga aaggtttctt ctctgctgag cctgcaggcc cgtcctgcct gcctggggtg   2220
cccgggagac gcgggcctgc tccggagact gctgactgcc ggtcctgtta gtcaggtgtc   2280
agccctgtct ctgccgaaga gactcttctc tttattttaa attaaaccct cagagcacca   2340
ccaaagcatc acttttctcc ctccattggt gttctcattc tttgatgtta cttgtttgaa   2400
caccactatt agtagttgga gatttgttcc tgagaaaaat ataaatacca cttaatttgc   2460
ctgtttgtcc cgcattcact caaaacagaa tgctcctgaa gacaagagag agagtaggag   2520
aacagacgct attccattac agtaacataa aagactggat tttcaggggc aaattattaa   2580
aataggagat gagctctttt aacagaaatt tgtttaaggc ctgtgtctat caaattcagt   2640
ggattttatt caagatgcac tttgtttagt gggagttttg tttggttctg ggacatgcta   2700
acttctagac ttgctgctct tagaggtaat gactgccaga caccatttca tgagtcctaa   2760
tccccacatt aagcataaga ggtgcacact ctcctcctat gggggaaact gaggtacgaa   2820
gaactaaagt gactttccca cagctggtgg gaggcagacg ggaaattcac ccaggggct    2880 tccaactcca gatccctctc tcaacttcca aactccactg ccttgtccga gttctggttt   2940
caggagatcc aaatcaggtg tgtgcaaatg tctaatgtca gagctggcaa ggggaaaggg   3000
cccagggagc cggctcatga cgatgagcct gtctgaagct tcaacgcggg ctgtccggca   3060
gtctgcattc ctgccgagtt cctcagccct gtgtgggtc accttccata gaggcagctt    3120
agtcctcagt tcagtgagca tggagtggag actgcttgag gggtgctgag caaagccctg   3180
cctcttacag gatgaaggtg ctctccagaa gggacactgg aaagtattcc aaggcgagtc   3240
gaattcccaa ctgagggagc tttgtggaaa taagcccgcc cagccccact tctggagacg   3300
ttcccattca gtaggtccga gctgtcttaa agagaaacca aagtggggat attaatggta   3360
tccaaagtga gatctacccc accctccctc ctcaaaggag gtcagatcaa gaaagcccaa   3420
gcccggcctg gcaattggga cctttcttct cactccagcc cagggtgaag gtggacaagt   3480
cactttgacc cttcaggctt ctgagctgtt gtttctgaat tcagtgaata tttactgagt   3540
gcatagaata tgctagatat tctgggctaa aggttgaagg gggggtgagt tttaagggtt   3600
tctgctcttg cttccagatt gctttcaaat ctggaaagga caccagtggt ttgtgtgtta   3660
gacccacact gccgtagcac agaatacaag aaactggctg agagctccaa taggctttta   3720
acagtaattt ctggcttcac gtatttagtt tcataactca tgattttca aaaacttctg    3780 gtttgaagac accgattgcc gaaagtccat tgtgctgcat aattacactt ggtccacgtg   3840
acagcactaa catgttctga aatgttttta gaagtagtct cagcaaagat gaaggattcc   3900
tccctgtttg aaaagaaaat attctttgtt ttttctttga tctaagctct aagactagca   3960
gctagcatct gaaactttt tgacgagagt gacaaaccaa ctctaatatt aaaggcaatt    4020
gatgattatg ggcactgaag ggaaggtaac cccaggctgg tgccccggaa tagggatggg   4080
tcacaatgtt gaggacattt cgcctgttgc agaacccacc tgcaacacag tgtggccctt   4140
gccatgtgac ttgtgtgtgt gcctgtgtgt ctgtgtgtgc gtgttttaat ttgacttca    4200 taagtactct agttatgagc ttatttaaca ttgggtttta ctaataggg  tatgtgttga   4260
```

```
gaaaatttca aagttttaga atatggttca cccacatgtt gcttccctgt aaatataatt    4320
tttaaaacca gattctgggc cgggcatggt ggctcacctc tataatccca aaacgttggg    4380
aggccgaggc aggcgaatca tgaagccagg agtttgagac caggctgacc aacacggtga    4440
aacccagtct ctactaaaaa tacaaaaaaa attagctggg cgtggtggca ggtgcctgta    4500
atcccagcta ctcaggaggc tgaggcagga gaattgcttg aacccaggag gcagaggttg    4560
cagtgagcca agatcgcacc attgcactcc agcccgcgcg acagtgtgag actccatctc    4620
aaaaaaaaaa aaaaaaaaac agattctgtt cctcagatcc attccatttt tgttttcctt    4680
tatcacttat ggacatttga aattatggta ataaacattg ttagtctcag ttaattatta    4740
ctggtttatt cttgaaccac taatccatag agaatagagt gtaaatctta acttgttcct    4800
gtaggccatc cccattaaac atcatagtgt tttctcattc gttcttttc gttttcctcc    4860 tacaggaatg aattttctaa gaaaattcca gcagttggct ctttggacga catctctaga    4920
ttgtcctcca ttgggcccat aggcacaagc tggccagttt gaatttgggc aagaatccag    4980
gcattggaac ttattcaaat aactagtttg cctgtaattt tcacttttc agagtcatct    5040 gataaagctt tcttgctaca catttagata gatacactca atccagttgt ctagaaagtt    5100
ccctgagcca gctgggagca ggaggggtag ttggggccag gaatattggg ggtgtgttta    5160
ctgagcccct agaaagtaag tgctagattt gacatttcaa tccctgaagg ccctgaagtt    5220
cagtatcaaa tgactggtcc tgtggactga gcatctgtga attgcatatg cttagagtaa    5280
attttactcc taccagtttc agcagcttgc tttagcaagc agtatggaaa cactaacatg    5340
ggggagtaga atttctctct ctgatccaag ttttatctca ttctggtggg ttttcaagga    5400
gagactcgga gtccaagtgt cctttctgaa tatatctgga acttctcatt aacaaaagac    5460
tcaagttata atttagggga caaggcaccc aatgagaatg ccttgcaggc agccctaagt    5520
acacctgcaa ttacaccatt actagcgcgg cagcacacat ggccctgact tagtttaaat    5580
aattacgtaa gtcaaccatg attgtttgcc cttttgcatag aagggcaagt attggtacct    5640
gttacaactt aggctttttt ttctttatgt ttgagccatg atgagtgatt tacactgttg    5700
catccatatg ttgagatgta agaataaatt agacttggta attgccctta agtgtctgga    5760
agtcaactgg ggaaagagag ctagagataa taagtgtgaa acaatgtcac agaatcaatg    5820
acggaactct tcccaggaca aaggatgact tttgagttca gtctttgcct ttaattctac    5880
atggggagga gagcacgttt agccacaaat ggaagggatt actcatttga gctatttggt    5940
tatatgatta ttccccaga gaataggatg tgcagggcat tacacaagca gtgccaatag    6000
cagcaaagtt cttgagagtg ctagtaattc aaatggcagg aagagaagga ataaatggta    6060
aggctaccta cagttcacag agagctccat cctcactgtg gctttggatt ttgtcctgtg    6120
tgaaagagaa gtgactgtga actgacatgc tgtgtttggt gttttagaaa gatggctgca    6180
gcagcggttt ggggaatgga ctgcaggagt ggcattggaa acaggaaggt tcatgactat    6240
tgccagagac agaggatgaa gcaggagcaa ggaagattca ggacagggga ctccggggct    6300
gatcaggagg cagaactggt tgataagtat atgtagcagc ataagaaaga aagaatccca    6360
gattgacacc caggcttctc acttggaagc ctggatagat actgaatgca atcacaaagg    6420
ctgggaagtc aatgggactg cagggaaggg aagggaaggg aggagaagag gaagggcagg    6480
agggtccaat atcaatattc agcttttaga tgtgttgagc ttgaagtgct cagatggaga    6540
agtccaggag gcagtagaat acggtggtcc agagcacagg agagcaatgt ggcttgagtt    6600
```

```
gtcatttgct cacatatttc cgtgtcagtt acttgtctta gatcacagaa caagttctcc    6660
tctcacagtt tcctggctcc acctgtctca tgctcaccgt cagcatcgaa attgagccac    6720
accaggggtt ctggatacca gcttctctct aggtgaggct gctatagtca gcagctgatt    6780
agttgcagtt atcagcaact ggtaatataa tatattgtgc atataagtgt accagaagtc    6840
atgtttatat attgctgcaa atactcggaa tggggatctc ttgttccctg cttaagacca    6900
catcacatta cttggttttg tacgctagtg gctgaaccaa aaaagtagg agatgatttt    6960 ttttcttttt tcttaaagca gtagcttttg aaccttgacc atgctttcta accagctgag    7020
gggcttttga aaagagggt gccttactgt gccccagacc aggacaatca gtatttctgg    7080
ggaatggagc ctggcacaca cacatttctt aaagctccct tggcaattct gaggagtgga    7140
ttacatgttg tatgtagctc gtaacgaaag aaatcttgtc tttgctctca gaccccccatt   7200 tcttactcat ctcatgagct ccttcgagat ccagaaacag ttgcatattt cattagtaaa    7260
tcagttccag agtcacattt tatttcacaa gttagtccat taaaagtttc ctgcagtgag    7320
gaaatagcca gaaagaacac tccacccctc ctccttttta taactatagg gtctggctcg    7380
acagagcagg agcatcgcca tcttggacaa gcccctcatt ctaaagttca ccttaataaa    7440
aaactgccta aattcaaact gcatcagcct aatggctaag gtcagcatga ccataaacca    7500
caaataacat ctccaaccgg aaacattcga aactcctcct cgaccagaga catgctagtc    7560
ccgagataac ccccctccag cagggaagat gccagtctcg ggataacctc tctctggccg    7620
gaaagatgcc tgccccaaga taaacttgcc tcctcccaga gatattccaa ccctgccata    7680
aaacttctcc ctcaaacagg aacattccaa aattctgata atctccctca ccctaaaacc    7740
aatatatact cctagtctgt aagagaaagc gctcttgacc aaaattcacc aggagtgcct    7800
cccaggtttt aactaaagaa aacctctctt taactgccaa aaaaaaaaag ggaaaaaaaa    7860 aagcttctg cagtggcttt cagcgggccc agcatggcag cagcacctga gaacctgttg    7920
gagatgcaca ctcttggacc ccaccctggc ctctgagtaa gacactggaa gggcaggccc    7980
cggtctgtgc acacaagtcc tcagggagat tctgactgat gcatgccaga ttttgagaac    8040
tgctgatata ctccaggcac atcgcatgct gggatctaga tacaccaagg gaacaaaata    8100
actgcacttg tcctctgagg accgacttac cttttggaag ggctgagaaa gagagacaca    8160
tacaagatca ctccctgtaa tgcaatgttt tataacagat gtgatttggg atttcagtgg    8220
gagcccaaaa gagggactga ctaattcagc ctctgtgaca aggggagttt ctcagaaaca    8280
gaatgcttag ctgggcctcc aggcacaggg acaggaatga ggaaatactt gtaggccctg    8340
tgctccttca gcaaaaccct cagtttcttg ttatttttat aaatgcaaac atcttattaa    8400
agtagatgct aaggcattag aatttcctgc tttattttc taaatgacca tgaggaaacc    8460
tggaatgtca agataaagt gcaacacatt ctgcatttaa aaattaaaat gatccttttt    8520
aaaagtagca accagatgtg aaaaattgga ctggagtcca ggttatagtt gatagcttta    8580
actttctccc caacagcaac agcacaattt tccctaaaat gtgttatgaa taagtaaaat    8640
gactacttca catcctttaa ctcttcctac agaaatctaa gagagaaatg aaacaaaagt    8700
ttgcacagtt ctagacacga taaatacatg tgaaatcaca caactcagaa aatgtccctt    8760
aaattaattg agccattggt acttgtgaat tagaagagac atctatgttc tgatccactg    8820
ttgaaagctg tacaatgtta cctatttatt tgcagacatc ctttggaaac aaataggtag    8880
atttgcaaca aataaagagt ggagtacagc tgctgacatt accttgtata ttcatgcctt    8940
tatgtaaaaa aaaaaaaaaa aatatatata tatatatata tatatatata tatatacaca    9000
```

```
cacacacaca tatggaggta aagaccactg cttgctttgc agttgtttta agagcattca   9060
tgaaggattt tattttataa gcagaaatgt gatatctgac gattttacca ctacatgctt   9120
gcaggccagt gcacagcaga tgacgtcatg attgttttag cagtcctatc gttttactta   9180
tgatgtcatt acaacccttt gctaaaattt cttttccttta ctccaggttt tggataaaat   9240
tgatgcattg cacatagtct ctctgataag acaaactggc atttgtatgt gaaaaactgt   9300
gcatgtttta gtgtctctgc tgatactcaa attatccatt attttagtgc tggaataaaa   9360
acaaaccact tagtgaattt gtgcaggtcc ttaaggacag gcaaggtgt cctgagattt    9420 tctgatcatt gtataccaaa ttttagaaac tttttcaaaa acattttttt aatttcaaaa   9480
acctggtttt gtttatttac cagcaatcat tgaatacctg aaagctttca ggagatttta   9540
ttacaatggt ttctattcac ttacaaaatt atctcctagt tcattctcat acactgtaag   9600
ccattgtaaa tgcttcaaat tgtgccgaac aagataaact agacaaacta ttttaagttt   9660
gttctagtgc taacttgcaa gatcaatgg ctccaactag atttttaaaa taagtatat     9720 tttaatatat tattagaaag ttaagcaatt atctgtttat aggtaacaaa acccctggaa   9780
ccccaatgtc agatgtcatc cacttttgat taagtccaaa catatgacag ataaacaaaa   9840
gatggttggc tgggctcagt ggctcatgcc tgtaatctca gcactttcag aggccgaggc   9900
gggcggatca caaggtcagg agtttgagac ttgcctgacc aacatggtga acccgcctc    9960 tactaaaaat acaaaaaaaa cagctgggtg cggtggcacg tgcctgtagt cccagctact  10020
caggaggctg aggcaggaga atcacttaaa cctggaaggc aggggttgca gtgagctgag  10080
atcacaccac tacactccag cctaggcgac agagcaagac tcagtcaaaa aacaaaaaaa  10140
aagtggtcat tggagaatta ttgtgtcacc tgttgttttt taatgtacta attttgagag  10200
gcttttaaat agagtgcact atagaacttt ttcttggctt caatttgcta caatgttaat  10260
agagaatcag aaaccttatc cttatagatg tttcttgatt ttttaattt ctggtgacat   10320 ttatgagtga gaatagtgta ttgccctgtt ttctttctta ctccccttc ttcttccttc   10380 cttgctttct ttcttcttcc cttccttctt tctcttcctc gctccttctt ttttacaagc  10440
tgttatgaat tagccttcac agagaaagaa aaattttat aaataactgg aaatgaaact   10500
ttgcaaagga ctgcagatga aaactttgt caaatgactg taaaaatata ctatataatt   10560
ttcaaaagtt agaaagtacc aaacacactc agtattcatg gttatacaag tatgcataca  10620
catgtattgc tccctgaaaa gtggtgttgt taagggagtt tttcttagta cgcggcttaa  10680
catatttttt tctgtaattt gttgttagtt ataatgggga gagaaaacag gttagagtct  10740
cccctctcag tttcaccttc cataaaacag ctaaactaga cgatcgtcag actccttcca  10800
gctgaaaaca tctgtaaaat taaaacaaa tctaaatgta tgcaagatat gtatttaaac   10860
atgctggtaa taagtgtgct gtccctataa tttagatgct aaaacattga tgtcataata  10920
ataacaacac ctcgcatttg tacagcacct catagtttac acaatgcctt aacattcttc  10980
tctctcagcc tcctacaacc ccacaggatt gggatagctt tccagattgg gaggtgaggg  11040
acccaggctc agagcgattc tgctgttgtc cgtaatcacc aggctggtga tcagtgggca  11100
ctgggtgctc tcctgctaca cagcactgtc tctcaacatg caggtcaagg ttacttattc  11160
ctccttcaag acgtcattgg gttttttagc tatggatgcc ccatcacttt tagttctatt  11220
tgtgaatcaa aggctaaata aagtattcct caaaatttgt tatacttctg ttactaatgc  11280
ttaatgtccc tcacaatttc tgtatatttc tgtgtatttc tgctctgttt tggttccttt  11340
```

```
cccaggtttc ttttttgtta tgaagtagtt tttagactca agtctcttct gtatgtgtta    11400
taactgccca ttccataaga tacagggcag tgaatttgtg agccttgaaa atatttactt    11460
tagaaatgag aagtatgact tttcaacgtt gtgtcatcaa cttctgtaaa ttttccagac    11520
ctataaatac ttgcagaaaa aaaatgaaag gagaaggcaa cttgatttag cagttgggtc    11580
agttagcaat gcctatggca agctgtagta attcccttac atagatttgt aagactcatt    11640
tctatgattt aaatgaaggc atacacttaa cctctttagg gtgtgaaaca gcttttacaa    11700
aaagagacaa acttaagaaa cagtgtggcc ctccaagagt gttcattttc catatcatac    11760
catttgtaat aagctattct ggctgggatt tacttgcaag cattggcttt taagaagaga    11820
tggtttcaca catcaaatta ttcacttgga ggcactttct gggttgaagg aatggaatgg    11880
agagtgcggc agtgagtaga tctctcagtg acggtgatgt gcctctccca gaagaaattt    11940
caaaatgcag tgttcatttt cctccacaag aaaggaagaa actgttttgt tattgtttat    12000
tcctaacata gtggaaactt ttcagtactc tggcagaaat ttcccaaaag caattttcta    12060
tttcatgatt ataaagtagc aaaggaaaaa gtcctgcact ccagctgagc aatggatctc    12120
cagttgttat ctaggtgctg caggtttaga gaggattgcc aggagaacac atcgattttt    12180
caggcctgtg atgacgtatc tcttgttgaa taagtaaacc cttccagtaa acagacagtt    12240
agtatattga tttcagggtg gctttagcca ctgaacctgt aagtcttgca aaggttactt    12300
gggcaaaagc atcattattt taccttcagt caacaaaaat ctacctggcc aaggcagaac    12360
agaaagttca gcaatttgat gaagtgggac aacatgaaga atcaggtgag ttgcctactt    12420
tttcacttca ctttccacct ttagagattc ttgtttagat gcagagtagt gacgtgcctg    12480
gtgtcaggga gagagttgaa tgagaaaagt cccagaaggg cagaagactt gggtgattat    12540
ctgagtccat ctttccttat cacatgacag agttcttgaa gtcttggcta ggaattctag    12600
gcttttagat tctttgggca atggctacta aatgttcata atgttgctca gttgcaaaaa    12660
caagacattc aaactatagc cagggagata agtagtcacg aactcaaggc ctaaattctg    12720
ctgatggagc cgatgagaat tgggtgctaa ggcaaagaga gttgccaata ttatattctt    12780
cggggttttt tgtttttatt cgcattttgg aaaaggaaaa tattagcatt cctctgactt    12840
aatattgaga agacattggg cactcttttt cctcccacac ttgtcttctt tcactaggtg    12900
acaagggaag aggtagcatg aggtggtggt cacaggtgag aggggctgtt gtgagcacag    12960
gcatgttgac tgcacattgg tcacctagta gaagttttgc aggcttggtg acttctgaac    13020
actgttttca aggttgattt ttagttgaga gaacctctag gtaccacgta atgttattaa    13080
cagtagtact gatctcacaa tcgccctatg tcccattcac aagatgttct gccaagccat    13140
aaaaggccca gttaagttta agagaagtct caaaagtaac agatgataac taattaatac    13200
ccagtgattt tgaaatgtag acatcaaaca taccaattca gtggtatcat ccttagaggc    13260
agacagagga tgattaaatc attcagccca tctctgtctg aggacgcagc ttagcacagc    13320
atggtggagg ctaaatgggc cttaagggaa aaaatgatat ctgaagatgc aatttatttc    13380
aaaaagagtt tgctcccgtg aattttcact ctctatgtag aacggcacca gcacacactt    13440
ttcctgagcc tttgcatgtg tggcaggcag cggcctggca tcctgggaa ctgaatgagg    13500 acgcagatga cccggacgtg ttcacagttt gacacatctg actcccagat cagggacagc    13560
tagctttgct ggctggttaa gttgatgatt ccatctttgc ctggttctct gactgtctca    13620
tgctttctgt tattactatt ttgcagcaga tatttctgct cattttttcaa tcatatatgc    13680 atcctggatg gcatagagtt gattctccta acaaatcagt gtcccttgt attttttct    13740
```

```
ggccataaga tagaatatat atgtcattta ttaaaaatgg agaaaatgtt caggagtttc  13800
ttgactcaga gagggaaaag ggatactcag ggcactttt cagccaggaa tttactacct  13860
ttgcagggta aagggactc accacgctgg aagtcaaaat aagccaccag tgccaagtgt  13920
tcaaagccct tagaatcaca atgctcttaa agcaaagtct tcaacaatgc ttgaaaactt  13980
ccactggttc tcagtatgtc caaaattgtc atgtctatga atgattttct caatctgaaa  14040
atttttatag caggctaaag aatgagatag gtcagtgtga ttctagaact aatcattaac  14100
attcaataga tgactatttt attctagaaa aagcagcaac tttctattta ctctctattt  14160
tgagggtaaa ttctctgtaa gtagaaaaag caaaatgtgg acatgggact aacatatgaa  14220
tatacaaagc aaatgtaccg aaaaaatctt aagacctgcc ttgtggtgtt ttttgttttg  14280
ttttgttttc attaaagtga cttgttagcc tcttgctccc tgtgaagcac agggaggtga  14340
cgtgatgtgc acagggcaga ctctgccata tgccctggcc ttgaactcag gccccctgg   14400 ggactgcagg gatgctggc catgctgagc aatgcctgtg ggtgtcagtt tcctcatctg  14460
cagaatgagg gtaggcctgg tgcttatttc ataggtcgc agagggatt cagtgacagg   14520 gtggtgtaga ggctggagcg tgccccatgt gtgcacgaca gccttccaac tagggaggc   14580 gggcctgggc tctcaccaga gagcctgtgt tctccatggc tacatgactt tgccccagac  14640
gtccttcccg tggtctggac cctgggaagt cgccaagagc cagacaggag aaaggctcca  14700
cttggctctc ctctttggtg accatccctt gcctccatgg cgggactctc aggtgacatc  14760
ccaccaaccc tcactttgct tccctggtgg gtctcacttt ccctcaagag tgttgctttt  14820
ttgtttcctg catagtcctg ggccagtttt gataaccctc ttcatttcac ttcagaaacc  14880
ctgatgattt cttcctgtgc tcttttttacc ttaggacttt tactatgacg actgtgactg  14940
gcccatttct tgtttttttt ctcttgctct gctttctccc ccatcatcac taaagcagac  15000
atggcaatga tggccatgca cactttccaa gggtccagct gtagatcttc atggttcccc  15060
aggtgcctgg accatcttgt gaggagggag gcaaacacac cctgcctgga gcacttggcc  15120
ctttcggcaa tgttttggct tcctcaagtg agaaaagaat ggatttgtat tcccctctg   15180 cattattgtt tttgttttgt tgtttgttt tgttttgtat tgagacagag tctcactttt  15240
ttccccaggc tggagtgcag tggcccgacc tcggctcact gcaacctcca ccttccgggt  15300
tcaagtgatt ctcctgtctc agccccctga gtagctggga ctacaggtgc cgccaccac   15360 acctgactaa ttttttgtatg ttttgtagag acagggtttc accatgttgg ccaggtgccc  15420
attattattt gatctggaat taactgagct actgcaggaa ttgcttgatt cactgatgac  15480
tggtgttgag ccagtacaca cccacaccca aggactgtga ctgtcttctg aggtccatcc  15540
tcagaaattc ctgtctcttc acctagtgtg taataaggcc tgcgcgtgtt atatggaact  15600
gtaaaaaatg cgccaaccat ctgtccttcc tctttatctg attacttatc attgttctct  15660
aagttgcaag ttaatagact gatcataaat taatgcatgc tggagacttg ctgtttccta  15720
ctagcagcat ataaaagtta ttttttaaagt tgttttaaat ctgtgagtaa aaataaattg  15780
ctttgctgca agaaacacca aacatggaaa agctaacggt tcaaagttaa taatttatct  15840 tatgacatc actagtggca tagttgcttt aaacagtgag aggatttaat agatatttga  15900
tttgcaagtg ggatgaaggg tggtctaacc tttgtcctgt gtttaccttc catgagatcc  15960
tagaggttgt acagcacagt agtggcatgt gacacacttg agagtgcctg ttctgtttgg  16020
aaacctggaa actatgaagg gaagtggcct tcgagcttaa cacataagac ttgggaggca  16080
```

```
aaaccttttta ttctctttaa atattcactt taggataagc attttttag gtgttaggaa    16140
cagggaaaac tgtgtggtta ggaaggaaga aagaagaaag ttaactgttg tacattccct    16200
aggtaatgtt tttaagcatt gttattcact ttcaaaacac attttattta tttggactta    16260
atattttgat cttattttt caatttcttt taatttaaca gacaggatga gttttttat     16320
agttgtatta cttagaaatt atactaaaaa tggccgagtg tggtggctca cacctgtaat    16380
cccagcactt tgggaggcca aggcaggtgg atcacttgga tcacttgagg ttgggagttc    16440
aagaccagcc tggccaacat agcaaaaccc cgtcttcact aaaaaaaaaa aacaaaaaaa    16500
aaactagcca cgcatggtgg caggtgtgcc tgtaacccta tctactaggg agactgagac    16560
ataagaatca cttgaatcca ggaagcagag gttgcagtga gcagagattg caccactgca    16620
cttcagcctg ggtgacagag caagactctg tctcggaaaa aaaaaaaaaa aaggataaag    16680
aaatcatact aaaaacaaaa cagaatgctg accaccttat agaaatagaa atagtggttt    16740
gctgtgatag caaattttct tgttaacttt ttatttttaa agaattgcac attcacagga    16800
agttgcaaaa aatctactgg gaggtcctat cccccttccc ccaacctcct ccagtagtaa    16860
catcttagta gcaaagtttt gtatatttat tttgatatca ttatctaagt ttgacatcat    16920
tatctaatat taacctaagc caaaagccca ctattttaat tatctagtga tgcagtgtta    16980
tagaactcat agccttttcac agcattattt ggaagttaat tttcttaagt gaaatgtttt    17040
tggtctttaa ggtttggagg ccatggaggc atgaggagaa atgggatgag ggagagagag    17100
ctaagataga taaagacaga gatggggaga tccactgatt cgttgaacaa accagatact    17160
tccttatagt ttttggatta acttacatga gctaagttta tattctgttc agatcacaag    17220
tggtcaagtt tgtgtgtgtg tggggggggg ggggtgggtg tgtgtgtgta ccactctacc    17280
catcctatat ttattgtcct gtatttggtc tgttctgcct tctttatttt caggataggt    17340
gtcctaaatg agggtctttg gaaagctggt gaggccatgt tgcccgtttc aggtgttccg    17400
tgctcaaatg tattcatttc ttgaaaaatt caggagtgc acacttttgt acattttcct    17460
atgtgtatat gataccatta tataaatctt aaaaatatat atggttcacc tgaatcccca    17520
gccatttggt agagaagata gaaaacctac agaggaggcc aagattttat tagaaaattc    17580
agcttctcga cggaggtatt ggctttaaag tcaaggcaat gcatctattc tttctttga    17640
tataactagc taaagatct cttaaattca aagtggccct catcttactg ttactgcaat    17700
ttactcttaa ttacaaatta tataaaaata ggttttgaaa tactgtagcg acaaagtaac    17760
ataccctctgc tccattacac agataaaacc tctaaggaac acctcctctc ttaacaggca    17820
ttaaccaact gcagaaactg cagaaggaca gggctatttg gaataacac agctcccttc     17880
cttgtctgtt ccctcccatt gtcaggcttc tgtggagcca tattcagagc aacataggga    17940
gggggaagag aaaatcaacc ccttggtgaa ggaaagctcc caattcacag agcaaacatg    18000
ggtactcttg tttgtgggag ctcccagggc ctcccagctc accgagcatt ctgagccctg    18060
atccttacac taattgtatt atgcaaccat aaatgatgtc tgctgtacca gcggggacag    18120
tttatttaa tagattggta taacttggca gaatcttatc tgcatgtttc atcttggatt     18180
tttagctcaa ttcaactcaa taggcatgtg tcaaatgtct actgcagact gagcactgaa    18240
aagctgctgg gtacagggtt acatggatag aaaacgtagc ctctgacccc taaggagcct    18300
gtaatccaga tccccattct ttccatccca ttctcccaag caagaattta cctaatgtgg    18360
tttgcgagaa tttaagagct ggaaaggtgg tcacgagaag ccggaatggg ttcgctaaaa    18420
tgtgtctata tgattaagca taacgtagct ttgcagcact cttcacagct tcctcagagc    18480
```

```
cttccgcacg cggtgtctca tttgaatact tgtgtgagga tagcctcata ccccctcagtg   18540 agctcttcat ggagtgatgc agtagacagc aagcctcaca cttctatgct cacggaagac   18600
caaatttgcc ttgaaaaatc tttatagtct cttcacattt ctaagttgac atcaaaaatc   18660
ggttaccata aaatcctaat agttgaagag atgtaatttc aattatttgg taaacctgac   18720
cttcattgtc aaagcaatta gtcaactcag atttactttc tcccagataa tagattctga   18780
cttctttttt tctgattaaa aaacttaaca ccttcctcag gagatctatc tcagttctga   18840
atgctgattc taactaagaa ggatatttgg ctacatgctg ggaagagggg tactgaggca   18900
cgccgcgatt ccactccagc atttccagtt agtcgggtgc ctctgcactc ccggtgttcc   18960
ggcgcccagt tagttgtgta ctctgggctg tccctatact ggagtcctaa aacacttacg   19020
actgcagata gggggaggtt tttcaaaacc ttggtctgaa aagccataga agggagatag   19080
gaaagcgggg gggtggagcc acagtacatt caggtggatc cgttttttgga aatagtacaa   19140 actggaggtg aaaccctgga aattgatctg tcgttcacat gcttcatgcc gagtccttgt   19200
ggacccacag agacacactc gccccagttt gaaggctgct aacttgattc tgaggacacc   19260
agtgaggtgg tagtgtgcaa atgatgtgtg aggaaacttt ggaggagtct caccctgcct   19320
ggagcacgtg gccctaaaa cagcgcagcc tcccaaagac agaagatgtg gactagtgag   19380
aagccaggta tggtgactgc tgctggatga agcttgtccc accagaggct cgcttgtttc   19440
attgagcacc tactgtgtgc ttgtgggatg caaacacacg tgtggtccct gccctcaggt   19500
taataggcag gggtggaaca gttatgaaac tgctctaaag tcattttctc aaactgggag   19560
tgacaaatgt atccacttgg aaaagattga gaatttttata agatttttaa atttttgttt   19620
attcacattg aggagaatct aaattctttt gaacttatgt atagatttca ccatttttata   19680 gtaataaatc agtcctcctg tgtgtgtgtg tgtatgtgtg tgtgtgtgta tgtaaacctc   19740
accttgcaat attattattt taaatagcca cttgcatctt aaggaaatta agaggacaaa   19800
agaaaagctg ctgttttgta tgtatccaca tatttaccag ctgcttccct gccggcaggt   19860
gctctggttc tgcactgcct gttgtccctt gcctgaaaat ggttgcctcc aatattttgc   19920
tcagttttct gattgtttac agtggcagag gagggtagat ctggtaccag ttagtaattg   19980
ccagaggtgg aagtctgtgg atgaaatttg tataacatgg aacgttagtt ccacagttaa   20040
tgctactcaa ttggaaccca tggaaattat ttttttggtga aaagggccca tgcgttatga   20100
aatttgagat ccatcacttt aagtgaatgt aggccctgga tacagtggga gctcagaaga   20160
gcaaatcagt tggtcacctt gctcaacgta ttttactaag gcatcagta aggctttcta   20220 tgacctgctc cttcaatgct tggttgacat ttggggagca agataaaact aaggattcta   20280
agttctgtcc tgtgatgctg taagggggaat ctcaaacctc taggtggagg agtgcagaga   20340
tgaccaggat ggtggaagcc tgcaggagag ctgaacacct gaagacaccc agtgggaaga   20400
ccaggacctt taacgcccat atctgctgct caagactggc agagagaaga gggtttgtga   20460
tgagaaaagg tggtgaaagg cacaaggagg cacagagcat gtcaggtccc atatcccaaa   20520
aggaatgtgc ttgggtgagg gagagctcct ccatggctgg aggcattcag agaccaggca   20580
gtcgcttgtg ggtttgtgat tagagtgagg ttcttttata aagggagtga gaagagaagg   20640
tctgtggata cttgagtgta tcggtaatta agaaataaat tgtgtacatc ccattctttt   20700
ccacattttc ctgggctgtc acagtggctg caaagaaagc agtccgtgaa ctgaactgtg   20760
atcccagaca ggcaagcaca ccaggaatct cttctcagct gttgataatg agggagcgct   20820
```

```
ggggagagaa atgggtcct ctttgagttt cctctgtgcc gatacctttc tctttgttaa   20880
aacagctaat taaacactga agcagtatag ctctcttact atacactggt agtcatagtt   20940
ctcttactgt tctcttcact gacagttctc ttactataca ctgatggtga cgcagaaatt   21000
cagaattccc cgcatgtgtc ccggtttgaa agccactgtg ctttgctgtg gattaggatc   21060
agacagttga gtcttgttcc aacaaggaaa gttgcttatt ggaaagtttt gctgcaggga   21120
gccttgagtt ctgcatcagg cttggaagtg ggctctgtgg aggtcagaag gaggatcccc   21180
cacccgcagc ctcaagaaaa atatgaaaag tggattatgc ctctgtagct atattgccta   21240
taaactttct gcagaatgac agtattcata tcctacattt tttcaaagcg atattaatcc   21300
tgagacctgc agctaaagtc aagtagaatt tagggataat taataggagg aaggtggggt   21360
tggaagatct gcatgattat agtcctctga tataactgga aaattctttc cattagcaag   21420
gagctttggt taatataaaa tggacagatt aaacctaggc aatttatttt actcattgct   21480 gtattttat ttcagagctg gttgaaaata ttacaaagta atatttaaa gtgcttatct   21540 aaactcttac tctgcatttt atcattgggt tatgaaatga ctggggaaag acttttcttg   21600 cttttattc tcagtgtcta cttataaaca tgtttttga actactgttt ttgtgacaac   21660
atgccttttt cccagaaaat ctcaggttaa cattaaatag gcactggatg tttatctgat   21720
cttgtttata gaaacacaag aaaattttaa ccttgtatat actttactca attaactagg   21780
taagaggtca ttgaaacatt tagaattcca ctctacattt caataattat caggtgaaag   21840
ctactgcatc tacatcagaa gatgtttgta atttatttaa gaataaaatt agctatgcaa   21900
gaaatagtat gtggagtcct atgtggaaat cacagaaacc ctgacaactt gatgatcttt   21960
ccgcaagcta aaaatatcac tctggatcac agcagtagag gactctgtaa atttaatctg   22020
tgtgtctcct gtaaataagt gcattagcag tacacaggtg gtgtcagagt cagtgatgat   22080
ggatagaaat tctacataaa atccaggctc agtggctcat gcctttaatc ccagcacttt   22140
gggagtctga ggcgggtgga tcacctgagg tcaggagttc gagaccagcc tggccaacat   22200
ggcaaaacct cgtctctact aaaaatacaa aaattagctg gatgatggca catgcctgta   22260
atcccagcta ttcgggaggc ggaggcagga gaatctcttg aacctgggag gtagaggttg   22320
cagtgagccg agatcacgcc attgcactcc agcctgggca aaagagcgac actccatcgc   22380
aaaaaaaaaa gaagtaagaa gttttacata aaaacgtgga gtgagcccaa ggtgccatt   22440 atccagccca tacacatcgt accatgtaca gagtggacac cagataaata cattgactgc   22500
atgccacaaa catatatatg taggcaccgt tgcattcaaa tacacatctg cagccctaac   22560
acatctttat ttgctaacga gcatcaatgt atttaaaaac aaacatgttt aaactagtga   22620
atgattagat tataatgatc ttaattcata agttttctca ttggcctttt gtatacttca   22680
attgtaatac ctagaaaaac agttatgtcc aaaggagtga ataggcctta tctgaaacag   22740
gtgagcgtga caagtgtttt cttacttatt ttacttttca gataattcat ccttaaagta   22800
cattagttta aaagtactgt ttaaggaaac agtacttgga ttaaaacttg aatcattgtt   22860
aaggaaaact ataccttaac ttcatgtaat cacaattaaa cctcttcata tagaaggatc   22920
taagaatttt ctgcagcatt caccagcacc aaaaagctca gagacatata tttctttctc   22980
tgtatatgta tttttaaattc aagttagtat aaattgacag gcaggtcaga gtaatatatg   23040
atcttctgag tcccccttagt aattaaaaga aatgattatt tttgcatgaa atatgataaa   23100
gtgattttaa gtgcctgata aaaagtctta accatgacaa ccattaaaga ttacatcaaa   23160
gaaaaataag tttgactttc atttaccttg gaaacagcta ttaactggta acctcaagaa   23220
```

```
acaccatgaa gagtcagttt gctccacaca tgtcttgtaa aagtcaaata actggtggtt   23280
atccagtaat gacaagaggt agaagttaca tccttgctgt ctgattgaac cttcccagag   23340
ctggcacaag gctgggaaga ccataggtgc taaatgagga actacttaaa gaaagaaaat   23400
ggaatttcac ggacaagaaa atccatgtcc atttggttct gtgacccaca tcctttgtat   23460
cctatgcttt tttacacttg gtacatggtt gcaagattgc ccctgttttc tacttatagt   23520
tccatgcagc atggatgtgg gaaaaagtct cctctgcaaa ggggttaat gcaggtcact    23580 ctacgtatgt gcacgaggtc gttataaagc tcgaaaatat gggctcacca accaggtgat   23640 tttttttaatt atccaaccag aagacataac ataggggga atcaaaagaa atctctgagt   23700
aaaataatga taacaggtca aactttgcgg tcccacgtga ggctggagat gcgtattgtc   23760
ttgactttgc atctacaagt ttaacaaatg atgctttctc agtttacctc tggaaatgga   23820
aattagcatt gcaaatgact tcatgaggag gtagaagcta tctgtgaatt cctttcgct    23880 gtgtttacga tagactctca cgtctagatg tgtcatgtat tatgttaaat tggtatgtct   23940
tgaagttata aagcacagcc ctctataagt atatatattc cacctctttc aaatcggatg   24000
gtacctatcc ttcaaactgc tatttaatga ctgtctgcta tgttcaaggc actgctctca   24060
atgttaatac ttgatgagat cgggcgcgtt caaggtggca tggccgtaga ctcaatgtta   24120
gtatctgaaa tatggcctac gagctgagtt gtgaatcaag ttaatagatt ttcggaatgt   24180
taaggtctaa accagtagct cttaactgag acaatcctgt cctcatctca cctgggagac   24240
atctggcaat gtttggagaa ccttttggtt gtcacactgg ggcatctagt gagtagaggt   24300
cagggatggt ggtaaacaag ttttttttgtt tgtttgtttt gtttttgaga cagagtctca   24360
ctttgtcacc caggctggag tgcagtggtg tgatctcagc tcactgcaac ctctgcctcc   24420
taggttcaag caattcttat gcctcagcct cccaagtagt agctgggatt acaggtgtgc   24480
accactacac tcagctaatt tttgcatttt tagtagagac ggggtttgc catgttggct     24540 aggttggtct cgaactcctg gcctcaagag aaccgccccc ttcttggcct cccaatatgc   24600
cgggattaca ggtgtgagcc accgtgccca ggctaacatt ctttaatgca taggacagcc   24660
cccaccatac agaggaatcc ccagcccaga atgttaatag ttctaaggtt gagaaaccca   24720
aggttaagcc aagtcaactt atctatcttc tttaaaattg cataagaatg cagtcctgtt   24780
cttcattcct cttgctttgc agttaatgat cctttgcctg gactttctaa gtgcccagaa   24840
gagcaacagc cagcatgcag gatggcattc ctgaccagtt gcacttggcc tagcattcca   24900
acctcacctg cctcagcttg ttcaacctga aaacctacca agtgaaagca agagccacgt   24960
gaagacgcct tagttatatg cacccacccca gacacttgct cagaaaggaa tcagtggggc   25020
cctggcctta gaaactggct ccttcactgc tgtagaaaca acataaattt aacataaaac   25080
acgtgctttt ctttttttctt cttacttttt cctgtcttgg caatgcaagg atgccattag   25140
gtaaagaaat ccttcaccac actaatcctg cagagccaga agagaaacca gcttgttcta   25200
acccagcttt gtcatggaga gaaggcagct gctccagtct gaactattct ttcttttggt   25260
agcagcctgc ccaagggtga aagtgtgtttt aatagtttga attacacaag tgaacagtaa   25320
atgtatgcct gtttctgctt tatgggactt tgaaataatt ttgtttgtgc caaggtttta    25380
gattactata cctaacaacc tagaaaaaga aatgaaaagg aagccttctg ccaggcagag   25440
gtcactacgg gcctggagct gggcacctga ctcagcagct gcccagatcc ccagagctga   25500
gaagtcacca tgcatttgtg gtgcttcgag cgagttacca gagtcctgga acagagcagc   25560
```

```
acacctgcgg ggtgtccct  tggcatttgg gcagggcagg tgaccaaggg tcttgttgga  25620
actgaagtcc agcttgaaaa gcaaatctgg ttgtgagcta gagtccagta acacttgttt  25680
cccgccgccc cccgcataac tcgtgtgtcc taaaatacaa taatttcttg aacttcagtc  25740
acttatgcct ataagcgggc atacaacagg ggcacaataa atgtttgtta agtgaatgaa  25800
ttctttcaga actagatggg atcttagtcc aactctctta tttaacgagg tccacagagg  25860
ttctgcgatt gtctaagaaa gaaggctgtg ttcatggcct ttgttgttta cgtggccctg  25920
tgattctctt ggctccgtga aagtcctgat gcagacattc cggccatcta gaaaggcatg  25980
cagacaagcc atccagctgg catgatcctg agtccagctt tctttaaaag agcttccaaa  26040
actgcttaag ctttgactgc acaaaacctg catcacctcc agttgagaaa ctcaagagaa  26100
taagtaagtt atggagttgg agaccccagc ttaactacta gttttaaaat agtgaaatca  26160
acattttcaa atctttgact tcactaagat ttaataaagt ttattaatca tatattatga  26220
gttattgctc tctctttatg tctgtaatgc agttgctcct ctctgtataa attaataagt  26280
tttagagatc caaaatgaga attttaaaat aaattacgta tattttaatc aagtttaatt  26340
tgactatatc cagctaaaca attgattgaa cttcacttgc ttttctatga caggtttttt  26400
gttcttagta aaagacccca gttttctcac ttgtgaacag aaggggttag acttcatgac  26460
agctaaggtt ccttccgtct ctaacaaaag tggcctgaag agaggcttct agactatact  26520
cacggtgggt tcttgggacc tcagagtcag ctccatcact taagtggctg tgtgattgag  26580
tggagacacc tcaatctctt tgtgcctcag tttcctcacc tgtcgagtgt caacatgatg  26640
gcacctaaag ctgttgagac ttcagaaagg taatgtgtga aaagtgaaaa gtgcctggca  26700
tccaggaagt actcaataaa taccaactat tttattgctg cagctgttct tatagatgtg  26760
atttctagaa cattgccttc taatagggta gccatgggcc acaattgttg gctgttcggt  26820
gtttcacata tggttagtcc aaactaagat gtgttgtgag tctcaaatac acactggatt  26880
gtgaagactt aggacaagga aaacaatgtt aataaaatct cattgataac ttttaaatta  26940
attacatgtt gaaatgaaaa tatttgggac atattgagtt aaataaaaca ggagattaat  27000
ttcttctgtt tctttctact ttttttatta gtgtggctac tcaaaaatgt gacattatgt  27060
atgcatctcg tattacattt ctattggaca gcagcgctct agacagtact atgggtagta  27120
tctgtgggga ggttctcaga aacatgtcgc atgctctttt agaaccttaa agtattccta  27180
gtctcctcta cttccagccc ttggctcttg ggcctcagtc ttttactttt gcggctgtg   27240
tttctctgaa ggcttggcat tagtagattg aaaagaataa ccatctaggg aaatgtgaat  27300
tcagtttctt tctgacattc tgctctctac aaggggatat tatgtacaca taaacctact  27360
tccaaaataa tgaagtgagg cctaattcct tactcttcag agagcccact gtggaagtgt  27420
cactgacctt gtgtatgggc tgcccttcat ggctctggga gtcattataa agggcagcat  27480
ttggcgtggt gcgtcctaag ccagtgtttc tcggctctgt tccttagaca tgtgttagtg  27540
ttaatagatg ttcttggaaa aaaaaaaaaa aaacagcatt ctgaggtcaa acatgctcag  27600
aaagcttgga atctgcacta cgcttctcgt acacatttca tattaaagat tttggaaagt  27660
cctgcaatac agagccctgt ctaatattgc cacaacccac aattgctcaa atgtaaatag  27720
atttgagttt attcacattc agatcacctc ttaaggcccc acctcccaat gctgtcacaa  27780
tggcaattag atttccacat gagttttgga agggacattc agaccacagc aggggaaagc  27840
agggtacttg ctgctttgca agtgtgtcca catctaatta atagtacagt tcttactctt  27900
ggtgtgtccg gtgatattaa aaattaatgt gccttattta gataagtaac ataaaaatca  27960
```

```
caaaatgtat gccttagatt tatatgtatt tataactagt ctatttcctg aaaacagttg   28020
agacaccttg taaaagttac cggtacgata gggccattcc aacaaagctg taaagtggtg   28080
ataacacagt cataaagaag aggagatagc tctgggagaa aaggtggccc agaaaccagc   28140
tctgagcctc atggctgcag gcaaggtctg caggttcctg gtcctgattg caggccattt   28200
gctgccttga gtggtggtta cacaaggcca gccctggggg tatcacccag aacacctagt   28260
acacgaattt cagtttagag gacgaagcat tactggagta ttgttatgca ggaaaacttt   28320
ttcctaaaaa tgccctgaaa agagagtagc ctaatgcatt caatcaaaat gtttttaagt   28380
ggaaaacata ttgtgtgtac ttgatctggc ctgctgcttt taaagattaa aaactgggac   28440
tgggcatggt ggctcacacc tgtaatccca gcactttggg aggcagaggc aggtggatca   28500
cctgaggtca agagttggag accagcctga ccaagatggt gaaacccat gcctactaaa    28560 aatgcaaaaa gttagccagg cttggtggcg catgccggta atcccagcta gttgaggggc   28620
tgaggcaggg gaatcacttg aacctgggag ccggaggttg cagtgagctg agatcgcatc   28680
attgtactcc agcctgggca acaagagtga aactccatct cgaaaacaaa caaacaaaca   28740
aaaaaacact ggggccaaag aactctgtgt gctgtatcac ctaaccacat tcatgacac    28800 ggctagagaa gaatcatgca aataaaaatt ccaacatgt tcgtaaactg ggaaagtatt    28860
tcactgggga gtgagcagaa aagtaatact ataacctcta tatctagaca aatgtgaatt   28920
cagtttcaca tataaatata taagtgaaaa aatatataaa tataaataat atgaaataat   28980
ggttatctca ccactttcta catcttttgt gaatatttta tagtgctcaa atatattagt   29040
gcactagtat atgtacatta cattaaataa ctaatcattt attaggagga tgtgcttgtt   29100
ttttgctaat aaagatgata ataaaaaaat ccttagaccc cccctcggtt tgttttcagt   29160
taggaattag ggatatttat aagaatatct ttaaatgaca catgccttgc tctgggacga   29220
ggcatctgca tgggtgacac atatgtgttg tgtgtacagg ctcccagcat ttccagggcc   29280
ctgctcagaa tgtaggcctt actgattctt acagagttac aagcgctggt gaggttggcg   29340
aagtttaggt aaacacagct gggaatgccc catggcctct gggtgacttt ggacatcact   29400
gaactttacc cttagagatg catacctgca tctttttac cctgataggg ccttccatga    29460
tgctttcaaa gtgttttgt ctgcttttcg gttaatagac tttcacagta gccaattgaa    29520
tatattggtt aaatgcatct ctttatacac agactggatt caaactgagg ttgtgtctct   29580
ccctggctgt gtgacgttgg gtatgatcca agtgtcagat tactcaactt caaaatgagg   29640
acagagcctt tcccttctag ggctgccagg aacattgaat gagagagtgc tggcagctta   29700
gtacaggtgt tcattgctct tgtatggtac tgtctgtggc acggctagat aaaatacagt   29760
agccactgat tcaaatttca actgaggagt aaaataaact gaataactta gaaagtttt    29820 cttcttttga atgactctaa gaatttaagg agcatgtgag tgttgatggc tctaaagggg   29880
taacagagcc caactagctc agttctcagc atgaaaatag tcatatggca cagactcagt   29940
ggagtgggtg cacttcaata actggaagca cagatgccct acagcagcat caaagatggc   30000
actctaaact actttcaatc ctttaaaata aatggaaacg cacatttagt atgcatatga   30060
caacacgaag gacttcgatt ttgctgatgc aatacagttt tacaggattt tttatactca   30120
aattagtaaa attctgtatt gcatccaaat tataaattat aatatcatct agattggaca   30180
taggaataac gaccactggt atctgcccag aaagctctac cgcctgttta taagctcctg   30240
caggagacac aaaaagaaga gaatttgaat ataacttgaa atgaccgtaa tctcctgccc   30300
```

```
caactcattt cattaccaaa ccgcctcttt cttcattatt tctcctgaag cacaaatcta    30360
tagagaactc agctgccagt ctctcccact gcactcagca gtgaaagggt taggcctagg    30420
cttttcaaac agaccagtgc ttgtatcagc ccttaaacat ctctggagaa ggaaatggga    30480
tccttctttg gtaattcatt tttgacagtt ggggattagg tgttctgtat ctgggggggcc   30540
ttgctgtctt ctctcctcct cctcccactg cagaccctct cctcccctcc cctctccagc    30600
tctctgatga ctgcttcatg ctccttccac ctgaggactg ccagcacagc ctattgcagg    30660
aacagccaat gaggggctgg ctgtgctctt ttatttataa aattataaac tcaagcaaaa    30720
tctagactat gtgtccccaa gatcagagga gcacaaatcc cttgcttaca gattgcatgg    30780
ggggcacatt ctttaaaatt ggtccctgat ctagactcta gcctgagaat catctttaag    30840
ttcagaattt ccactcatga cctcacatct gtgggctccc acattgtctt ccaaaacaca    30900
catggcatct ggcatcacct tcaccccac cctcagagcc tcatctccct gcaggtagat     30960
agtcaaggca acctcttcac tcttctgcca agcctcctct cctcagctct tcccttcctc    31020
tctcttttg aaaatatttt taattgtggc aaaatataca caacataaaa tttaccatct     31080
taatcatgta taaagtggga gttcagtggc attaaataca ttcacgttgt tctatagcca    31140
taaacaccat tcatctccag agctcctttc atcttgcaaa gctgaaactc tgtccccatt    31200
aagcaatggc tctgttttcc tccgttcccc cagcccctgg ccaccatcct cagttttctg    31260
tctctgtgag tttgattact ctaagcacct cttataagtg gatcatacaa tgtatctgtc    31320
tttttgtgac tggcttgttt cacttttccat aatgtcttca aggttcatcc acgttgcagc   31380
atatggcaga acatctgtcc atttccaggc tgaatggtac tcttttgtac gtgtggacca    31440
catttcattt atccattcat ccacgggagg gcacttgggt tgcttctgct ttttagctat    31500
tgtgaataac gctgctatga acatagctgt atgcctttgt cttttaaagc ccaaatctga    31560
tcaagtcact ccccagctta aaaccttcca ctgctcccca gcagtgggat aaaggccagt    31620
ctcccctgta ggtctctccc gccagccctg ctcagtcttc ttgcttgtca tccttggcta    31680
ggccttgcat tgccatagcc ctctgcctct gttcacgctc tctcatcttg gagcatgagc    31740
cttccatcat ctctaccaga tgaactctca tttcttcttt caaaaaataa aaacccaaa     31800
aaacccagag atcccaactg tcctggtgtc tgcatagtct gcagcacacg cccctccat     31860
ggcccttcct ccataagcag aatcactcct cactgttcct gcagcacctc ctgtgtgccc    31920
acacagctgt cctgcggtgg gctgtgtgtg tgagtgtgcc ccctctagga cctgagctcc    31980
ttctggaggg tgggcacagc atccattcat tctgggaatc ctggtcggca ccatgctaga    32040
acttctgcaa gtgagtgcct ttggtgctgg cccatgggag agctgttggt aaggcatact    32100
tttgcagatt ccagttgctg ctgaggttgt tgctctttgc acaagtttct tctagtcacc    32160
agtgaagtga catgtgtggc aggcatggcc cagggaggct ttttcataaa gaagaggttg    32220
aatctttggg gctgtggttt gaatatgtcc ctcaagctta tgtgttggaa acttaatccc    32280
aaatgcaata gtgttaggag gtggggccta atcacaggtg attaggtcat aaggctctgc    32340
cctcatggat ggcttaacat gtttagtgag gcagtgggtt agctattgtg agagtgggct    32400
tgttagaaaa ttgagtgcag ccccctcttg cttgctggct accatgctct cttgcttttc    32460
tgccttctgc cgtggggtga cacagcaaga agaccctccc cagatgctgg caccatgccc    32520
tgggactttc cagccttcag aaccacgagc cagacaaatt tcttttcttt ataaattacc    32580
cagtctgtgt tattctgtta tagaaacaca aaatggacta agacaatctt ctttcatcaa    32640
gttagggtac caacctttaa agactgccag tccaaggtta aggaaacttt tcaagagca     32700
```

```
gtccaaacat gatctggccc tcagctactc tccagggtca tgccaccta tcacccactg   32760 gctcacacag acgctgacca ctgcttagtt tctcaaactg aagttttcct cctcagagct   32820
tttgcaaaac cttttctttg cctggaaaac tcccccaca aatcttagt tgtaggttcc    32880 ttctcatctt gcagaattat tagtttgctc ttcaaatagt ctctccagct agactatcaa  32940
ctccaggagg gcagagttct tcttcgcttc cttcacccat gtgcccactg agtccagaac  33000
tgtatagcag tttgattgaa aaatccaca gggtggagga tgagaggacc ctggatccca   33060
gcctcacagc ctcttacttc acctgtgtga ttttggtcaa gtcctttatt cttcctgggc  33120
tttagttttc ccttatctaa aatatgagaa aagttcccct ctcctgggta ttctgggaga  33180
ctcatgtaaa aggcactgag ccagtgcagc acatctatga ccaggaaggg tcagcttcct  33240
gccttgcatg agacacacat tcccttcttc atgcacagtt attcatgagt taaatatgta  33300
ttgagaagtg ggttctcagg agatgatgca tccacagcat tgtttgtatg cctctgtctt  33360
tgatgtccct gcctgagtcg cccactttag agcccttctg ttcttcagaa accagacttt  33420
tctttcaata gtttcagtaa tcaatcgatc aatcaatcaa ccaatcaaca gtgataataa  33480
tcatgagtga gccctgccc gtgctggctg tgtcctgctg aaggcacact aagtgctgcc   33540
cttcccagaa gcctcaggaa gcttgcgaag ctcaggtgca tggatgcctg gtggaatgag  33600
gaagggatgc agccaggtag agaaatgccc tgccatcact tgcatcagca tctgtgaaga  33660
gctggccagg cttttgctca cagtggttga cacagtcaag gagcaagggc cccgtaggag  33720 agggagtca agggctccgg gtgggaatgg agctgggggc tgatgctggc ttctggagca   33780
ctgtaatgtg actgagaaag gtgaaggagc cgttctgaaa aagaagaagg caggagctcg  33840
cacagctctt gactcatctt gacttctttt tcctgcttca tccaagcagg tcgactctct  33900
cgtgatctca gagacagagt gaagtcatga gtgggagggg agcacagaaa ataagacctt  33960
gattcccagc attgggagac tccctgctcc cctgagtctc ggaaaatagc acccttcaaa  34020
tgttttaggg atccagattt gatgaagaga tgttattttg gcttttagat tcttaggaga  34080
gatttgtctt tctcaggtca ggaagaaaat gctgcccgct gcacattctt cgggacagac  34140
tcttttaatt attactagtt taatgtatgt tttgcttagt taaggaaaac ccctgtggtt  34200
tcttgacgtg cttcagtatt ctaactcaca gctgattcag ttcaggggc tggggagatg    34260 tcctcgacct ctggaaagga gggtgcatct ctagaaataa ggctaagtat gccactgaca  34320
ctgtctgcat aaacgtgtgt gatctcaggt ccaaaggatg gggcctggtc taagccaggg  34380
acgtgggaaa tcattttcct gtggcaactt gtgaagacca ttctgtgacc ttggtgtctc  34440
tgggccttct cttagatttt ctaagttggc tagtcagtgg agctgccatc cctccttgc    34500 ccatgttcta ctcccagagt tcctccaaga aattgcggag caatgcctgt tcatgagag    34560 ctgagtttgc tgtgtcttcc acttagaaac aacactgtgg accaggagga cacacagctc  34620
ccagggccat caccacacaa agtgaaggct ggtgaatccg aggcttctag cccttgccgg  34680
gccaggcccg cagcactccg ctccccaacc cagccgctgc tttgtcgcag gaacctcagc  34740
agggcagggt gtttcctagg aggacatccg attcccagcc attcctttca gtgaatcacc  34800
tgagctcaca ttcttttttc ttttatttt gaagctctta gccaatctgc ttcgcgatga   34860
accagttttg cttgaagcag acaaacccga ttgtcaggag acagtgatga tttcttcagt  34920
ctctgaggaa gagttttcat tttccccaat tcgcaaaaaa agtcaggtcc ctccctccct  34980
ccctctccgt agaatatttt ccatgtgtgt taacaatggc tgagcgtggt agatgccagg  35040
```

```
aatttctgtc aaccctcaaa gaggaaagcc ctgcctaatg gtctgcccgt tcttgttcac   35100
tccctgcccc aggctcccca cccgccttct ttctggaagg tataaaggct cctgcttata   35160
cctggcactg cacgcttcgc tccctctgat ctcctgactg tcatgcccag tgtctcagcc   35220
tatcattcta cctctaactc gaccttgagt gaccttgagc aagtttctca ggattccacc   35280
tccaagtcac tctcccttttg ggatatgcag cactaagtta agcttgcctg gaaaacatca   35340
```

```
cttgaagctg gaaaaccact tttaacacag cgggaaaagc tatttgttca gacaggagtg   35400
gggtgggtct gggcagagca ctgctctaac ttggccatgc cgtggcagca gctcctttaa   35460
tgccactttt tcctggcgcg cccgcggggc ctggagctca gaaagagggg aacgctccct   35520
cgtctctcaa cagttgctcc agacaggtca gcaaacatgg aattcagaat gttcattaaa   35580
cactggctgt gtcttttgtg ttcaaaagca agacactctc tctgaaccat gcccccacag   35640
agagtgcaga atgtgtgaaa cctgccggga aggtctggac cccttgcggg gcagtgggca   35700
gcaccgtgcc tccgttcaca ccactcacat ggctgtgcct ctgcttcctt ctggcatggc   35760
tgcttcttcc tcaggtctca accatctccc tcagatgctc tttcccatgt tgtggctac   35820 aggtccccgt gacctgcaga ggcagagcac tcaccagcag cccagcctcg ttgcgcaccc   35880
atgtttgcat ttgcaggccc tagaaccact ccaagctccg tgtggcgaga tgcaccctcc   35940
tgcccttcac tggggagctg ccctcctgtt cacagcggca cctgagtcac acatctggag   36000
ccatcctgga ctgcctcatt tccccgatgg ggggtttccc tgacttcatc catcctgtct   36060
tttgggtccc cataataact gacatgggtc ggcccgtacc agccctgtg agaagggctt   36120 taactgcctt cccaccccct gctcatctta gagtctctct atagtgctgc tgaaagaatc   36180
tctaaatcag tggttctcaa cctcagccgc acattgagaa tcacctggga cccttaaaaa   36240
aatcttaact cttggtccaa gaattctatt acaatcggtc tgggatgggg ccctacaggt   36300
atttttttaa agctctccag ttggtaatgc atagctagag ttgagtatcg ctgttctaac   36360
gtgcagatct ggtcatgtta ccagccttt aggtggtctt cttttggcttt ctctatctaa   36420 agttcaaaac cgaacatgtg cgcattcagt gcacccattt tcaactgtgc attaacacat   36480
tcagcccacc agcaagattt atgaaccatt ttctgctgtt gtatataaca tatcatatgc   36540
ataatggcat aggttattgt tttcttcaaa atatatgaga tgtgagtcct tctacgaact   36600
gactcacact gattgcccaa cttcctctct cgaggtctca tcctctttcc ctgcagccgt   36660
ctccctcttg cacgcacaca cacacacaca caccacacac acacacacac cacacacacc   36720
agggtcgatg ccatctaccc tggacttcat cttgaactcc ttcgagtgtg agtcattact   36780
cctttgtgca cctctgcttt ctcttctcaa gatgttcacc tgcttgaggt cagttccttg   36840
agcgtcttcc acttgccatg ttcaccacag tgctcaacat gcctgaatgc atggatggcg   36900
acttctcaga tcctcagtct cctcatctgg gtaataaggc attgggttgg cgggtccatc   36960
tggtttcttc cagctctgag agtgcatttg ctctgtgatt cattcgttcc acaacacttc   37020
accaattaaa gagagggtac aaaaggtgaa catccttggc tcccagcaga tgctcctcaa   37080
aacctgaaaa atcagatagg tgagggaaga ttgaatgaaa ggcctcttat gattctgcag   37140
caattttggt ggtttaagaa ctctatggaa aaatcatcag tatttctgga attgaagtaa   37200
aatggatagt gagcctctgt gtatgtgaag gcccgcatct ggaacatgaa agaacctgtc   37260
tgatgtgttc tagtcaggaa agcaggtagc caatactatt tatagaattt acagaaactg   37320 aagatttgt ttctactgat tttcaaaata gtattatgtc tgattttttt cctcagaaat   37380
atacttcctg ctcttctcaa caaactcatt tgaaaatatg attagaacat gatagaattt   37440
```

```
tactcatttg ccaactgcgg ttcccatttc acatattgtt agaattctgc atggtggctt    37500 tgcccttaa ccactaactg ataaatgatg tagttagctt ttaaatgtgt ggaaaaatat    37560
aatttcaggt tcaaccatag gtcagaagta cacgtgtttt gttagtctat ttgtctctca    37620
gtcatctcat ggaaaattct cagcttttgg tatggaaata attttcttga aggcaatatt    37680
tgttgagtga ctgacggaat gaaaaacgcc agttgcgtaa gtgtgaaaaa gatctgggtg    37740
ttttcattgg atccaaattc cacatgagcc aacaacagcg tggtgtggag gctggagcac    37800
attaataaga acagtgtcct aaattcagga ggtaatgctc tgcccatgcc ctgtgcagct    37860
cagacggtgt gtgcagtgca gtatgtaacc cagggcacat ttcaggggcc cacagggagc    37920
tgcagcttgt aaggtggagt gcagccaaca gagcagagag tcagaatccc cgcagagtgg    37980
ttgaaggcac aaggatgcgc agcaaggaag acagacttat aggtggtgcg actgccatcc    38040
tctggtactg aaggtgctat catggaggga gggaagtaga ttgaccctcc tggctccaga    38100
gtacggaact cagacaaacg gtcagaagct tacaggagg ccaattttgg atcaacttta    38160
agaagaattt tttaaaagct agagcaatcc taaaatggaa tttgctcttt ataaagttgc    38220
gaatgcctca ccctggaatt gcttaagcaa agttgggacg ggcagttgtg agtaatctcc    38280
tttccaatcc atacccgcaa tcaccagaaa cgtggacttc cctgacactg agcacctctt    38340
aattaagcat ctcataagtg aacaaaaccc agcccttcaa agaagtcact ttatttatgt    38400
gtgggtctgc agcttggatt tcttgataat gttaaataaa actccatcta ctcttccaca    38460
aacacttcaa gaaacctaag acttttggcc agagtaacac cgaggtttga gagaaaggat    38520
atgtgtgtga gaggtgtggt ttcattagaa catattattt gacttcatgt tgaatcaaca    38580
cttttgtgca aaatgcagtt ttaccagcct cttttccttgt tttggtcaca taatttaact    38640
taacattctc ggtacttgat tttctaacat aaaatgggat tgagagggga attttgaagt    38700
tcccatggtc tgtcctctac attctgacag ctcattatct ctgcggtatt gttctcacat    38760
ttaagtgagg ttagcggagg cagaggcctc tcaggcctga agatagcctc tgttttcagg    38820
gaaatactag actgtgagat ctgtgacact gaagcactaa gttcatctca caaaagcaac    38880
gtgctctttt taaatggttg atcaaagtta ctttcaaaag gaagtgttag ttttttgttat    38940 tagccgaaac aagagctgct ttaatgtagt atatttaaaa tcatatctca attaagatgt    39000
tattcaaata ctatttgacc caccaatctc attactggat atatacccaa aggaatagaa    39060
atcattctat tataaaaaca catggctggg cacagtggct cacgcctgta atcccagcat    39120
tttgggaggc cgaggcgggt ggatcacgag gtcaggagtt caagaccagc ctggccaaga    39180
tggtgaaacc tcatctctac taaaaataca aaaattagcc aggcgcggtg gcaggcacct    39240
gtaatcccag ctactcggaa ggctgaggca ggaaaattgc ttgaacgcgg gaggcggagt    39300
ttgcagtgaa cagagatgaa gccactgcac tttagcctag gtgacagagc gagactctgt    39360
ctcaaaaaaa aaaaagaac cacttgcata tacactattc acaatagcaa agacgtgaa    39420 tcaacctaaa tgcccatcgg tgatagactg cataaagaaa atgtggtaca tatataccac    39480
gaaatactat gcagccataa aaagaacaa gatcatgtcc tttgcgggga catggatgga    39540
actgcaggtc attatcctta gcaaacgaat aagaaaagaa aacaaaatac cgcatgttat    39600
cacttataag tgggaggtaa atgatgagaa cacaaggata cactggggcc tacttgaggg    39660
tagagggttg aagggagaga agcagaaaaa ataactattg gggtactagg cttagtacca    39720
gggtgacaaa ataatctgta caacaaacta ctatgacaca agtttacctg tttaacatac    39780
```

```
ctgcacatgt acccctgaac ttaaaaaaat ttttaaaaag atgctatgca ataaaattct   39840
caattaagaa tttaacttgg taaatgttca tttaatgatc taaaaatatg tgtctggatg   39900
gctctagcaa aaaaataaat aataagtttc tcagagatgg taaggctgaa ataaatgggg   39960
aaaaatctga attgtaatcc tttttctgtt ggacctggtg ttggggtttc acacttgtgg   40020
gtgaatgtgg gcctcctgtg agcaccagca caaaagacta aactgaacaa aagattaaat   40080
gtcacctcta aaattctgtg caacaagact tccagccaca gaatgtgcaa ctcagatttc   40140
caagtaaaaa cacaccagga agcagatctt agatctctgt tatctccttg gcaccagctg   40200
gtattcatcc tcaatgctag ctagagttga aataaagagt gaaagaactt tctcttttat   40260
tacttaataa acttcctttt ttgagctgtt ttaggcttac agaaaaattg agtggcagtt   40320
tcagggagtt ccagcacggc ccctgtttct ttctcatggt ccctgcaggt ttcccctatt   40380
attaacgtct gtcattagca tggcacattt gttacaatta atgagccaat attgatacat   40440
tattcactaa agcccacagg ttgcgttagg ggtcattctt ggtggtgtac gttcttcagg   40500
tctggacaaa tctataatga catgcattca ccattactat atcacgcaga gtcgtctcct   40560
ggccctacaa gtcccctcct tccccacctg ctcactcctc cttcccaccc tccccaaact   40620
gtggcaacca tttaactttt gactgaatgg atttattctt attctgcctt attgtatgta   40680
caccatattt taataagata aaataatagt ctatagtaga cttctgtaaa tactcaatga   40740
ataaatactt gcatgaatgc aggaaaaatc aatcagtctt gcaggatttc ttatgcgtta   40800
catcgtcctt ataagaaagc agtcattctc accgagatgt gctgagcaga tactggacat   40860
gttctgaccc agataagggc tgggtggaag tagggctgga gacacagaga cccagtgcca   40920
acttccagga cctcggaaga actgaaggca gagaggtcct ctcagtgtgg actgggcctc   40980
tgctggcagc caccagcggg cacagagctg atgtgtgtta tgccacgtgg ggaaaaccta   41040
cagacgattc tgagaaaggc tcacagggac accctctgcc cctaaaagaa caatttaact   41100
ctaatttatt tctgtcactc tgcatttttct gacctttccc aagtgtacag ttttatatgc   41160
atttaactgc caaattgtca tgtgagatta tatggttata tttcattaat atattctagt   41220
ttgttcagct gttcttactg ggtgaatttg tgtggtttcc tgacattttt gttttttagta   41280
gtgcctcagt agttttatac ataattacgt ttcccttctg gattatttcc ttagtatcta   41340
gttcaagaag tgaaatcgct ggattcttgt ggtaaatttt tgaatttcac agtataatgc   41400
tgattttctc aaagtctcac attctaagaa agtataatga ggcaaaacaa acaacaaaca   41460
tcttaagttg attttttcct agcatctttt ccttccatct ttgcttgtag aatctagact   41520
atttcatgaa cccaagatat aatcagtatc cttcttcagt atggccaaag tgagtttctc   41580
attattttac ctcccctcca ggaaatgact tttcatcttg tgttttggga gccatagatg   41640
gttctgggca ggaaactggc tttggataga cccagcatgt agatggctat ttggccttgc   41700
tcccagtata acgatgcagt tccctgtgaa agggtatgag taggttttgg ggctctggat   41760
accgtgtggc ctgaagagac aagggctcaa tgccaactct gcctgtttcc aactgtgtaa   41820
ccatgtgagc gtcaaaaatc atggacgtgc tctggttaac actgagtggg agctcaacaa   41880
attattattt ttaattgtta cttggacatg gccaagttga ctacacttta tgttctgcta   41940
cctgccagtc tgaaagtgac gccacagaag gtgaaccgca tgttgggaga tgctcctcat   42000
ctgcttaaat gaggtgcaaa cacagcccat gcgcctgctc ttcatgactg tatctgtacc   42060
agcaatattt gtattggcaa atcacatgcc ccagtgggaa ctacttaagg ggaattcaat   42120
ggatttcatt ccttttatgt aattggccac ttagtaatag acgtgtaggt ctcttgtgtg   42180
```

```
gataaggatt ctgccttta tgtaagatat gtgttgcaat tcagctttca ggtcccagcc      42240
ccgggaaggc tccaggcctt cacaaactgg cccacccacg agaaggaaag caattgtcca      42300
aatgtgggta gcttttcttc ccactgttgt cagctgcttc caattagccc ccatatacat      42360
aatcccagtt tgtgtctgta tcagtacaat tctcccatgt caatgtgaat tttaagccac      42420
agagggaaag gggacagaga atatgctttc attcagctct cctcgtctca cacctcttgc      42480
cctgcatgca tttctttgct ctgattaaac gagcatttta taagccacat ttgctgtgtg      42540
aaaggcaaag tcttccctcc cacggatgac ggtctccagg gatgtgtgtg tgtgtgtgtg      42600
tgtgtgtgtg tgtgtgtgtg agagagagag agagagagag agactgtaaa catatatctc      42660
tgtgaaactt cattttccat atgtgaattt ttggaaccga gacaaatgga acttagctaa      42720
aagatgggaa aggtagactg actctgactt aatctactta acctaccagg caatttataa      42780
cttgatggcc taattttgc agcacccaga agcaagcctg tttcagcacg gcaaaggctc      42840
agctgctaag tgggcagcat tgttggaggt gagcagctta ggctgactgt tcatcaaagg      42900
accaagcgct tgaggttcgc tcatcgctgg aggccagagt ggggagggcc atttaactgc      42960
tcaaggccat ggaactctac tgtcagtttc agggaaattt gggaccctgg agcacaaacc      43020
aaaactccaa ttaaccagga gaggaactcg atccccagga gataagtgaa gagtaagaag      43080
tctatcttta gaaacaagag atgtccaagg ctagaaagat ggggaaggag ggtgaactg      43140 ttctggaagt gggtctcaat ctcagcacca gcagctctca agactttcta gagaaggaaa      43200
cttcatttct gaattaaaat tagtcttcaa tgacatggca gggatttcgg cacactctct      43260
tgcgtcatag gccactgtgt tggaggcagg agtgttggct ttggaggcat agagattaaa      43320
attagagtaa cacgtgagca ctgaaaaggt taaacagtag agacatggag gactcccgac      43380
ccccatgtac ccctttctta acctttaat taagatcaca gccctagaaa tagcttgcaa      43440
aataattaac tactgatcat ttataccta gtgcttctgt gagcatgttt tctctttcat      43500
tgctgctcat ctgcatggaa aaatgtgcat gggtttctga atataactcc atggtgcttg      43560
cttccattat atttgtgcca tttggatcat aactgataag caaccaaaga gtcccatatt      43620
actgcacgtt cccatcgcta ttttatgtga aggtggtcct gggggctgtt ctgaattctc      43680
agtttccttt tttcccctcc ccagttcttt gaaaatatca gaaacggact tgtggcatct      43740
ttgaaaagct acttaaaatg tgctgctgtg ctctgaactt gaaaatgtgc ttttaataca      43800
aagtttgtgc agcccttgct gctcatacga gatgaatctt accatgtggt ggatgcccgt      43860
ctcatgccag gcactgtgct ctaagcccat tggtttattt cagtgcttga aattggcttt      43920
cgagagaggc accacggttc ccttttaca ggagaggaaa caccagagga tcagagatgg      43980
agagtctttc tccacaaact cacagacccc aaaggcaagc tcagggttgt cagcttccaa      44040
agtctgcctg ctccaggacc tcatgttgca tctccattct cttcactgag ggtcaaatgg      44100
aaagaacaca tggggtcaa gtttcagaaa ataagagaaa tgaagaaata tgtgcccgga      44160
agcaagaacg accgacctca ttaaactggc tcccttcacc tcctctcaca tcttttctg      44220 ccttttggcc aagttttctc tcccccgcat ttcctccttg atctcgtttg aatcctcttc      44280
cctggtgaag tcatttaggt tcaggctctt attttacttt ggtccataat ttagatcgaa      44340
ccacatgtgc tgatgtgatt gaaacgatgt ggaattctct ggacagagat agaattatgg      44400 agggggttagt gtgtgtgttt aagattaaaa gaccaggtgt atgggaggaa atataatgaa      44460
caaaaaatag tattttaaat gaatactaaa cttgcactca tggaaaaagt tctcttccca      44520
```

```
tgaggttctc gcaaagcatt ttaccatcag cacacgcagt ttttctcagt tttctgagat   44580
ggggccatct tgaatccaac agacaacaca cagcatcagc cagactaaca caaaggacgt   44640
catgggcatg gacgtaaata ctggtgtcaa cactaggtct gcacctcgag aggagtggag   44700
caaaaggatg gagtggcaga tgaaggtatg ctgttcagaa aggaggcaga aatgaaagga   44760
agaccatcag tgcgctccac agcttgagga ccgtcctgga gggcaaatgc cagctgctca   44820
cttctgaaaa gaaaaattcc agtgaaatga gtacagtcat tcttaggatt actcacttga   44880
tactgtgtat gtctcttctt ggcttctcat ctccacacaa aaccctcagg tggtaaaaat   44940
ctaattaaaa aaattatata aagtcttgta gatttattag cctgaacata atagattttt   45000
tttaagcacg ttaagtcttc catggactaa aagaaaactt gtaaacctaa gagaacctct   45060 attttttgata tacaaaataa tacatttcct taaactatga tcttgatact agaattttaa   45120
ttaaaaaata cctgcagttt atatgcaaag ttatagatta atgcttaaaa ataggttgta   45180
tgtagtatcc acaggtcatg tttgactgtc aaatagatgt aatttttaatt cataataatt  45240 gtgtcgtgtt cttccccact agaagccaat tatgcaagct tcaccattca cacatggaaa   45300
ataatttaat ggagtactca ttgcaatttc acttatccag aattggctgt tgttctcaga   45360
gcagcttgtg ttgccttgtt aaggagaata tgttagtatc cagacatcca gaaggatcc    45420 tttactgttt cagagtccat tttccccact tttgaaatac acacacaaac acccattcat   45480
gcaaaccaaa cagagattgt aaagtgattc cactgacatt tatgcacttc ttttttctct   45540
ttggttcttc aaactctcag tcagtgcgca tttactctta atttagatac ggtttaaacc   45600
taattagaaa ccagaagctc ttgtatttcc acaaaggatt atgacagccc caagaaaaga   45660
tagtgaaacc attatataac aagataaagg cttcttaaca atacaaggat ggattttctc   45720
attgatctta gccttctgaa ttttagaaat tgccatttca aagtctaaaa caaggaaaa    45780 tcagggaata aaagaatggt aagtagacac aaacctactg gctccatcat ttctgttta    45840 gcaaataacc tgccacatat accaatagcc caagagatgg gcatgtccct gcatttcctg   45900
gtcaaggtga caacactgcg tcctcctgga agaggtctgc cactcaccat accacaaacc   45960
aaatataata aaatcagaag gcacactata gtgaattttt tagaggcatg tattgaaaag   46020
catctcaaaa agcattctcg aagcttccag aagtcaactc aagttatctg aaaagtgaca   46080
cttttgatga ttgctcgctt aatactggga gagccagatg aagattcctc cccacttcct   46140
cagatgtgca actctggaat tcttagtgt tactggagat tcctgctgca ttctgggcct    46200
ttaatgcata aacactgaga tgttctaagg aaaattactcc ctaggagga gaggggtgga   46260 cgaggagtaa gctttgctgg tgactcatgc gctgtgtgga aactccctgc acaagtgagc   46320
tgcgcagggt gagtctaaag ggttaatgca ctttcaaaag cctctaattt gttattccag   46380
aagagtaatt tactcactag aagtatctgg gtggctacta acacatttgt gtctttaaaa   46440
agatcagttt tattttaaga ttaaaaatat aaagcaagag ctggaaagtc actaaaaact   46500
gacagccagt ttcccatttt caagagtatt tattaaaagg ttctggttgc agaaggaata   46560
agaaatggct tgagatcatg acacagtgaa tcatgttgta aacatgttag ctatggctgt   46620
gaattcaacc agcgatgagt tcaagcgtcc ccagaaggtg ttgggggaat tagggacatg   46680
gctgtgtttc cccagagaaa agtggccatt ttactttccc tcttcactaa catgcttttg   46740
acatgcatgg cagagctgaa ggcaagggga aggggacaac atagtaagtg actaagtggc   46800
tttttttttt ttttttttgc caagtgaagc tgagtcatat ggcctctgtc attccaaaac   46860
tattctctac ggctgcattc ctttcgctct tgccttcctt tagaaccctg gagaaggcct   46920
```

```
cctgaagcct ggccctatta tgtatcctga caaagataaa cttttccaaa aagctgcatg   46980
ttgtttctag cacagttttt cctcgcagtg actacgtgat gaaagtacca tgcagaggag   47040
gtgtctgact gaggcgttcg tggtgtgtga cagagtcccc tgcacaggac agccgcactc   47100
ccctcttgcg tcctttcctc ccatgtttgc aaagcctctt tccctgtcag caggggtgt   47160 tctggcagtt gacatttctg aaaactacag cctacatttt taaaaaatcc agtaagtgaa   47220
aactaaaaaa ttaataccgt ggtcataata gtgtggcatt tgataactaa tgaggcactg   47280
tcgtgccagc tattattttc agacatttac agtccttttt taaatacaaa gaaatatttg   47340
gtgtgaaatg ttccccggga gctggtgcaa gcagaggcga cagggcaagg gagcttgggt   47400
tgtagcctcg aattcctccg ccagggcta ccgtcagcct gcggcacaca agtaaatcaa   47460
atataaaacc aaaatttctg taagcaaatc agtttctaac tcactgtaac gaattatctt   47520
tcgcacatca cagaggcatc tcttttcact gtcgagtttg gtttgcttgg ttacaaaaag   47580
ggcagttcaa aagctttggt tgctattgtg aaagtcagct gaattccttc caccgtgctg   47640
gggtggggtg gggttcacgc aggttctctt ttgtcaccag gggtgctgtg gattcacaag   47700
taagcaagag gctcctcagg tcaagcctct ggctgctccc tgaggtcagc tgcctagctt   47760
ctcctcctct gagatagacg ggaacaaagt ctttgatgtg tgcatttctc aagcttgaca   47820
atgatacagc tacataaaaa cccatgattt catatagata ttccaaaacg taaaagtaaa   47880
ccatgcatcc acagagacat ggaattacag aactggatgc tgagctggtc acttgggagg   47940
caggcgtcct tgccattggt ttatgcctca gccccaccat gcagtggctg gccaggtgac   48000
ctaggccagt cctgcatcct cggctcctca cctgcctggt gggacagtga catctctcct   48060
gcagcactgc tgtcagggtg agggaggtag ggcgcagttt cagaaaacca ttgggctgca   48120
cctgcgtgag cacagctgca ggagcaaaag tcagaaaggt cagcaaagga tttcaggagc   48180
aaaggtcaga agaaaccctc aaggtggttg tgtctgcagg aaagtgctgt cgtctcctgc   48240
aatgctttca agactattca gaagcacagt gtgaagggag agccggagcc catggggaaa   48300
tgactccaga gtgttccacg tgttggaagg catctgttgg aaaacggaca ttcaagcaaa   48360
tagttgcctg catagacaac gcagaatgac tgggaaagcc ccaacaagtt acctactggt   48420
aaatgaggtg agaagcttaa agtgagaacc ccattgctgc ctctttttca ctttaaaaac   48480
atttaagttt tgaattatgg taaaatacac gtaagattta ctactgtaac catttttaag   48540
tgtacggttc agtagtgtta agtatattca cattgctaag gaaccaatct gctacttttg   48600
tttattaatt ttttcctgag gggaaatatt tttaaatttt aaaatattta attgacaaat   48660
aaaaattgtg tatattcaag gtgtagaaca tgatttcata tgcacgtaca ttgtatactc   48720
attaccacaa tcaaagaaat taacacatcc aacccaccca tagttgccat tgtgtgtgcg   48780
cggatgtgcg tgtatgtgtg tgtatgtgtg cacgtgtgcg cctgtgtgtg tctgtgtgtc   48840
tctgtgtata cgtgtgtgta catgtgtgta cgtgtgtgtt cctgtgtatg tgtgtctgcg   48900
cacgtgtgta tgcatgtata tgggtatgtg tgtacgtgtg tacgtgtgtg tgcatgtgtg   48960
tatatgtgtg tctgtgggca caggtgtgcc tgtgtgtatg tgtatatgtg tatgtgtgta   49020
catgtatgta cgcgtgtgca tacgtgtgtg tgtgtgcaca ggtgtgtatg tgtgtgcctg   49080
tgtgtgtgtg tgcatgtgtg gtggggacac taaaaatctc tcatcacctt tttagtcaaa   49140
agaacagttg ttttggtttg gctcttctgt tttaaaatat cagaacaata ataatttccc   49200
acagacaaaa tcctcaatcc tcaccatcct tctatttcct atattcatca taaacttcat   49260
```

```
gcttgatgtt gaaattgttt tctgaaaata gagaatacaa agaggagatt ttaaaatgtc   49320
agtggcagcc ccacactcct ttttaatctt atttcctgat atcttgagtt tacttggacg   49380
tagagttttc cttgactatg gttatttctg gtagtagcag ctccagatta ggcaatggtt   49440
ttcttcagag atagcttaga gtgagcccca gaacaaggtc aatgcgaaga ttgcttgtgt   49500
ctgcgtgtcc agggcacagt gatcctcatc actagccggg gggctccgtg aggatctgct   49560
cctggtcgtt tctgttctgt atcttctctg cagcccttac tgaagccgtt accaactggc   49620
acaattcaat tcctactgta cccatcatgc acagatggct gaagtattga gaacgctcca   49680
gtgaccggga ggcaatagtc tgtccacatc taagaacaca cttggaataa ccttagagaa   49740
gagagagaga gagagaatgc atggttagta ggttatcaaa ctcctatgac ttttcacagg   49800
aaaagccctc atccacacca actttaggaa tgtgtagaaa gaagggtcag ggacaggggt   49860
gagtggtggg cagagcagtt ggagggcaca gggaaaaggc atctggtcat gtatttggag   49920
taggaggtct tgctttacta ttgaattgca gggacacttt gggaacagtg ttcacttctt   49980
tttgcaacca tttcttcaga gaaaagtcat gatactcaag tcttcttaca aagcagtttg   50040
aggctttgag taccagactg attacagaga tgagtatgaa gcattattgt agtattttta   50100
agtgaaattc actaaatgca aataaaccta gcaaatgctc tatggttaat ttttttctaa   50160
aattcagata attaagacaa ttcattctcc tgaaactgct gttcatgtaa aaaggaattt   50220
tatcgaggtg gcccttgagt gccaaacagc ctgtcctcag ctgcaaaatg agtcgttgat   50280
gatcctccag caagggatac ttttttagctc gtgtggtgat tgctgcacac gggatatgtg   50340
cagcaagtat ctgctgagct aataataaac agcctcagac agaaagacag tgggcacaag   50400
gtcatgctta aaaagacccc ttgttctact gcatcccagc tccccaccat ggggcctcac   50460
aggccctggt gaccaagcac atcagacctg gttcttgctc agtcctggga gccacagaac   50520
ccagcacgta ctttaccccc aagaccagac tccagcttgg cttttgtcct cctctccagg   50580
attggtgacc tcctaggtcg tgaagctgtg atgagcaaag acacactcct ctccattctc   50640
ccaacttcag gtcccttga cagtgtcagc aggcatttaa atagcagacc acccacagca   50700
gggctggtag atgcagtgaa ctcaggaaga tgcctgcata gactctagtg ttaaagacag   50760
aatccttaca aggaaccccc atagttacct aactgctgtc tccagtggtc atagaagtgt   50820
gataacccac taatcatcat tctctgtctc tctgtctttc tcatacacac ttacacacac   50880
atacacacaa ccttgttgct taattttcag agagtctact ttcagaaaag ccttcaggaa   50940
tacatcatgt acaaaactga gaaattacct gaagtatctt taaatttagt aaaaagttgc   51000
attgtttttt gaacatcaca cttgaaaagt acatgaatac aaacatactt aggaaaaaaa   51060
gctttaatta atttaaaaag gagaacaatg ctatatgctg tatcccacct ttctctgaat   51120
gttacatttt ctcccctatc ccaggctgca tctaagaaaa ctcagaggga atatgctatc   51180
tatcttttcc gagcaatgaa agctctgggt tttttccttg cttttcaggg cacaatactt   51240
ctctttcttc ctggttagac aggataagtt ctgagtcccc tggtatcatc agcttacttc   51300
ttctctgtta atattcaca aaaaatcact aactttcatg cctcagcaaa cctccactgc   51360
ctaaaatata gtgaggtcat tcatcttcgg acaaattgcc ccaactacgg tgggaaagaa   51420
accaatgtgt tggactattt atctaatttt tgtttagttc ggggatacaa ataaatgcat   51480
agatacatac aaacatgcgt acataatagc agcagcagcc tgtgaaacat tgacaagacc   51540
tggagttgga agaggacttt gccatcctcc agtccaacag ttgcctgtca cagattgagc   51600
gactgggatg tgcgcaggcg attatttgca aacggccctg agtcccccag tttatgtctt   51660
```

```
aattcgcagc cagggctgat tgtagaagca aatttgcaaa catgtgcaag aagaaatcac   51720
acatcctaga gcttggattt cctcgtttct tgctatttct atccgtagac agaaccattg   51780
ctgagctgtt aaatttgtct ccttccccta taccagtctt gaaaaaggaa aggaagtgga   51840
gcaaagaaaa agaaattaat aaagccggca gatcctagga gaatcttatt taatccaagc   51900
tttgtaaagt tttgctttat tccatggcaa catgggtata cacatcccac cggctgtttc   51960
agtggctcag agcaggtaag gcctgtgcca acgccgcta gcaggaggaa caacgtggag   52020
acagccccag aggtggaacg ttggcccttc tgtggctccg gtgtctcagg acctccctaa   52080
agcccagccc tgacactgag caagtttcca ccactgttag gaagaagtag aaaggaattt   52140
ggagggttgg tgttactgtt caagagctgg aaggcttctg cccccattcc cattccatta   52200
attgcgtgag gtagagaact catagaagat aggaacacat atgctgattt ccaaaattgc   52260
ctttgtatat tttcacgtga agactttagg ggcaaaagaa aagaagcaag catttt gaat   52320 atgtgtttca atttgccttc tgttatataa aattgtattt tgcctattct ttttt catta   52380 ttcggaacct tcaagaaata aattaagttc tctcaaaaat gtgttttttg aaaagaggac   52440
taaaacagat ggcctggctg tgttaaacac agggaccaga ccagcaccca cctctccacc   52500
tgccctgcct tcactggcag aattgtgatc catcatgttc tctgttcaat gtcatcatcc   52560
ctttcagagc atgggtctct tccttt ctag gcagtcttac caggatgcat gggtgtgcct   52620
gcgtaggcac acgcacagct cccaaggact ctaaaaaaag atattttt ct gcttatatac   52680 taataatatg ttagagattt atgtttcaaa ttagtacaga atcacatggt tctctccaaa   52740
ttatatttga gagagaaaga atagaacaaa atttattt ta caaaaatact cagtacattt   52800
agggcatata caaagatgtt ccagaatgta gcttatctct ttaaagacaa ttaacacagt   52860
ttctgggcaa ggcaaggcaa atattcagt aacttagcaa caccaacaga agacagccaa   52920
tattgcagca catttttctc ttggattggg tcagagagta ctgcagagaa aatggagtag   52980
agagacctga aatactttcg cacacactgt ggtcagtgca gcgtccactg tgtgccacag   53040
taatactaga aactccctgg ttaggccttg gaatccagct ctcatttcgt atgtgacctg   53100
cagggaagta agttaaatgc acacgtttta tcaagttcaa atgcaaactt aattttaaat   53160
gtatgcaaca tcagtttaag cgttgtagct attactagca attgtaccta ttactagtct   53220
gtactctgca caactttgga gtatactgcc tactcaaggt ggattttaga gctctatttg   53280
tggcattata tcacggacaa aagcacgttc atcagagtca gaggaatgtg gtgcaaatcc   53340
cagctgtccc acttaccagc tgtgggactt gagtaagctc ctgaagcagc tgcacctgca   53400
ttttctggtg ggcaccatgg agctgtcagc agtgctttcc tcagagggct gcgggctgga   53460
tgaggtttgc tggtgcatgt gaagtgtcaa tcattgctct catgagtggt gatgctgatg   53520 ccgttcccctt ttttagggaa gtgatttttcc cttacaaagt taccaacagt ttcatgttgg   53580
cccatttttc tattaattgt ttccactaat aggaccaaca gtggtagtcc catcatttta   53640
ttactgcttg tcgtagcaca agcagttgct tcattgtgtt tagataaata ttgacggctg   53700
cttttaacag tctgctgttt tgtctccttt tgaggtcctt aaagtaatcc ttaaaaagat   53760
agtgcagatg gaaagatgtc tggagtcagt gaacctgcct tctttcctgt gtgcttgtca   53820
gtttctaaaa tgccatacac aaaggacttt catgatttct ttttaggtac atgattacag   53880
ttcaattcac ttcactgtct ggaaaatttc cttataatca ggatgaaatt tctcatgtta   53940
gcctttcaca tttcactact tttagataag gaattctcag gctttgctat atctgactgc   54000
```

```
tcttggaggc tgagcttttg gctaactacc tgactacttt gtcgtttctc ttcccttgga    54060
atgaagcaaa tatctaactt ctcactcatt gtttctgcta ttttaccatt tagtcatctg    54120
tgattttcct aaatactgaa agacttccct caattcaaac tatgtgccgg atcaaggaaa    54180
gggcagttgg atattgcaga cagcatagtg caattgtgaa gagtgtctgc ttaccagcca    54240
cgctgccttg cacaagttat caagcctctc aacccacttc ctcaatctgt aaaataggta    54300
tgagtgtagg accttcccag gggattttt tgtgactata gaatgattct cagaagactt    54360
tcaggcagta tgtgggtgag gcacatgctg gaaaggcttc tgcaggtgca gtgatcaatg    54420
cttttctcag tgtgtacatc ccataataca gacacgttac cagaaactcc ctagccagga    54480
ctttgattgc agctcacatt ttgtatatgg cccatagggc aatgaagtgt gtattttta    54540 taaagttcaa gtgttaactt aatttggaat ttactatcaa atctcagttg ttatgggcat    54600
ttatagctat taatacttcg tcccatgtgt cccatgagga accaaggaa cagaaattaa    54660 agttctttct ggagtcccct gaatctcgtt cctgttcttt tgcaccctgt taattacata    54720
gagacattca cagctcttct gaccttatca gcgttaagga aaacagaaaa ccagcgtgct    54780
atttgttctg tcccttagtc aagccttctc aacatatatt tttcttccaa gattttgcat    54840
gtgcacaggg atgcctatcc tctacaagaa acacatttta ggcaaattat aattaaaatg    54900
ctgtttacat ctcttcacct ttagaattta aagaatgatc atttcttaga ttgcatctca    54960
gacacaccct tcccctagtc tggagagggc gaggcccatg ggtactgcaa acagcctgac    55020
gttgtcaggg gcggtctcaa cggctcattc accacatctg cctcgcgaag gctaagccat    55080
gtgctgttac ccctgctgcg ctctggctca ttctaaggta cacgctatta accttgtgag    55140
aaaacaaaga ggccagcccc acccttcctg ctcactctga gtcacggtga aaatgtttca    55200
ggatctcggg ttcgaccatg agtcctgtcc aggtccagga ggaaattcgg aaggaccaca    55260
tgttcactct gagatcccac tttcatttcc ctcctggttg agcagcatta atactctggc    55320
tagatttaaa ttctggcttt ctccagttag aactgaaagt tatgacaatg taatcaaaat    55380
agaatgtggg tttacagctg gcccctggc ctggtttgtg aacataaaac agaaacagaa    55440
agtgtaagtg gtgacatcat attctctcat tcaatgtgaa aggccaccga agtcttccca    55500
gaattatttt tgagaataat atgaattttt aaaaaatacc taattatttt aaatatcgtc    55560
ttgcttgctc cccaaatacc tactgttttc aacttggata tacgcacatga ttaaagaata    55620 tctaatattt gggaatgcat actttaacct tataaactac cactgtaaat agacagactc    55680
attaaagtga aaggacattt taaatcaatt agtaagcaaa tcaattaggt ggcaaagaca    55740
agattatttt tccttatggt agttgaagaa taatgcttaa cctgtcattc taattaccaa    55800
gcacggtgtt ctctttggaa gatcatttca acaaaacatt attttcatcc agaatttgaa    55860
ccttgagatt gcatggtatt ttagaaatct attttagaaa tctttggcaa aggttactat    55920
taaaacaatc acattcatgg aaaatcagta taagagcaac taaaataact cacaatacca    55980
gtaaaatcac tttgtcatct tcttaagact tttaagagc atttgtaagt aactgaatag    56040
aaggccaaag ggtgtgtagg tagcccagac catcagtggg cagccagggc cagggcaggg    56100
gccacggttg cagcctgcat tcttctaaag ggcagagcaa attaaagttg aagcaggagc    56160
taaaaaaaaa aaaaaaatg tttcaaagaa ttccaccaac cagaggatac tacctaggac    56220
agtttgggcc taacttatct gtgaaggcct ccagcttcct ccacaccggt ggccactttt    56280
cattcactct gaacccttct ttgtatggag gtcatttat taattgagct gtgaccaaca    56340
tgacagaatt tcctgttta gggcttttat aatatagata gtttatatct aatttcagaa    56400
```

```
tatattcact ggggaatgga cttagcaacc actaccacaa caatgcaaca atgtgttttg   56460
gaacaaattt accaatctga atttcccct agattaggtc acaggaacat tgcagctgat    56520
gtacagctat gttcctcctg aaacttggag acacatcctc ttgagctggg ttataatggg   56580
ccacccaaag ctcgagttcc tgtaatggat acactcaggc agcagaacct accaccgtag   56640
tgaggacagc acccagagcc ctcagaggcc atcacaagtg caccacagct gccttctctg   56700
gcacgctcag agctacacag tgtactctgg gattggaact ctttattttt ttttcagttg   56760
atttgtaaat aagattgcac aaaaatccat gcacatcaac tctccaaatc agaatttgct   56820
gagctaaaaa gagcattaaa ttagatgggc tggctttcaa ggggtggggg tgcaatagtg   56880
gaactctgca caacagttct ttacaaagag acaagcaagc atcgcgtg gaaatttcca     56940 ttcaactgga aatgtccaag cctgtttacc tcaattaatt gtccttgttc acttgtccag   57000
cctagcaatt gtccattagt aatttgttat aaatgagaca tttggtatta aagcatctct   57060
ttgggatact ggtatggttt attataacat tctgttagta gtgttgtaca agcttgagat   57120
gtattaatac gaaatccaag ctgcatgagg gctttatttt tcaagcctac accttgctga   57180
aattctgaat taaatatga ttctcagtac aaatgaataa atcaacagaa atggtaacgc    57240
atgtcaaata ttcttaaaac ccaagaaagc cttgtaactt ccttcaatct aatgggaaat   57300
gcaggcaaat acaagactga tgtccttgag ttttattatc aagactcaag ggcaccagta   57360
aaatctagtt tcattggttg gaaaaaaaat cctgataagc actgttaggc atattaactt   57420
taatgattac aatttttagg acactctgtg gcctagactt agaaacacaa ctaatgtcca   57480
gaaaaagatt cctctttta ttccatcatc tgataggcct attttacac atacacacca     57540 accaaaagta gccaagcaaa caaaacaaca tactcacacc ccttcgccta ttatcatcta   57600 ggtgatttc aatgctcatt gcaatgaaac ctacttattg tgcatggcac ccacccccac    57660
tgaggaatac tgtagtttct ttccctttga acttcattag tagagcacat ggttcattca   57720
ctcctgaaga gttcttcgta tgtcagaata tatatactac aacataattt ccatcagagc   57780
tctgaccacc cgcttatcta ttttcataat gcctgccact ccatcattag ctgttgtcat   57840
gtaggctatc aataaatata tgacaaataa acagttagg gaatgaggga aattgactag    57900
cagccaaaga cctaagccat cctctgcttg gacattagaa aactgagttc actacagtca   57960
taagatacac aaaggcagaa tgtaagccat acaaaaatcc atgtcaatcc caatatgtga   58020
gtacaactat tgaacaccat gtactaatgg atgagttggt aaatcattca atgtcttcat   58080
gaggtcaatt acagattatt atttagaccc caaagattcc aaagatggta tttcggtcag   58140
atcttcatcc tttgtaagcc tagcagaaaa tatggcagtt ttattgacta ctattctttg   58200
ctgggtgtgg tatttttaaa ctgagacatc agtgtgccta gcacagggcc tcaagcacac   58260
agaaaaattc cttgataata attaaataaa atttcagcaa aaaatatcat cttaaggctg   58320
tgaaattatc ttcctgtgtg gctaaaatag tgaataaaat tcagcgcaat ataaatcata   58380
gtacaatttc atcactaaat tttctgatct tgatcttgtc attttacatt ggaagtaaaa   58440
atgtgtcctc cttttttct ctgacagtga aaagtgtgtg tgtgttgtgt gcccttttgc     58500
acaccctgcc tcacacttgc tggtctaatt ccttccagca tgattatgat ataattaaat   58560
gacagaaatg tttacttcca agtggaacta agccagggta actcagggta gggcagctgc   58620
ttgcaccgaa agaccaagac tgctagagaa ctaggaaaca ggcggtgcaa gaactccagg   58680
ctctcatgga agagcgggag gcttctatgg ggctgcagaa actctttggt gcttgggaa     58740
```

```
aaaatgggtt aaatgctctt aaaaaagaaa cctgggagag gtagtttcca gatgcaggcc    58800 cgtctttttct tttaaacaga ggcagctccg aagagctgga cattgaaccc tgagcaggaa   58860
ctggaggccg tcagcgcagc tttgtttggc gagcggagct ttgcaagggt gtaatgctgc    58920
accagggaga cgctatctgc agggaccggt gacgccgtgg gtgtggaggg ggaggcagtg    58980
gctggccctc ttggggtaag gtacgcccag gaacagttta gaataacgtg cgcgagtcaa    59040
agggaagaag aagctcctgc agaccttctg ggcactgtgc agggtttgct cctgtccacc    59100
gtgccgtgtt cctgtcctgg ggtatttggg tgtgtggcgt gtggggaggg gagaaggagc    59160
aaggcggcag ggaggggatg aggaccaccc tgtccatggg acaggccctg ggccccgcac    59220
acaccccaag ccccgcgtcc cgcgtcctca ctgtcctggg acacccccca ccccacccca    59280
ccgccacagc ccagagcggt gccaggaagc cgcctcgacg cagccgtatc ttgaggctcc    59340
agccccatcc ccagggtacc acgccacgta gagacactat ttttcacttc gtgtttgtca    59400
ctcctaaagc atgtgtgcta gctgcaccaa ccctgggatg cctcggtgca tagggtttat    59460
gtgcgtcctc ctccttccct ctgagctggt ccccgtgggg gaactgctgc ccagactgac    59520
ctgcgtcctt ccgcacgtgc aggaaaatgt ccacgtgcac ttgtcagggt gggggccaca    59580
cgggcaccac cactgatcat ctgtgggatc gagttactgc ccatgcagat cccacgtgca    59640
gggcccagtc gctttggtga gagagtggac gctgtggtga ctccacggtc tgtggctgtg    59700
ctcaggagga cagagagggg acatcctgag atggtttggg cagcccgcgg atcctgtgca    59760
tgtccccaga gcgtccactt tctccatgga gcagtggagt ggcgttgctg agacagaaag    59820
ttcaggttct ccactcccca tgcagccccc actcccctgt ctccggccag gcacgcgtct    59880
ggggtggaga ctcccggtgc ccggggccct ccagacctct ttccccaccc caggagcag    59940 gcgggtactt ctattccgtt tggcttcaga agggaaaaga gaacgtaagt tcagggagtt    60000
ctcgtccatt cctctcccgt gggccgggca ggcagcaggg acagccttca ggagccagga    60060
ggggctcgag ctgcgaggcc ctggaatgag gcaggcatgg gctgaggctg gagggaaagc    60120
cccgctaagg ctgggcgggg gcgggaaaac ttaccaccag gggactcgag atggggaagg    60180
aaaggtcaga agaggagagg ccaggcacgg ggtgtgggcg gcctgcagag ctggagcagg    60240
tgctccgccc agagccaggc atgcacactc agagtaggtg gcctgtgcag cggggaagag    60300
gggcgggtcg gcgtgctgct gaagatgcag gagctgcggc ctgctctgtg cgtgctgaag    60360
gtgtggtgag aagcacttac aaaaagaaat ggactgtgtt aggattgcac attttacttt    60420
gtttctccca aatacgtgtt cttttgaattt ttttccttcc agggccagga ctggagtgat    60480
ggttgagaca ggcacgcact gggtcttgtc tgcatttaca ttttgagatt ttgttcagca    60540
tggattttat ggcgtttttt tgtttgtttg tttgttcgtt ttcaaaatac tgcacggttt    60600
atcgtgaaga cagggtcctt tgctgccgtc ttaagttttg ggcccaagaa cgtgcccac    60660 cctaggcccg ggcctgctgg cttcatagct ctcatcattc ccacgaacc ttaagacctg    60720 aggacagaaa ggaaggaaac aagcccagta gtccgtgaaa atccagggtc ccgccactcc    60780
aggtgtctgc agcagagctg aacacacgta ggctcttgcc aggaggggca tttgtatgtg    60840
ctgagcattc cttatattct caatatgacg cctttgaaag atctgtggtt tgcaaatatt    60900
tactctcagt ccataactta tctttccaac ctcttaccag gctcttttgc tgaataaaag    60960
ttttaaattt tgaagtctaa tatattttta attttttat tttatggatc atacttttg    61020 tgtcaggttt gagaagtctg caccaaagta tgtcctgtgg ttttcccta ggtcatcttc    61080 aacaagtttc atagtatttt gtttagatgt aaatctgtgg cccatttga gttagttttt    61140
```

```
gcacaagagt tgaggtcaag gttctttttt tgcctgtgat gttcagtggc tctggcacca    61200
tttgttgaaa acatgatagc caatgtcaag acttaatagt tataataatc aggagctttt    61260
gtttcttttt gttttgtttt tagtaactgc cagtcactgc ttgtggtata catacacaat    61320
ggaatactat tcagtcttaa aaaaaaaaaa agaaggaaat cctgtcattt gcatacctgg    61380
aggacattat gttaagtgaa ataagccagg caccaaaaga aaacattgc atgatctcac     61440 tccttcatgg aatctaaaaa attgtattca gagaagcaga gagtggaatg gtggttacca    61500
ggggctggga aggtgtgagc ttggggagat tggtgaaag acatagaat ctcagttaga      61560 caggaggaat aagttaaaga gatctattgc acatcatggt aactgtagtt agtgacaatg    61620
tattgtatac atgaaaattg ctaagagagt agattttaag tgttctcacc acaccaaaaa    61680
aaggtatgtg cagtaataca gtcattaatt agcttgatgt agccattcca caatggatac    61740
atatatcaaa acatcatgtt gtataccata aatatatact gtctctttat gtaaatttaa    61800
aaataagata aaataaatgt tattcacttg tcgtggatgt ggtggggaca ggtgtgggat    61860
agccctccct gtacaactag gacccagggg tgatctagtg acactagcca tttatcagga    61920
cgtatgggtg ccagtcagga tgataaagct tccttttggc cactatacta cttagaaatg    61980
ccctgcaaaa ggtgcacatc aaagattgaa agctcaatcc tggattttaa gtgcttcaaa    62040
agtgcactta attgccacat ttttgtcaaa cattttccca ggtagtattt ttcctcatgt    62100
aaaacaacag caatttaatt tgaacagaaa gcattttgaa acatactttt ggcagggttc    62160
cttgcagatc agaatggaaa tgattaacag ggcaattatc aatcatggac ttttggcggc    62220
agaaggaact gtattgtttg gtacagtctg gccagggcc acaccgta acggagatac       62280 tctattctgt ggacggttgg aggggctgt gctgagcagg gtaactgcat cttttcctag     62340
actgttcaca ctgctgccac gaaggagtct tgtttagact ggacctggct ttcttcttcg    62400
caatgagtgt tgcagactcc cgacaaaggc caggtggtaa agtgtggtgt ctgtgagcga    62460
gagcctgaga tgcctgagct gacctgtcct cagccacctg ccatcgtgca gaggtgagag    62520
cagcccctga attctgcccc tcggtctctc catagctaaa gcaaaaccat ccttccgtgc    62580
tcccaggaca agcaggctat taccaaatca cccactaacc ctgggcgagg aggggccatc    62640
actgcacaat tcatcagtgt ctgtgacagg aagagattgt tttagactgg ttttttttt     62700 tttatttgca agcttttttc tctctccaaa acgtgctgtc agtgtgttct aatttactct    62760
gtaaggaatt ctggagctaa tcataggctc acaaaaagca gcacaggaaa gtttcccaga    62820
taacatctat ttcagtggct ttcaaacatt tttgacctta ccaaagtaag aaatacattt    62880
taatatcatg gcacacatac agctgtatct aaactttcat aatactgcct ttacgatatc    62940
actctgatat tgtctattct tttctgttta ttttctttt tgttccttgt tatgctggtt     63000
gtgacccact ccagtgattt cacaatgcag gctgggtggt gtcccacagt ttgaaatccc    63060
aatctagggc cttcctctca ctgtacaaag taggtaactg gggacattag tggatcagtg    63120
atcaaaccaa agttatttga tcttaccaag tgatatcagg atgagaaagc tgttagagtg    63180
tcagatatgt gaaggaactt gggtcattcc tgatacctca aagagaaaaa aggtagtcct    63240
tgaacacctc ctacttgtaa aggatgcaca atcctacatg cccctccctt tccttttcctc   63300 ccctctgtac cccacccctg cccacatttt cttcataagc agctttggtg ttttggcttg    63360
tttgtttccc ttgtctccta cctgtgactt tatagccttt tggagactca cagcaatagt    63420
tgtatttaaa ctcagtgggt ggcatccaag gctaaaaagg agattgccta gacacaaaac    63480
```

```
cacccaaggg agaaagcagg acagcatctt actatgattg tttcttgttt cttcctgtct    63540
cataaggatt attacccagg gttttcattt ttttcatttc atggttcatt ttcgctccag    63600
tgtagacata caatagacca ctcgtccctg tggctccggg cagcagcctc atctgagacc    63660
ctcctgagac atctcgtgca gggcagccgt agtgtgtggc ttccccaggg ctgctctaac    63720
agatcaccat ccttgccatg gcttaagaag ctgcagattt atttgcttac agctctggaa    63780
gccagaagtc caaaatcaag gtgtcagtag agtctctctc tctgaaacct gctgaggatg    63840
atgcccctgg cctctcccca gcctctggtg ttcccagcag cccttggcat tccttgcctt    63900
gtagatgcaa aactccgatc tccacctcta tcctcacagt gagttctcct gcatgtctgt    63960
ctctgtgcct tcacattcct ctctgtgtgt ctgtgtttcc atctccttat gaggacaccc    64020
atcactgaat cagggcccac tctataccag taagacctca tttcaactcc attacatctt    64080
caaaaacccc attctcaaat aaggttactt cacaagtgct ggaggttagg acttgaacat    64140
accttattga acaatccaac tgatgacaca tagtaattta tgcactcgtt cttggagacg    64200
ttgactttat ttagtagcat taaccatggc aatgtcacca gcatcgctga cagcctgaag    64260
catatgatct ccagaatgta tttcaatcat catgttcact tccttggtat tctttagaca    64320
ataactcagc cttgaactcc agtaaagggt ttccctggga ttttcttctt gactcactcc    64380
actgtggcct ccctcatcca ggactgtaac agacgcctga cgtcagtggt ctagacctct    64440
ctgctgaatg tcatctttgg tgaatgtctt atgagaaaac acatggttgg tcactcttag    64500
aagggcatga aagcctgtct gcagtataac caaaacaggc acatggcgag gcacactgtg    64560
cgcatgtgtg tacaattaat atcatggttt taaattattt tcaggccaag gggagatctt    64620
tgctgcatct actgaagaaa gcgaatcttt ttcttcctga aaaaaaatgg ctacttatta    64680
gtcgaatttg tgttttaaaa atatgtgaac taatataatg cagacatgca ttaatgttta    64740
aatatactgg aagttttggg taaaatgaaa cccattgtct ctgttgatta ctttgatgag    64800
tcaagaagta acatcctggg aatgattggc cagtttaaat gagtgcctca ggttttgga    64860 atacaagaaa tcaagaggaa gggattagaa catataggtt agcaagattg ggatcctaaa    64920
atacagaccc aaatgaatgg aacaaaatca gggaatttat taataacagg gtcaaggcca    64980
aatcagtaac aaatatcctg agtggaagaa aggtggttta acaaatgccc ctatgaaaga    65040
tagagattgg cttaccatga tgagatgtaa gcccaagtta tgaggttggc acacaaaacc    65100
acaaatgtca tagcttaaaa caacacacac ttcttatctc tgtttctgtg ggtcagggtc    65160
tgggttctca gggactcaca aagtatgttt tcatctggag ctccaggtcc tcttccaggc    65220
tcataagggt tcttggcaga attcagtttc ttgaggctgt aggactgagg tcctggctcc    65280
tagaggccac cctctcccata agcagttctt agcatggccg cctgcttctc caggcccagt    65340
gggaaagcat gtgcctccag gagggctcag tccattcttc atggctttta cctggttaag    65400
tcaggcccac tcaggataac ttcattttgt attaaatcaa aaccagctga tttgggatgt    65460
taattacatc tgcacaactt caactttgcc atataaccta accatgggac tgatatttat    65520
catgcatttg ggtcaagttg cattaagaga tataataaag ctggacaagc ttctgttgat    65580
tagaagagtt cagttacaag gctacacttg ggaggaatgt ttacaaactg gaatggtcag    65640
aggatgggga agacacttga gaaaagtcaa gtgacggatg aaggcaaatg tggatattta    65700
tctgggagaa aactaagagg agttataata gctgtcttca aatatttaaa gggcttttat    65760
taggaagagg aatttggcat attggatttt gccttcagag aagtgagtc ctgagatgct    65820 cttagccatt cattccagcc tccagggctc acctgctgtc ttctgtccag gttctcggta    65880
```

```
gcagggcagt acagcccat ccgtgatctt ccatagtcag gcatattgtc acactcagtg   65940
agcggagagt caaccgggag gaaggcacag tttctctgga atgacctacg gaatggtacg   66000
ctcaaatgca aattctcctt cccttcccca gtccttgtcc ttcagatggt aatttaggag   66060
ctgaaggtca gggcaccagc agcctttgga agcctacagg acaacagtca gcctggctag   66120
aaaaaaaaac aatgtcacag gcatgttgtg tttaatcaca tgaaggatat ttgcattgtt   66180
ttccaactga tgccagcaga cacattgtca gtggtatcat gcctgggta tcagagttga    66240 cattgggttg ccccttctct gaggcattca tgtaaatcct tttaagttta taaaacctcc   66300
atgtggctcc tgcatgcttc atcatttgca tgtgtctctt tttccagggg aggcagcatg   66360
gggagcagga tgctggtggg ctccaggtgc agagagcagg gtgggcgtca cccccaggt    66420 ccactgtgca cgccctcttg tagagcccgt tccgttgtcc atgagatgag gagtgttctt   66480
atctctaaag tattatcatg aaaacctaac aatgtagaaa gactaaagca catgggtggt   66540
gcttcataaa tagtatttct cccactttct gaaaactcct gctgaagtaa ctgcacaaga   66600
atccttgaac atttagaatt ctggttttag ccataccata aagtcagtag tgcgtggtgg   66660
aattctgcta acgaaaattg cgaaggatca aggcagagta cagagctggt gtgtagcggg   66720
taccttctgt ctgctggcac taggtatttt acacattaaa tcagctcgtt ctcacatcag   66780
ctcttttaaa aataaggaaa tgaggagcca cagtggccca actgatgcag tgcagaagt    66840 agaatttgag cttgtgcaga tgtgcctccg tgttttgtct cctgagcatg ctgccccaag   66900
tttgacaata ccaagatttg tactggaaca ttccctccca tccccacccc ctagaagccc   66960
ctcttcctcc cttagatttg acacatagtt tgaaaccact attaactacc ttatgagagc   67020
cactgtttgt gaagtgctga ctatgtgcca ggtcccgtgc cgtgcaattt ttgtgaatta   67080
tctcgtgtct acagtgcctc acaatttctc tgctcaatac ctccatgtta ctgccgagga   67140 aaggaagct cagagagagt aagtaatttg ctcgagttaa agagctggcc aggacagcca   67200
ggggcttgca ccccggagcc ttcatccact acactgtcag ctggtatctc aaccagccat   67260
tacaggctgt aaaaaaatta tataagatag tctatggtaa tgcagaaaag tgaggttatt   67320 ttgctcccctt tccctttgaa gaaaaaagcc ctggaaagac atatcacttg agtatgggaa   67380
aaaatgaagc tgtggctttt ctgtgagtca attctttcct ggcagcttct tggaataaga   67440
ccaagtatag cagcagagtt ttctgtttta atttgagctg cagggtgact tttttcttc    67500 tatgctttca tctctctgtg gcttcttttg cctcgttaat ttcatgccct gcccaggcgg   67560
gctactgtgc tgcccagtca cccgggtctg ggcggccac cgctggccag caggcaggcc    67620
ctccagaggc agaggtggcc acgcttaggt cgctcccgct gtggaggcgg cacacttggg   67680
tggcagcaca gctgtgatgt ggcggcagct ggcagcccca tgggaaagat gtgtgaagtg   67740
tggggtttga cgacccatgg gagaacagac ttcttcctc ttcttgtttt cccttcaaag    67800
ccgtgagtca acctcaaatt ctctgtcttt tttctccacc cctcgtgcc tctctccctc    67860 acgctctgca tctctcattg caagcttgca tttttttgca cacaacacta tcttaatatt   67920
tctcttttct gcaggcagga aatgagaagt cattttttcag ggtcattcag gaagtcatcc   67980
agagttataa tggcccatta tctactggtc agagtttact taggctttca ctacttccac   68040
tgcccacttg aaacagggaa aaatattttc ccccgcgct gtgagtgtgc tatttagagc    68100
tgaccacaag cggggggaag agaggatggc tcggatgctg catttccact gagaacacaa   68160
ggctggcaaa gcttgtctgc tgcccagcaa gcacttcagg ctcacaccat tttaggttca   68220
```

```
ctttaagtag tttctcaatt gttaaaaaaa aaacaaaaaa aaaaaaacct gtactctgag    68280
gatatgctta taatcccata gctaacccag aatttcttag agaactgatc aacatcagca    68340
gtggcactta ctgaaaatgc acattctcag gccctgcgta gggcctactg agttagaata    68400
ttagagagca ggtctcagaa acattctatc cggcagtctt attctatgca cccgaaggga    68460
taagagccat gctttcatga aacatgggtt gtgtgtaaaa tgtttaaaag gtatggcaaa    68520
atgtgtttga ttggcaccaa ggattttctgg ttcctcctag aatcattaat caaactttga    68580
aggagaaata agagagtcgg cattttcttg cacattcttt gtgatgttgt gatgagttgg    68640
aaacttcccg attgggttta ttagagcatg aacacccagg cacccagctt ctagccagcc    68700
ctgtcaggca gagtctcctc gaagatgtgg aaaggactga ccaacagctg aggcctacag    68760
gaacctgagc aggcaagggg agaggcaccc cggaaccagg agcaatggcc ttcccaccct    68820
ccctcgtcct ctcctcttct cctttggag ttgcaggcca cagaaaggaa gtgacatgag    68880
tcactttggg ccttcttaat tccttcatca aaggcagcac aggtgtgtat gtgtgttggt    68940
ggctaattga ggtaggccca cagaggagat aacagatgga catactattt cctttcttcc    69000
attctgatat aattcagggt ataaacacac acacacacac acacacacat tctcacttct    69060
ttggcatcta ccacacctgc cccagtgccc atttctctcc cacctgaata aaaagccccc    69120
acaaagcctg aggtacatgg aaaggagcag tggtctggct cccaggagtg tgagaagcag    69180
ccatgttttc agaggctgta ttccacttgg acttggccct acgctgaagg taggagcgga    69240
tgggggaggc ccccttcgca caaagagccc catgaaagag tgcacagtcc agtctataaa    69300
acagacgcag aaaatgtgtg taggacttct tcctgaaaaa gagcgtggtg cgtccagtac    69360
ctccatgttc atggaacttc ccagtctgca gtttacccct ttgtgcaact cccttttggt    69420
aaagccctgg tcacacttct ggttgttcag attatacagg gataattcca gagtgatttt    69480
aaagtcaact gccaggcatc cgcacttgca aattagatgc ctggcacatg cttgtgttaa    69540
ggtaataatt cattacaata caaattacag gggagttcct ctgggcatgc gacctttccc    69600
gtcatttggc tttccctgtg attatcaggg gagcttccat cgtgctgcta atgggacctt    69660
aaccatgtgt caacccatgg ctgtaatgct gacactgttt tctttctgga atgaaaggcc    69720
ttcgcaattg aaaccaaaat gttatccaac tcagtcctgt cccttttgacg atgaaaacat    69780 caagttctgg agactggcca tccagcctcc ctgcctcatc tcccacgccc tccatcattt    69840
tttgtctcta cttacttatt tatttggctg tattttacgt acatcatgca aaaatattcc    69900
tctttgtaaa aagtataatg atttcaggaa attagagggt aaaaagcaag aaccatgctt    69960
tcactccact gtcaagagtt gtggaagaat ccttccagca ttttttctgt gtattttaca    70020
tacatacaaa tatatgtaca aataaaggtc gatcatttag gttttgttta tatttttgta    70080
tatatgagct tatgtcattc atacatattg ttttgcctct tgctttttt taacttaatt    70140 ttactttgct tgagagcttt ttgaactgaa gtacgtgtaa gtcagcctat gcatgtaatg    70200
gctccctcat cttctgtgag gctgtcacta aaagggggat ttagcttgtt ctgggctttg    70260
cagcccgtac actgggcact gttcatacgt acttctctgt gcacgcaaag gagggcttgc    70320
tagggaggcc tggcagaggg tgccattcaa ataggatttt caatgaggaa attttttaaat    70380 tttcagttat ttgaataagt tttaatatat atccagaacc ccaaatcatc aagtttgttt    70440
tcttccacat ctgtccttcc atttctgaac tattttaagg ccagtcatgt ctcatccaag    70500
aaatcccatc ctttcacaca acactatctc cgtttcatgg ttatgaatct ctaaaagcat    70560
gattttaaaa acataatcac aatgctgtca tcgaacttaa aaaattagcca taaatctctt    70620
```

```
atgttaccca acaaccagcc tactgacaca tctccagttg tctcaaaaat gtgttttcca      70680
ttgtggtttg tctgaaacat gatccaaaag tcagacccac ctctcacctt tccctaacct      70740
gccggagccc atgtttcttt ccagccaggc ttggagacca ccacacggga tttgcttctt      70800
ggggcctccc tctaaccagc tatgcaggat gccctctttc ctgtcaatac aagctgctca      70860
aaggactcat tcagttcaaa ttcacctatg tgagcctagg tgatgctact tatttattta      70920
tttatttatt tatttattta tttatttatt tattttgaga tggagtctca ctctgttgcc      70980
caggctggag ttcagtggca taatctgggc tcactgcaag ctctgcctcc cgggttcaag      71040
tgattctcct gcctcagcct cctcagtagc tgagattaca ggcacgtgcc accacgccca      71100
gctaattttt atagttttag tagagacagg gtttcaccat gttggtcagg ttggtctcaa      71160
actcctgacc tcgtgatcca cccacctcgg cttcccaaag tgcttcatgt tttcaggagc      71220
tgtacgtgca ttttagttt tgatgaccag gtccttttc tgttttttaa agaacttcaa       71280
atgatctcca gggtacacag cgcttgtgtg ctgatgaaaa agctggcagt acaaaggcca      71340
ccagccaagg tcacacagcc aaaaagcccc tgacctcggg cccttccca gaccctgggt       71400 cttttgctgc cacatgaatc ttcttcaagg tcctatgtgt agattttctt gacttggcca      71460
tattatttag gattcagata taataacaaa atagatgtta aagcataaca tgaaggcatt      71520
taaaagggta gaaagcacat gatttactaa aaccataaat cttatgacct gaaagtttca      71580
cctaatctct taaaaaatac cgtactaaac cctgattgaa aatcagagct cagacataca      71640
gcctgagatg ccaaaaaatg gccaggcttg tctgttgaga aagccatatg taactaactg      71700
tttggaaatt caaatatat cttatcattt taaaaacatc tttcttctaa agacaatcat       71760
cttggcttca ggaatgaggc tagtaaaaag tgaaatactc ctacttgtgg aagaaatcct      71820
cattttaacc atgaagaact gaaaaatgca ttctgatgtt gatggaccca acctatattt      71880
gggtatttta tgatgtacac aatatacttt tgtatatgag attgttatta aatgtgactt      71940 tgcttttca agacatacaa tgttcctccg ggggtcaggc actgtgttta gcactttgtc       72000
ctgacctcat ctgacttctc agctgtccct gagaggtacc agtgtgcaag atcgctgagt      72060
tggcaagtga tagtgacaat attttcaccc caatttctaa tttaaagacc ccgatttcta     72120
gttttgtttt gtattggatt tgcacaattt cacgttctga aagaggatgc cctcaacttt      72180
gcaaaatggg cctttttgaat gaaaaggatc agtcatgtca ggaaaagcgc tacaatgatg     72240
aaatatgata aataagtcag tctttcatct gtaattatct actatggggt aaaaagtgat      72300
gaaaactacc atcttgaaag gttctggtga tagtggttcc taatgcagtg aaagatgtgt     72360
aagtcaaaga tttgtaacca gccagggaat gagaggcgaa gccatagctg tggcgggg       72420 ccacatctgg gtgtggggag gccacagttg ggttgggggt ggggcctgca gttatccaca      72480
cccctcccac ctcccttcga cagtacaggc ttcctggtta ccttccagag agtaaggcca     72540
gggagagttg aataagttga gaaatgtcat gtcgaagcta ttggtggaaa gagttccatt     72600
aattgacaat acaagtccct actacattct aaaatctggt cctgactagt ggcaagccgg      72660
gcccaggagt agcacttaaa caatggcagg cttgtgttgc tggcaggata cttcagcctc     72720
agaggagctg tgtgcagctg gggagactca cactcagagg atttcaaagc agagggcatc      72780
tcgtagagca acttatccaa acccctgaccc actgtaaaca cacacacaca cacacacaca    72840
cacacacaca cacacacaca ccctgagaga gagaaagaga gagagataac taaagagaga     72900
gaactaaagt ttggcaaaat aatacatgct ctaatgaagg tttattaatg attaatctac     72960
```

```
tcctagcatt tcctagtcca ctctatctcc ttaaaaaaaa attctggttg cagcccacta    73020
acttgattgt acagctgctt aatggatagc aggctgtaat tttcagagaa ctgtttaatg    73080
cgggctacct ctgttcttcc atgctgcttg tggttcctgc tctgctcagg acagaatggg    73140
gaggaaaaca ggctctgcgg cacaatattg gcaagtgaaa ttttgtaaac cggccctccc    73200
ttccttttgc atttggtctg aaaattcaat tagatgctga gtcctacaat gtatttgaga    73260
agcccaggag tgccctagag gatgagactg ggtggctccc tgtcaggttg aacatttgcc    73320
ttaattactt tggcaagatt tgcatcagtg gtattagtcc ctgcctcact tggaggcctg    73380
cacttaagtg gccacattca ggctccaatt tcctggtgat ttcatagtgt agggcacttg    73440
caatcaaaac taggcttaaa gcccaaccct cttacatttt acccaccccc acaaatgcag    73500
caaataaaat gactctgatt ttcattccct agacctcttt tctatattta ttacattatt    73560
gttaagacag tttttgaaga agctgtttt atttaacaaa atagctttat ggaatcaact    73620
tcatatatct tctccgccag atcaaaacaa gctcgtagta ttagatgtca ccgagcacca    73680
tgacaggcag atgaacatca tccctgtgcc cggctaatga tagctcggcc tgccccggcg    73740
tcagccgctc ctggcagggc cagcgggcgg tgtgggaccg gcaccgtatc tccagcaatt    73800
cgcagataac aaatatggtt ctgatgatgt tactaaagat ctgtcccttt caagattgga    73860
ttagacatta ggaatttgga gggcttttta ttgctagcat tttttaagaat aaccaattag    73920 agtattgatt ctaaagtctg aaagccacat ggacagagtt catgtaattg gctactttat    73980
gtgcctcttc ctagattgcc ctgcatttc aaaacaagag cctttctatt ttaatcaaaa    74040
gaatccagaa tgaaatgagg ctttgaaaac tcagcctatg tttgtcttga tttccttaac    74100
tgacatctag aagaaaatat gagctcaggg gtccgctggg ttccttccag cgcctaagcc    74160
tgtaagctct tcctgctgga accaagcttt aaatgcactt gtcagtcatg tcccatgaga    74220
atagatactg ccttccatgt ttttttgttc tgatttccgt gtttgaaatg atgaaaatca    74280
tttttctgtg cttttaaaa atggaattgc ttttgtgttg ggaattgtgc tgttcatttt    74340
tactctacct cgttttggaa tcactaatgt ggccaattta tagccaaaaa tcagtatcgt    74400
agagtgagca atgaatggca tggtgactgt gtgagcgaat tcatgccctc cctccccacc    74460
gctcgccccg cgtctcagtc ctcagtgatg gtaaacagaa tgaggacctt ctcccgaccg    74520
tgatgcgcct cagccctact tcccttgtcc tttcctatca taaaatcttc tttcatagaa    74580
atggtcattt ctgttcatat ctgtggactg taaataacaa ggaagtcatt tttgaggtga    74640
aaactgcact tagactcatt ccaattttga tggaaacttt tagctggtgg atggcatttt    74700
gttttgtctt agttttgcaa ggagttatct taatttaggg agatgaaact agtctgtgat    74760
ccgaggtctc acttccatac atttctctcg ggcagtgtgg ctgcctgaat catgcctgga    74820
tgccacaggt gcttagccag ctggtcctgt cgtaactgtc actggtagct cagggagtgc    74880
agaggtgcca gcagacacta tgaaattggc ctcgtaaagc atcagttatg ttgtgatggt    74940
ggcaaagctg caggcgagat gggaagtgca gccactgaga actcacagta gagcgtgtgt    75000
aacgtaaaaa gatgaaaccc attgtacaca gctgtgtact gcctccttga agtcaaattt    75060
cccccattac caaggaaaag ttttttctga aggggctgc ttgacaggat gacatctggt    75120
gatatcattt attcctttgg aaatcaatct gtggaagtga gtttccactg actgatgagg    75180
agaaaaatga attggcttca cccagcatcc agcttcttat cctgggagag atagctcttg    75240
gtctgtcatc cacgcagctg cctggtgcaa gagccaagtt tgtgcagcct gcagagcact    75300
cttcctgagc tgtgggctgc caggtcgggg ggcaggggg gcctcactgt gcagcctcct    75360
```

```
gccacccact gatcatctgg ggagactggc ctatcctgtc aggagacgca gttgcccaga   75420
cgttttcaag ggcctaagat gtaggcagtt gatccacaga tttttggaga gtccttgagt   75480
tggagattac aggtgacctc agaggaggga gtgagaacat ctgggtcatg ggtttctact   75540
aggagtccac agtgaaaaca agaagaggaa tttacgacaa gacagtccag caacttcctt   75600
tctaacttct cctttcacat atgctggata ctccaagact ttgcatttac atggacatca   75660
cagatccact ttgagagaag tagggtaaaa agaaataaat acatagtgct ttaggtgtat   75720
ttctatacat cttaattgat atgggattac attttcactt gtgtttactg tacagactct   75780
agacagatcc tgctcttttg caggtaaaac aaatatttct taaaacctag aaagacccaa   75840
aacaatttaa cagaaacatt ttggaccatt ttggaccttg gcagttaggc cccagtgcag   75900
cagcggcaac cataaacctc tccataggtg ctgaacccag gtgatccctg gcaccggcag   75960
ccttatgtca gggctctctt atcgctggtt tttatttctc ctaataaaag tgattaaaag   76020
attcatcttt taaagaaagc aaggacacag aggtggattc tccctgacgc tagcacagct   76080
catgcccaag ccactcctgc agggctctgg tctaagtgca aaagctggaa aagctgcagg   76140
tcccgcaaga cacagagcaa ccctgcaagc caggtcacct tccctcttct ctgctgtccg   76200
actggccctc caccatgtga cattcaaaag ctcaagttac ttaacctctc aaaactcagc   76260
atccttttct gtacagtggg gaagatactg gactgttgtg aggattaagt gaggagagtg   76320
gcccaatgag gttgacagtt attactgtca ttgtcattat ttgccttctc acaggcaggc   76380
gtgccacagt cattttactg aagctgcttc agtgggtcct gaattaggcc ctgtcctttg   76440
ggagagacag tcctggttca acacacagct ccctgcccag ggcagcttgg gagtgtgggc   76500
cagtttcgcc tttagaacca caattctctg atatgtgcaa tgagagaatt aattatagac   76560
tcaaaggatt gcatgcagac acacacagat acaaacacat acacacaaca cacagagtta   76620
cacacagaca tgctcacaat acacagaaat acacacagac acgcacac agcacacaga    76680 gatacacaca gacacacaca cacacacaca cagacatacg cacagatggg cacacacaga   76740
gacacactca cagagacaca cagatacaca caggcacaca cacagagaga catacacaca   76800
gcccacaggg atacacacag acacacagag acatacctac aacacacaga gatacacaca   76860
gtcacacaca gagagacata catacaatac acagagatac acagagacac acagatacag   76920
acacagacag acatacacac agacacgggc acacacagag acacacagac acacacaggc   76980
acacacgtgc agataaggta atattagcta gttcaggagg agaaagagat aaagataaag   77040
taatattagc tagttcagga gggagtgaaag aagccttgtt tttctccact ttttatagaa   77100
gagaaagtga agattcgatt tgaggtgagt tcagcacaaa agcgtatccc aggccctctg   77160
gctccaactg cagcccttte tacctcattc ccagacccca cctaagcctt ttctcttcaa   77220
aatcttctca ggcacactga tacacatacc tcagattttt aattctccgg ttgtgttcac   77280
caggtgcttg gtcatgatta agaattccgt gatgtgtacc ccatgtgttt aaatttgctg   77340
ctgagttaac tttgtggcgg cctgtggact agacctctgc acatgcaatg cagaacggca   77400
gggccagatt tgaaatcctg ctatcttttc ggctgccttg taaaaataac atcaggcgat   77460
ggggatacga tgccagaggt cacctgtgat aagttctgtt tatggccatt ttacttctag   77520
gaagacagga agtgtcagga tctcagggat ctaggaagcc aaaatgtttt tccactctga   77580
aataaagtga ctgaccagga gttcccggcc acgcagccct gtgggaactg ccgcacggcc   77640
acttttatga agtggacacg tgttggtccc actgaaaaga aactccccac ccatggctcc   77700
```

```
ctcacgctgc agcagaggcc ctgccacagc acctgtcagc ccctgccagc ttgcaggggc    77760
gcaggcgcag agcggtttgt gcccttgctg gagccaggga agggcacagg gtccctcctg    77820
gagtcatggg aggtgcagcc gaggttctat attaaaatac agaggctagc acatgtgctt    77880
ggggaatgca gctacagtag tggaatgaaa gtgctgtccg ttccttaccc ccccagctcc    77940
tcacctgtcc tccacacgca tatccctggc tccctttccc tagtaaggag actgaattga    78000
aattgtggct tgcccgaggc tgcatacctg tgctcttct gaagcccaag tcactggctc     78060
tagaattcta acctgtgagg aagccactga ggatgtttgt caaaatacat atttctgtgc    78120
cttgccccag ttccacggcc caggaatctg cagttttcac aagcaccccc aggtgattct    78180
ggtggtgtct ttgcacttct tcaaggcagt actgcctgga acgcagaatc ccagcctcct    78240
ctatcctcct tgcctaatgg cctggatgct ctcagatcta caggggaagg gaaggtcaca    78300
cagtcatcgc aatagtaacc tcagctgata aatcctcccc cataaaactt attccccagt    78360
gttttttaat aggaaacaat aaaactgtaa ccagcccaaa tatccatcaa agagaaaatg    78420
gagaagtaaa tcatcgcaca ttcacctgga ccagatctat tgtaaagcca ataatactga    78480
agccccttcc aaggccctgg gagtcctaac agtgcactgg cagtgtctat aatttatatt    78540
atgaaatttg cataaggaaa acattttgtc tcatttgtgc aatttctcct tctaaatata    78600
cgtgtcactt tgtacctgat ttctataaga cccaggacct acaaaccctg tgtctgcccc    78660
tgcagccacc cagggaagga ctgcacagca gcaagacaga ttgccatgga gcatgttgtg    78720
cccaactagg gacagcgcag atagattctg taatttgcct aacaatgtct ataggatgat    78780
cccatttgtc aaaaaaaaaa aagaactggg ctttattgat gtcacctaaa tgcacctaaa    78840
cttctttttt gccccatgct cttctgtact cttgatcttt ccccaaattt ttaaaaacat    78900
gacactcatt cccttatttt tcctacttag aaaagtgtag atggttttat cataggaagt    78960
tcaaaaaaat taaaatataa tgaaaaatac tcaaatagtg cctcacaaca gtaactactg    79020
ctaacataaa taaaatccat atttcctctc atacagaccc cagagttgct ttgcctgaca    79080
gtgtagttga tggagaaaat aatctttatc cttagcctcc atctggttgc agaccataaa    79140
gacagggaaa aaatgagggt gttggtagct tcgttagaaa ctgaaagctc actgattttt    79200
tcaaaaccta aatagcctgt gtttctccaa ataactaatt tgcagccttc ggcagccagg    79260
actggcaggg atgggctag ggggactggg gagaactgct ctctcctgag ggtggtctga     79320
cccgacagca cgcatgacct tcccacagtc aggaactgct cagagacgtg atggcaactc    79380
catagaatga aatactcttc agccagtaaa atgtattttt ggataaatat ttgctttaaa    79440
aaactttact atatgttgtt aaatgaaaaa aaaaccttaa ggcatcagaa attatgtgca    79500
gtaaaatctc acttttgtaa ataaatatac ctgtttacta cgtatgcata aaaagaatcc    79560
tgagaaatat aagtactgta tgcatattgt tgttaagtat ttttctgtt tgcttatcta     79620 taattctaat tttgcttcaa agaacaagtt actccggcaa tataaaaata aataactaa     79680 tttgtcttgt catcaaacag atagtaagaa caggcaaacc tggccctcca cactgccagc    79740
cttttgtgat tcaaggcttc agtttcctcc acttgttaaa aagattcaac aaagtagttg    79800
aaatagtatg tgaaccagta aaccctaaaa ggtgtccagt gttgtctgtg agctaattaa    79860
gtgatttgat tctgactccc cgagtcttct gatttcgaag cagtggggag tcagacagga    79920
gcctcaggtg gcctctcctg agaggccctg gaaagtgatg agaacctggc ctctggcagc    79980
tcttcataaa cgtccatgtt ttccctctac tctctcactc ttttcccagg gcctcaaaca    80040
gaagatgaaa atcaatttct aaaacagccc tctgtgtgct ctctcgtatc tctccttttc    80100
```

```
acacatcgtg gtggtggctt tctctgtgtt cctctgttga ttcagtctct ggaattaacg    80160
gatcaggatt ccatgcccag aatgctacaa agactgtgct tgagttctcc cacatctcac    80220
tcaattacac agaagtttca gattatgtaa cagatgctgt gctgggttag gcagagccat    80280
ctgacttgtt ttgctttatt ttagaccatg agatgggtga gtttttcttt ttaatgccac    80340 attctttttaa gaattaaaaa cctccacttg gctgtcagca ttggaaatca gagtgatggt    80400
gcaagccctg atgaggacaa tgtccttgtc tatgaaaagg tgaaatcatt gcttgaaatc    80460
gctaagcagg acatgcagtc ccagatggag ggggaattc gggagctggt tggaaaagag    80520
tatttggcac tttgcagcct tgagaggtgc agaagagaca ccgaggggtt caccaccaga    80580
gccaccattg tcagagaggc gtccagctgt gtccacctgg gactctgcct tcagggcttc    80640
ttgcctggct gggagctgca caggcagact cctgggacgg tgtgccgaca gctctgggca    80700
cccccttcta ggatctgatt cctgaggaat cacaatgtgg atttcacaat cacttccagt    80760
gtcttttgcc aacctctgtg aacagatgtg caattaaaaa aaaaaaaaga aaggggccca    80820
attctcaaca ctgtaagtgg aaacttttta atggaaaagg ataggctaat gaattgaatt    80880
tgaaatctga cacagaaccg atgcatcaaa tgtgctggtg tttacagata atacaagggg    80940
ggctgcatct tatggtttca atcctttttt aaattttttgt tctgagagac ccagccagca    81000
gactgccgcc agtcttgtca gagatgtcag tggtggccac tctgaatgga aagcagcatc    81060
tctcagcatc tctgaggcac tgctcctcag cggagactgt ggtggctttg cctttcagca    81120
cgcatccttt ctacgatgcc tgacagtgcc cagggaatgg gcagagctgg gagctctgaa    81180
gccctttcac ctaaaccacc ctgggtcacc tgacctagtt ttcctcccaa tttttaattat    81240 gtcaggcact tcacaaaggc ctccttgggg acaccatgag ctcactgtca tcagattgct    81300
ccaatcacag ctgtggcttg cacacaaccg ccatctctgc cccagcagat gctgtgtgta    81360
aacagttgta ttaattacat ctcaaaaaca tggttcttgc cagatcctca ggatttgggt    81420
gcagcctctg aggtgggtgg gaggccctcg agggagaaat gtctgcagga aattcttccc    81480
ctacgagagg tctgttttct aagttatcta agagctactg cagctgttta ctgcagagtg    81540
accctgctca aagctgtggt cacccaaggc tttgaaaggg gacctccact tccgccctgg    81600
gtggagcacc gtgctggaga cccacgcctg ccaaggcctc attgtcatct ccacacgccg    81660 tccttgggt gggccactcc tgggacacgc agacaggaag ccggccacct gagccactcg    81720
gaggctctat ccagagtcag ctgccaagcc tcacgtcaca catcactgtt agtcttggag    81780
ggctggcggg gccctgaagt caattgaaca cttggatgac agggaacttg ccactgccag    81840
aggcaatatg ctccattttt ttgacagttc caacaatttt tctttaaact gtcataaaaa    81900
attgctgctg tgaataccag tgtcggcgtc cctgcctcac ctttacctgg tgcttttcca    81960
ccacacaaaa ctgtttctcc tcgtgctggc cttgggcttg cagacagctg attcttctcc    82020
tcccgcggct gagcagcctc ctccgagcaa ccctctgaca actctgctcc ttctgacaac    82080
ctctgcaagg gctgccagat gtgaacaagg ggcccgggca gaaggtatcc aggaagactg    82140
gaaactcgag gaagcctgcc ctgtcctgtc caccagactt tacgcttgcg tcactgggct    82200
ttgggaccta agtcctcgtc atttgttcct tttgcagttc ctactgttct cagcacttcc    82260
ttccagctta ctgaggtaca ctcagatgtg atatgccatc ggtacagaca cagttctgct    82320
ccagcatttc cccgtgttct ttctgtcgct ctatttactg aattaccgtg aggatgtgga    82380
gcgaggctga gttctgtatt ttaacaccat tttaattctc acctactgag aaatccatcc    82440
```

```
tcttatcact gtgctttttt taacctgtca cgaatccatg aaatcctatc agccagcctg   82500
catacttcct tttaaggtgc agttgaatca ggagaaactt gccgcacatg ctgcgtccgg   82560
gcacagcatt ggctgaggct gctgccctga cctgtccgct ttgtagtact gcccagctat   82620
gaaacaggtt agccacacat gacctgcatt taggagtaac aagtctgtct gtacatgcac   82680
atacagcaac ttttttaaac tgtctatatt ttttcctgag ataggtattt ataatatctc   82740
catcttcttt cccatttga aacttagaac aagtttgcct gtcaacagtt ctccacagca    82800
tactgtgtat tctaggattt tctaaggttg agcaacggag gttcagcaat tttgacttaa   82860
tttcttccca tcccttttcc acgcagccca gaagccttgg atcacgtggt gaggggaaga   82920
ggttgtgcta tgtcgggaaa ctctgtatcg aagctcggct cagatcatga cattctcttg   82980
actaaaaccc tcagtttcca tcaaacttgt cactctggca ttaaagcctg tcactgtgtg   83040
gctctgaaaa cctctctgaa cgtgttccct gcctctgccc tgcaggtccc tgtgctccac   83100
agaagcccac ttatgtgacc cacccccact catcaccacc ttccctcacc cagagcctca   83160 gctcccccact cccacctgta agaccctac tggaaagatt cccacctgcc cctcaagatt    83220
aatctccaag gacatttcca aattcctctc cccatctctc agccagatgg ctttgctccc   83280
tccaggaacc ccagccacct tcgacctcca gcagggcact ccactccaca ttctcctggt   83340
ctgtctggct catcttacct gagccatgct ctccaggtga aggactatgt ctaactcaac   83400
tctgctttaa aagcagctaa cacattgctc tttgcatatt gttcactcac taagttgaac   83460
tggacttgga catgcacact gaactgcagc gtctgctgct tcttggtggc ccagctcgtc   83520
aaaagaataa gatttcagca aaacaatgta acaattttt ttaccaaaag taatgttaac    83580
aatatatggt tttcccctga tgtttgcgtc aaaatgcttt ttggaaaaaa cattttcaa    83640 ctctttaggg tcagaattaa gcaatgaaat ttatatacca catgtataat gtgtatgttt   83700
atctaagtat ctgttcattt atatatctta aatagaaatt ttaaaatttt ttttaaaact   83760
cctgataaac attctcagga ggcacactat gtaactgttg gttgatatac ctagctagat   83820
ggtgaaatca gattttgttt aaagcatgga ggagagggaa aaattaaatc ttgcagattc   83880
tgcagtcctt aacatcttg aaagaggaac atttcagaca atgtaataag aaggccacgt    83940
gctttgactt ctgtagattt taaaaatact tctgtatagt ttcttcttcc tttgaagaag   84000
tttggggagt ttgggaagat ggagaaagat ataagaatag actccccata tgggtcatga   84060
attatctttt tgcatcagaa ctcttagtgc agtttcagta ttttcttcct caggagggtg   84120
agctgcttcc gaatgtcctc cccttctttg aggcatcctc tgttggtgaa cttgagagc    84180 atccatttat gaagttgatg accttccca gtctctgcaa gcccttcagt gtgtgtcctc    84240
tctgagcaaa tctgaattgt gtgcttaata catggaaagg gatttgggag ggttgctttt   84300
taaactgatt tcttaattaa tattatggtt tagttaacta gacagtctca ttgcagaagt   84360
gcataaccat aatatgtctt caaatatatc tcccttccta acaccctgta atatactttt   84420
gtaaagatac ccttacagaa tgtgatccac catttatgaa cctgcagcat tgcattcaga   84480
gactaagtga aaagctggca gattttcatt taaagcacaa gctaaggaag aaagctggtc   84540
tagaaggagc tacagaaggg taatgcttag ggagggaatg atgtgcctgt gggtggtggt   84600
agttaaatct aaccaaagaa tgatgtcgtg ggtgtttgga tattggatgg tccacattgg   84660
gccacattct ttcaaacata agagtctgta gaaatatgac ctgtaaaaga ctcttaaata   84720
ttctggaaac tgtttcttcc ttgtcacatc cttatatata cttgaaccta tgcctaccag   84780
acatgacatg tgactattca tacagatttc atcatctctg gtttaagaat aaaggatgct   84840
```

```
gcatagaagg ctcacatctt ttaattcaca agactgaaac tgttctgaaa tgacattgtt   84900
tctaaaaatt cattacttgc attatattca tttttatttt tccatgccag aagggtagaa   84960
gttcctgtgc tcatattaag aaacagcaat gtcaatcgag gcccaactca aatccaattt   85020
ataggagtta taaagggcgt gtgcctgttt tgtctagaag cagtgttggg cagcactgag   85080
taggatagac cacctgttgc taccgataaa ggagcagctt ctcgaatgct cctgtctggt   85140
aggcactatc ccgagtgctt tggcccctca tccacaatct gtgtggcaaa aggcattgca   85200
ggcaattcag tgaggagacc gaggcatgga gagcaagtgc catggaattc cctaaggccg   85260
tgcagggagc aggttgccaa gctgggttga aaccgtcctc cgtaggctcc caactccgcc   85320
gtcgctgcta ctgtgctgga tgatgcctgg tagatgcaga tgtggagccc catggattct   85380
gagacaggcc gggtttcagt cctgccctag ctgcctattg gctggatgac cttggcaagt   85440
tgactttcgt gagcctcatt tgtctcatct ctcaattaag aaaacctaga gcctatctgt   85500
gggggttatc tgaaggattc cagggatgca tatggcactg tctaccgcat gcggtaactg   85560
tttcacaaat gatgaggagc gatttatgtt cttagtggaa atatgtcggc gtgtgaagtc   85620
ccaaagctct gccctgcctg gcttgatcca gtgcctaggc actgcccctc ttcccctctc   85680
tcccaaccca ctgtaagagg ctaggctgcc tcagtaactc tgaggggcat tgactctttt   85740
catccaaaaa ttcatgttac tgccccacat ttttctgtt gttttacaac gcagtaggaa   85800
gtgggcagac tgtcaggaaa agtgatttat agtcatgtat tgcttgtgct ttggcttcat   85860
ttgatccaat gcagatcagc tgcactcaga aaactactca agtgaaagag aaaaagtaac   85920
tgaaggggga aatctggatg agtaagaatt ccagggatag gaatattaat agcaagcttt   85980
ttgcctgata tagtcacttt atgctgcagg ggtgcccctt tataaagtgc ttgtacaatg   86040
gatgtttgct tttgattttg gatttggagt ctaatgaatg ttctaaatta ttattagagg   86100
agcttgcggt tgttacatgt ctgcctttat tgcttatttt tagccatctc ccctgatgtc   86160
aaatgctcag gcaagaatga tacattcatt tataatgtgg ctccttcaga aatataccac   86220 atacctttg gtgtggtttg tggctgagaa gagtggggaa tgcacaagtg gaaaactgca   86280
gaaagattat gccttcatca cttcaagtat ttgagatgaa actagatcat ttgctgttgc   86340
tttttattct cattctaagt gcttttcaaa gtcagcgcta agattttaaa atggttttct   86400
gttgttggca gagagggaat tactctatta cttttctgata aaacagagtc tttcatgatc   86460
aaagagaacc aggctctagt agttccagta tcctaacgtg gacactaatt gtttccctcc   86520
ttttcttcat gaaaacagct tctgcacaaa tgatagcctt tgaactagc catgggcaca   86580 actggagaag catttaggga gctttagtgc aaattgagac cacctacaca tctgactcta   86640
cagggtttga caacatccag ggtgaatcac aaaacatcag tctaatcagg gcttatatag   86700
aaagagtgaa agaactctga tttcatccta aagattattt atattaacca ttgttccaaa   86760
tgcattaact attttaattt agttgttttg attgttaaaa aaaacacatc tgtttggtag   86820
ataagacata atttaagaca aatgttctat ttgataagct tttagaaaca acttattttt   86880
attctttcct gtgagataac tcagatgtgg agaatgtgac aaaattttaa gcataacatg   86940
agaagggctg acacacatag atttctgtgt gcttacttga aaacaacaaa atttaagaat   87000
ttggtatagg agttgtatca ggtagtgcag agtccccagg agacctagag acccaggtct   87060
gggagcctag cggcaagggc tgaatgtggg atgacatcag cagaaactca cagccactgc   87120
tattccaaaa acccagcagc agctcagtgc agggcagtgc tgatagtaca gtgcctgcaa   87180
```

| | |
|---|---|
| tcctggagtg gatttggatg tgtcaggtac gcacacgctc actgctcccc cagcagtacg | 87240 |
| ttgaacagtg tgcgtccagg tgtctgtagg gcccctcgcc ctaactcaca aaaccattct | 87300 |
| gggtcagaag ccaccaatat tgtcatcatc ctcccttttc tgagaaccct agtaagtccc | 87360 |
| tccagtgggg caagcccacc tttcccttc attctgtggc aatatgcctt catttcctaa | 87420 |
| tcagttttgc cctgctcatt caatgcaaaa tggatctgct ttccttgggc accaatatgt | 87480 |
| ccagggattt tttatcaatc ttcagttctg tttccttac atatccctcc aaaaatcagg | 87540 |
| cctgcactgc ctgtgcactc cacaatccac aggcctgaag gaaatgttat ctttgatgta | 87600 |
| gagacttaaa gtaaaactct tcaaattaat tatttcatgc aaaaggctag tcctgactct | 87660 |
| aattctaaga catgtctcct aaactctgga agtctgatgt atcctattat caacatttat | 87720 |
| ccttaatgtg atggtttatc atttatcctc aaagctgcat tgtaaaatgt acactgtaaa | 87780 |
| gtgtacattt taaagtcggt tttaaaaaat catatttaga gatcctggta aaaatctatc | 87840 |
| aagtcaagac attaccttat tacccatgga attgtcttca actcttacag ttcaaatatt | 87900 |
| cctgaattgg ctttcacaat aaacatccta aatatgtaag tagaaacata tatattgcca | 87960 |
| actttgtgcc ttcccaagca aaattaaaat acaggaaaag tcagtttgtt ttgcccataa | 88020 |
| ataaatatat gtgtgtgtgt atgtgtgtgt atacacatac acactcagaa aagatagaag | 88080 |
| cagcagcata ttttggcagc atctggttta ttggaactca aacgttctga ttgtgcatac | 88140 |
| agactagtta atgtggtaac aattatgtat ttcttccctg ctccttgcct tctttccctc | 88200 |
| cccagttttt ttcttcctga tagtaggtgt gtactttttt cctatttcca ttggcaagcc | 88260 |
| acatgacaag caaaacgatc actcgaagaa tattgttccc tcaatcaaga aaaatgccca | 88320 |
| ttgggttttg ttatttgatg ttatttgatg acagagacct attgttttc cattttctt | 88380 |
| tttttgtttt ccgtggcacc tatggaatta agcaatataa aaaatctatt atttcagatg | 88440 |
| ttcacgtcta atgaatttca tgtgaaatac tggcagtata accccaaata gaggaaattt | 88500 |
| gtgaagagtg gatgctgcag ggcatggagac atctgcacag agttcatctc ttccagcatc | 88560 |
| ttgcatgtcc caagcactgc cctgccaggc agagaatgct gcagatcacg gcagtgaatt | 88620 |
| ccagttgttc agagcacatt tgacttccaa attctcaagg ccacagattt gaggacagaa | 88680 |
| caatatttgc atttgaaatt ggaagattat ttttttgcaca agtgcctata tgctatatag | 88740 |
| agtttgccca ctctgcatta tcttcccct gttccccgt tatctggcac aagctattca | 88800 |
| aaagacacgc ctacttgtaa aataaatggt ttgcaaacta aggaaaatac ttaaatctca | 88860 |
| tgtaaatggt actatactat gtataaaaat gtgaagaaac acagaacagc tcatgaacac | 88920 |
| ctccactgct gtataaaaga accatctttt ttctggctcc tattggatgc cttagaaaaa | 88980 |
| tctgtatttc ctcttagtt attgtgtttg aaagatgaag ttgagacaaa agttctattc | 89040 |
| tttttaagtt ggcagaactt ctgaaaggtg attttagct gcagtgtgac tcattccaaa | 89100 |
| tgcagaaatc tctgaccctg agttagtcta tttgtcatgc aagagcctag aaaagccctg | 89160 |
| agtgataaga aatggccata ggccattccc acagaatttt caacaaaaat agaatcatgc | 89220 |
| ttatgttcta gtcatgactt agaacttata actcatgttc ggaactgtcc atgttcacgc | 89280 |
| acagggccg tatcactccg ccagagctgc cctgggtgcc ggtgtgcaga ggggtccgag | 89340 |
| agtgactgtc tcttcctctg ttgtcgaatg tgtgggttat ctccataaat ggctgccatg | 89400 |
| agcatccttg ttcacacatt tttaggtact tgagtgagtg tctgtggaat aatttttggga | 89460 |
| agtgaaatct gtggtcagag gtttgtgagt tttacatgct acattttcag aagttgagaa | 89520 |
| atagcagtag gctgaaggca agtcgccatg cctggaattc atgaacacta gttgaaagaa | 89580 |

```
ctggcgtgag ttagtcatga caggagagat ggggaaggga gttgcaggta ggagggccat    89640
cttcaaattc tcaaagtata gtcactccaa accaaaattc gatttaatct gtaggactcc    89700
attctcaaag cacagtcact ccaaaccgaa attcgattta atctgtagga ctccaggtgg    89760
cagaataaga ggcaatggat gggtggaagc gaaacagggc caaagtttga cttcatgtgc    89820
aacttcctaa ggagtgattt gaactccaca acatgaact  aagcacctca acacaggctg    89880
ggcaagttgc tgttcttttg gagcttacat cttagtgggg aaagagaaat gcctatgtaa    89940
acatataaat cagcaggata cattgtgagg acggtcattg ctcagtgaga ctgcaataga    90000
gtgatacgct ggaggggggct gcaagggaga aggtgggagg acagcatttt agcagaatga   90060
gcagcacagt cccataggaa gaagaattta ttgcctcctt aggcaaataa attcccaaac    90120
cttgaacatc agaaaggaaa tagattaatg tgcacagagg attaaattat gtgatctgca    90180
aagtcattta aaatctattt ccacataaaa catattaatg caacctaaac aaaaggggtc    90240
tggataccct catcttcttc ccaagcatca agtctttcta tagttaaact gagatgcttt    90300
tattcttgga aaattttaag gactatctac agcaatggaa gaatcgggtg ttgggatgtg    90360
ttcccaggta ataatgactg caggctgatt tggcccttga ggtgtggcct catgcccctc    90420
tccaaaaaaa atcaaggacc tgctacaaag cacaaagccg actgcaatgc ttgctgctta    90480
ctggttaggg cagctcctct ttgccagcga ccaagcagaa agcaagacaa gacaggttct    90540
gaagcagtaa ttcaaagcct tcctcgcttt cccatgtgag tcattgctag tcagaatatt    90600 accttttgcag agaggcttaa ttccaaattt gctcttaaag ggatatcctc tcctggttta    90660
ggtataaact tttgactcac aggacaaatt ctatcattcc tttgggccta ggattgcatt    90720
tatttccatg acaaagggc ctgtctggtg tttcagcaaa tgaaaacaaa aatataaagc     90780
ccatctcctt ttgaatgagc tctaaaacag ttctccactg gacttcagaa caagagggag    90840
ctctgggctg ctggctggtt gtgcatttgc tgtgggttcc ctccggcagg cgacctctcc    90900
gcgctgagaa ggttatccgg ataaccaagt aagaaagtac atgaggaggc acagaaagaa    90960
aaatgtgaga gataacagca taaacacaca gtgtatgttg ttatgaggca tcacatgatg    91020
agatactgct ggggagggaa gaagtgagga gattcctagg aatcttatga gaatttccag    91080
agacaacaag ttttgagctt ttttttaatt tagaaaattt accttatttt taaaagaata    91140
tgtaacatat cccatgctat aaaattctag acatagtaga tttaaaacag cataatgaaa    91200
aatataaata tctattttct tttcctattt atgtattctg tgccagtagg aatgtagcca    91260
aaaagagaga aaaggggtct ctgcagacat ggatgtctct gtgacttgat cactgctaac    91320
ccaagaagat aataaagcag aagcatgtat ccaggttgct gcagccaagc ctgcccggtc    91380 tgcgggggcgt cctcacacat ggggcagctc tcccacccca cacactggga aaggcggaca    91440
gaggctgggc aaagccccca attttcgttg gcactgaccc cgatgattta taggcctttg    91500
tttcccatgt taaatgtctt acgatcatta aattatttat agctcaatta gcatgtgtcc    91560
aaaaccagga agttcatagg agactgtgtg actgggaatt aaggagcaaa gcaactttcc    91620
agtctgtgat ttactgggtt tccattctgt ttcctgttcg gatccggaag tagaatttca    91680
aatattgctt ttcatgcttt atttgggacc gattttagcc ccgctctcct ttctcttgcc    91740
attcgctggc cattagccac cagcctctgc acaatgacca gctggcccct ggcagatctt    91800
gggcccaggt gtgaagtcgc tggagaagca tttcagggcc aagatgggag tgatttcatt    91860
ttccattgac actatgcaga aatgaagggg attcaagtgc cttcagaaaa gcttccttcc    91920
```

```
agcgaatgga gttttggggg ttttccagac ttgcaactgc ttttattctt ggaagcatca   91980
ttgttgcttt ttccccccctt ccatttatat cccaggaact gattcagaaa ccatagaaat   92040
tggatttgga atcgctgaat gctagcagac agctgactgc actcttccca agaaaccctg   92100
ccagctgggt tcgggtatcg cgcggtgtgt gctctctctg cctggcccgc tgagtcctct   92160
aactctaatg gattccttct tacaccaaag tgcactagaa ctaaagtgtt ttgcttcatt   92220
ctttagacat tttgtggttt agggctcaat cagccagggt atgatttgca atccacagta   92280
accggtttca gagcagctgc ccagcgaggc aggtttcatc tcgcttgcta gacgttttgt   92340
tttttttttt ttctaaacct cacacctttt atttattaga cttggattcc agtttcctga   92400
gcctgtttgt gccactgatt agacaggctt gaagcagaac ccaccaggct tcctgaataa   92460
aatgcagcag tgattgtatt aggggttttt aaattgctca aaatactgtc taaaaaacac   92520
taaaaatcat gttactttct agattgaata aaatcctata gaaatgaatt cctggacttg   92580
atatgtagca agctggcatt ggctcgggag tgagtgggct cagttaagtg agctaagatg   92640
agatggtgca caggcgagca cccacctgag gagtgtttgg atgttatgat agccagctcc   92700
tctgtaaaga cctgtccttc tatgtcagca gcccagcaga taaatgacgt gtaaatacca   92760
catttaggag ggcttatgat gatgccaatt aatggagacc tttttgaaac aggaaggagg   92820
tgaaacatat tccttttgctt ctacatcact gtgtgccagg cactgtttac agcatctcgt   92880
ttaaccagca gtcaccacct gacgatggc tgatgtgggg tggggtccca gggtgggatt   92940
gcgtgatggg cttggggtct ctggctgatg ggtgccagag ctgggactgg aactcctggc   93000
gtgactgagg cagacacctg gctacccag cctcacccac gacgccctca ctaagtgacc   93060
cacaggactc accggaagca gggcagcaag gtccccctac agaggtcccc actgcaaacc   93120
gatacccagc ttagacagca gttctgcagt cggcgtctca ccccttcggg tctcattgtg   93180
actcactttg atagccacac gatttaaggg tggttcagta gtgatttgat gagtgctgtg   93240
gctcagggtc attcccctgc ccaagcattt caaattccag aagttcatgc cctgcatggt   93300
gggtgaaaag tctcaggcca accatgagca cacagcagcc aggcgactga ggcagctgcc   93360
cggggtggca cgttgctcaa acccatcatt tggagtcaaa acaaacagat gattagctgg   93420
ggtggtcact ttcaatcaag agttttcaca tcgcctagac atggcctcag aatcaggcct   93480
ggtgtggcca ggggctgatc tcacagtaga caggaagtgt ggcccgaggg ccatggctgc   93540
cccctcagaa ggccctgtgg agtggctggc cgagcctcag cagcctcctg tgaagcgagg   93600
aagggtcttc ctgccggcct ctggagatca gtatgggaat gcacaagtag gaaacgctgg   93660
atgggaatcc ctctgccctg tgataccaag gcagtgagtt tgtagactat ggaattgctg   93720
tcggagggct ctgtaaccgg ccaaggtcac acaggtagcc attggtagag cagggactgg   93780
aatcccagac ccccaacttc caggactgtg cacctttctt tatcccatac agccttacag   93840
tcaagtgcca gtgcaacacc tgattcccag gttccagcct ttgtctttta taatgggaat   93900
caaccttatc ttgacgatcc agagatagtc atcaaggaag attaaattat ccccttagac   93960
tcagagtgac catatcattt tccctccaca caaggacact tttgagaatg aaaggaggga   94020
gatgtctgta ccagacgctg gatgacaggc accgacaggc tgtctgccag gggagcagcg   94080
attcctgtat gttgtagaaa gttttcaaa agtcaccttg gaaagaggtt tgttccttta   94140
accttctgtt aaataggaag ctccgtgaat gaaaacaact cccttcccta aacattctag   94200
taatgaccca acactgccaa gcctgccagc tctgcctcat ggtcgtgttg actgtgtgag   94260
actatgtgag tgcctgctac acagtacgct ttcagtaaac atggtattgc ctcgataatc   94320
```

```
ccacaaaaat gtcctattca aatcacctgg cacccaggaa atttccttct tttttttccc    94380
aggtgaaata tacagttgaa aacacctgac agcaattccc ctctcccatg tgtttgcagg    94440
atggtggttt tggttcctcc atctttgatg tgtacaagtg tgatgttttc ccccacaga    94500 caagtaaacc acattctctt cacattccca atgttttgtc aatgtacctc cttcaataga    94560
ggatcgataa ggaaaaaaat cattgacaat ctcaattaga ttcactattt catccaaaag    94620
catagcttag aactctagtt tttgttcaac actcttgccc tatgagtgca cagaacttta    94680
attctgatac aaacatccct gaatgtttag ctttgacaga gattccaagg tgatttgata    94740
agaagcaggg ctgtgtttgg gctctgggag ttttttgatat ggtttcaagc cccatccaaa   94800
acccacagac ctctagaaag taggtgcctg ccttcctgca gcagccctgg agcctgctgg    94860
gggctttgag cagctgctgc caagccaggc ctcacccgac actctgatgg gcacggccat    94920
ggtggcaggg gcttggacgc tgccaggtga ctctaacttg tggccagggt gggaagcact    94980
gctccacaga ggtgccaaaa ccaggttcct tcctgtgttc tcacatttca cagcctcaat    95040
gtaaaaagta agacatgggc actctggaat attacaaaaa tatagaaaag catgttatag    95100
taaataaaag gctcacagaa ttttgtcatt taggaacaat gattattaat atattagtgt    95160 gtgttttgc tcattaacag tatatcctga gatatttcct ataccattta atattttaaa    95220
agatgtttac actggccaca gtagctcata cctataatcc caacacttta gagggcaagg    95280
caggaggatc acttgaggct taaaaattag ccaggtgtag tggcacatgc ctgtagtccc    95340
agctactcag gaagctgagg ctggaggatc acttgagccc aggagttcaa ggctgcagtg    95400
agctataatt gcaccattgc actccagcct aggtgacaca gtgagaccct gtttctaaaa    95460
taaataataa ataaattaaa acatttaaaa atacatgatg tttaattatt agaggactca    95520
attttatatc tatgtataca ataatttta agtttcttaa tattggactt ttagtacctt    95580
tttaaaaata ctatttttaa aaaatctgt atttctaact tttataaca aggaaccttt     95640 ggctttgaga tgactgggga atccattctt tcctatagta tccatgtcca atggacttaa    95700
agtattaatc aatgtgttta tgttttgtta tttttctggc attacaaaaa attctaaata    95760
tattgttacc gcctgtataa atatcagctt ttgagagaag gacattgtgt agaaataatg    95820
aaacactgca acttgtattt gtattattct tttttttttt tttttttttg agatggagtc    95880
tcgccctgtc acccaggctg gagtgcaatg gtgcgatctc tgctcactgc aagctccgcc    95940
tcccaggttc acaccattct cctgcctcag cctcctgagt agctgggact acaggtgccc    96000
gccaccgcgc cgggctaatt ttttgtattt ttagtagaga cggggtttca ccatggtctc    96060
gatctcctga cctcatgatc tgcccgcctc agcctcccaa tgcactggga ttacaggcat    96120
tatattattc tttaaattca catgagaatt tagtatggct tcaaaaaata ccataagtta    96180
aaatatcacc aagactctgt tcagacaaaa gtatcagaaa agtgagccag gcactcacat    96240
agtttatagt ttataaaagt gagacaggca tgatctctta acctcactat agtcctgtga    96300
ataaggttta tttacatttc attttacctg ccaggattat tgtaaaaacg ccaagcacat    96360
tgcctacaca aactaaatat tcagtcaatg gctgctattt tcatgagttc gttttaacat    96420
atatttattg tcctctactg gatttaagaa gttatattta ttatcatcta agattttagc    96480
tattccttct cttaaaaata gattttataa tcaatggcag taagggagag taactcgcag    96540
ttctctgaat ctcaagggggt tcctggaagc cttcctgaag gtatagtgaa atttcagctt   96600
cacattccca tccatgagct ccctgcaaat atcccggtct gctctcagga cccagtgact    96660
```

```
tacctatgca gaggctgtag atagcacctg gagcttcctg tgtgccctcc tcaaactcag   96720
ccaatgccgt catacagtag caggcaggtg tctttgctgg gtagttggac tggatgtccc   96780
tgggattgca gaactggaat ggggagtgac atcaggaaac tataatcatc aggacaacat   96840
ggtttgccat aactttaagt tttaagcgac cgcagattat gcggagagag atgcatgccc   96900
acagccatgc ttcccatgta actggagagg ggtctgaagt ttgaaacaag tgttcctagg   96960
cacgggttac agtgtttgtt atcatcatac ttgatttaga atggggcaca acatgtggat   97020
tcatggtaac tgttacaacc ttactcattt taatacctga aaacatgctt tccccatgct   97080
gggaatcgaa agattctcct aggaaaagaa aggcttgaca acatcgattc aaaaagggca   97140
tgcattttcc tcatttaaat aactctaatg tgcaagtaga tcccctgacc tcaagctcag   97200
aagagtccag gccttcacac cttctctgct tctgctctgg ggccagctat tgagattcct   97260
gtgcccacgc aatgcgcaca tcccacccct ggccgctgtc cacaagaaat ccagttgcac   97320
caagcacccc acttttttgca cctctcattt atgtactcct aagagcctca ccacaactcc   97380
cttctaaaaa catgagttcc tgactgggaa ttcgatgctg cccaggcagc tttgctcaga   97440
gggagcagcc ttctagaaat gtttcaagta aactttcaag tataactaaa ttcaaaaaaa   97500
acacatacac acacacacac acacacaagt caaaggtgtg taatttggcc aatatcacaa   97560
accaattagc cctttgtaag tggcacccag atcaggacag ctgaccatac cagcacccta   97620
gaagcacccc gtgctgcctc ctgggacagg gctaccacca tcctaaggcc agcacgatgg   97680
gccagctttg cctgctgttg aattttgctt acatagaatc ctccagtagg tactcctttg   97740
ggtcaggttc tttcactcaa cattatgtgt tgatatttt ccatgctgtg ctgcaaaatt   97800
gtatttcttg cattccataa ctgggcagtt ccatcatagg agaataccac actgcgttcg   97860
tccattctac cgccaatgga catatgggtt cttctctttt tcttgcagtt acaagtttat   97920
gaatattgtc ccacgtgtcc ctggtgaact tttgtttgca tttctgttgg gtacctcaga   97980
gtggcgttgc tgggtcagag ggtactggtc gctttagtag ctttgaaaga tattgccaaa   98040
acatttccca gcgcagttat agcaaattat acaccaccag cagtagaaaa catctcctaa   98100
ttgctcacag taaaccccca aagattgcca catacatctt ccatatcaat tacttaacta   98160
ttcagcaaat ttgaagggaa atatatttaa tcttttttatt caaatagttt ataaagtgga   98220
atagagatgt gggtaaaagt tgtcttgcca ccttttttaga tcggtaaaag tttgttgaat   98280
gcaggcaaga aaagatgaga ataatggta cccaatgaaa gacatagcag tctacaagga   98340
ggggcatttc ccggggtggg ggggacccac actctgtaac tcccacattc aattagcatg   98400
ttataggtaa gctgcagaaa acgaggcagc ttgtcaaaga ggaacggctc ttggccatgg   98460
ttgctgccct aggaggatat ttgatactag cagagctggg gcaaccctgg aggaaaccac   98520
ctggaatgat gggagaactc ctccagggaa catggccctt taatagatct ctgttataaa   98580
aaataatccc aaagcagcca ccagggcata ctgctgcgat caagtcctag gcggtattcc   98640
cttctgcgcc atagaccctg tgcagagtgc cctcaacgaa ggagcaagga agaccaagtc   98700
tcccgagggt ttgcatatgt gtatgtgatt ctgcagtcat ggtgaatgac acagtcaggg   98760
ctgcggaaaa gcattggtaa agtgtatatt tgaggcttca gaagtttgaa aaggctagat   98820
ttcctaggcc aaaacactga aaatttgcaa ttagaacttc agtgctgatg ctgggaagac   98880
tggagttagt ttgagacatg cacctgtgca gaactgggcc cccagaaaag gagaaggaag   98940
ggaatccaga ccagagtagg gcctgacacc actcagactc ggcgtgtcta taaattgaaa   99000
ttgcgttaca attacacttt gacatttttag tggttttaa agtgcccagc acaagttaat   99060
```

```
ttttcattaa tgaatccttt attcataaaa tgcttagatg gagattaccc ttttgagcat    99120
tttgccagtg cttctgaaat taatggggac ctcctgttgg aggacacagt ctgttgcaat    99180
aggtgaccac tgctctgaat ctatgtcacc tctccaggac cacgggcaca accatcacct    99240
gaggcatgtt ggagatgcag atggtcaggc cctcctagaa tctcagaatc tgcattttag    99300
caaagtcctg ggtaattcct atgtccattg gagtttgaga agcactggta atctcaaata    99360
cttttaaaga ttactagagt aagataggct cagtaggtac ctgaaggcac catcccaaag    99420
accagagtgg tagaagcagg tggaccagcc tctgaacaca tttctccccc actcccggc     99480 tgtgtggaag gttgccacct ttggggtagt cattcaacaa acacgtgtca actgtccact    99540
atgtgtcagg ccaccactgg gcactggctg tggctagctg atagacacc atttctgccc     99600 tccagaaatg tcatgtccac tggcacatga caagtcacta agtcattcag agccatgggg    99660
gacagctcca ggggccgaca aaggagctgt gatctcacag atccacagag aagtgtccca    99720
gggcgggcgg gaaccaggac tgcacaggga ggggtgaagt gacacataag aagtcagccc    99780
atcagcctga aatgctcccc caaatcttcc cattcagtgt tttctcagta gcaaactcgt    99840
gggaaaattg gttattttac ttaaaaaact catactagaa agctagttta actttaaaaa    99900
taaattttaa aaacatttt attaacaaat cctacctttc ctccaaagtc aaggagaaaa    99960
gaatagaagt gaacaatgga ccaagtaagc ctaaaactct gctctttccc ctgctcattt    100020
tacagttcaa gtgccattca attatcctg gcaagaagag gaaggcatca tcaagaacctt     100080 aattttctaa tacatctgat ctgagaagaa tgtgaaagct ataaaattaa tttttgatca    100140
ataactacag gccttttgag agagtgccct cctaatgaat tgagtaccta tttctccata    100200
cacagtgtct atcatgacct acaaacccctt ttcccatgag gtgtaacaga gagagattac    100260
agccttggaa ctggatgtca gactctcctg gtttaagaca ataagccatg acatagagcc    100320
tgaaaccaac acaatcttcc gagtggttcc agaaacatat aggggataat gttggctctg    100380
atgctgtaca tccccaacaa ccatcaacta tttggaaact agaatttcag cataattgga    100440
gttggtgtta ccctagcaaa tgctgtggga agagagtctc actgtgtatc ttctcctgtt    100500
taaagcctga atttgttcag aatgtaatat ctctgtttag ccactctact gaaactgatc    100560
taggaaatgt tcaaaaaaag gtatcccaag gatcccttg tagctacatc tgtgggattc      100620
ccctcgctct ggcgtggcct ggcccctctg catttgacaa tacggtccta tgcttttgtc    100680
ttcctgggct gcgtgaaccc accctgccct ggttcacctc tcctcttgac ccatccttat    100740
cagtgtcttg aaaggtcctt ctattggagg acacattctg ttgcagcagg tgaccactgc    100800
cccaaatctg tttcacctcc ccagggccat gggcacaacc atccctggag tgtgttagag    100860
atgcagttgg ccaggtcctc caaaatctca gaatctgcat ttttgcaaag tcctgggtaa    100920
ctcctatgtc catgagagtt tgagaagtac tggtctcatg agttcctgac atacaaatag    100980
tgctgaggcc agtatgctga ctgggtagcc agatacaagt gaaaaccttc ctgttttttg    101040
caaacctgga tggacccgag gccgctgacg tgggccagga caagctactc ttttttcagtg   101100 tttctgttgc atcgctgtgt ctctctgtga tcaggtgctg ccctccctgg caggaggact    101160
gcagacagga tgaccaagag cactctacac agcctgctct ccagtgttgg gggacgccac    101220 ccacccctcgt ggttcctgtt catctgccta cacgtggagg gcccaagagg gctaatatgt    101280
gactatctcc acttcctggt accctgtgtg aataacttca cttactaaag ggatgttgag    101340
caactttatt aataatgaag aaagcacttt ggtttgacaa ataatcactc cattttttca    101400
```

```
tttgaaagtt aactcttgtt agtagagaaa gcaatgtatt acaaccacaa ggacgtttac 101460
atggaaatga accatctgca aagcatcccc cattttcctt ttaaatcagc caatgggtgg 101520
tggtgggaga atattcacc agagtattta acatctatcc cccttcctag actgtcagct 101580
ccatccgggc ggagactgtt ggtatctcca cagcacacac agggcctggc acacatccgg 101640
ggctcagtga gcacttgctg aatggtgaac agattagctc tcctgggaac gttgttgaca 101700
catctcataa cactggtttg gagtggaggg cattcatcgg gctgcatatt cctattttta 101760
attgtattct ccactggtta cagcacctac agttataaag acattgttaa cattgcttat 101820
aggaagacat ttgatggaaa tgagtccaaa ggcattacgg ttagaaactg gccaggtgtc 101880 attttgaga gattagataa ctgttttccg gtagagtgaa ttgcctgttt gttgcaagtt 101940
gggactttgc tgggctggtt tacagggcca aggggaaaga gataagtgga tcttctagtg 102000
agaggtcatc tgttttgaaa gcctggaaga ttccatgaac taaatccaag tcttacaaca 102060
cagggaagtg tgtcatactg tgcagggatg aagtctccaa tttagcatga aaacaagagc 102120
tcctcacact gtcctcttca gaaagcccat acaatccaaa cttctgaatg cttagctgct 102180
tacaaccata catagattga gggataaaac tctgatatgg aagagaaggt aaacatttt 102240 tggcagacat tcccaggaaa aggcggctct cttctctcat tgctgctgct ctttcagaat 102300
ccatttcaac agaggaggag tcaatgggag ccccgtgcct ctggcagata tcatatggcg 102360
tttcagtggc attgtgtgtt acccttctta ggtaacagct cagccattag aagaatgtcc 102420
tacacacctt ctcatttct gtgatgagag gaatgtgagg tactgcccctt cgagagctgt 102480 catttgtcct agtagccagc agcgtgactg tgctgtcttc tgctctgtct ccctgtcagc 102540
cttctgccca gccaccacca ctatagtttt gttctctcca ttggaactcc tggttcagag 102600
aattaccata aaaaacagac ccctagacat acaacactct atcacataat ggtgactttg 102660 tcttctatt tggattactg agctttcttg ggtaacttcc actaaatcga agttaatatt 102720
agaagaactt cctcttacta gaatcgaaaa gcatttaagt gatgcagtca agtttgtacc 102780
ataagtaatt cagtcattta acaaatatat atggcctctg tgcgacagtg accttgactg 102840
ggaatgaagc tgtcccatgt ggggcctgtt cttcaaaggc agttccctgc tgcccagttc 102900
agtccagtgg atctgggcat ctctcttaa tccgcattag gggctcttta ctgattcttc 102960
actatccaaa aagacttgga ggggagacct gagcccactt ctggaaggaa atgataacaa 103020
tttatttaga taatctttgt gcaacaagtc aattcactga agagatctgc tctctaggag 103080
cctctgtgac cccaccataa ctgggaaggc tctacctctc cagtcttcgg gccacatttc 103140
tctctggcct gctgtcttcc cagcactctc agccttgctc atggagcact ctagtcctcc 103200
gtcgaccttg gcctttggta acgtgatttt tcacctggca gctcccatct ggtctcactc 103260 cctcttttg tccagtctgc atgacacagc ctcacatcgt tagtgttccc tcactcccct 103320
cttactgccc aacctgcaaa gtccatgcct gggccagtgc agcatgtgtc ctcaatgggc 103380
tgctggtggc agtgggggga accgcacagc cacgctgtgt gctgctgaag aaaatgcacag 103440 cctcctaccc tcgccctcaa gaggcagcca tggctgcgca tttctgccct tctgagctcc 103500
gctcactttt ggcagcagcc gttccaacct gcatgggatc ttcactctct cacagatgtg 103560
ctgactcctc ctgctgcctc ccctctctgt gccttctcac tctctgttcc cttttgccctt 103620 tctccccttt tctcctctgc ctacctccaa gccatccatc acaggacagc tcaagcatca 103680
gatcctctgg gacactttcc ttagttgttc agtctgatga ggtgtccctc atcctctctt 103740
agctgaaaat cagcagctgc ctcaacttct tttccagcat gtctcatgag tattgccaca 103800
```

```
acagcatctg tcacaatgtg gggtagtggc tgacttgctt ttctgccatt caactgagtt    103860
ccctcagtgc tggggccagc gtgcagtgtc ttgtattcag tatatagctg attaattgat    103920
gaattgatta attaatggtt cacactagca cagtgcaacc ttcaatgcaa agatctcatc    103980
aaaataattc acatggtggg atattttaga aggatgacca ggctagtttg tagtaagaaa    104040
aaatcaacaa gactaggtca ggaattcttt ttttgtctac aggcttgcta tagaagatat    104100
tgaaaatcat ctacctaatt acctttattt tatcaggttg tgtattaaat atcacgtctg    104160
ggggaagaaa atgtgatatg tgattacaga ccttcctgg tacaacatag tacgtttcag    104220
attaactcaa ggtattgtgg tgatattgcg gtcaaagcca ggtgattaaa gagtcattct    104280
ttgaaacaaa tatctgtgca atcaattaag aaattaattt gcaaatttta tttgcttaga    104340
gtaattgata tatcattcct tttacaaaca aatataaaga aaacttaact aaaaatactg    104400
catatctctt tcagattata tatcccagaa aggatatatt tttctccttt ctggtcttcc    104460
tttttggtgt agcatctgta ggaaatgcat ttcttcatag ctaagtgtac ctccttgtga    104520
aatatcttca gagtctactg gtgcacataa gcaattgctg gcagcagctt gagggtctcc    104580
atctcacatt tatcatatgc cttattgcat gaggctttgc aagaggaggt ctagagctac    104640
aatatctcat ggatatgaat gtcaattcaa atcccagtgg cagtttatga gggggaaagc    104700
ctagaagaga agaacctag aggaatcaag caggagggga gagtaataaa agactagagc    104760
agcaggtttt tcttaactca aactagaatt aaatctctgt gtgtgtgtgc atgtgaatgt    104820
gcccgtatgt gcatgcatgc acgtgtgtaa atggatgtgt gtgtgtgtgc atgtgtgtgc    104880
aagtaagtgt gtatacgtgt gtgggcatgt attgtgtaca tgtatgtgtg tttatgcat    104940 ctgtttgcaa gtatgtgtgt atgcacataa aagtgtgaat gtacatgtgt gcttggtgta    105000
tgtgtgtgta ttaatgtatg cgtgtagttc tagagtctag ttagagaaag tgcataaaga    105060
aatagggaaa ttaacaagaa agctatagct taaattatag gaaaaacttt tctccctatc    105120
agtcatggtt ttaaaatgtt cagacttgat atgtttccca gtgctattgt cagaaaatgt    105180
ccctatgaca ttccatacta cttcaatcaa atctaaaacc tttgttccaa catgtttttat    105240 tgatatgagt atatttcaaa tttctaccag gtttttggag aggtattttg gccataaaat    105300
tgactaaatt attcaaaata aaaaatgaat aagcctgggc caaggcttgg agacttgctt    105360
aactcagttc ttaaattttc agattttcaa aattacaaat ttaagctcta aaatcatggt    105420
gctgtgtatg atattcttttg attgcaactt atggttgaaa aactatagag ggctttatgc    105480
taagagttgt ggatcttagg attttcatga aatctgcatt atcatcatct gcaagtttag    105540
atggggcata actgatccaa aggatggatc cctcggggc aattcaactg gctgattcca    105600
gccaagatga caacagtcag gatccgttcc cttctgatca tccattgggt gccctgattt    105660
cctctacagc cctagctgaa agaccagaca ctatctcagg ctggctgccc cacatgcctt    105720
gctccacacc aaattcacag tctataaacc tgagcctcca gtgctcctac taccatactc    105780
actcgaacat tcccgattct gacctggaga tgtcaacagc tacttgatgc cactctcttc    105840
tatctttctg tagctaagcc atccccaagt ttgtcgattc accctcttta accctgtcg    105900 gggtgtccat tgtgcccctt caccctgcca tctccctggt gcactgtttt gcaaagttca    105960
gcatacatga gcgtcacctg ggaaccttaa taaagtgcag atgttgattc agcaaatctg    106020
ggatgccctc gggctgcatt tccagcaggc tcctggggat gtcccgctg ctgtgctgca    106080 gatgacactc tcagtggtgg gactccaggc tctgctgtcg cctcctaggg gtttctccac    106140
```

```
actccctgga ggcctaatgg gcccttctcc acatggcagt aagatctgtt tttgtgtttg   106200
tgtttcaagt tgggagaagg agattattta atactaaaat gtgcaacatg ggattgagaa   106260
aactaattat tagtcataag ttgagtatgc aacattgaaa ccacatgctt taaaaaatta   106320
taagaaaaaa tcatagtatt tgaaagttac aagctattat ggctaactcc atttatctca   106380
gttagagaag aagagtcacc tgtcaccagg gcactgccag aagccaggct catttccaac   106440
agcactgggt gctccagctt tggggtgcca gctcctccca taaagcaaac acatacctag   106500
ggatgatatt tctttgcaag ggctctgccc tacagcttgt acatctcaag aagttatgta   106560
attaaactgt ctgttttgag aaaattgtag attcacacat actagctgta agaaatgatg   106620
cggataaatc cagcgtacca gctttcccca cggagacgtc ttgcagcgtc acagccagga   106680
tgaggcattg acccaggcga agtccagagc acctgtgcgc tacagggccc cttgcactgt   106740
gctgtcacag acacgcccac ttccagatgc catctaggac cccctccaaa aagcagaggc   106800
attcttaaaa acacacatct gcacatgttc ctcttcattt gaatctgtca gtggcttctc   106860
agtgcctttc aaatgaaatc taaagtcctt acaagccttg cagcaggaac ctctccatcc   106920
cacttcccct cacactctca gcttcatctc tgctaggctc tgttcagcca ggcagccttt   106980
cacagtccct ctcctcctgc cctgccagga aggtcccctg cccccaactc ttccccacat   107040
gtggcggggc cccgcttgtc cttagaagcc cagctgaact gcttcctgaa ggaacccctc   107100
cagaacctct cagaccaggt caggtttctg cactcttaga tcatccccat ggcataatca   107160
cagttgtgat gttgtgatga ttcagtgaat gtctgtctcc ccactggatg gtaagcttcc   107220
tgagggcagg aacagcattg gttccagtca atgctatgtc ccaggactgt tcgttttgc    107280 acatactaat cctaaaagga cgatgacaac agcaaccact tacatgacct agatgctctt   107340
ctgggtgttg tgcaaatatt aacaatttaa tccttgcaac aatccacgag ggaggcattc   107400
ttctactccc acttaacaga caaggacagt gaagctagta aagagaagtc atttgcccaa   107460
ggggacccca ctactgttgg cagagctggg tgcaaacgca ggcttgtgaa gccaggaccc   107520
atgcattcaa agaccatgcc aggtgccccc actgcacacc tcatccccac ataccagtga   107580
gggggagaga aatgctcctg cactgcctct gattaactgc tttcctagaa gtcacacata   107640 taaagggat ttaattctag tgggattgaa tctcaatagt ttccttatta ggttgatttc    107700
tgttaatagt ttaagtactg gatatacatg aattagaaaa tctagattat tagcaaatgc   107760
aaactataaa gtatttttata atgttatct tgtttgtcag gggatgagtg agatattcat    107820
tatacaaaaa gtagtgtgga ttttgaggta gaaggtttac taaggatcat accgtagtat   107880
gaaatagcca caaacattca gtgaaaccaa acaccccgc ttaacctcaa actaacacta    107940
aataataagg aatagacttg ggggcagtgc aagtgtattt ctaatggtga aaaccattcc   108000
ccagtgaaaa ctaatgtacc atctagttaa taagagctcc tctgacccac gcacatcaat   108060
acttacatcc caatggtgat gtgacatttt gggttttgta tttcttttgc aaattgagct   108120 agcattttg atgagtggca gggctctgct acccaacctt tggacagttt ccaagcataa    108180
aatcacaatt ccagataatt ctgtcacaaa gatctgggtc tcattaggaa ggagaggaag   108240
ctgggagatg atccagtcca acctccccca aaccaaacat cacggccttc tcagttgttt   108300
caccaaccat ctaaatgttt tagtaattct aaaaattgat gcgcttttc cacgaaagga    108360 agtgttacca cattttccaa gtgggaggca tctatatcct tactccttca tcctctcctt   108420
cccaccccct caccccccac cacccacaca acatctgcaa ttcttaaact aaagcacaaa   108480
ttgttacaaa agttaattgc actttcaaag gaatgcttgt atagaaactt tctcggcttc   108540
```

```
aaggaaaaat aatacgcttt gaatggctgt tcaacagcat agaaattagc tgagtagaag    108600
gcactcatat agccattagg accaatcctt tctgccgcca acacccccct tataaagact    108660
tgacagtggg ccagaataaa caacttcagg atgaattcag ttgagacaca aagtacacac    108720
ttccagtttt tcccttctct ggttactggc ctcaataacc aggcagtcaa cttaaaaaga    108780
aaaacaaaag cttgcttcag attacagatt gcagacttct tataatatgt ccatttcacc    108840
aggccccgct ctcagcccg  ggaaaggcca ctggaaacca cctcacatgg tagggccttg    108900
cgggagccag taataacctt atctccgtca acatgttctg tcagattgaa tggggcagcc    108960
agagaagcca gagttggcac aggaaccaaa acaaaggctt cccatcctcc tggagtgagc    109020
ggttgagcct ggattggtgc ttagacctat aatgggtgca agcagcgttc attcatagtg    109080
gctttctaga cccagggact tggccccagc cctgctgctc cactcctctt cttgcttcat    109140
taccacgagt ctcctagacc accgaacgat gcctgcattt gaaagacact tctgctgatc    109200
aaagcagctg atgtgtccct tgcggttca  tttctaattg tccccaagga ggagaaattc    109260
aaatagttta ttactgagag ttaaagaaat ccactgaaat attctttggt ctaaaattac    109320
tgtcatggcg gagcagcttc accttagtca ttgcccttaa atatgaaagc tatttaagaa    109380
agtttgccct taaatatgaa agctatttta aaaagtttaa tgaaagaaga gaatcacaaa    109440
acattttcaa aaagcaaaag aaaacctaag agaaaagttg aaagtaggaa ttttttaaag    109500
aatatacgac gtgtgttctg tgactcaccc ctgcaagtta tttgtgtgta ttcccttgca    109560
tagtaattaa taatgaagca aagcatggca atgatatctt tcttgtcta  gtattctaga    109620 agactccatg ttttggaaa  atatcactct agttagatct caaatatatt caatcagaaa    109680
atgggttttc tacaagattc tatatctgta gtcaatagca aatataattc tattaagcta    109740
gtaggatgtg ataggaaact aaaacctagg ggagaccaaa gcaaggaaaa atacttcctc    109800
atccaaactt gagagcaatt taccgtcagg cctactatta atagatggaa tacagattcc    109860
attttcatta ctcaactgcc atattcatta ttacactgta cagaaaaggg aatcacatct    109920
gttgaaaact tatatatgat gttcatgcat gcattccagt aattcaacaa ttttttattta   109980 tcttttatt  gcttgctaat ttttcaaaat aataagctaa agaaaacaaa atgtttgtgc    110040
tgttctcaga tgacatgtta tctctttaaa ggacaaaatg tgctgtgaaa taatagaatg    110100
ctttcagcac tcaagtgtga gtgagtgctc atacatgaga gaaagccgtg gggactacag    110160
aagccaagaa gcagatctag ctggggaggc cttttgcagag gatgtagttg tgtggagagg    110220
ccacacacgt ggaattccca ggagggctgt ggaggcgggg aatctgcagg aaagcactgg    110280
ggtgagaaac gtgatgagaa acaattattg tcttaaaata tctgcagggc tgtaaggtag    110340
agaagcaata cgttgcatct gtgttaagtc aaacaaaatt atcaagggac tggtttcagc    110400
ttaacataag gaacaattat gtgatagggt tgtcaataac aagagtagac tgcttcttca    110460
cacactccta gtcactcaga atggtccagg aggagtggac aaccatttgg tagagtatgg    110520
gaaggcaggg gccctgggtg ggagtggtga gggtagggag tgagtatccc aatctagaag    110580
taaattgtgc ccagcacgga gctgcaacac tgccctgcac acaaacacac acaaataaca    110640
atccccagcc cctgcatttc cctctccggt ttcaggacct tgtatcttac ttcaattcct    110700
ttatttagct gatgatgaaa taggaagagc ttagcactaa gaaaatcctt ttggagtttg    110760
gccttggggg aaaatgaatc actccaacca ggtctgtctt ctagaaagta taggatgaaa    110820
gggctcctca tcacatactt cctgacctcc tgctaggcct ttccctaaaa caggggctgg    110880
```

```
caaagcacaa cctgtgggtc acgcctagcc tgccacctgt ttttgcaaat aaagttttat   110940
tggagcatga ctatatgtat ttgcttacag tctgtggctg cgttcacact atcccagcag   111000
agttgaataa ttgggacagg gaccatatga tgggtgaagc tgaaaacatt tactctctgg   111060
ctgtattcag aggaggttta ctgagcccct ctctgagaca tggcaagcgc tgcttcaggc   111120
tcatgcttca ctagattcag gcctggggca gtaaagagcc agctcaggat agcactcccg   111180
actcactcat tttttcaggc aggggagcca tctaatgtca agtgcctacg tgcaggaact   111240
ggtctgttaa ttagcagctc tcctcatgga agggataata tattctagaa acaggagtgc   111300
ggccctattg caagaatgtc ctgagccaaa attaagattc ttctatggca gaaacttggc   111360
tggggcttct cctgagttaa cttggtagtt gttagtgatt tttgagtcag tttttccttg   111420
tcaacgaccc caggaatgag tttgggatta caggtagcc agggaaaggg aaagcttcac    111480
gcccgccccc gggacaaggt ctgtcttcac actgctacat cccttcaccc actttaaaat   111540
gaaacttaaa aggaggattt cagttgagta ggaagtgaga agagggctca ttttaaaaca   111600
agcgttaaat gaaaacccac acacactcag agcacacaaa tccaaccacg cttacaaaac   111660
catcacagag ggtcaggcga ggccctttc taaatgaaaa agaacagggg tggagactgt    111720
tctgagagca tgctgggttc cctgaaggga attctcagct gtatgtgccc cgcacaggat   111780
ccctgctaga cacaaggcca gctgccttcc tttcaagccg cagacgcatc cctgtgtcca   111840
ggcgggctgg tcagctgcgg tcagcaccag cttccccgct ccatggtgag gtcatcacaa   111900
catgtgagca ggagggcagg ccggcaacct ctgagtgctt agagaaaggg acgggattcc   111960
tcctgtgcaa cccctctagt ctcactcaga ctcaagtctg actaaggggc caggtgcttt   112020
gaccagggac tctcccctct cacttccctc ccaggagtca caggtacatg agtccttgtt   112080
ttacaaatga agaaaacaga cccaacatga ttaagatgtt gccttcatag gggtggcacc   112140
aggattccaa accatggact ccactgagcc cagtgcccac tgacatgtgc cagtaacagt   112200
gcagctgcct gtggttctgt cgactaaact gccggcagag gctggctttc caccttcttt   112260
tttttttttt cactcttcaa acactttatg acatgaacat aaactactgg ctgcatcgtt   112320
ctgctgacaa catgacatgt ttctataact tgaaaaagc aagcagtgga ctgctcattg     112380
gtaaaattga gtcagtaatc ttttaggaag gttattttc ttccttttac tgcttctcat     112440
ctgttccccg cagtaaagag gacaagatga cgacgactca gggaacacct ccagcctgaa   112500
gcagcaccat gcgagcttag accttagggt cggcttagaa accacaggcg gggcggcttg   112560
ggccctcgg acactccctc tcgaagctgc ttctccccaa gctacccaa aggcactgag      112620
cgccctctgc cccccagcaa ttcaattcac tggctgtcct gctcctgtca gtactgagag   112680
ttgcatgttt gaccctcggg ggaaaagtcc agaggcctg gggtgtccag catgctctga    112740
ggtccctgct gctgaccct tgcgctgtca gcattcagag acattcacac agcacagcct     112800
cccaggctaa cagctgtcat ggaacagtgg agcagctaga cgtggccatt ctgtggccca   112860
gtgctgcaga ggtcaaaggg acaagcgcag ggagcatctt tgctttcaga aaaaaaaaa    112920
aaaaaagaa gcacactggt gcactgacct gctcctggtg tctttgtgat tgctcttttc    112980
tttcgatttt tggttgtctt ttttttttg aaagaggggc tttatgctt ttttcctaat      113040
gttcatgggt aaaccaatgt aaatgtgtgt atgtttatag atggctttt aaatcgcaat     113100
tctgcagtag agattgattt tttaaaaaac atgggtaaaa attgaagaaa attttaaaa     113160
gaacatttaa accatcttgg gctagggtg gatatgcacc accccacgga agccaaacaa    113220
aatctctctg cagataaaca tttgcaaaaa gaatttccaa tcccaatttt tgagtcagag   113280
```

```
atcttttatt tccttgcaaa ttacatatct gtttcaggat ttttgactat aagaagaatg   113340
aatgaagatg tgtttcttac agataactat gaacaaacca ggaaggataa taacttgtat   113400
cccccaattc gaatccagag gatgggaagg cataaaaaaa agaaatggaa gaaactttat   113460
ttttagtggt aaatggtggg actatgtatt ttacgtatgg tgaagtcacc aagcccaaca   113520
cttggcactt gtaggcaagg tagtcttcta atctgaatgt gaagtattat gttttcattt   113580
gcttggtaat gaggaatatt ggtgcttttcg tcccagttct cgagctgact gacttctctt   113640
tctgacgtgt gttcctttag cacacctcta cactgcatgg ctctgagatg tcctgtgact   113700
gtttcatgtg taaagttgcc tccccaaagg actcacatat tccttcaggg cagtgagtac   113760
ttctgattca tccttagcag ctaccttcgc gctactttac tagatatgtt gtagttgaat   113820
taatgaacaa aagaacaagc aactttggtg cctggtgtgc atctcagagc agggtggagt   113880
gagcctggcc aaagggtcat catgcaacct ctgtggctga ctccatctgg ccacggagct   113940
tctcagccat gcttggtatt cacatgactt ctagggcgac agctcaacca gcaaataaac   114000
agcttcatat gggaaatatt actcagcctt tgtcatcaag gagtgagtca cgggcctgaa   114060
ctgaatagaa gatagaggag aaaaggtgtg tggactgggt gagacagcgc ccagcgaggt   114120
gaactcccgg cagccctgcc tgtctttacc tgcacatcac cttgctaggg tgccttcggt   114180
tgtgagggcc tgtctaggaa gagaagagtt gcaccctggc aggcagcact gagctgtctc   114240
atgcaaagct gaggaagaaa gagtgagctg cccagtgagc ctgctggggt ggtggaggct   114300
gggctgggct gtgcagtctg cagccccccag cagcccttgg cacctttcta ctgcctggtg   114360
ctcaccagct ctccagtaac aaagagggac gtgaagtcag aggggaaggg aggtagcaca   114420
gggcagtctt gactttgaac aaaagagctgg cttcctgaag tcagctggcc gggttttgaa   114480
gccgattttc cagcagtgat ctttgatgcc aaccccattt aggaattctg tatctccccc   114540
taccttctac cagatgtctc tgagctcacc tttggtgata atcatgcaat ctccgtcatc   114600
cccacgtcca cactgcccca ttctgtccca ccccgggttc tgtggtgctg tcggctcccc   114660
agcgagccag gaagggagag gccagctctg ctggggctcc tgccgccctg gctctgcact   114720
gcccttctct ggcaggtctg aggcgccact ggaggagcca cacggccctg aagcagcaag   114780
gcagatgccc tggacacagt ggaggcacag agtgcaagca ccggcctggc ccacagactt   114840
ttggagggga agtggtatta ttcagttcaa aagtatgcct gtgtgtaaag agagagcccc   114900
tgaacatgag taagcaaaag tctcagcgca gagattagac aagtagaatg ctggcccgag   114960
aggaggcgtt tactcaccct ctgtctagga aggaaagcca ggcccagcac gctcactgct   115020
atctatcctc tcacacagag ggattttgaa tcgaagccag catcctgtcc tttctccaat   115080
gtcccctgct caggagtcag gactcagcaa ggcccacccc agccacacac agatacagtt   115140
ccaggactca gaactcagcg aggcccaccc cagccacatg caggtccagt tccaggattc   115200
aggacacagt gaggcccacc cgagccacat ccaggtccag ttccaggact caggattcag   115260
tgaggcccac cccagccaca cacaggtcca gttccaggac tcaggactca gcgaggccca   115320
ccccagccac atgcaggtcc agttccagga ttcaggacac agtgaggccc acccagcca   115380 tatccaggtt cagttccagg taaatcatct gccttcctcc gtccaaaagc cttgtttcct   115440
gtgtgtcctt gtgtttaaaa tggaaacgtt atgagaaact gcctgccagg gcaaagggtg   115500
ctgcccggca cacagtaggg actcaaaatg aaactattgt attgaataca taacagatca   115560
acgggtattg ctttctgaaa tctttttttag cccaattttg tttcttatag tccaataaca   115620
```

```
ggtcaaattc atttctgatt tactagccat tcagttgccc ataaaaaatg gaaagtgatt  115680
taagattatt agtttaaaaa ccaatgaagg taaaacagtt atcattgaag cacataggc   115740 agaaatagat tgcaatagtt gctgccatgt gaagcctcag tgtcatgctc catatttaga  115800
gagatctatg atttctgagg cccttcatg tccatgatct cagtactgct cacaactgcc   115860
ctgtgaaatt cgccgagctg gccccatgtc aatcagagta cactgagcac tgagacccag  115920
catgttgaga taactggcta gagatcatcc cataatggta ccatcacaat cttcacactg   115980
tagaagtttg atgatgtcac tggaagcata ttccacagtc ccttgtgaac tggccttcct  116040
gtgatcagaa gcatcagtga actcccaaga gggtgggaac tcccaagagg tattctcact  116100
ctacttagtg tatattttac aaatcacaag cttggctttg gattctttta atggctagaa  116160
ggagaatcat ggggttggaa gtccaccagt ttgggtattc tgttccctaa ctcaaaataa  116220
agagatgtta ttttcaagtc ttctgcttgt taacttaatt agagatacat gagtttgcag  116280
ctgtgctggg catgccgcag cttggcatgt ttagtccaga aggcatatta taatgtacat  116340
ggaagattgt cagaaattca aaaggacttt ttgagtatca catgtgtatt ttcaagttcc  116400
aatatagatt cacattcagt ttgacaggta tctttggatg cctatcagtt aagaactatt  116460
tattagttgt ggaataaaat agggtaaaat aaggaacaac tgaggaaaaa acataaaatt  116520
tgctttgtga ataaaagttg tcttcaaaat tatgactttt tccatcccac aaaagttttg   116580
attaaaccca caatgaaaat ttaaataagt gtatttactt tggttaacc acttatttca   116640 ttatgactca caactatagg ttttctagtt tccattatta caaactattg tgtggtttaa  116700
atcaatttca tagactagtc tagttctata gtcacaattt ataaaattt tttatgtggt   116760 aaattgagtg tcttcataga tgtacatgat tatttctcaa tttttaagga atgtattttt  116820
taagatagcc ttctttagcc ttctttaaca ctgatttttg taaatttttt acagatttt   116880 ttaaattttt ggtaattttt tagcataaag taatacatgg tcactatgga aaacataaaa  116940
acacaaaaac tatgaagagt aaataagaaa acacccaga aatttaccat tcagaaaagg   117000
tcattgttaa caacacggtg tatcttcctc ctgtcatgct tccgtgcatt tgagcacatt  117060
tgagatgtgt atacatgttc actttgagat tttagtatag caaaagaaat gaccggtcct  117120
gattcaatga aacctctggc aaactcgcta tatttccctt acatatttt aagttcatcc   117180 tataaatgaa ctatccattc atcttatttg agatttctct aaatcttcca gcaagaaagc  117240 gggaaaaaa tcctcctctg gcctttaaag cctaattaaa tatatgacta agctagaaat   117300
attttataat gaccaaccag aaagtggcaa ggactgtcac tcttcccata cagcccacct  117360
cctcctctat ctccctcagg cacacggaaa cgagaaaggc agagaaaccc aggacaagtc  117420
atccaagact ttggtcacat ggccatccat tgctttcaca acaaaaatat aaatccaaca  117480
tgtgtgtgtg catttcatac cagtaggtcc aataagctat ctatatatac acatatgtgt  117540
acacacacac acacacatcc ttacagacac tccccagctt actacagttt gacttaagat  117600
tttttgactt tacgatggtg tgaaagcaat gcacattcaa tggaaaccat acttctaatg  117660
ttgaattttt tatcttttct tgggttagtt gatgtctgat atgttacttt cttgcgatgc  117720
caggcaatgg ctgggagcca gagctcccag tcagccatgc aatcaagagg ctaaacagct  117780
gatactatac agtggactgt gtcaccagca ttttgggat attgtgtttt gtgttttga   117840 atcctatcat gtctacaaaa tgccattttc gactgctatt ttcaatttag ggtgggtta   117900 tcaggacata accctatgga aagttgagga ccatctgtat atctggtagg gaagatgga   117960 taacaaattc ataggcaaat aataatttca tgattattat taagttattc ctacttaata  118020
```

```
ataagtagtg atcactgcca gggagcagag aatgcaggat aatgtgacag atgtaatggt 118080
gggtacttaa gctaatgtag ttgcagaaca ggcttttcta gagggtaggc ctttaagcgt 118140
acctcgaaga tgcaaaggaa gcaaagatgc gaagatctgg gctggggatg gaagcagaga 118200
caacttggag gccaagggga gagactgaca acagcccagc tcatacctca gcagcctttta 118260
atgcatagct aagaaaacaa caaattaaaa caattatagt ttacttagac gattctaagt 118320
gtctaagtgg atttgggcaa atctggagaa acttgttcta atactgtgtc ttaataagta 118380
atatagattt gcccaggctt gtgggcagag tggtatacac cccataatag cagaggaagg 118440
ccacagggcc taccctacaa aaccagaggc atttaaaaac ttaaaggagg cagattgctt 118500
ttattttcag ttaaaataaa gtgaggagtt tctcaagaaa aataataacg agaccaccgg 118560
cccgccctag atgtccaaca agaatgcaca gataacttcg tatatccact ttcctgaacc 118620
tgcccctgac agccaagtgg agcacaacaa cagagatgaa cctcaaaact actgtgctgt 118680
gacataaggc ttgctcaaga ggacagtgtg gtgtgagtcc atctatgttc taaagcaagc 118740
aaagctattc tgtagtgaaa atggatcagg acagcagttg cctctggtgt atgggggcag 118800
ggatcgactg ggaggggcat gagggatgac agttagggtt tcgatcatga caggaattca 118860
gattactcca gcatgtgcat ttgttaaagc tcatcaaatg ctacacttaa gattaatcct 118920
ctcacagttt gtggatgtta ccttaaaaac aacaatgatg actgcaaact aatattgaac 118980
tctggttagt gatataccaa tgtgaagtat agtgatatct ctactttact ttaaaatgca 119040
tccaaaggca gactagagga ccatatctga cagacagaaa aatagatatg tgataaggtg 119100
aatgtagtaa aatgctaaca taaggatgtt tgcggtacaa ttctttcagc ttttctatac 119160
atttataaat cataataaaa ttttaggaca aaaagttagt gctttgaagt cctaagtcat 119220
agggcctgct gctcttgatg cagtagaatt tgtcttcaga tttgcaaagg gtaaggcaaa 119280
ccactagcat tttgtatgga acttgatgca aatacttta attgtctggt tttcaaatgt 119340
atagacttaa agtaatatca actctttctt tgaatcaact actgaaatac ctagtcttaa 119400
ataaatattt ttatgtaatc cttaaagtac tatgtattca ttttctttc ttctttcttt 119460
tctggtttga taaatattct ataaagtaac tgtgtttaat ggccaacatt tgagtaagtc 119520
catatgcaga tccaaacatc tcagtttaga caataactta agacaatata gagtggctga 119580
catcccctaa cgtgggtcca gatgcatgtt atgttatgtt tctgttgcat tctcaatagt 119640
taactttaat aaaagaaagt caaaagctta tatattttt caatcttcaa acatttctg 119700
ggaggttgtc ttagttaatt ttatgttgct atacccatat cacagactgg gtaatttata 119760
aagaaaataa atgtatttgg ctcatggttc tggtggctgg gaagtccaag agcatggcat 119820
tggcatctgc ttggcagctg gtgagggcct tcatgctgtg tcaatctatg gtggaaggtc 119880
aagagagcat gcatgtgagg tggtgggaa gagaaaaagc gggtttaact catccttta 119940
tcagggactc actcccgtga tagctaaccc attcttacat gaatggcatt aatccattcc 120000
ttagggcaca gctctcatga cctaattata ataccctctta aagtttccac ctctcaacac 120060
tgttgcattg gtgattaagt ttccaataaa cgcactttgg aaaacacatt caaaccacag 120120
cagagatcaa cgttattgtc accattttca tatttgagga aagcatggca cagagagctt 120180
ggagaagtac ttcaaggtca cccaatgagg aagtggctaa acaaaaacct tatcttaaat 120240
taattaaaaa cctcttgctc tttgcagttt tgtcttaaat ctacctaatt tgtgactgta 120300
atttttaagt aatttactca tataagtggt ctcacattaa attttctcat tgctttatat 120360
```

```
ttctaacatg agatatttgg tataaggatg gaaccaagat cataccttgt tttaattaga    120420
aaacctagac caagtcattg tgatcctcat cctagatttc agttaaatgc tgctgtctcc    120480
ttttgggtat gtgacagggg aaagcctcag aagaaacaac cttatgtgtt ttcttttgat    120540
actttagtaa ttaacccagg atagtattca agattgacat gccttatatt gaatcaaata    120600
gcatatcaac tgccttctta ttctcaagta tagacatgtt gggtaattgg gcatttaagt    120660
ttctttgcaa ttttttccat tattaacaaa attaatgagc aacattctgc ataaggtctg    120720
tttcctcaga atacgtttcc caaagtggaa tcatcatgac gtagaattta agcatactta    120780
cttgtttaaa caaattgtcc agttgcttcc caaaatgttt tgtgaattaa gatttacatc    120840
aagaatatgt aatgttgtta ctgtctccca aatacaggat cttttctga atataaaagt     120900 tatacatgct aattgtagac aatgaagggt cattatcctc atagataatg aagtgcttct    120960
aatacttgtg ctttattca tttattcaaa aagtgctaaa taagccctga aggggctttt     121020
ggggggtcat ttggggctta tttagcactt tttgaataaa taaataaaag cacaagtaca    121080
gtttttttaa aatactgttt tctataatag attaatctta aatggcatgt tttcctttat    121140
tttactgaca aaagttactt actctgtgat tgaataataa aaattctttg gttcagctga    121200
gagaaacttg caagctgacg tccttgatta tttaaaatga aagcagctgc ctgttttcat    121260
ctctctgcat cctgaggaaa ctcttctgca acgtgttcca gccctaggtt ctagctgacc    121320
ctgttcatct gtttggcacg aggggcccaa ctaacacttg cggctacctg gacgacagcc    121380
aatctagttg gaatgagagt tagaggccat agtctgtcag ctgggaaagc agcttttatt    121440
ccaaggtgtg ccaaccgaaa ggccacatgt tattgtcaca acctggtacc tacatcagtg    121500
ctgacatctt taagaacctt agaattggga aatcagttta gccctatctg catgtgtagc    121560
cgacaaccac acaattgttc caacttgagg ttgcattcag agcaacctca tttcccccat    121620
actcctgagg aaaagcagac cagagacgct gggtcaatcc agagttatgg ttggaaaaat    121680
gatggaataa ttctgcccct ggtgatagga gagagggact ccatcttgtc aactgtcatg    121740
gttcccatgt gaaagctatc attatcactg aaattgaatg agaacacaga agggaagaac    121800
agggaaatcc ccacagagtt aaagaggatg tgaagattgc ttcatgttta atgtttgtgt    121860
aagtgctttg ggttggttat gtgctgtctg aacatgtgct catttccatg gctcattgag    121920
agggcagaca gtccaatgat actctttaga atcattccca tggggaagga acaaagaagc    121980
ctgtaaaata gaaatgcaca tgtaaaaagc attgaagaaa gtgccagtgt attgattttg    122040
gccatggttt gtgctctacc acctggttac tgtgattgca gaagtgcctt tgcagatgag    122100
gaagaacctg gccaaggctc aatccaacat ccaaagccag aggccatatt tcttcactct    122160
taagataatt tgggttcaaa ttatagtccc tttacacact ctctgcctca aaaggcccaa    122220
gactctcttt tgttatgctt gcctaaacat gcctttcaaa gaactagttc tgtaaataca    122280
actttattat aaacctctcc tttgctttta aaaatggatc accacgtcca tttctatggt    122340
ccaactttgt cccttaattt aaaattttt cttggattaa gttgatgcc ttgaaacatt      122400 aggaactcaa gcatacaaga ttgtatgctg gtggtgaggg aagtaactgt gcctccgcct    122460
gtgctgggtg gatcaacatg gagtgtggac gagcataggg atgtgtgggt ttctcactag    122520
ctgagagtgt ttttaaatgt tgtatttga tgtttgttat tttctgaata ttctacagtt     122580
agacctttga tttattcttt gatgcattca tttgaataat attttaatc tccagccagt     122640 taggttttta atttacactt ttgtccctga ttttaggtgt agtgttgtgt acactactgc    122700
ccagtgtatg ttatgtttgt aaacattcat tgcacgcaca acaatgtgac tcacaatatt    122760
```

```
tttgagaagt aaaaagttca ttatatagtt attaactcaa ccctacagtt atattcgtga   122820 ataccttgt gaaatttatt ttttgcctac tggagctctt acaggttaat cctgtcttca   122880
agattttcat agaattttca tctaccaccc acccctttaa atttcaacat ttttttattt   122940
tggcatttta atgcaattca atgcattata gggacaagct atctcttatt atgaattgca   123000
ccttatataa acttaaagat cttttatcac aaatttcttt gctgtgtcct ttagtgagaa   123060
tttgtattat cagtcactaa agctcactaa gttagtaagc tttgcgccca gatgacctgg   123120
gcaggaatgg gtgagtctct gtgtggagag agtgaagaaa ctgctaccct taatacctgg   123180
accttgaggg attgttttat tttagttttt ctgcatttct cagtatttca tgtgatatct   123240
gtcttttcct tccagtttgc caaggcacga gtaacaagct cacgcagttg ggcactttg    123300 aagatcattt tctcagcctc cagaggatgt tcaataactg tgaggtggtc cttgggaatt   123360
tggaaattac ctatgtgcag aggaattatg atctttcctt cttaaaggtt ggtgactttg   123420
attttcctac acaaataaaa ttggagaaaa tctaagtgga gaaaggcctg ggcagaattc   123480
cacttgaagt gtgtttattt ttgctatggc aatgacaagt cttacagagc tacaaacgag   123540
agttttatga gaaagccatt ttaccagcta atgtcaagta ataactagaa aaggatatca   123600
aatagaaaca ggctaatctg gagttccatg tcatcataga cactgacgtt tatccctgac   123660
cattacctca gtcatgatgt gctgccatac tcgctcttaa aaactttttt taaaagccct   123720
gctttgcacc atttgcctat tcccttagtg taaatactcc tactatagct gatttcaagg   123780
taccaagttt cactcagctg gtcacagaat tcttatttca cgataggcgc taatgacccc   123840
ataggagcca gctctgaagg cttcagagtt tcactgaatt ttggatgggg tttacttagc   123900
cttcttctgt ttttctttta cctttccttt taaataaga aataatgcaa gacagataca   123960
aagtaattct ttttaatttc cattttcact ggagagtgtt gaacccgtg aggcatgaga   124020 gcacagtgtt ccagaacaat gcttactgct cattatcaca ggggtcaaag gctaacgtgc   124080
agggattgtt gcagatcgtg gacatgctgc ctcctgtgtc catgactgca atcgtctacc   124140
tattttacag ttgttgagca ctcgtgtgca ttagggttca actgggcgtc ctagggctcc   124200
ctggacccat tttagacctt gagttcttga gttcctcaaa agagaaatca cgcatttatg   124260
ttttctcttc ttagaccatc caggaggtgg ctggttatgt cctcattgcc ctcaacacag   124320
tggagcgaat tccttttggaa aacctgcaga tcatcagagg aaatatgtac tacgaaaatt   124380
cctatgcctt agcagtctta tctaactatg atgcaaataa aaccggactg aaggagctgc   124440
ccatgagaaa tttacagggt gagaggctgg gatgccaagg ctgggggttc ataaatgcag   124500
acagcagttc cgatggctcc cagcgagctt gtcactcaat tccacctcgg agaaggcttt   124560 tattttacc cagtacacgt gcactgagtg ccggctgtgt gtaagatact gcaggggaag   124620
ttactgagaa gatggcagat actggaatgg gaagatttaa gcggggtacc agtgtttaca   124680
tggacatgaa aaaatactga gagatagtaa gaaatcgtaa agattctgag taaaagagag   124740
tatgaccaaa caagctgagc aggaatcgtg aatctatgtg tgtaggcagt gaataaactg   124800
ccagtcttat tacctggacc tcaaggataa aagacataca gtaaaaatca acccacattg   124860
aggacagttt cgagagtcgc gctgctacac agaaagccct gtgtaagtta aggatagaga   124920
atgaggtgtt ctagaacttt gaattttgt gagcaggact cgtgaggttc ctgtgagagg    124980
aaacaatgaa ggatgataga aaagaaggga aattgatttt aaaaaactgg agatagcagt   125040
gattgtgcct cactgtgcag tgggtttggg gccaggaatg ttaaattggt aacttcattt   125100
```

```
aacgcccaca accttctctc aaagtaggca ctgtacagat gcccttgac ttatgatggc  125160
atcctatctg gctggacccc gccgaggtg aaggcgtcat taggtcggat ttcagggcta  125220
attgaatgta tattgccttc acaccatggc aaagtcgaaa atctgtgtta aatcatgcta  125280
agccggggac tggctgtgct ctgccatcgt acaaataaat aaatggaagt caagtaactc  125340
ccttgagggc cccagctagt gaatggagag gccagctatg gccaccactc tctgcccag   125400
ggcgctcaac gcccctcctg tgccatgcag ttctgacagg gaggcagtgc tggtaggaaa  125460
ggggtgtgat gaaaggggtg cccagcagag ggagtcatat ccggagtgac aggagcccaa  125520
cagggggtgca gcgctggaac ccaagccagc acctctggtc atggctcctc agttcaccgc  125580
ctataaaatt gtgtggttcc cccacacccc ttgctgctca gagcagccgc gcacatgctt  125640
gtgctgtgcg tgcctcctgt gagatggcct ggtacaccgg ttcctacagt gcgcctcaca  125700
cgctgtctcg gagggaggca gcctgtgcgg gtgcctggac ctccgagcca gaccctctgg  125760
gttcctgcct ggccccgtcc ctcagcagcc agatggctcg ggagcacatt ctccaatccc  125820
tccgtgtctc tgtttcgtca tcttcaaaaa tgtggatggc atagctgcta aaaaatggtg  125880
acatacttcc taggtggtgc agaaaattaa gtgactgtag gaacaggcct cagcagctcc  125940
ttccacttcc ttggtatgat tgtttttttaa accaaggctg ggattgtata gatgcagatt  126000
agttaatgtg ataccattaa tagctaacct agtgcctgct gcagggtgag cctcccctaa   126060
gccaccggga agcggctcct gcagcctccc tcacgtgtgc tggccctcct ctggcagtca   126120
ttgcctgtgg tgtgctgaag gcccagctct gactgtgcct ctgtgctctc ctcgccccgc   126180
cccctgctct ctctcaggtc tttggtctgt tgtccgagct gccacagcag cctggacatc   126240
cctgttggtg tttccagccc tgtcctctcc tgagttccat ccacctgtgc atggcttttt   126300
catgagtgtt ttcacggatg ttctgctgt catctccaac ctgataaaca aagcaccacg    126360
attcagccct tatgacccca agcttccttc ctcagttcct tgcttctgtg catccactga    126420
agaagcctgt tccactgttt ccctgcactg ggtctcctgt ctgcaggaag ccttcagccc    126480
tcacttccac actcctctaa gatgtgtgcc tgtgcccttc tggggaagct cattttccta    126540
gcagcctcca ggatcttcag gggtgaatcc ctccttttccc acgttggtac tctgtacaca   126600
caacatgccc attccctgcc tggggagctg ggcattgctt catgaatcag aggtcaattt    126660
tttctctatt aaagtcacag atgctcattg caccattgtg agaatgaatg aagatagtgc   126720
ttataaatca gccagcaagg tacccagcct cactgtgtca gggtctccct gggcatgagg   126780
tggttagagt gtgtgacatg tctgtcccca agctgtcag ctcccagatc gaagccagtg    126840
gatctcattc atcctcgcag cgcccacagc acttgcacag ggttttgtac acataagtca    126900
ttctgtcaat gttcatgttt aatgtcatca gtggaacact cccactttgt aaagacttga    126960
atgtgttcat ccctgacttt tccacatctt gttagttctt ctttggaaac agctgtacag    127020
tttcaccatc ctgtgcatcc ctggagtcta cctgtctctg tcatacattc agattcttct    127080
tgtttcgtgt cactctcata tccttttctc taatgaaaag ctccgcctgg gcatgcaagg    127140
tggagccctg gatgccagcc cctcacctgg catccagggc tgtagcactc aggaactgcc    127200
tccctgccct gcctaccccc tacatcatgc gaccattcca gtccagccaa tcagcccctt    127260
gggacccagc ttaccacatg catatcattt atgctgtgac cactgactaa accattctct    127320
tccttcctcc ccatatttct aaatttctaa tcattgctca aagcccaatt cagagaaaac    127380
cctagctcct ccatggcacc atcattaaca attttatctg gccgcccccc gggaagttca    127440
ctgggctaat tgcgggactc ttgttcgcac catggcatct ctttagcaga acataaatgc    127500
```

```
gaagagcaca tgcatccttc atgggaattt aaaggagctg gaaagagtgc tcaccgcagt  127560
tccattctcc cgcagaaatc ctgcatggcg ccgtgcggtt cagcaacaac cctgccctgt  127620
gcaacgtgga gagcatccag tggcgggaca tagtcagcag tgactttctc agcaacatgt  127680
cgatggactt ccagaaccac ctgggcagct gtaagtgtcg catacacact atctctgcct  127740
ccagctccta tggggacag ctctacagca ctggggcagg ggagagaagc catgtttagt  127800
aagtcacatt aatcagaaac aaaaagtagt aagcaaaata tctgaccact agaaaagcat  127860
gtatttacca cggacataga gatcgttttt ttgtggcggg tggcagccca gctggttggc  127920
agtgcaggcc accggaggca gatccctgc agggacagca gagcacttgt gtcctgagaa  127980
gagctgctgt tcatggggct ggcagcacca gggcctctcc tagcctgccc tgctgacact  128040
ggccagactc ctacatgctt ctgagtctcc agaggctacc cggccctcct gaagcaccag  128100
ggctgaatcc accccagct gagggcatga acactgccac atggagtcac acacacagct  128160
gggcactgcc atggagagga agtctgtcca tgtttccttg aatactggtg gcctggtccc  128220
tgtcccattc cccagtgagg cagcctgtgg ggaagcctgg cagggaacca ggcgcaggtc  128280
agcgtggcgc cctgactcag gccagcactg atgggggact ctgagacgca agctcacact  128340
cacccagctc ccctgggctg cgcccgttcc tgatcgcttg gactttctgt tctttagagt  128400
aagaagtgat caccatttcc tgcttctttg tttctccaca actgtgcagt ggatgcctgt  128460
ttgttttctg ccctcagaac aaaaaaaaaa aaaatagag ctgacgtgaa tcttcaaaat  128520
catcaactac agggctttgg attttgtgt atttgtttta ttttcatttt atggatggat  128580
tgtgatgaaa tgcccgtaat acaagatttt ccatcttaac cattgtaagt tacaatgtca  128640
gtggcattat acatccacat gggtgtgtgg ccatcaccac cgtccacaca cagaactctt  128700
ttatcttgca aagctgaaac tctacccatt agacagtaac tctctgctct cccttccttc  128760
ccagcctctg gccctggcag gcaacagtcc acttgatgtc tctatgaatt tgactgctct  128820
ggggctctca tacaggtgga atcatgtagt atctgtcctt ttgtgtctgg cttatttcac  128880
ctagcaaaat gtcccgaagg tttatccatg ctgtagcacg tgttaagaat gtccttcctc  128940
ttcatggctg aataatattc cattgtatgt tgacactaca ttttgtttgt ccattcacct  129000
atctacagac actggggttg cttccatctt ttgactgttt gaataatgct gctgtgaaca  129060
tgggtattga ggctctttgt tttatagaca tattattcca ccagatacc atcctgacac  129120 ctactatgtt tgcaagaaac tgaaagcttt attttacatt gcaaatttc atattatgag  129180 atcaaggtta gcatttcctc agctgtctgg tggacaatgg ggaggttaaa ctgtgcacat  129240
tttatttttt tttaatgaac ctggaacggt tatgggcca gtgtttgcca tggatcaggt  129300
caggcagccc acaatggcag gtctccatgt tctgtacaac aactgtggga agacccaca  129360 gagaaagtgc tggaaagggg aatgatgggt aggttcatgc agtaaaaaga ttcaaatact  129420
acagggcatt gaactatagg ccaatatagc attgctttaa gaataaacaa aaataagac  129480 agtaagaata agcctagcaa atcaaaagt ctataaagaa ctgacatttc aagccaataa  129540
gagaataatt ccttattcaa taaattgtct ggaatgactt aactattagg ggtgaaaata  129600
tcaaagtgag agaactataa agggttttta aaaggaatt aggtatgttg ggttagtcgc  129660
attggagagt gcaaattcac catcgacctg atacctgaaa tttcctcctt accatctaga  129720
ggcaagttgg gaatgctgcc aggctcctgt ggtaaaggaa gctcctctct tgactggtgc  129780
tttatggcta cacgttcctg ctcagaatgg atctcattta gtcttcacca aaaaaaaaaa  129840
```

```
tctcatgaga tgatttaagt gttttatgga caagatgtct aaaactcaga aaaatttcac  129900
agtgtgccta gcttttatgt ttatgttgaa gttgggcatt agaagttaga atgaatgggt  129960
ttacttcaga gaaaattaaa tccatcaccc actccttgta ctatgaattc caaatacata  130020
ttaaatacat ataataaaat atttaatata tatgtaagtg ccagaaggaa acataaatat  130080
gaatattttg taatatcaag ttgaagaaaa gccaaaatct gacatcataa agaaaactt   130140
tcaagtaaaa tatgttaatg ctaccagga aaatattgtg caatgtctga ttgccatgaa   130200
gagggttaat atccttgcta tatcactctg tgaagtcatc tttaaaagac taagaaaaag  130260
atgaatctct taataaaaac ctggcccaga acatgagcag cctctctctc tcactctcac  130320
tgtctctctt tctgtcacac acacacgc acacatacac acacacac aaatatggcc       130380
aagaaataaa gtaaaatgtt atttctaatg taataagtag gtcaaaatag aaaaagaaag  130440
catcacacct tcctttgcaa agtatttggg ttccttttgc ttttaaacac ctgggtcagc  130500
tggggtgtcg agaaacagaa attctcacgt tctgcttgtg ggcatatatg ttaataaaac  130560
caagcttggc aatatgcctg caatatgtat ctaaagcttc aaagtatgta tagctttgac  130620
caatcaatat cacatttcgg aataagagaa aaagaaataa tgaaagtgaa aatcataaga  130680
gatgtagaaa catattctta tacaagaatt ccttgcagcc ttatttataa taaattttgt  130740
gaacaaatta tatatctaaa aataagagat tggttgaaaa aattatgcag cagccatgct  130800
attgataatc atgttagata gaagcatatt taaaggcatg gaaaaattgc catgttttat  130860
atgggttttt aaggttataa cacaatgtat agtgggattc caattcctgt atatacatag  130920
acttatatgt ctatattgat taactctgga tgagtctcat gtcttctttt tgctttcttc  130980
tattatccat attttatacg atgtgcctgc atttcttttt tgtaacagat ggtcaatact  131040
agaatcataa acagatcttg tttgtttatt ggcaaatgtt tcccgttaga aaagatgca   131100
ttttcttttt aaatatttt atttttataca atgattacaa gcttataata gaaatttgaa  131160
aattatatgt gagtacaggg taaaaagttg aaagaatggg attgcacgct acagatctag  131220
ctgcttttag cacgcctgcg taggaccttg cttttctctag acctctgttg cagtctctct  131280
gcctacctcc tcacaacgtc catcccccgc ggtcactgtc gtgatgccag cctccccggc  131340
cttcatgtct ctaaggagca ccagcgcggc aattagcgcc cttttgccttg gtggtattct  131400
ggcttcacag tcacatggga gatcaatcgt cagcttttct gtttgaaatc taaattcttc  131460
ctgactgcag gggacctcgg gacccatgaa cacctctagt ttactatgtc ttcacagtaa  131520
aagatatctg catgactgga ctctttaaca aatttggtgg ttaacctact cttttctatat 131580
agatatagca cttcgacctt cagacttctc aatactgata aaagaaaac acgacagatg   131640
acaggaaaac ctttgcagct ataatttgta atcggccaat tataaaaact gcaaaaattg  131700
accagatagc taaggtttta cacagtcatg aaagtgatct gcactgttaa catttcaccc  131760
tctgtgcacc attctgtgct tctctctggt ttggagtcta gaaggttta tttacaggct   131820
atgacttaac aatcccagaa cggctgacac atgcagtcac tcaagactgg acacagcaag  131880
gaagtagtgg gtccatgcca aaggctcagc cagacgagac actctagctg tggcaggaga  131940
tgccagggaa tgctccaagc ctaagcagat tgtaaacaag gaacctcaaa ttcatgaaaa  132000
attcttgctt atgtggccca tgtcagtaat tactctctgc ctcagtttcc gcagctgaca  132060
tgtaaataaa agcagttcat ggttcatctt cttttcttat cggggtctca agtgattcta  132120
caaaccagcc agccaaacaa tcagagaata agttgaaaag attgtcttca tttattgaat  132180
gtgcttaact caggcccggg aaagggcgtc atcagtttct catcatttca ctgagatatg  132240
```

```
catctattac ttttacattt caggccaaaa gtgtgatcca agctgtccca atgggagctg   132300
ctggggtgca ggagaggaga actgccagaa acgtaagtca gtgaacagcc tcagacccat   132360
gtgtgaccgc ccctctcttc cttcacttgc ttaggtgatt ggatttgttt tccctctgaa   132420
gactccaaag agttacttta ttacagggtc agatgtgaac cagtaggtga aggacagtct   132480
tgcaaatctc accgcatgca gttaatccag ggtgggctat tttgggagct tcagcctatc   132540
acaaataagt gaacatcagc aggggctggg cgcggtggct caccccctata atcccagcac   132600
tttgggaggc ggaggcggtc ggatcacgag gtcaggagat cgagccattc tggttaacac   132660
agtgaaacct cgtctctact aaaaatacaa aaaattagcc gggcgtggtg gcgggcgcct   132720
gtagtcccag ctactcggga ggctgaggca ggagaatggc atgaacctgg gaggcggagc   132780
ttgcagtgag ccgagattgt gccactgcat tccagcctgg gcgacagagc gagactccgt   132840
ctcaaaacaa caacaacaac aacaacaaca ataagtgaac atcagcaagt accccagccc   132900
tgtcctctga acacagcaca ctttcccagg aatggaagac ttgctcctgt tgacagcagt   132960
caccagactt cttgtttcct ctccctccct ggctttcttt ggtacccacc tacacagaag   133020
cctgagcacg ggttctcatg ggacttttc catgtggacc ctgctttacg atggagaggg   133080
ccattctcct aggtatggtt gtctggctca gcctctcagt ggccaaggaa cctggggaca   133140
tgagctcaaa aacggacact atgtccttaa gctgaattgt ggggggggctg ttaggccctt   133200
ctaaacacta cttcccagca ggtatttttg ttctttgtat gtgctttctg cattgcccaa   133260
gatgcatcta attatttagc aggtctcaaa gtctagactt gatctcatga gttctcttaa   133320
gtgattaaaa ataaatcagg agaaaaaaga ggcaatcaga aaagggcatg gtttgactta   133380
gtttgaatgt ggtttcgttg gaagcaaatg tgtcttcact ttttcatgaa aaagtctgca   133440
agtgctctgc gacatccctg ggaaatgatc ctaccctcac tcttcagctc acagggaacc   133500
tttgctcttt ttcagtgacc aaaatcatct gtgcccagca gtgctccggg cgctgccgtg   133560
gcaagtcccc cagtgactgc tgccacaacc agtgtgctgc aggctgcaca ggcccccggg   133620
agagcgactg cctggtaaga tgcccctcca gcagcctccc tggagcaggc tgggctgca   133680
cccgccccac ccacaccagg acagaagact tcctgtgggg gagctgtcaa ttagcatttg   133740
tcataacaga caggatattg ccctctgcct ggtgacaaag tatctttagt atcctgcctc   133800
caccactcac tgagaccttg ggaaaatgat gggactacca tgcctccatt tccttacctg   133860
acaatgatgc ataacaaagt ctctcccagt tgaatgctta aatgatgaga tgcctgtgat   133920
gtccgtcatt aggacctggg cacagaacaa gcactaaata ctacatgcaa gtatttgtca   133980
tgaatgtgcc ttgttgccag cagcacactc tctttattgt ttgacttcgg ctatacctct   134040
agagacttga cactgtgagg tccctaagag acccatggag agccacacag gtcttgctgg   134100
ctggggctgg gttagggcct cctgacacgg atccctcggc tcctccacca tgctcaggc   134160
acctcctgag ctgcaccctg ccctcaaggg gtcctgaagt actcactgtc gccccattgc   134220
tccagaaagt gccagcagaa gccttgctgc cccagcgggc tctgagcagc actggagggt   134280
acaggtcaga agcgtcttgg aagtcctgga gacgccaagg ctggtggatg tgactcctgg   134340
agtgggagct ggtgtgacga agcccttcct aagactaaat ccagagcact ctgtggtttc   134400
agagaagatt cctaaattcc agagtttgga cccagaccca ggaattgtga cttggttggc   134460
ctgagctgtt tctaatgtga gccccaggga gaagactgtg cgtggggttg gtcctaggaa   134520
aagccctcgc tgtattgggt ctggctcctt tacacggcat tgttctagca aggctttctg   134580
```

```
ccattcagca atacattata aaatataccc tcaattgtac tttataaggg aagcccaatg   134640
tcctttataa gggaaattaa acataatttc attccatagt caccgctata atgtgtgaac   134700
tccatcatct atacgttagt aaacagacgt atttttatca taatccataa attatgatag   134760
gtgggacagt gcacctaaga aaaaatgga cttttagag aagggtcttt ctgactctgc     134820
agagggcgcc agctgggttt tcccacacta gtggaacact aggctgcaaa gacagtaact   134880
tgggctttct gacgggagtc aacaccgtgc tgcgcttcct ccgtgtgtgg cgctgagtgt   134940
acttacctca cttgcccagc gtgtcctctc tcctccatag gtctgccgca aattccgaga   135000
cgaagccacg tgcaaggaca cctgcccccc actcatgctc tacaacccca ccacgtacca   135060
gatggatgtg aaccccgagg gcaaatacag ctttggtgcc acctgcgtga agaagtgtcc   135120
ccgtgagtcc tcctctgtgg gccctctaac tggtcaggca tccttgtccc gctctgtctc   135180
ctgctgagcc ctggagtatc ccatcttgga gagtctttgg gtggatgtgt ttgccttgct   135240
tggaggaggc gaccctgtgc ccgtccagge acacaggcga ggggaggggc tggcttgcta   135300
ccgaggagcg ggcaggtggt ggccatctcc acccatgggg gctgctcagt gcacagggca   135360
gatctgggtg gccaggccac ctcacaggag aaacacctgc tgctcagccc tcaccactca   135420
tccagcagcc acagccgtgg gtattcagtt gtctgctggg cacaaagccg tgggcatgcc   135480
actgtttagt gcttgtgcca agcaggtatt taatacaccg aaatcagaga gtctatcaga   135540
agacctgcct tcttgagtgg ttaaaattct agtgaaagtt atgcctctta ggagtattgc   135600
agaggttttg tttttgtttt tattttgttt tgttttaatg gtttgggttt gagttttgct   135660
tgtttgtact tacatttgta ctggtggctc cagggtttag ggaaattgtg acataaaata   135720
attcctgaca gagaaagcaa aactttgtct aatgaaagag ttttagaagc cactcttgat   135780
ctctagaagg ggagattaac tgagaaaaaa aattgaaaga acaattatga gggggagatt   135840
ttaccctgcc agatttgtgt acatgaaaaa ttttacattc cgtatggaaa aaaaaaacac   135900
aaaataataa gccattataa ggtaaatgac aaacaaagct aaagaaaaat gtgccacagt   135960
gatgacacag atatatcttt gagatagggc ttaacagagc tttaaaatcc ataggaaaac   136020
acttcgagcc tgagatacca agagcagatg gttcacagaa gaatcatcaa tgtcctataa   136080
atatttttga ggatcttctt ggggaactta aaacaggaac aggccaggca cagtggctca   136140
ttggctcatg cctttaatcc cagcactttg ggagactgaa ggggctggat tgtctgaggt   136200
caggagtttg ggaccagcct ggccaacagg gtgaaacctc gtctctacta aaaatacaaa   136260
aattagccgg gcgtggtggc gcacgcctgt aatcacagcc gctcaggagg ctgaggcagg   136320
agaattgctt taacccagga ggcggaggtt gcagtgagct gagatcacac cactgcactc   136380
cagcctgggt gacagagcaa gactccatct cagacaaaca aaaaggaag acatagagct    136440 cctaaaaata acgcagaagt ctgctattaa tacaaatgaa ttactttaaa ggtgagagca   136500
ggtggaggag agggctgagg tgcctgctgg gacgcaaaac agctggcccc tcaagggacc   136560 cagtgttttcc tgccatgatg aaacacctgt attgtccaca ttgcggccta gaatgttatt   136620
aaactcttga acgggattcc ttctctattt gcaacctttc attctttgtc cttaaagtaa   136680
ataaagccaa aggaggatgg agcctttcca tcaccctca agaggacctg gaccgcctgt    136740
gtgaggcccg agcacctggt gccaccgtca tcaccttcct ttcatgctct cttccccagg   136800
taattatgtg gtgacagatc acggctcgtg cgtccgagcc tgtggggccg acagctatga   136860
gatggaggaa gacggcgtcc gcaagtgtaa gaagtgcgaa gggccttgcc gcaaaggtag   136920
gaagcccgcc ggtgtgcgga cgaggcttgt tctcggctgc tgaggctggg ctctcatgcc   136980
```

-continued

```
acctccaaag gaacacatct tcctcttctc attaaaaaac aactatacat atcgtttctt 137040
taaaacagaa gataaagctg taaagctagg ttaggcaatg ggaaggcact gaaggttgtg 137100
acggggtggg gggctctgat gagaacagtc acagagccag ccccgctcag cagctgccag 137160
gtgcccagcc ctggggagaa tccagggaag gcagagctgg aagcagtgca gctccaagcg 137220
gcccatggga aataatgagg agaacgcaag gtcagtgtga ggtgacaggg atggcatctc 137280
ctacaccgcc gtagcgcccaa agtgtactat aggtcctggt gtccccctt ccgcctgca 137340 ctctccccag cccttcagt gtttgttgag tgaatgaagg atgatgtggc agtggcggtt 137400
ccggtgaccg gaattccttc ctgcttccct ctgcctgtgg atccctagct attcttaatc 137460
caacaaatgt gaacggaata cacgtctctc ttatctctgc agtgtgtaac ggaataggta 137520
ttggtgaatt taaagactca ctctccataa atgctacgaa tattaaacac ttcaaaaact 137580
gcacctccat cagtggcgat ctccacatcc tgccggtggc atttaggggg tgagtcacag 137640
gttcagttgc ttgtataaag aaaaacaaaa tctgccttt taactggtag agattggtga 137700
tcaataatca ccctgttgtt tgtttcagtg actccttcac acatactcct cctctggatc 137760
cacaggaact ggatattctg aaaaccgtaa aggaaatcac aggtttgagc tgaattatca 137820
catgaatata aatgggaaat cagtgtttta gagagagaac ttttcgacat atttcctgtt 137880
cccttggaat aaaaacattt cttctgaaat tttaccgtta atggctgatg ttttgatatt 137940 tttcaaagt gcagtttctc ctgcaggcaa aaggggacac gttaagtcca ggcttgggtc 138000
attcactgcg gtgtaaacac gctttctccc tcccgcccgg ccccagccag ctgccttggt 138060
ggcccataac ccctgagggt agaggaggg acagggta ggtgacaggc agcctgggcc 138120
tcaggctttt gaaactggac gccagagcct tgtggggcca cgggcaagcc tcgggtctat 138180
gactgccgcc tgagctccgc ttccttcctc tctaaaatgg gaagattaga ccaaaataac 138240
aagactgttt taaggttgga atcaaataag gaaaatttgt aaagctcctt gtatgtgata 138300
ccagatccac aattggcaga taatcgcagc aggagcctct tcggggtaat cagatacgcg 138360
gcgcagcagg ggtctcaggg ccacagccag ggggcggcg ggagacatgc ggaatcgcag 138420
cggaaggcgg gaggcagctg tgaactgtgg ctcggcctgc gtccgccctg cgcatgtaca 138480
ctcagagaag atgataatga aaagaaagc aaatccaatt ttcccactta ctgttcatat 138540
aatacagagt ccctgagagt ctagagtaat gtctcataca aaaagaaac tcctacgtgg 138600 tgtgtgtctg aagtctttca tctgccttac agggttttg ctgattcagg cttggcctga 138660
aaacaggacg gacctccatg cctttgagaa cctagaaatc atacgcggca ggaccaagca 138720
acagtaagtt gaccacagcc aaagcctggt agattacatt tgccttttta gttggaaatt 138780
aggcttaaca ggagagttgc taagataggg cacagagctc ctgcatctct cgccggcatt 138840
cccaaatgct atctcacatg agcaggcaca gggagcaaga ctgcacgacc actggcacag 138900
gctgtccgct aaaccacaga cttctcagcg ctcgccagtg cttctgcttc tgtgtccact 138960
ccagatccca cattgcactt agttgtcaaa tcttttcagt ccatttctaa cctatattag 139020
ctcctgtgtc tttccttgtc tttcacggcc ttgacactta caaaacgtgt gggtcaggta 139080 cttttgcacac tgtctaacca tgtctgttca gctggtgttt tctcaggatg caattgaggt 139140
tatgcacatc ttatcacagg gaccagagag acttttttagc accactcttc aagaatttcc 139200 acttttcag ctttgacagt ggaatagaca tgcaggtgct cacacacaag catctttaat 139260
atggtaatgg taatcatcag tttagtggtg tggaggagga gatgggaatc tcttagtgaa 139320
```

```
acccgccttg gaagcagcct cgttatgaga actgctgccc ctacttgact cttaaagcac   139380
tagataatac tgtgcaacat taaagagaat aagagtgcgt gaaatatgca ttgcctccca   139440
taaactccct tggctctgaa tctctgatac taaatatgtg gctaccgttg cttcccagaa   139500
aggccttttt gctctgaatt ctctggaatg ctttctttga ccaagattct tataaaaata   139560
agagatttag agcaatttc ttggatggct ggtatgagcc agttggctta gttgtaggga   139620
tttaaacaag ataaggtta cttactttc acatttaatg agaagtctgg tgattccagc   139680
tcctactgag acagggtggc cacacgttcc agggtgtgac tcactgaggc cccagacctg   139740
ccctgcaagg aaaacctggc tctgccctgg tgtcctggcc tccctgggca tatgtggggg   139800
agaattccta atggtattgg ttacaggctc ctatgcgaga ccactcatct gtgtaggaga   139860
aaggaaaaag atgggggaaa gaagagcagc agggagagga gaagcctctg gatgatactc   139920
taaccccctg ccatccaaca cctgaacatc agtctcttca tccagtgctc tcagctggcc   139980
cagcccccag cctggggtca gatgagagct tcctgcaaat gcagatctct ttcctgtggc   140040
tccttctcaa ttacagacag ctcctccaca aggtgcactc tggccttgtg ctccctcccc   140100
aaaccagccc agccctccca gcctgcatca tcgtggtcct gtaggggcta gaggttctca   140160
cacccatcgt ggtctggcag aggctggtgg ttctcacacc catcgtggtc cggcaggggc   140220
ttagtggttc ttatacccat cgtggttcag gaggggctag tggttctcac acccatcgtg   140280
gtctggctgg ggctagtggt tctcatgtcc accgcgtgct ttcctgctcc tccaggtggc   140340
tgaggacatc ccccttcgg tctgaatgac ttccatccag tcatctgata tacacattgg   140400
accacccaat agcatcctag tgtcatgttg gatggtgaag aaaatgccac agttactgct   140460
ttcagggcct cacaaccttg ggcatagctt tttggaggaa ggccccactt cccaggcatc   140520
cctcccagac ctggtcagag gcccctgctc tttgcttcca tgttgcccac actcactgtg   140580
ctcttcacac cggctcaaaa tgatctgctt acggggttgt gtcaccacca gatcaagcgt   140640
cctggagagg aggaaacata tttaacctgc acagaatttg ggacagagaa cctcagtgt   140700 ttgttcaata aatatatgaa tggatagagg gacaggttgg gtggtggata gatggatgaa   140760
cccacacctt tgaagtgtat ttggctgttt gagaggttag aatatgttct caatttccag   140820
gcaaaatgaa aatggagaaa atataatgac attaaggcat tttattcatc ctccccatct   140880
gccactgggt taaagatact aaataaacaa ggaactatct tttgcctgga ggaacttaa   140940 aaacacctgc agttttcaaa aggtgcagtg tgtgcctccc acagcatgac ctaccatcat   141000
tggaaagcag tttgtagtca atcaaaggtg gtctggagaa acaaagtttt cagggataca   141060
ttgtttttat aatttttcac cacatgattt ttcttctctc caatgtagtg gtcagttttc   141120
tcttgcagtc gtcagcctga acataacatc cttgggatta cgctccctca aggagataag   141180
tgatggagat gtgataattt caggaaacaa aaatttgtgc tatgcaaata caataaactg   141240
gaaaaaactg tttgggacct ccggtcagaa aaccaaaatt ataagcaaca gaggtgaaaa   141300
cagctgcagt aagtcaccgc tttctgttta gtttatggag ttggttctaa tgggtccttt   141360
atttgtattt agaatattga agggctattc ccatttaaat tactttttc agttccttaa   141420 gaagcaaatt aaaatcttaa gattcctaac tgtgaaatta ccatgtgaat tccattaaaa   141480 cttttttccag atcattacca ttcaatggga tgaattacc ctgaggttta ggctaccaat   141540
tatttgtaat gtaagtaact aaatttagta ttagttatat tacctttag ttgtaggtca   141600 ctctctgctc atttcagcct gtaaagacta cagctacaca catacacaca cagaggaatg   141660
gaatgagcac tttacatcaa cacttcctgt tctggctcta gagcctcagc ttttgaagct   141720
```

```
ggtgagagcc tggcctgtgc tgggccttgg ccacgggcag cgtcagcttt gagtcaagtg  141780
ctggtctggc ctccctagct ttgagcctct gtcaattccc ttaatctgtt taggctttgg  141840
cttcctcatc catagaatgg agatatgaat gattcctacg ccgtagtgct ttgagagaat  141900
tcagtgaaat tcctgtgtgt aaaacccttc catggtgcct agcacacagc acacagccaa  141960
tggcccaatg gctcctatca gctgtgggat ttgtcatcag aacaccacca gctctgctcc  142020
aggctgccct gggtaccatc aaaacacacc ctgtgcccag cagcacctgc tcctctgcac  142080
acctggttcc ttcagcaggg gcagtggccg tgggagcaca gaaaacatgg agtcccatct  142140
ggtttaattg atgccattgc caaggggag gactcacggc accccctctc gggtgccagg  142200
gtgcctggct cccaccagga ggaagacctg tcctccactg tcaggcacat ttcagtcttc  142260
ccagcagcca gcacaactac tttgtccttc cagtcacggt cggcctctgg aagcccagt   142320 ctgtgtcctc ctccttcagg ggtagccagc atgtctgtgt cacccaaggt catggagcac  142380
agggcccctc ccgggaaggt gccgtctcct ccggcccctc gggtccctgc tctgtcactg  142440
actgctgtga cccactctgt ctccgcagag gccacaggcc aggtctgcca tgccttgtgc  142500
tcccccgagg gctgctgggg cccggagccc agggactgcg tctcttgccg gaatgtcagc  142560
cgaggcaggg aatgcgtgga caagtgcaac cttctggagg ggtaggaggt tatttcttta  142620
atccccttgc gttgatcaaa ataaggctc caggttgttg ttatagcttt acaggcattc   142680
tgtttgattt tctcttcctt ttattctttg cccttggctt ttggaggttt tgggttttct  142740
gtggggagac gggaagttgt ttgattgcgt tattttggc aaatttaagc acaataggaa    142800
ataagcaagt attattgcct aatataatcc aataatttat agaatctctt ttcctggaag  142860
tatcttaaat ttttctaagc tacaaaaagt tcctaagaca aatgagacag tcatcaatgg  142920
ttcatctagc caacaccgtg gccatttggg cttttctttg tagtgcccga ttcctggtgt  142980
gtgaaaataa attaacacaa attatattgc caagttaata tctgttttat gtgccccag   143040 catgtgttga acatcaaaca gtaccaggga ctttaaatat acccacggac aaagaaataa  143100
ttcataatga tgtttgttga atttagttgc aatcaataaa aagtgcagtt tgtgaatgct  143160
ctgaggttct tgatattgat gtaaggcttt gaacgacaaa tgaggacaaa acataaatag  143220
gaaagtaaaa ctgaaggata gaggccaagg ccatgtttta gaagatttaa agaaaaaggg  143280
aaatttggtg agcaccatag gaattacaga tggctgtagg aattcttcct gttttactct  143340
ctgggcatgg accacagctt ggatccagaa atatttagga gcaggataag aggaccaagt  143400
tcaattctat aggaatcctt tagctgatag gctcagaaca aatcacataa ttgatagtgc  143460
tgcttcaact tcaagtaagg aatattgatg caatccttac agctacaaat ggacagtggt  143520
ctcatgtttt cagttttcaa gtgtttctta agaggcaagg tgatgaaaac gcccacgtgg  143580
ggagccccat gtccttccat tagtgtagag aaacctggtg tccagcagca cctgctccct  143640
ctgcaagccc agcccccttc agcaagggca gtgacccaga gaagaagcac agaagacaca  143700
accctgtatc acattttgtt taatggtgcc attgaccaaa ggggaggatg aaaggcacac  143760
acttttttgt tgtttttttga gacagagtct cacgccatca cccaggctgg agtgcagtga  143820
tgtgatctca actcactgca acctctgccc ctgagttca ggtgattctc ctgcctcagc    143880
ctcccaacta gctggaatta caggtgtgca ccaccatgtc cagctaattt tttgtagttt  143940
tagtagagac ggggtttcac cacgttgcc aggctggtct caaactcctg acctcaagtg   144000
atctgcccgc ctcggcctcc caaagtgttg ggattatagg cataagccac tgcacctagc  144060
```

```
caaggcacac actttggaga ataaacactc cttgttcgct gctggagggt agaactatgc   144120
ttgactacta ggcagagtcc agtcttactg acaaacagcc gtacatctgt tctgtctttt   144180
caatcaaaca tcagcttctt gcttaacatt gatgtgtaca tcttgaggga tgtcaaaata   144240
ttgtaagcta agttttcat acctgtgttc cacactcacc attttagta ataaccattg      144300 agcgagttca ttctccctcc ttcctttttc tatcacttaa tctaaaatta tcattttcc    144360 agcttaattt tgataaccat gaatctggta ttagaggcag ggaacacctc ctcaggacta   144420
tcttttcttt tatcatttgg cttgcttacc caatatgcaa aaactatgct gtagaaaaag   144480
cagaaaagat atcttgatta tgaatgaagc tcctgtgttt actcagagag aagatgaccc   144540
aggattcagt taacaaaatc agctgattat attactatat agtcctggag tcccaactcc   144600
ttgaccatta cctcaagtta tttggaattt tgaagaggtg atttgtgttc ctgcaataat   144660
gtctcagggg tgggctgacg ggtttcctct tcctcctctc agtgagccaa gggagtttgt   144720
ggagaactct gagtgcatac agtgccaccc agagtgcctg cctcaggcca tgaacatcac   144780
ctgcacagga cgggtaagag ccccttgctg ctatccacgt ccatttcatg ggaagggcct   144840
tcacagaagc cgaacagtga tgatggccca gggcatcctg tgtgggcagg acggccatca   144900
gagccacttc ccagaggaga cggcaggcgc tgacagcgct gtccgggcag ggtgtcggtg   144960
acattagcac acacattagc ctgcgatgaa cattcactct ttctgctgac accccaacc   145020 ttatctaagc ttatcaaatc ctcacattta acggaggctg ttttcacctg gtttccccca   145080
tccctgacct agtcagcatt gctttatcgc tttcatcaaa catcctcaaa ttcttaacat   145140
tagcttgtaa ttaattgaag aatttttaaa gaaattgcta gcaaaacttt ttaaactgca   145200
caactttgta tctatatgtt caataacata tagatacaat attctttaca ataatctttt   145260
aaagaatatg agtgagaatt cgggcccctc tcacaccaaa tgtcctgatg ttgttaattc   145320
tcaatgttat tatataggga gctctgtttt cttgtgagct tcaacagcca gttctaaatc   145380
tactaactga aaacattttt tagacattct ctaaattggg cagaagatga caggactgtg   145440
ttttgaggga taggctgcca gcgtggctgc ttacaaagta aagacttggt ttataggttt   145500
gcatggtgtt gggttaaatt tctgtcatta aaataattgg cgatattgac atagtcatct   145560
aattatgctg gctctgggca cacacagccc ttgagtggac aaaaccaaca tgagagaact   145620
tagccaaggg gaaagccttt ccctgctggt tttatttctg ctacttctga agtgtggggc   145680
acacaacctg agcagtgctt ttatttgagt cccaatgctt ttatttgagt tttgcaaggt   145740
tattccaagt tttacaaata gaaggtagcg tatgactcag tccttgatat gccaaccact   145800
gcacagagac ttgccacctt cctgtcactg gagaaacact catgtgggtt ttcttaaatt   145860
tgcctccctc tgagcttccc tttaacttca actataatat gcaagaaaga ctatctgacc   145920
ataaatacac atttgggcca atcaagatgg ttttgccaag gaaagatgcc cacaatggtt   145980
aagcagaatg caataatgta gagaaatatca tttctttcat gctggtgtat atcatatgca   146040
ttcaaaaaca gggagaactt ctaagcaact aacagtgacc atatcaagca ggtgcaatca   146100 cagataact ggttttctcc tttaagaatt tttctatcat ttggctttcc ccactcacac    146160
acactaaata ttttaagtaa aaagttactt ccattttgaa agagaaaaga aagagacatg   146220
catgaacatt tttctccacc ttggtgcagg gaccagacaa ctgtatccag tgtgcccact   146280
acattgacgg cccccactgc gtcaagacct gcccggcagg agtcatggga gaaacaaca    146340 ccctggtctg gaagtacgca gacgccggcc atgtgtgcca cctgtgccat ccaaactgca   146400
cctacgggtg agtggaaagt gaaggagaac agaacatttc ctctcttgca aattcagaga   146460
```

```
tcaaaaatgt ctcccaagtt ttccggcaac aaattgccga ggtttgtatt tgagtcagtt    146520
acttaaggtg ttttggtccc cacagccatg ccagtagcaa cttgcttgtg agcaggcctc    146580
agtgcagtgg gaatgactct gccatgcacc gtgtccccgg ccgggcctgt gttgtgcaat    146640
gctgcacatc acaacaggag ggtaggggga caaaagagca caggtcctgg cagctgccac    146700
agtctccagg ggcttttgcg tttctctcca gatttctaag gttaacatgg ggattagctg    146760
ttttgcaatg aataaaaggt aacattgcct ggaatgttgc ttaaagacac ttttttaaag    146820
ctagttgatt gttaagctgt tgctacttaa attaaaacta ctttgggcca gacgcagtgg    146880
ctcacgcctg taattccagc actttgggat tccaaggcag gcagatcact tgaggtcagg    146940
agcttgagac caggctggcc aacatggtga aaccccacct ctactaaaaa tacacctgta    147000
gtcccagcta ctcaggaggc tgaggcagga gaattgcttg aacccgggag gcagaggttg    147060
cagtgagcca agatctcgcc actgcactcc agcctgagca ccaagagcga aactctgtcg    147120 caaaaacaa aaacaaaaaa aaagctact ttgactggaa ttagcagaag cactctgatt    147180
gtgtgtatct tatttactgg aataataaag ctgtcaatca aactggatcc cactcaacaa    147240
tcagaaagag aagttgagct gtcatatagt agttcacact tacttctgtt tctcaaaatc    147300
ctcagctttg tttggaactg ttactcattc tttctctgaa tccatctgta tgagttgtgt    147360
gcccttgggc aagggtctta ccttctctgt gcctcacttt cttttctgta aattgggata    147420
ataatgctgc atagctcaca ggattttat gaccatgagt taagatatgt catatactta    147480
aaatggtgcc tggaaaatgg tgaatactga gtcaatgata gcatcattga tggtgggatg    147540
gtgatgagga ggtgggagtc acaatggtgg tgttgatggt ggtgatggtg gtgaggaggt    147600
gggagtcaca gtggtggtgg tgttgatggt ggtgaggagg tgggagtcac aatggtggtg    147660
gtgatggtgt tgatggtggt gaggaggtgg gagtcacaat ggtggtagtg atgatggtgt    147720
tgatggtggt gaggaggtga gagtcacaat gttggtggtg ttggtggtgg tggtggtgag    147780
gaggtgggag tcacaatggt ggcagtgttg gtggtgagga ggtgggagtc acaatggtgg    147840
tagtgatgat ggtgttgatg gtggtgagga ggtgagagtc acaatgttgg tggtgttgat    147900
ggtggtgatg gtgatgagga ggtgggagtc acaatggtgg tgatgagggt ggtgatgatg    147960
atgaggaggt gggagtcaca atggtgtcag tgttgatggt ccgatggtga tgaggaggta    148020
ggagtcacaa tgttggtggt gttgatggtg gtgatgatga tgaggaggtg ggagtcacaa    148080
tggtgtcagt gttgatggtg gcgatggtga tgaggaggtg ggagtcacaa tggtggtggt    148140
gatgacggtg ttgacagtgg tgacgaggcg ggagtcacaa tggtgtcggt ggtgatggtg    148200
gtgaggaggt gggagtcaca atggtggtgg tggtgatggt ggtgatggtg gtgaggaggt    148260
gggagtcaca atggtggtgg tgttgatggt ggtgatggtg gtgaggaggt gggagtcaca    148320
atggtggtgg tgttgatggt ggtgatggtg gtgaggaggt gggagtcaca gtggtggtgg    148380
tgatgagggt ggtgatggtg atgaggaggt gggagtcaca acgttggtgg tgatgatggt    148440
gttactggtg gtgacgaggt gggagtcaca atggtggtgg tggtgatggt ggtgaggagg    148500
tgggagtcac agtggtggtg gtgttgatgg tggtgatggt ggtgaggagg tgggagtcac    148560
agtggtggtg gtgttgatgg tggtgatggt ggtgaggagg tgagagtcac aatggtagtg    148620
gcgatgatgg tgttggtggt gaggaggtgg aagtcacggt ggtggcgatg atggtggtga    148680
ggacgtggga gtaacaacag tggcagtgac ggtgattgag acatgatgat gatttgtcaa    148740
ctttctagga aaacaatcat ataatctcca acagtgatat cttaatatct tttccaaaag    148800
```

```
tatcagatca tattataagg gccaagtttc cagaataata tcagacataa tgacagtgga  148860
catcagagct tggcatctaa aggtaatggg aatagctcta atgtctcagc gtgaaaaaca  148920
acatttgcta ttagtctgag atactaatta tctagttaag gaagtactca cctataccta  148980
gtttttaact gttttttaaa atctggaatt gattttgaat tttaacaaat atttccctgg  149040
gaacaatgta agattcttca tattttcgcc tttgggtata ccaacatgcc agctctgttg  149100
gccactttgt gagctcgatg aagcatggta taaaagatgc tttgctagtg tttcacgtaa  149160
tctatttcta taagcaattt tggagctaag cctctgaaac agaattatat tatctgtata  149220
gaataaatgt tttatcttcc ccctttttctt tcttctggaa tagatgtgca tcagtatctc  149280
tgcatcaata tctctatatc agtatctctg tgtcagtgag catatgttgc tgggcttagg  149340
ggaggtccag aaagtgattg ggttttggca ttttcaatac acttactttg tataagaaat  149400
agtttgccaa atatagaaag aggggattta gtcaagattt aaattaaaaa tgttagtggt  149460
cattttctta atgtctttct atttttttccc aggtcctaat aaatcttcac tgtctgactt  149520
tagtctccca ctaaaactgc atttcctttc tacaatttca atttctcccct ttgcttcaaa  149580 taaagtcctg acactattca tttgacatat ggaattttat aaatattttc tttagtatgt  149640
gtgattacat tcctgattct gagccttttt agatgagtat atagtttgat ataatcttgt  149700
tattgccacc tgtgtcttct cccaaagcca ttaattatat aggaattaca cgatagaaat  149760
gggtttaatt tttaaaatac ggccaagtgt tgatgagagg gaaaattttt ttaatttctt  149820
tcactgagta tttatgacgt gcacaacatt cctgaatata ttgtctctct catttctcag  149880
atgggatgta ttgccttctc catttctatt gttaaagaaa cacttacagg ggtttcttta  149940
acaacttgtg aacagcagca tcagagccca gactacagca taagcagctg ctgattccaa  150000
aagccctacc ttccaaccgg gcaggtgcag ccacccagac gaggggggagg aaccctggag  150060 gaatagctat ttcttttttt tttttgtcga gacggagtct tgttctgtca ccctggctgg  150120
agtgcagtgc cgtgatcttg gctcactgca acctccacct cccaggttca agcaattctc  150180
ctgcttcagc ctcccgagta gctgggatta cagacacctg ccaccacgcc tggctaattt  150240
ttgtattttt agtacagaca gggtttcacc atgttggcca ggcttgtctt gatctcctga  150300
caagtgatcc acacaccttg gcctcccaaa gtgctgagat tacaggcgtg agccactgcg  150360
cccagcagga atatctattt ttaaatggaa ctgtgttttc atagtacacg gtgaggagaa  150420
agttgctttg aaatctttat cctaataaac caaataatat gaaaatttgc ctattttaat  150480
tatatgtaac aaagtttagt tactgctata attgcaaata tgtataaatt ccttaccaaa  150540 aaaaaagaa tcaagtggga gccagagaat aatttttctg acagaattaa ataacatgct  150600
atagctgctt gagttcatac tcaatagtca tttctgcaga gttaccgagg gcctcatcag  150660
cgtcagcagg agccctcgc cttctgacgc tctcacatcc ttctctcctg cagccccgtc  150720
ctgccactgt ccttgtccag cttctcttca agggtcaact ggtctacctt tccctacaag  150780
tctgtcacag cttcttgtta gcaatcccta tggttgccca aaagcatttt cagagcctgc  150840
ataagactgc atcttgtaga aaatttgcag tttcaatctg ccctccctct gccgggtgtt  150900
cccattgtat tgcattcagc aggcagggag agactgctat taggtctgtt cctgagtgac  150960
tgctttctgt ctcagactgt ttggtgtctg taggaggtag tggggtgggc agtaacgagg  151020
tctcctgtat attccacccc tacgaagcct gtgtgtttgg tttatgaact aagctcaaaa  151080
gcaccacagg ggtaagactg cagtacatga caccatggaa aagagggagc acccagccc  151140 ccaaattaag aagagcagtg tagagaacag agacctggag agcagagata gaaactgtta  151200
```

```
ggatcagatt atagtgttac accagggctc cccaggcctc tcacatattg aaatgtactt   151260
gtccatcttt ctccaggcca ggaaatgaga gtctcaaagc catgttattc tgccttttta   151320
aactatcatc ctgtaatcaa agtaatgatg gcagcgtgtc ccaccagagc gggagcccag   151380
ctgctcagga gtcatgctta ggatggatcc cttctcttct gccgtcagag tttcagctgg   151440
gttggggtgg atgcagccac ctccatgcct ggccttctgc atctgtgatc atcacggcct   151500
cctcctgcca ctgagcctca tgccttcacg tgtctgttcc ccccgctttt cctttctgcc   151560
acccctgcac gtgggccgcc aggttcccaa gagtatccta cccatttcct tccttccact   151620 cccttttgcca gtgcctctca ccccaactag tagctaacca tcaccccag gactgacctc   151680 ttcctcctcg ctgccagatg attgttcaaa gcacagaatt tgtcagaaac ctgcagggac   151740
tccatgctgc cagccttctc cgtaattagc atggccccag tccatgcttc tagccttggt   151800
tccttctgcc cctctgtttg aaattctaga gccagctgtg gacaattat ctgtgtcaaa    151860 agccagatgt gaaacatct caataacaaa ctggctgctt tgttcaatgc tagaacaacg    151920
cctgtcacag agtagaaact caaaaatatt tgctgagtga atgaacaaat gaataaatgc   151980
ataataaata attaaccacc aatccaacat ccagacacat agtgatttta attatttaag    152040
agtagtttag catatattgc tttatgattt aattaaaaat ctccaaaata tatgccaaag    152100
aagtagaatg agaaaaatgt atatttctct ttcacttcct acagatgcac tgggccaggt   152160
cttgaaggct gtccaacgaa tgggtaagtg ttcacagctc tgtgtcacat ggacctcgtc   152220
aagaatgacc acactgctgt gggtgaagat gctttcctgc atttctgact gtcctctgtc    152280
ctgatcaagt ttctatggct ctgggccagc ctaccctcag ccagggtttc tgcagagact    152340
gcccagctgg ttccacgtgg ctccacgtgc caactttgtc ctcagtggag ggaaagttgg    152400
acacacagtg ctgggctgc tccctgctcc gccgttgctc gatgcatggc ctgcctctga     152460
attccttggt tccactggtt ttgctgggtc cttctgtgcc tctagctcct cttttttct    152520 gtccacttac cccattggtc ccatcacaag cctgtgtgtg agtggccttt ctgttcgatg    152580
acaacctcca gcataggga gtgtttctc ttgctttctt tcccagacac actgcccagc     152640
aaaggcaaaa gggcttcctt caacatcagc tctggccagt tgccagagc aaagccctga    152700 gaaaagcaag gttgaaaagt cttattcaaa ctcaccagga aagagtggtg ttactctcga   152760
tggcgtctag ccaggaatca tggaattata caccgagcac ctgtttgcca tttggatgt    152820 ttccaaacat gaaccaaact tccaggcccc tctgccatct ctggtaacat ttacaaagtc   152880
ccttcctcac cactgccctt ccttcatttt ggcatgctcc tccgccccg agttgacagc    152940 catagctctc tctcctgcca ccagtgtcac atgatcgagg aagaaggcaa cttcaaaaag    153000
actgggtccc cttccactcc catctcttca gtgagctgct aggacaccca gcagaacttc    153060
cccactccac actgcaatct cagggatctt agtcacgggg ctttccacca tgtctccacc    153120
tggaaaccag tcatggccat tccttcttac atctgctctt ttccatcttt ttcttctcct    153180
cctgttcacc cgcccttact cttgtggcgc cctatggata tgcgctccat agcaaatgat   153240 tcttatatc ttacggtatt ctagtgagct ggcacatgtg gcttctggtt tcctctctct     153300
ggaactagac atgacctctg tgggagggag gattaaatgc accctacagt ctgaggctgc    153360
atgatgacat cactcatcac aatgatgctt tctatgtctg aatcctattc ctttataacc    153420
cctttcaagc tcgttcagag agtatttcac acaatccatg tgctcatctt aaaagccaag    153480
gacccagagg agtctcagca ttgccaaaaa gtcccttcac ccagcctggc cagaggcagt   153540
```

```
gcctggtcca tgtgtatgga ctatggcact tcaattgcat ggaaatactc ttggaatgaa    153600
caaaatacca atccatgaaa aagcattatt gaagtctaag ttattttttg aatcatattt    153660
tgttaatcaa caaattgaaa aatactcatt atatggagag gtccagataa agcctcaatt    153720
ttaaaaaatg aggaaaagtg tgcctggtag gggactgggg agagcttgag aaagttggaa    153780
acgttgcctt agaagcctgt tttttctcct tttagaagct acatagtgtc tcactttcca    153840
agatcattct acaagatgtc agtgcactga aacatgcagg ggcgtgttga gtgccaaggc    153900
catggaatct gtcagcaacc tcacccttcc ttgttcctcc acctcattcc aggcctaaga    153960
tcccgtccat cgccactggg atggtggggg ccctcctctt gctgctggtg gtggccctgg    154020
ggatcggcct cttcatgcga aggcgccaca tcgttcggaa gcgcacgctg cggaggctgc    154080
tgcaggagag ggaggtgagt gccagtcctg ggtgggctca ggagccctcg caccccgaca    154140
ggaacaaggg ccagccccga gaacgggcca ttagcagttg tgtatgttag atacataatt    154200
gtattatgat gcagaaagaa tctctgaatg tgcagttata cccagttggt gacatgttgg    154260
tacatccatc cgaggaaatg gcaatgtttc taggctgcac ccttcaatgt ccacaaagct    154320
gtgtggcatc tgcttaggac ccggtgcctg tgtgtgcata ggaggaggc caggaagcct    154380 ggctgttgat cccatgctgg cactgtggcg aaggcgagag attcctgctt tggaaaacac    154440
cattgtccac acagtggctt tgtccatgat ggacttcgcc acagcccagt cctgtgctgg    154500
aagccatgtt ctctggaaag agcaacccag cggctcataa gcataagcgc gtgtgatgtg    154560
ccccaaccaa acgaccgcca tgcacaactt ccctaccgga gttttcaatc cagttaatag    154620
gcgtggaaac agacatagaa attgtgtttg ttgaaaggta gctgttcagt taaagaacac    154680
ctgtatcaga gcctgtgttt ctaccaactt ctgtcaagct ctgtagagaa ggcgtacatt    154740
tgtccttcca aatgagctgg caagtgccgt gtcctggcac ccaagcccat gccgtggctg    154800
ctggtccccc tgctgggcca tgtctggcac tgctttccag catggtgagg gctgaggtga    154860
cccttgtctc tgtgttcttg tcccccccag cttgtggagc tcttacacc cagtggagaa    154920 gctcccaacc aagctctctt gaggatcttg aaggaaactg aattcaaaaa gatcaaagtg    154980
ctgggctccg gtgcgttcgg cacggtgtat aaggtaaggt ccctggcaca ggcctctggg    155040
ctgggccgca gggcctctca tggtctggtg gggagcccag agtccttgca agctgtatat    155100
ttccatcatc tactttactc tttgtttcac tgagtgtttg ggaaactcca gtgttttttcc    155160 caagttattg agaggaaatc ttttataacc acagtaatca gtggtcctgt gagaccaatt    155220
cacagaccaa aggcattttt atgaaagggg ccattgacct tgccatgggg tgcagcacag    155280
ggcgggagga gggccgcctc tcaccgcacg gcatcagaat gcagcccagc tgaaatgggc    155340
tcatcttcgt ttgcttcttc tagatcctct ttgcatgaaa tctgatttca gttaggccta    155400
gacgcagcat cattaaattc tggatgaaat gatccacacg gactttataa caggctttac    155460
aagcttgaga ttcttttatc taaataatca gtgtgattcg tggagcccaa cagctgcagg    155520
gctgcggggg cgtcacagcc cccagcaata tcagccttag gtgcggctcc acagcccag    155580 tgtccctcac cttcggggtg catcgctggt aacatccacc cagatcactg ggcagcatgt    155640
ggcaccatct cacaattgcc agttaacgtc ttccttctct ctctgtcata gggactctgg    155700
atcccagaag gtgagaaagt taaaattccc gtcgctatca aggaattaag agaagcaaca    155760
tctccgaaag ccaacaagga aatcctcgat gtgagtttct gctttgctgt gtgggggtcc    155820
atggctctga acctcaggcc caccttttct catgtctggc agctgctctg ctctagaccc    155880
tgctcatctc cacatcctaa atgttcactt tctatgtctt tcccttttcta gctctagtgg    155940
```

```
gtataactcc ctccccttag agacagcact ggcctctccc atgctggtat ccaccccaaa  156000
aggctggaaa caggcaatta ctggcatcta cccagcacta gtttcttgac acgcatgatg  156060
agtgagtgct cttggtgagc ctggagcatg ggtattgttt ttggtatttt ttggatgaag  156120
aaatggaggc ataaagaaat tggctgaccc ttatatggct gggataggt ttaagcccct  156180 tgttatttct gactctgaaa cttgcattca attcactcca ccaagttatc tcatctttga  156240
aatggctttt tttaaaggtg cctagaatat gatggcgtgc agtctataaa ctgttgccca  156300
ccttctgtac tttctctcag ataattcac attcttctcc agtgtctgtt gattgttact  156360
ttgtggaata agttcttgga aaattccaca agattattgt tatcttctta ctaccaattc  156420
tattgaactt tctccacctt ctctgggcct tccccagcca gtggtgggaa gatgctggct  156480
ggagtctgac agagcctctt ctacactggc ctgggcttgc tgtgagttgg tggaaacctt  156540
tgctcttgtc ccaacacaga gcaagtgaaa gaggaggtca aggggctcag gcagcggact  156600
agggaagcag aatcgaggaa aaggaaaaat ggctgactta ttacctcaaa actctagaga  156660
atttagttga tcttacagcc aagaaggaca aaagccagag agtaatatcc tccgcctcat  156720
gtctaaccca cagaatacat agcaagtaaa gagaacatgg gcctttataa aaatgtctta  156780
agatacaatt ttttaattgg aggaaatcta cagtttaatt ttctctgggc agcttttctt  156840
ccttttatta tagtagggga aatcccatgt tgatatactt ctaaatgaaa gatgatgaat  156900
tgatataata caataaaaaa tctgtaaaat tgatgatata cttatcaaga aaaattagct  156960
ttcattttaa cggtttacaa attgagtcaa gtcctagtaa caaaatgtta agtctattaa  157020
cataaccaca agaaatacag gaagacgggc aatctgtgaa gcctttcact acaatctct  157080 ggcccctcac ctgtgctgtg taggaaaatc tttgtgcaca atttgcttcc ttaattcatt  157140
ttttattcat tcaacacatt ctaataaatt atacaaaatc atgttgaaat gtgaatttca  157200
gtggtattta taaatgcagt gtgaggaggg tttggatgta ttctaagaca atagttgtgc  157260
tttgggaagg aagcagtgtt cactgaaaag tgccccagg accttttaat tggaggaaat  157320
atgcttctgt ggagttggaa atggggtaga agatagataa ggtcaaggct taaaagttaa  157380
gtgcacccaa catctgaagc gtccatgggc ctggcatggt ggctttcgcc tgtaatccca  157440
gcactttggg aggctgaggc aggaggatcc cttgagctta ggagtttgag accagcctgg  157500
gcaacatact gagacccagt ctctacaaaa aataaaaaat tagctgggtg tggtgtctca  157560
tgcctgtagt cccagccact caggagatgg gaagatggct tgagtccagg agatctaggc  157620
tgcagtgagc taaaatctca ccactgcact ccagcctggg tgacaaagca agaccctgct  157680
caaaaaaata gttagatata aatattaata tagataccta tatatatctg aatatagata  157740
tctatatata ctctgtatat agttatttag atatataaat atatatgata tatatttaga  157800
gagatatata tttagagaga tatatattta gagatttata tatattttat atatatttag  157860
agatatatat ctctaaatat atatctctct ctaaatatat atatatctct ctctaaatat  157920
atatatatcc ctaaatatat taaataaata aagaaataa aagaaagctc agtttggcct  157980
cctgcttgtc ctgtctcctc atcccctctt ccccctccat cattttattt ccttgcccca  158040
tgtttcttca ctgcggccat gtccccctc ctctccaatg atggatgtca tgtctgctgc  158100
agtcagaggg cgacaagcct ggagtgttcc ctgaagcctg tggtttgtgg tttgtcctgc  158160
agctcaggct gccaggcct caccagcaat cctggcgggc agggcaccac actgggatgg  158220 agaggggggaa gctggaggag gcactttctg gtaaagaaag caaagccag cagtgcccag  158280
```

```
gccaatttca acagggagtt aaatagcacc ttaatcctgt ggcaggacag ctcatggggc   158340
catgtgtgct cttagaaaga ctcacatgca cgcatgcacg gcagcaatga ctccatactc   158400
acgttcccct gcagacacca ggcccccaca gccggcacac acactgcagc cccagttcca   158460
tgttgctagc agtggcttag tgaatgagta aagttcttaa aatgcagggg acacctgccc   158520
ttcattcata aggctggacg tacacctctc cttaaggagt tcaagagcta gtggaatccc   158580
aattcatacg gtagagccat tcacagatga gagagacaag ccagaaggaa ggaaccaaaa   158640
gtcatgtcag cagttaggac aaaataacag gctttcaagg tcacaaagcc tcagggacac   158700
tcctgcggtg ggactgggct aggagccatg ggggctccaa ctgtgcgctc tgcctgccag   158760
cctgtgggtg ctgggctcc acgaagattg ttgtggaata ccaagcatgc ttgctgtagg   158820
tcacggtgca cgtttactac ttccaagaca aacagccgag aacaaagctc gctttagctt   158880
ctgcgtacac cgaacgggac acacgactga acagcgttcc cattgtgcct gctgggtggg   158940
gaggaagtga tggcccagtg ggtctatcag atgttagtag gatggggcct ggcggggctc   159000
caggctctgt gtggccgaca cccacgcccc ccgctctgct ccccattccc agccccaggt   159060
cagccctgcg aggccctgca gcagatgggc tgctcaaact gctctggttt gcagattttt   159120
cttccctctc aaatgaatac aatatgtttt caagtctcaa ccagatcttg agaaaatagg   159180
aagagccaga gggtttcttt ggtgttatgg ttgtacagct tcccagactc cggggagag   159240 atgtgatttg tgctttctgg caatcccatg gcgtattaaa ttttcatagg cttccagtt   159300 taaatttagg gtaggcaatg aagggaacg caaaacagat ttctaggtgt actgtgtgtg   159360
tgtctcccac gtctaaagtc tgttaactgg agcacccaac aggcccccaca ggctgccttc   159420 acacagagga cctggggcgc ctccgaccca ttggggtgag cagtgggcca tggagggagc   159480
cagggtcagg agacctggtt gtgggcctga cctgaccctg tcagggtgg cctcaggtgg   159540 gccgttcacc tcgtcagcct cagcttaccc tctgactaca gtgacctcag acaaaatacg   159600
cttcctggcc ctgtccagtt ctgactttt ataaacaagc acttatccaa gttaaaggga   159660
tattttcaat atctactgag tccacagata ttaaatatct cctctcttct ttaaaattgt   159720
ggcattatct ttagaatata aaaggaaaat aacacacact ctccttgaaa atagagagcc   159780
taaacactct gcaggaaata tttaaagcta tagtttttgt ttgtttgtct tgaatgcaag   159840
tggcctggac tttgacttgc tttgagtctt tgaccttcat gacttcagta cagttcaacc   159900
ctgacagttt tgaagtaggt atgtgcctag atctgcccta gtccctgctg gaatgttgaa   159960
gaagcaaagg tccaggccct cagagcactt gccacgtact tgccaacaga tacggggcgg   160020
agacttgagt caacgtaaga gcaagtgtgt gccgggtgat ccgacactgc agagcgccag   160080 ctagaccctga gcgtgtgct aggggctgac caagccgttc tttcctcaaa aacttggtgg   160140
ggagggtatt tttaaaatca cacaaatatt taagtacaga ttatgatgac tgcctcaaag   160200
cagtggctct tcagcttcat caagcttcag agtccagagg gttgttcat atggaaggct   160260 aggcctgtct cctgcatttc accctcttgg cctggggcg ggacccaaga atgtgtggct   160320
ctaaaaggtt cccaggcaat gctgaggctg ctttctgaag gaaaaactgc aagataccag   160380
gagagtttca tttagattga agagtcgagg aaggctcctc tgagaaagag tctgctaagg   160440
aaggaggagg tgggttctgg ggacagaggt tctcccgtgg gtaagggtgg agggaagctc   160500
tcctggggag aaggtgggca ggaggaccag aggctggagg gaggagggca gtcagcctcg   160560
gggcttccca ggaacaggga cggccaggc agggtttagg gcaaggaaag cgtgtgagca   160620
tatttgtatt ttagtaaata tttacagttt gccctccatg tctgcagttt catatccatg   160680
```

```
gattcaatca accacaatga aaaacgttgg ggaaaaaaat tgcatcggta ctgaacatat    160740
acggactttt ttcttgtca ttattcccta aacaatacag cataacaatt attcacatag    160800
catttgcact gtattaggta ctataggtaa tcaggagatg ctgtagatgg gaggatgtct    160860
gtaggttaca cacaaatgct gtgccacttt atatcagggg cttgagcatc ctcacatttt    160920
gatatttaag ggaggtcctg gaaccaattc cccagatact gagggtccac tgtctgtgtc    160980
ccctcgcccc accttgcctt tgtctcctgt ctcctatctc caccctgcct cccgccagcc    161040
tgttgctcct gacctgcccg ggcaccctgg agcagcaccc tatctcagag cctggctcag    161100
tgtgttcact tctgcagaga aactaacttg cccaagtcca cactcaaaac ataggcattg    161160
ctgagatgtg aaaagcagct gtggatgctt tctgctacag tctgtgtgtt cttttccata    161220
tctgaataaa aggtcaccac catttgtatt taaagagaa agagaattta tgggtggaaa     161280
ttggggattc cctcattctc agtcagacag aaaagagggc cccattgtgt gcctgattgc    161340
aaataaattt agcttcctca gcccaagaat agcagaaggg ttaaaataaa gtctgtattt    161400
atggctctgt caaaggaagg cccctgcctt ggcagccagc cggaattagc agggcagcag    161460
atgcctgact cagtgcagca tggatttccc ataggggagcc tggggcaca gcacagagag     161520
accacttctc tttagaaatg ggtcccgggc agccaggcag cctttagtca ctgtagattg    161580
aatgctctgt ccatttcaaa acctgggact ggtctattga aagagcttat ccagctactc    161640
tttgcagagg tgctgtgggc agggtcccca gcccaaatgc ccacccattt cccagagcac    161700
agtcagggcc aagcctggcc tgtggggaag ggaggccttt ctccctgctg gctcggtgct    161760
ccccggatgc cttctccatc gcttgtcctc tgcagcaccc acagcagcg ttcctgatgt     161820
gcagggtcag tcattaccca gggtgttccg gaccccacac agattcctac aggccctcat    161880
gatatttaa aacacagcat cctcaacctt gaggcggagg tcttcataac aaagatacta     161940
tcagttccca aactcagaga tcaggtgact ccgactcctc ctttatccaa tgtgctcctc    162000
atggccactg ttgcctgggc ctctctgtca tggggaatcc ccagatgcac ccaggagggg    162060
ccctctccca ctgcatctgt cacttcacag ccctgcgtaa acgtccctgt gctaggtctt    162120
ttgcaggcac agcttttcct ccatgagtac gtattttgaa actcaagatc gcattcatgc    162180
gtcttcacct ggaaggggtc catgtgcccc tccttctggc caccatgcga agccacactg    162240
acgtgcctct ccctccctcc aggaagccta cgtgatggcc agcgtggaca accccacgt     162300
gtgccgcctg ctgggcatct gcctcacctc caccgtgcag ctcatcacgc agctcatgcc    162360
cttcggctgc ctcctggact atgtccggga acacaaagac aatattggct cccagtacct    162420
gctcaactgg tgtgtgcaga tcgcaaaggt aatcagggaa gggagatacg gggaggggag    162480
ataaggagcc aggatcctca catgcggtct gcgctcctgg gatagcaaga gtttgccatg    162540
gggatatgtg tgtgcgtgca tgcagcacac acacattcct ttattttgga ttcaatcaag    162600
ttgatcttct tgtgcacaaa tcagtgcctg tccatctgc atgtgaaac tctcatcaat      162660
cagctacctt tgaagaattt tctctttatt gagtgctcag tgtggtctga tgtctctgtt    162720
cttatttctc tggaattctt tgtgaatact gtggtgattt gtagtggaga aggaatattg    162780
cttcccccat tcaggacttg ataacaaggt aagcaagcca ggccaaggcc aggaggaccc    162840
aggtgatagt ggtggagtgg agcaggtgcc ttgcaggagg cccagtgagg aggtgcaagg    162900
agctgacaga gggcgcagct gctgctgcta tgtggctggg gccttggcta agtgtccccc    162960
tttccacagg ctcgctccag agccagggcg gggctgagag agcagagtgg tcaggtagcc    163020
```

```
ctgcctgggt gctggagaca ggcacagaac aacaagccag gtatttcaca gctggtgcgg    163080
acccagaaag acttctgctt ttgccccaaa cccctcccat ctccatccca gtcttgcatc    163140
agttatttgc actcaacttg ctaagtccta ttttttttcta acaatgggta tacatttcat   163200
cccattgact ttaaaggatt tgcaggcagg ccctgtctct gagaatacgc cgttgcccgt    163260
catctctctc cgacagcagg gcaggggtc cagagatgtg ccagggacca gagggaggga    163320
gcagacaccc acccggcctg gcaggtcct cctcattgct tgcatccgcc tggttagcag     163380
tggcagtcag tcctgccgag tcattcgtga ggcgctcacc caactccagg cagatgtaaa    163440
aggtgaccta caagaagaca aacaaaaaca tctggagcgc tcttatgcca gcatctgccc    163500
ttgacaccac caggcaggct gttgctggga gccgtggtgc ttgggtaagc tccttcccat    163560
ggcagagctc ctgggacgca ttgtagaagc agggaccacc tcccaggata accagatagc    163620
agcacaccct gcacagcccc ttttactcca gcatcatcgg gcattgatat ctcagctgca    163680
gccacaggcg gcccccagca ccccaggaag tggggagcgc tcatgcttct ctgagcacaa    163740
aaatcactga atattttgc cattctcatg gtcataaccc gggccacaga gtagaacact     163800
cctatcactg ttgttagaca gtggtcctgg gagagggtct tgtgtgcctc ggatgccagg    163860
gcctcttttt attgggaggt gcttgttatt tctgtgtgtg gctgcatttg tttcccaaga    163920
ctgccacaac aaatcatcac caacttggta gctcaacata gcacagcttt attccctcct    163980
ggctctggag gccaggtgtc taaaaggcca tgctcccaca atggttctga ggaggatcct    164040
tcctgcctct ctggcttctg gtggctccag catccctggg ctgtggctgc acctccccat    164100
gtcaacctcc gtcttcacaa ggcctttttcc tgtgtctctg caaccacagg cccctctcct   164160
ttctcttaat aaagatacca gtcattgagt ttgaaaattg ctaagagagt ctgttgtaaa    164220
tcttcttagc acaaaaaaaa atgacagata tgtgaagtgg tagatatatt aattagtttg    164280
atttgatcac tccgctatgt gtataaatgt caaaacaaac attgcactcc ataaatatat    164340
atattaaaaa agatcccagt cattgcattt aggacccacc ctaaatccag gatgatttca    164400
tttcaagact tttaactaga tttgcaaaac cccatttcca aataaggtca cattctgcag    164460
ttttgggtag acgtgaaatg tggagacact gtgcaaccca ctgtcttggg gaggggtgg    164520
tcagcctggg gcagatgttg ctgggtgtgg agctacatcc actcatgccc tgacctggaa    164580
cccagacctg cttccccagc tctcctcctg gttatctgaa gcagggaatg gagagcactg    164640
ccctccttgc ccaggcagtc tctatcacct ggttttagtt tcttcttagc acatattgcc    164700
ccagaatatc tggttggttt atggcttact tgagtttgtg cctacctgtc caacccggga    164760
ggtgagccct ggctattccc caaacccggc cctgcatgtg ggagctgccc ttcctccgtt    164820
catcagaggg ggccaacagt ccacagctgt tcttaatcat ctcccagtaa ccccagctc    164880
cacaaaggtg actccttaca tggtggagag gtggtcgggc catccgtgtg aaatgtgtat    164940
gtgaccgttt tccttaaggg gcacgtagtc ttggcaggtt tcgctcaata taggatgagc    165000
tcaggactcc agtggactgt ggattcagat ctggattctg gcgcattcgc cgtgtgaacg    165060
ggggcacgtt gctggcctgt ctgcgcctcg tctcccgact gtggagtgtg ttctgcccct    165120
tgtctttctg ggaggtaggg agggcagtga gccccttcgc atcgcccacc acaggcccag    165180
cacatggctg atccccactg agtgttcttt tcctcctttg atcccctttg gctgacctag    165240
gttggagcag ccactaaaat atacccagaa acatcttcct aatctacatc tgtgccaacc    165300
ctcattccct ggcgcagcat gaccatcaca tgcccgccat tgttcctgat ctctgctgct    165360
catgacctgc tctccagcgc tccttctcat gctcacattc cagttggcct gacctagata    165420
```

```
agtggaggtt tatttgaccc caaaaattag ccttctacaa acgaatataa tagtgtccat  165480
tacagagaat aaacttagtg cgtgtcccat ttaagcagaa gttactgaaa gcctgagttt  165540
aagtttccag ggcctgaaag ttttccatga cagttttctg cataatatta cctacaattt  165600
caatctgtta tttaaagcca ttcttgtgtt tgttgtactt tgattagctt tattttgatt  165660
tgaagtcctt ttacattacg ggcagttaac gctttgtctc tgttagattt gcttttagt  165720 tcacaagaga aacctcattc ctctgtattt gaatagttgc aatgatggaa cagctgtccc  165780
tggagggaaa tgaaaacagt gattccccaa attgtgacaa tagaaatttg ctcttgggtt  165840
acttacaatg tatctgagta ttaaaaaatt ttcttttta acgtttgaag taaaactacc  165900
cagaaacact tagtggctga ccagaaacta aactcctggc atcctcaaaa tgggatttat  165960
tggcttataa atgtcctgtg ttgactcaca aaggcacaaa ctatctaggt aagttttctt  166020
ctaaatgttg atgggagagc tggccactgt tatgcaagtt tcattgtcct gactaaactg  166080
ccaaagagat tacataaaat tatatcaact agacaaaagg aaaaggaaa aaaaacagag  166140 gtgtcttggg aggaatccat atgagaccag tagaccatga gagagacatc ccttgccatc  166200
tacaaggaaa atggattttg ttctccatat gcaaaaccat ctcaggagct tgcggagaca  166260
ccacttgctt actagccaga aagagcaggt gcctcctaaa ttccccacac aggagctcac  166320
agtggctttc atgcactggg attaagttag acttaagaaa gcctgtctac tcttcctggg  166380
atttacaagc cagctagtaa atcccagaat aaatcacacg gcacagtcat ccaaagatcc  166440
cgtcatccgt gccgtttgga aagccctgct cctgtgccac cctctccccg tggagcctcc  166500
catgcccagg actgcagagt cctgccattc agactgcaac tcatctcaca ttcttccaaa  166560
ctatttggac aacagagctt tctcatcacc taatgcagat tacagtctca cagaattgag  166620
tgttcaggca gacactgatg tggttctgta gtacagcaaa caatatcagt ttacagtcct  166680
gaggccaggc ctggtgaaca acgcacggta gcggtggggc agggttctca gaatgaaact  166740
ggcttacaca tggcactctc tgaccacaac tgtataagca ccaaactaca cttagttcca  166800
tctatgaggt aaaatttaat gcagatgaac atcaaagaaa acgtcaaagg ctccttttta  166860
caagtacgtg ggctacttaa tttggtccaa gtccatttta aaaagcccta ggtgctttca  166920
cggctctgct actgacaaga agccccagtg cctgtgagct gctaatggga gggagaggaa  166980
gatgagctga gtgggccggg ctatcccgtc cacaccggga gacagggaag gagactccaa  167040
gctggtggtg ccagcacatt ccaggccact caggcctatt cctaggtgcc aggtcacgaa  167100
aaccacgctg acagatcgtg ctgtgtgcgt gtcatagcac acaagcagga ctgtgagaga  167160
gtgaaagtga cactgggtgg agcactgagg aagggccaca gtgtgttggt ggagataggc  167220
tgtcatggag aagagaccct ggcttgctct acattgcttc caatgcaact gcaaggcagg  167280
tcccagaggg ctccggcctt cgtcatccag gtttgctccc tcccctcatg gctttcccat  167340
cctcagatga ggactcggca gagcctaccc ctgctgacta actgtggccc cagggtggtg  167400
actcagccct gcacctcctg atcccgtctg cactgggcca gagaggatga cttacccagc  167460
acgttcacat cacacagctt tgtggattcc taggtccaag gaccagagat ttcagttatg  167520
tgagttattt ttttatttg ttcttgcgta ttccacaaag ggtcgcagct aaacttaacc  167580
taatgatcac tttagtatat cactaaaaag acaaagctca cagtgctgtt gaagcacatt  167640
catcatcttt agacattttg actagttatt tcttaagcat ttacctgcta gtgttaagca  167700
tcacatgaaa tacatataga agtaagacaa aatttcttat ctccccaagt ttgccaacaa  167760
```

```
atacagagca ggaagggaag caggtcagag caggaggcgc agctatagtg aggccaccat   167820
gcaaggcaca gggagggtga gctccaagtt tgaatggaat gggtctgtca gccaagcccc   167880
ctggctctgg gaagatagca gtgaacaagc cagatggccc ctcaccctcc agagccgtga   167940
gtcctgcaga ccaaacagcg tgacaggtcc tttccctgtc caggaggcct ctgtgggtga   168000
gagttggctg cggacagggc gtgaaggcac ttgagggtgg ggaagtgact ctgactggga   168060
gatgctgagg acagggagga aaccaccaga taagggacac tggggaggag gggtggaccc   168120
ctcagggcca agcacatgga gcctcatcac aaaggcaaga tggtggccaa attcaaggtc   168180
gctgcaaaag gaatggagaa gagagaatag atttggcatt tggaggaaat ggtgacaatc   168240
atgagcacct acccgggact ctccatgggt gctatctcta cataaactca ttccaccctc   168300
tgattaatcc attctacata tggggaaaca aaggcatgcg gtgtttacgt cacttgccaa   168360
gatctcagga tttgatccag gtggcctggt tccatggtgc agcctctcag cctgcatgga   168420
tgccccagct cagagcatga ctctcaggac aggggtccca gcagccctcc ctccctgagc   168480
agcagggtgc ccgtgctgca ccacttctgt ctaggaatag acattctga cacttttcctg   168540 cctcttccga ggtctagcac ttactctatg cctgcctggg aaggtggcaa gctggcctga   168600
ggaacagact cttccatttt ttagggagct caaggccaca gatgctctga gatctggagt   168660
ccagagacag gagcggaggc ttctcctggt gaccactctg cttaaaaact tcatcagatc   168720
cgtagtttca gagccccct gaaccccatc ccttacctct accagttgca ggtgggtctc   168780
tggggtgggg ctgccctccc caccagcacc ccaagggcta aaaggttgag gggagaacac   168840
catcatttgt acaggggat cctggaagat gaggcctgag aaagccctgc ggggcccctc   168900
accttctccc tagctgtggc caagagtgtc tggccttgcc tgcctcagga ccagcccaaa   168960
gtggaggtga gaggtgagcc ccagccccca ggggaagggt gatggtggtc ttggtctcag   169020
catggttctg gtagaggtgg gttattttga agatgatgaa ccttaagcct ctttctgatc   169080
ttgctttaaa taaatacttc tgaacaacag caacaacaga atagtgttga taggaaagcc   169140
ctccactcca ccagaaccac gcggccttct cgtcctcccc tcctccactt ccttcctaag   169200
tcactgctcc atgagctctt ccacaggaga tttacaaaat agaacacaaa caatccagtt   169260
cccgcctctc actctgaact cctcccaaga ctcgtggggt gcggcagccc ctgggaacac   169320
ccagcccttc aaggtcaaac acagccccg cccctcactc tggggtaccc tgccagaata   169380
agccccgaca gccatgtgga gcagagcctt ctttttgta agtggaagtt ccaggctggc   169440
ttttcaaatc cccttttaac ctcagtgctg tatttcaaaa ttcattccag ttttcctgta   169500
gtaattaaca aaaataaata ttttaatttc aattaaagtg agggtctcgg agaagaagca   169560
ggaactgagt ttcctgagag gccccgctga ggctttgttg atatttcttc ctgcgacctc   169620
tgctcggacc ctgggagctc acaggccgta tcgcagctct tatctttggg gaccagttaa   169680
agcataactg cgccaggcac agagttgtcc tttcaaatgt gccggcagtg ggacgggac   169740 ccatgcgtca agtctcctct aagttcacat gggattctct ccttgtccca aagctgtctc   169800
tgacttaaaa ccctccaact gattacctga attccagaat atgtcctgtg ctctctgccc   169860
tttcccacgc ctttggtgaa gaccggtgtt ctgaggaaac agacactgtg tagaaatggc   169920
tcaggtcctt taaagccctg gtgtgaggag tggggaaggg ctgggccaga ggtcagctgg   169980
atttgttaga ttgacagagt gacgcggact tccccagagg cacgggacca aggtgcatgc   170040
tcacgctgtc tcatgctctc acacataatg tgtgtgtgtg tgtgtgtgta tatatatata   170100
cacatataca tatatatata tacacacata tgcatatata taaaaccccca agcagcctct   170160
```

```
ggcttagcag gtgcatttcc cagcagggca attaaagcca tggtcccagt agtggtcttg 170220
gggtctcagg gtatttggtc tgtgcagcca catgcttcag tctctggacc ccaggtcatc 170280
taacgaggtg gtcgtgtggg gactgggata gaaaaggtgt ctgcacggac gtgtgtgaaa 170340
gggctggcac atcgccagtg ctcagcactg tcagctgcta tcaccagtca ttcaatcatt 170400
cattcattca gttgttcatt cttcaacagg ccgttttaaa aatgtgccca gtataccaaa 170460
atctccgcta agcatttaaa gaggcagaat gaaagttagc agtggtggtg aaacgaagct 170520
gggaatgtgc tctgagggcc tccttgtggg cttaatgaat atgtagaaac cacgcatttt 170580
aaatagagag ggagaaaggg agaggttcct ggtcctctgc atggggactt gtgtgtggct 170640
ctttactgta ggcctgtgcc actcctgctc aacagctacc acagaggacg ccttcaacaa 170700
atgtgaagaa cgaacaaaag gtacaaatgt gaagaacgaa cagggtagaa agaaaggaga 170760
aagcaagggt gagggtgaga atcaaggga cagagaagag agaagaggag atagcctggg 170820
agttcacaca gccaagaagg tagacactca gttgaaccag caagaggctg agcctaactc 170880
tcccttctcga atgggcagga gttcatgata tttaataaac agaggccttg ctctgtaaga 170940
gacagggtac caggcagaga gcaagtcagc atcgcaggag tcaaacgagg cagacagcgg 171000
gggcagggag cttgcctctg aaggagaccc aggctgccag agtagcaggg agtctgggcc 171060
agtcctcttt tgggaagcgc ttcctcggct tctgccccc ctctcctctc cctttccacc 171120
caccatcctg acataatact tcctaatctg gaagtgttgt ccagagaaga acctgctcat 171180
ttcctcttaa gtaggcaggg aagcactaac gtccagcagc atcggaaacc cgtaggagcg 171240
ctctcggcag tgcagggtga ggggacagtc catgtagtca tgagacgtgg gtgtcaggca 171300
agcgtctctt ttccaaaaga gaaaaacatt aaaggcctca caaacggcgc ccaaagacta 171360
attctgcata gcatctttgc gagaccctag gttcttatga tgactggttt tgcctgagaa 171420
agaaaaaatt ttaattttgc tctgacatgc caattcaaca aatcattttc acataatatt 171480
catgcaaaaa aaaaacaatt tgccagaaaa cttgggaatc catccacatc tacagctttt 171540
ccctgcagtc acactacagt gggatccctc catacaggag cggcagagtg gagcaggcta 171600
gagatgcctg tttgtttctg tttgctgcac cgcagcaagc atttctgtcg tgcccactct 171660
gtactagaaa gtacatgaac atcagccata aagggaacta gaaaggtggc ccaccctctt 171720
ggtggagaga gaagagagtg tggtagaaac aataataaga agtctgcaga acttgacccc 171780
tcccagcctc tcccacctgc cagcctggcc cttgcagaga gatgcaggct gccattctta 171840
ggccaaagcc tgggacagtt gggctcagca aggtaggcat ccgtcaagca aggaggagca 171900
ggggtcagca gtgaccccag cagccagcag ggagaaaggt gcatgtgaca aggacaccag 171960
aggccgtggg tcaggatcag ccagggtcag ggtagcattt ctaggaattc actctgttgg 172020
gcgctgtgct ggctgcttct cacatattat tcctttctta ctctcagagc agagatttca 172080
attgcagcga gattgtggag gcagccaggg aggtggggag ggtggtgtct tctaaaagca 172140
tttttcagtat ccatgtggtt tcagtaataa taataataat aaaccagtga aagtaaaac 172200
aggacaaaaa tcttcatagg cagtgaacca tatcagagag tccaagaaag cacaatgaga 172260
gtgtggctta aaaccctga cgacattcc tttgcaccag cttggtgagg agggcatggt 172320
ccccgccacc ccccaccccc actttgcaga taaaccacat gcaggaaggt cagcctggca 172380
agtccagtaa gttcaagccc aggtctcaac tgggcagcag agctcctgct cttctttgtc 172440
ctcatatacg agcacctctg gacttaaaac ttgaggaact ggatggagaa aagttaatgg 172500
```

```
tcagcagcgg gttacatctt ctttcatgcg cctttccatt ctttggatca gtagtcacta  172560
acgttcgcca gccataagtc ctcgacgtgg agaggctcag agcctggcat gaacatgacc  172620
ctgaattcgg atgcagagct tcttcccatg atgatctgtc cctcacagca gggtcttctc  172680
tgtttcaggg catgaactac ttggaggacc gtcgcttggt gcaccgcgac ctggcagcca  172740
ggaacgtact ggtgaaaaca ccgcagcatg tcaagatcac agattttggg ckggccaaac  172800
tgctgggtgc ggaagagaaa gaataccatg cagaaggagg caaagtaagg aggtggcttt  172860
aggtcagcca gcattttcct gacaccaggg accaggctgc cttcccacta gctgtattgt  172920
ttaacacatg caggggagga tgctctccag acattctggg tgagctcgca gcagctgctg  172980
ctggcagctg ggtccagcca gggtctcctg gtagtgtgag ccagagctgc tttgggaaca  173040
gtacttgctg ggacagtgaa tgaggatgtt atccccaggt gatcattagc aaatgttagg  173100
tttcagtctc tccctgcagg atatataagt ccccttcaat agcgcaattg ggaaaggtca  173160
cagctgcctt ggtggtccac tgctgtcaag gacacctaag gaacaggaaa ggccccatgc  173220
ggacccgagc tcccagggct gtctgtggct cgtggctggg acaggcagca atggagtcct  173280
tctctcccct cactggctcg gtttctctta gggaccctca cagcactaag gggtgcgcgt  173340
cccctgtcag gccctcgaat gccctcccac agccaggccc ctctgaggtt tcactctggc  173400
ctgcttggct cctagcagcc accaacccat gatgctgggc cctgaaaaca cacgcagacc  173460
tggatgagtg aggccactgg gcacaaccag ggctcccagc tcaccagagc agcctgggac  173520
acagagggtg ctcagaaacc taccagagca gccctgaact ccgtcagact gaaatcccct  173580
gttgccggga ggaggcgccg ggcctggggg acgggtcctg gggtgatctg gctcgtctgt  173640
gtgtgtcact cgtaattagg tccagagtga gttaactttt tccaacagag ggaaactaat  173700
agttgtctca ctgcctcatc tctcaccatc ccaaggtgcc tatcaagtgg atggcattgg  173760
aatcaatttt acacagaatc tatcccacc agagtgatgt ctggagctac ggtgagtcat  173820
aatcctgatg ctaatgagtt tgtactgagg ccaagctggc ttttattgtt agttaattta  173880
cattatatcc tctgacatgc aagtattttc tttcgagata atgactaatg ataatgtaat  173940
cattgctgtc tatctattgt actgagaaaa cacggcagag gaaatcgagt ccagctgccg  174000
tccaaaagtc actggagatt gcaatgagct cgtctggcag ggtgggggt atgggaggga  174060
aagagcttag gaaacggctc tccctgcaaa gtccaaccaa actttaacgt taaccaaacc  174120
attaatgttg ccatgaattt gaagtgaacc agagggaggt ggcagaagaa gcttaatggg  174180
gaatagttcc ggtagagaaa tgaggcttaa gatgaactac cctggccctt atgtgtcaga  174240
gagaacggct tgacaaacac acactgagga tgtctgcagg gataaaagaa gaagggaga  174300
tgacccttgc ttctcgctct cgggaggacc atctggtccg gccctgggga ttctctgttt  174360
cctcttctga atcccagtgt tgcccagcac tggcctgtac ccatcctcac gagggccgct  174420
ctcctcaccc ggcccctaggt ccctgccctg tcctgagcct acaggggcct cccatgttga  174480
gaaagtgttg ctgacacatt gtctctgacc gctgtgccag gcattttctg ctgaattacc  174540
gcacttggtc cttgaatttc acccagcaac ttactgaaag gctggaaccc atgaacctac  174600
cccttcactg aggaaaataa gttaccccag ccatctacag cgacaggagc aagggaggag  174660
tcgcctcacc tctctagaaa tgtgtatttg aggagaacac tattgaaatg aatttccaag  174720
aataatctag tcagtattac aaaagcaaaa ttatttggga tatcgtcctt ttttacttag  174780
tatttttct ttttcctata gcattattaa ctttctgatt ttccaaatac atacacattt  174840
ttaaatttcc tgagtctttta tctcttctgt taaaatgtaa gatttatgat acaaaggcag  174900
```

```
agatttgtgt ccatgaataa gtgaagtttg gtgtgcacct gtgagctgag ccacctcaat   174960
taatggaaca gataaggaaa taaaggtctg ctgatgcatt gttatttaca gccattttca   175020
gaatgtatct cctctccacg agggaactgc agggtcctgc cccaagccat ttattttgtc   175080
ctcaagcagc ccgcccctcc cactccaggc acagcccggt ctcctgctgg tctcccctct   175140
tcccacttgc tcccctcat ctatgctcca gacagaggcc acatatattt tttaactttt    175200
tttttttttt ttttgagaca gagtcttgcc ctgtcaccca ggctggagtg cagtggtgca   175260
gtctcggctc actgcaacct ccacctcccg ggttcaagtg attctcctgc ctcagcctcc   175320
tgagtagctg ggattacagg cgcacaccac catgcccagc taatttttg tatctctagt    175380 tgagacaggg tttcactatg ttggccaggc tggtctcgaa ctcctgacct catgatctgc   175440
ccgcctcggc ctcccaaagt gcatattttt aactttatc agactttttca ttctctgctc    175500 aacatctttc tttggtcctc caggtatgtt cagataaaac ctgagcacct ggccatgact   175560
gatgggttgc tgggccatct ggccctggca actctcccgt ccaccaggtc cccctcccgt   175620
cacgctccag gcatagcctg tgtgtgccag cgcaatgccc acactccatg cacaagtgga   175680
agccctctca aagtcagtgg cttagtgcct tgatgtggtc acacccattc tcaggaagtc   175740
cgttcccact gaaaacattg tgtgttttca acatcattga ggctgccacg gcagattata   175800
atcactggcc taggcagccc actggaacta ccagaccatg agcctgaatt ttttgtttaa   175860
aaatcatatc ctgttttctc tactctctag tctctagtca aggtgaatta ttcaatttaa   175920
taaattaggg gcctagtgtg ttgtaccaag gagctaaaaa gagagaactc gcaacacctt   175980
ccagcccatt ctccacctaa cactggctat actggctctc ctctctctcg ctgtttgttc   176040
caaaatctaa taacctgtct tcccactaga attcatcata catgtttaaa aacctagtta   176100
aatagtagtt aaactgactg catagatctg gaaatgagac agtctttctt ttacaaatcc   176160
atatagacta tgagttgggg gcaggggatg acacaagaat ctattttctt gcccccaaac   176220
cattgctttc cttccaatgt taagcttgta ttctgtgtat taattcaggt ggttccgttt   176280
gggaatggcc tctgttaccc agagatggga gggccatcag aactcggggt tgtctgaaaa   176340
aacactggtt ctaaaattat cactgctttc acttgttttt aaccatcata gttgtttgat   176400
tttgaaggaa aaacatgagg gttttttattc tatgcttgtt atatctatat tgtggttcg    176460 tatttttag attttagtac ctgacatttt tttaactttt attttaggtt caggggtaca    176520
tgtgcaggtt tgttatatag gtaaatttgt gtcatggggg tttgttacac agattatttt   176580
atcacccagg gattaagcct agtacccatt agttatttt cctgatcctc tccctcctcc     176640
catcctccac cgtcctatag accccagtgt gtgttgttcc cctctaagtg tccatgtgtt   176700
ctcatcattt agctcccact tataagtaag aacatgcggt atttgatttt ctgttcctgc   176760
attagtttgc tagggatgat ggcctctagc tccatccatg ttcttgcaaa gtacatgatc   176820
tcattctctt ttgtggctgc ctagtgttcc atggtgtata tgtaccacat tttcttatc     176880 cagtctgtca ttgatgggca tttaggttga ttccatgtct ttgctattgt aaatagtgct   176940
gcagtgaaaa tacgcatgca tatgtcttta tggtagaatg atttatattc ctttgagtaa   177000
tgggattgcc gggtcaaatg gtagttctgt ttttagctat ctgagaaatt gccacactct   177060
tttccacaat aattgaacta atttacattc ccaccaacag tgtaaaagca ttccttttc    177120 tccacaacct caccagcatg tgtttgggatt tttttttttt tttactttc aataatagcc    177180 atctgactgg tatgagatgg tatctcagtg tggttttgat tttatttct ttaatgatca    177240
```

```
gtgatgttaa gctctttttc atatacttgt tggctgcatg tatgtcttct tctaaaaagt   177300
gtctgctcat gtcctttgcc cacttttaa  tgggattgtt taattttttc ttgtgaattt   177360
acttaagttc cttatagatg ctggttatta gacccttctc agatttgtag cttgcaaaaa   177420
tgttcaccca ttctgtgggt tgtcttcact ctgatgatag tttcttttgc tgtgcagaag   177480
atcttcagtt tagttagatc ccatttgtca attttttgctt ttgttgcaat tgcttgatgt   177540
gttttcatca tgaaatctta gcccattcct atatccagaa tggtattacc taggttgtct   177600
tccagggttt ttatagtttg gggttttaca tttaagtctt taatccatgt tgagtttatt   177660
tttgtgtatg gtgtaaggaa ggagtccagt ttcaatcttc ttcatggcta gctagtcatc   177720
atttattgag tagggagtcc tttattcatt gcttttttt  ttttgtcaac tttgtcaacg   177780
atcacatggt tgtaggtgtg cagccttatt tctgggctct ctattctgtt tcattggtct   177840
gtatgtctgt ttctgtacta gtaccatgct gttttggtta ctgtatccct gtagtttaaa   177900
gtcaggtagc atcatgcttc cagctttgtt ctttttgctt aggattgcct tggcaattca   177960
ggctcttttt tggttccatg tgaattttta aattgtattt tctagttctg tgaagaatct   178020
cattggtagt gtgataggag taacattgaa tctataaaat actttgggca gtatagtcat   178080
tttaatgata ttgattcttt ctatccatga gcatggaatg ttttccatt  tgtttgtgtc   178140 atctctgatt tctttaagca gtgttttgtg gttcttattg tagagatctt tcactttcct   178200
ggtttactgt atttctaggt attttattct ttttgtggca attgtgaatt gaattgcatt   178260
cctgatttgg ttctcagctt gactgttgtt ggcatattgg aatgctaatt atttttgtac   178320
attgattttg tacaactgag tcttcactga agttgtttat cagcttaagg ggttttgggt   178380
caagactatg gggttttcta gatataggat catgtcatct gcaaacagag atagctgttt   178440
tcctctcttc ctgtttggat gtccattatt tctttctctc acctgattta tctggccagg   178500
acttccaata ctatgttaaa taggagtgtt gagagaggga atccttgtct tgtgtcaatt   178560
ttcaagggga atgttttcaa cttttgccca ttcaatatga tgttggctgt gggtttgcca   178620
tagatggcta atatgttgag gtttgttctt taaatacctta gtttattgag aattttaaac   178680
atgttgaatt ttattgagag cctttctctgc atctattgag atgatcatgt ggcttttgtc   178740
cttagttctg tttgtgtggt gaatcacatt tattgatttg catatgttga accaatcttg   178800
catcccaggg atgaagccga cttgattgtg gtggcttaag cttttttgatg tgctgctgga   178860 ttcgatttgc cagtattttg ttgaggattt ttatgtctat gttcatcaga gatattggcc   178920
tgaagttttc ttttttttgtt gtatctctgc caagctttgg tatcaggatg acattggcct   178980
catagaatga gttaaggaag agtccctcct tctcaatttt tttggaatag tttcagtagg   179040
aatggtacca gctttttttg tacatcttgt agaatttggc tatgaatcca tctagtctta   179100
ggctttgttt tggttggtag gctatttatt actgattcaa ttttggagct cattattggt   179160
ctgttcaggg attcagtttc ttcctgaggt ttttatttt  atcaaatgga acttaagctt   179220
tttcatttcc aattttttta tgatctaaaa atgtgcagtt tacagccctg ttcagaatct   179280
gcatcttcct cattctgcag atacaggtcc ctcagagcag gtgactgagt gtgtatcctg   179340
tctggagcat aatacttatg ctagtagagt tactgttgtc tttattgtta attaccaaag   179400
tttaccactt atcagtcact tactacttgc tgggcattgc actaagcatt tcagttgtat   179460
tatcttgttg ggtccttaca gcaatcctgt gaaacagata ctgctattac cccactttat   179520
agagaggtag actgaggctt ccagcattga agcaaattgc ccaagactac agaaatgtag   179580
gtttctaaac atcaagaaac agtaaccagt aatgatgact aaagcaaggg attgtgattg   179640
```

```
ttcattcatg atcccactgc cttcttttct tgcttcatcc tctcaggggt gactgtttgg   179700
gagttgatga cctttggatc caagccatat gacggaatcc ctgccagcga gatctcctcc   179760
atcctggaga aaggagaacg cctccctcag ccacccatat gtaccatcga tgtctacatg   179820
atcatggtca agtgtgagtg actggtgggt ctgtccacac tgcctagctg agccttggtg   179880
gctgctctta gccaaacagc tgaggccttt gcatccctgg agaaatgtca tcacattact   179940
taaggcaggc acacaaatcc agaaacatct gtaaataccc cttcaagcat tcttttaaag   180000
acacttcttg actcattggg cagtatgacc tgacatttgc ccatgtttgc aagcaaataa   180060
ataaaactaa agtcttccgc aagccattac accaaaatat tctattcgct gagttactca   180120
atgaaatacc gagttgccct atattttgaa gcctgttacc agagagactg aatgttttta   180180
aatgcatggc agtgagtaac aacataaggc taatagagtc aacatttctg ctttgactta   180240
aaccttttaa accagtggat ttatgtgaag tctctgcagt gtggcattta acatttcaa   180300
tctaaataag agtgtgtaat ttgattgatg ctattattct accagattca cgagtgcagt   180360
gggctctgga ggtagcatta catgcatggg atgagcattt gcaaagaaa gttgtatagg   180420
gaatatgaca gagccaagtt aatgtaaata ttaatgcctt tctgaactct aggccacaga   180480
gttgatcttt tttaacttcc ttggtttggg ctaaggaagc tgtgatccag agaagccacg   180540
tgatttgtct aaggtcacat agcagtctgg cctaaaatag cttgatatgc tgtggatgga   180600
aaataaatgt gatccctcaa gaggcatgag gatttccagg cagtagccat acctccaaat   180660
tgtttaatct ggatttagat tgttgggtag tcacatgcag cagcacagtt aacagtgtgt   180720
cctcctgtgg aagttgccag cacagccagc cctctcactt gcatgcatgc ccaccagcct   180780
tctcacttgc atgcatgccc actgggtatg tgctgtactg gagacgccgg gggtagggggc   180840
ccagtcccaa ccccaaattc tttaaagcct atttttctaa gttgcatctg gtttcctacc   180900
tgaaggaatg ctaagggtgg atgttgagtg aggaccttgg tgcagggcac cctgcagtca   180960
ggatagttca tggagagcaa ttgtacagac ccacactgct ccatcccctc aggcgtaaca   181020
caggatgctg accccaggaa gagtgggcgt agaaaaacta gagggcatta ttgttattct   181080
gattcaaatg tacagtgctg gcatggtctt taaacagtaa ccagtactag ctggccaaga   181140
cagaaaagtc taccacaaag acttggttct ttcatcactt atttgactgg aagtgtcgca   181200
tcaccaatgc cttcttttaag caatgccatc tttatcattt cttccagtgt tctaattgca   181260
ctgttttttc tcattccttc cccaggctgg atgatagacg cagatagtcg cccaaagttc   181320
cgtgagttga tcatcgaatt ctccaaaatg gcccgagacc cccagcgcta ccttgtcatt   181380
caggtacaaa ttgcagtctg tgcttccatt gggaagagtc cctctaatga gcatctcatg   181440
tcactgtgtt ctgtcacatg ccagcctggc ctccctgtgt cccagatcgc attattaaac   181500
cctccagcgc attagagcaa gcctcagtaa ggcgcaggcc acatcgtgaa ctaagcagca   181560
tccgtgagtg gggcccaccc aactccatct ccccctcccc gtctgaactc tcctctggtg   181620
ctcgtcctca ctgtccggct agccaaagcc tcagctgggt ctaagagaga agcatggtct   181680
attgggcttt ggtgtcaggc agacgtggct tcacacccct gactctccac ttcttcgcat   181740
cacccaggca gccgatccac ctatctcctt ccataacaca ggaataccaa aaccaagctc   181800
acaggattgt ctcaaagatt caataaaata tgttgcaaaa tacgctccct aacacctcac   181860
agcaaggtgc acactcgatg aatgctgcag cttcttccct ttctgtttcc tcagaagcta   181920
tttgaatctc atgtaggggc tttcaagcat caaaggatgg ttcatgtttt attttaaggc   181980
```

```
acccacatca tgtcatgagg ggaggcagct ataatttaga gaaccaaggg ggatttcatt   182040
ataacaaaat tggcaaacac acaggcacct gctggcaata acccctgct  cctatagcca   182100
agaagtggaa tagcatctct acgggccatt ctaatagcct caaaatctct gcaccagggg   182160
gatgaaagaa tgcatttgcc aagtcctaca gactccaact tctaccgtgc cctgatggat   182220
gaagaagaca tggacgacgt ggtggatgcc gacgagtacc tcatcccaca gcagggcttc   182280
ttcagcagcc cctccacgtc acggactccc ctcctgagct ctctggtatg aaatctctgt   182340
ctctctctct ctctcaagct gtgtctactc atttgaacaa attgaatttt agggaaaata   182400
accatctagt gaaactcaca tggatatgaa gtcaatttta accaaatggt aaaatcaaaa   182460
tcaaaataaa ttaagtgtat taattatttt gttgcattgc aacaacttga ttgtaagcct   182520
tttaggtcca ctatggaatg taattaaatc aaaactaaac ctagttgctc taaaactaac   182580
gattaagaca aaaattaaac accttcacaa tataccctcc atgaggcaca ccacctgcat   182640
tcaggaaaag tggatgagat gtggtacaag cattccatgg gcaacttctc tgtttctttt   182700
tcagagtgca accagcaaca attccaccgt ggcttgcatt gatagaaatg gggtatgtat   182760
gaacacctta taagccagaa tttacagctc tccactatgg ctctatttta catggaaaat   182820
gccttaacct aaataatttt aacccagata atcttgagtt ttcttcctgt gtgggttttt   182880
ccctgcacgg ctgtcacgcc tcacagtgcc gttcaaagcg tgactcctgg accagtagta   182940
gcatcgcctg gccttgttag aaacgccatt tttcaggcca ctgccccagt ttgaccaaat   183000
caggacctct gggggtggca cccagtagtc tatgtttgag ccactttcca ggtgatgctg   183060
atgtctgttg aagtgtgagg ccgtggtcta gaccgcactg tgccatgcag aaaccactag   183120
ccacatgtgg ctacttcaac ttaaatgtta atgagttaaa atgaaataaa atataaaatt   183180
cagtttctca cacatgtgaa gtgtccagta gccacacgtg gctagtggtg accgtattga   183240
agagcaccgc tcatagcaca cctccctcac tgcggaaagt tctgctgtac agcacccagc   183300
acagccctgc tgcccaccct gcagcctgtg gcccagtagc accagcaccc accagggtgc   183360
agactctcag gcctgcccaa cctactaatc agaaccagca tctcaaggag atctcgggtg   183420
atttttgcaa acactgaagt tggggcagcc ctgaccggag taaccttccc tcatttcctc   183480
ctgcagctgc aaagctgtcc catcaaggaa gacagcttct tgcagcgata cagctcagac   183540
cccacaggcg ccttgactga ggacagcata acgacacct  tcctcccagt gcctggtgag   183600
tggcttgtct ggaaacagtc ctgctcctca acctcctcga cccactcagc agcagccagt   183660
ctccagtgtc caagccaggt gctccctcca gcatctccag aggggggaaac agtggcagat   183720
ttgcagacac agtgaagggc gtaaggagca gataaacaca tgaccgagcc tgcacaagct   183780
ctttgttgtg tctggttgtt tgctgtacct ctgttgtaag aatgaatctg caaaatttct   183840
agcttatgaa gcaaatcacg gacatacaca tctgtgtgtg tgagtgttca tgatgtgtgt   183900
acatctgtgt atgtgtgtgt gtgtatgtgt gtgtttgtga cagatttgat ccctgttctc   183960
tctgctggct ctatcttgac ctgtgaaacg tatatttaac taattaaata ttagttaata   184020
ttaataaatt ttaagcttta tccagatact cataacctgc taacacacac acatatacac   184080
acacatacac atacacacat atacacacac cacacacata cacagacacc acacacatac   184140
catacacaga cacatacaca tgcacacaca tatacacaca cacctcaaat acatacacac   184200
cacacacaca tacatgtata cacacataca cacaccacac atacaccaca aaaccccac   184260
acacatacac atatacacac cacacacacc atacacacac acgtatacac acatatatac   184320
acacatacac catgcataca tacacaccac acatacatac agacacacca cacacacgta   184380
```

```
cacacaacac acaacacaga cacgtacaca cactacagac atgtatgcac acatacacac    184440
acaccacaca tacatacaca cagacacata tacactacac acaccattac atacacacgt    184500
acacatacac cacacacacc acacatacac acaccacaca cacatacgcc acacacacac    184560
cacaaaaacc gcacacacat acaaacatat acacactaca ccacacatac acacacacac    184620
cacacaccac acacacacat acacacacca cacacaccac acatacacgc accacacata    184680
cacacacgta gacacaccac acaccacaca gaaacacaca ttaacacacc acatacacat    184740
atgtatgtgc atatacacac ccacaccccca cacacacatg tataaagatt tagatatata    184800
taaaacatat gttatatata tgttgatgta atatctaata tctatatatc taatatgtag    184860
tttattagct atctaatatc tatgtcatat atatcaaaat cttttatatat aaaaatatgt    184920 agaaatcttt atacatatgt tatatgtata taaagattta gatatataac atatgtaagt    184980
tatatatatg ttagtgtaat atctaatata tagtttattg gctatctaat ataatataaa    185040
cagattatca atattataag ctattagaaa aatgcaagtt aaggcagatg atatacctct    185100
ttacacacca actacacaca ccaactacac acacacatac acacagacac acgacaca     185160 caccatacac atgtacacac acaccacata tacacaaacg tacacacaca ccacacacac    185220
atacacacca cacacacacc acacatacat acacatccac acaccacaca tgtacacacg    185280
ccacacacac acatacacac cacatacaca tatgtatgca cacatacaca ccaacaccac    185340
acagacacca cacatgcata aacatataga catatacaca ccacacacca tatgtacaca    185400
tgtacacaca caccacatat acacacaaca cacacaaata cacacaccac acacacacca    185460
caaaaacccc acacacacac aaacatatac accccacaca tacgcatata tacacacaca    185520
catacacacc acacacatac acaccacaca cacaccacac atacacacac gtacacacac    185580
cacacacaca ccacagacac acaccacaca tacatacaca tacacacacc acacacacgt    185640
acacacacca cacacaccac agacacacat agacacacca catacacacc cacaccacac    185700
acacacaact catccacacac atacatacac aatagacaca tacacaccac acacaccata    185760
catacacacg tatacacaca ccacatatac acacacgtac acacacacca cacacaccca    185820
catgcacaca ccacacacac atacaaatat accacacaca cacatacacc acacacacgg    185880
tgcacataca cacacatata cacacaccag acacacatac cacatacaca tcacacatat    185940
atgtatacat gcatacacat acacacacac atacacacac tctcctcaag gcagtttatc    186000
ctctgagaac tttaaattta caaaagacac atatgtccat tactttgaga aggacaggaa    186060
agaacccact ttcttttgca gcaacagcaa gagggccctc ccgaggctcc tgctcccgt     186120 cataagtctc cttgttgagg acattcacag ggttcagaac ccagggatcc tgcatgggat    186180
ggtgctttgc tgattacttc acctctgatt tctttccact ttcagaatac ataaaccagt    186240
ccgttcccaa aaggcccgct ggctctgtgc agaatcctgt ctatcacaat cagcctctga    186300
accccgcgcc cagcagagac ccacactacc aggaccccca cagcactgca gtgggcaacc    186360
ccgagtatct caacactgtc cagcccacct gtgtcaacag cacattcgac agccctgccc    186420
actgggccca gaaaggcagc caccaaatta gcctggacaa ccctgactac cagcaggact    186480
tctttcccaa ggaagccaag ccaaatggca tctttaaggg ctccacagct gaaaatgcag    186540
aatacctaag ggtcgcgcca caaagcagtg aatttattgg agcatgacca cggaggatag    186600
tatgagccct aaaaatccag actctttcga tacccaggac caagccacag caggtcctcc    186660
atcccaacag ccatgcccgc attagctctt agacccacag actggttttg caacgtttac    186720
```

-continued

```
accgactagc caggaagtac ttccacctcg ggcacatttt gggaagttgc attcctttgt    186780
cttcaaactg tgaagcattt acagaaacgc atccagcaag aatattgtcc ctttgagcag    186840
aaatttatct ttcaaagagg tatatttgaa aaaaaaaaaa agtatatgtg aggatttta    186900
ttgattgggg atcttggagt ttttcattgt cgctattgat ttttacttca atgggctctt    186960
ccaacaagga agaagcttgc tggtagcact tgctaccctg agttcatcca ggcccaactg    187020
tgagcaagga gcacaagcca caagtcttcc agaggatgct tgattccagt ggttctgctt    187080
caaggcttcc actgcaaaac actaaagatc caagaaggcc ttcatggccc cagcaggccg    187140
gatcggtact gtatcaagtc atggcaggta cagtaggata agccactctg tcccttcctg    187200
ggcaaagaag aaacggaggg gatggaattc ttccttagac ttacttttgt aaaaatgtcc    187260
ccacggtact tactccccac tgatggacca gtggtttcca gtcatgagcg ttagactgac    187320
ttgtttgtct tccattccat tgttttgaaa ctcagtatgc tgcccctgtc ttgctgtcat    187380
gaaatcagca agagaggatg acacatcaaa taataactcg gattccagcc acattggat    187440
tcatcagcat ttggaccaat agcccacagc tgagaatgtg gaatacctaa ggatagcacc    187500
gcttttgttc tcgcaaaaac gtatctccta atttgaggct cagatgaaat gcatcaggtc    187560
cttttgggca tagatcagaa gactacaaaa atgaagctgc tctgaaatct cctttagcca    187620
tcaccccaac cccccaaaat tagttttgtgt tacttatgga agatagtttt ctccttttac    187680
ttcacttcaa aagctttta ctcaaagagt atatgttccc tccaggtcag ctgccccaa     187740
accccctcct tacgctttgt cacacaaaaa gtgtctctgc cttgagtcat ctattcaagc    187800
acttacagct ctggccacaa cagggcattt tacaggtgcg aatgacagta gcattatgag    187860
tagtgtggaa ttcaggtagt aaatatgaaa ctagggtttg aaattgataa tgctttcaca    187920
acatttgcag atgttttaga aggaaaaaag ttccttccta aaataatttc tctacaattg    187980
gaagattgga agattcagct agttaggagc ccacctttt tcctaatctg tgtgtgccct     188040
gtaacctgac tggttaacag cagtccttg taaacagtgt tttaaactct cctagtcaat    188100
atccacccca tccaatttat caaggaagaa atggttcaga aaatattttc agcctacagt    188160
tatgttcagt cacacacaca tacaaaatgt tccttttgct tttaaagtaa ttttgactc     188220
ccagatcagt cagagcccct acagcattgt taagaaagta tttgattttt gtctcaatga    188280
aaataaaact atattcattt ccactct                                        188307
```

<210> SEQ ID NO 2
<211> LENGTH: 18
<212> TYPE: DNA
<213> ORGANISM: Artificial
<220> FEATURE:
<223> OTHER INFORMATION: Mt-R2 primer
<400> SEQUENCE: 2
cacccagcag tttggccc         18

<210> SEQ ID NO 3
<211> LENGTH: 22
<212> TYPE: DNA
<213> ORGANISM: Artificial
<220> FEATURE:
<223> OTHER INFORMATION: Mt-R3 primer
<400> SEQUENCE: 3
acactaccca gcagtttggc ac        22

```
<210> SEQ ID NO 4
<211> LENGTH: 22
<212> TYPE: DNA
<213> ORGANISM: Artificial
<220> FEATURE:
<223> OTHER INFORMATION: Mt-R4 primer

<400> SEQUENCE: 4 acactacccca gcagtttgga cc                                              22

<210> SEQ ID NO 5
<211> LENGTH: 24
<212> TYPE: DNA
<213> ORGANISM: Artificial
<220> FEATURE:
<223> OTHER INFORMATION: Mt-R5 primer

<400> SEQUENCE: 5
ttagtagacc cagcagtttg gccc                                             24

<210> SEQ ID NO 6
<211> LENGTH: 20
<212> TYPE: DNA
<213> ORGANISM: Artificial
<220> FEATURE:
<223> OTHER INFORMATION: Mt-R6 primer

<400> SEQUENCE: 6
ctattccagc agtttggccc                                                  20

<210> SEQ ID NO 7
<211> LENGTH: 22
<212> TYPE: DNA
<213> ORGANISM: Artificial
<220> FEATURE:
<223> OTHER INFORMATION: Mt-R7 primer

<400> SEQUENCE: 7 acactacccca gcagtttagc cc                                              22

<210> SEQ ID NO 8
<211> LENGTH: 24
<212> TYPE: DNA
<213> ORGANISM: Artificial
<220> FEATURE:
<223> OTHER INFORMATION: Mt-R8 primer

<400> SEQUENCE: 8
ttagtagttc cagcagtttg gccc                                             24

<210> SEQ ID NO 9
<211> LENGTH: 22
<212> TYPE: DNA
<213> ORGANISM: Artificial
<220> FEATURE:
<223> OTHER INFORMATION: Mt-A primer

<400> SEQUENCE: 9
ctgtgaccca gcagtttgac cc                                               22

<210> SEQ ID NO 10
<211> LENGTH: 23
<212> TYPE: DNA
<213> ORGANISM: Artificial
<220> FEATURE:
<223> OTHER INFORMATION: Mt-B primer
```

<400> SEQUENCE: 10
atgtgaccca gcagtttgtc ccg                                    23

<210> SEQ ID NO 11
<211> LENGTH: 24
<212> TYPE: DNA
<213> ORGANISM: Artificial
<220> FEATURE:
<223> OTHER INFORMATION: Mt-C primer

<400> SEQUENCE: 11
ctaccgcacc cagcagtttg tccc                                   24

<210> SEQ ID NO 12
<211> LENGTH: 18
<212> TYPE: DNA
<213> ORGANISM: Artificial
<220> FEATURE:
<223> OTHER INFORMATION: Wt-R1 primer

<400> SEQUENCE: 12
acccagcagt ttggccag                                          18

<210> SEQ ID NO 13
<211> LENGTH: 22
<212> TYPE: DNA
<213> ORGANISM: Artificial
<220> FEATURE:
<223> OTHER INFORMATION: Wt-R5 primer

<400> SEQUENCE: 13
attcactcca gcagtttggc ca                                     22

<210> SEQ ID NO 14
<211> LENGTH: 19
<212> TYPE: DNA
<213> ORGANISM: Artificial
<220> FEATURE:
<223> OTHER INFORMATION: Wt-R6 primer

<400> SEQUENCE: 14
atacacagca gtttggcca                                         19

<210> SEQ ID NO 15
<211> LENGTH: 21
<212> TYPE: DNA
<213> ORGANISM: Artificial
<220> FEATURE:
<223> OTHER INFORMATION: Wt-R7 primer

<400> SEQUENCE: 15
gactacccag cagtttagcc a                                      21

<210> SEQ ID NO 16
<211> LENGTH: 21
<212> TYPE: DNA
<213> ORGANISM: Artificial
<220> FEATURE:
<223> OTHER INFORMATION: Wt-R7-2

<400> SEQUENCE: 16
gactacccag cagttaggcc a                                      21

```
<210> SEQ ID NO 17
<211> LENGTH: 21
<212> TYPE: DNA
<213> ORGANISM: Artificial
<220> FEATURE:
<223> OTHER INFORMATION: Wt-R7-3 primer

<400> SEQUENCE: 17
gactacccag cagtatggcc a                                              21

<210> SEQ ID NO 18
<211> LENGTH: 22
<212> TYPE: DNA
<213> ORGANISM: Artificial
<220> FEATURE:
<223> OTHER INFORMATION: Wt-R8 primer

<400> SEQUENCE: 18
attcactgta gcagtttggc ca                                             22

<210> SEQ ID NO 19
<211> LENGTH: 20
<212> TYPE: DNA
<213> ORGANISM: Artificial
<220> FEATURE:
<223> OTHER INFORMATION: Wt-A primer

<400> SEQUENCE: 19
gactacccag cagtttgcta                                                20

<210> SEQ ID NO 20
<211> LENGTH: 21
<212> TYPE: DNA
<213> ORGANISM: Artificial
<220> FEATURE:
<223> OTHER INFORMATION: Wt-B primer

<400> SEQUENCE: 20
actacccagc agattggcca g                                              21

<210> SEQ ID NO 21
<211> LENGTH: 24
<212> TYPE: DNA
<213> ORGANISM: Artificial
<220> FEATURE:
<223> OTHER INFORMATION: Wt-C primer

<400> SEQUENCE: 21
gactagcacc cagcagtatg gcca                                           24

<210> SEQ ID NO 22
<211> LENGTH: 17
<212> TYPE: DNA
<213> ORGANISM: Artificial
<220> FEATURE:
<223> OTHER INFORMATION: 3T-EGFR-858-R2 probe

<400> SEQUENCE: 22
ttggcccgcc caaaatc                                                   17

<210> SEQ ID NO 23
<211> LENGTH: 25
<212> TYPE: DNA
<213> ORGANISM: Artificial
<220> FEATURE:
<223> OTHER INFORMATION: EGFR-L858R-F2 Forward primer
```

```
<400> SEQUENCE: 23
aggaacgtac tggtgaaaac accgc                                              25
```